US012037463B2

(12) United States Patent
Park et al.

(10) Patent No.: US 12,037,463 B2
(45) Date of Patent: Jul. 16, 2024

(54) ANTIMICROBIAL OPHTHALMIC DEVICES COMPRISING POLYSILOXANE-POLYGLYCEROL BLOCK COPOLYMERS AND METHODS OF MAKING AND USE THEREOF

(71) Applicant: Clearlab SG Pte Ltd., Singapore (SG)

(72) Inventors: Jong Gu Park, Singapore (SG); Yeong Shenq Chow, Singapore (SG); John Christopher Phelan, Singapore (SG)

(73) Assignee: Clearlab SG Pte Ltd., Singapore (SG)

( * ) Notice: Subject to any disclaimer, the term of this patent is extended or adjusted under 35 U.S.C. 154(b) by 0 days.

(21) Appl. No.: 18/114,564

(22) Filed: Feb. 27, 2023

(65) Prior Publication Data

US 2023/0227613 A1      Jul. 20, 2023

Related U.S. Application Data

(63) Continuation of application No. 17/158,290, filed on Jan. 26, 2021, now Pat. No. 11,649,325.

(Continued)

(51) Int. Cl.
*C08G 77/46* (2006.01)
*A61L 26/00* (2006.01)
(Continued)

(52) U.S. Cl.
CPC .......... *C08G 77/46* (2013.01); *A61L 26/0019* (2013.01); *A61L 26/0066* (2013.01);
(Continued)

(58) Field of Classification Search
CPC combination set(s) only.
See application file for complete search history.

(56) References Cited

U.S. PATENT DOCUMENTS 3,408,429 A    10/1968   Wichterle
3,660,545 A     5/1972   Wichterle
(Continued)

FOREIGN PATENT DOCUMENTS

EP          0802852 B1       4/2001

OTHER PUBLICATIONS

AATCC Test Method 147-2011(2016)e, "Antibacterial Activity Assessment of Textile Materials: Parallel Streak Method." 2021, pp. 286-287.
(Continued)

*Primary Examiner* — Peter A Salamon
(74) *Attorney, Agent, or Firm* — Meunier Carlin & Curfman LLC

(57) ABSTRACT

Described herein are antimicrobial ophthalmic devices comprising a silicone hydrogel composition and an antimicrobial agent, and methods of making and use thereof. The silicone hydrogel compositions comprise an actinically-crosslinkable polysiloxane-polyglycerol block copolymer crosslinked with a crosslinker. The actinically-crosslinkable polysiloxane-polyglycerol block copolymer being derived from: a polysiloxane prepolymer comprising a polyglycerol side chain, the polyglycerol side chain comprising an ethylenically unsaturated group covalently linked thereto, wherein the ethylenically unsaturated group is actinically curable.

20 Claims, 3 Drawing Sheets

Related U.S. Application Data

(60) Provisional application No. 62/966,233, filed on Jan. 27, 2020.

(51) Int. Cl.
*C08F 293/00* (2006.01)
*C08L 53/00* (2006.01)
*G02B 1/04* (2006.01)

(52) U.S. Cl.
CPC .......... *A61L 26/008* (2013.01); *C08F 293/00* (2013.01); *C08L 53/005* (2013.01); *G02B 1/043* (2013.01); *A61L 2300/404* (2013.01); *C08G 2210/00* (2013.01); *C08L 2201/10* (2013.01); *C08L 2203/02* (2013.01)

(56) References Cited

U.S. PATENT DOCUMENTS

| | | | |
|---|---|---|---|
| 3,699,089 A | 10/1972 | Wichterle | |
| 3,835,588 A | 9/1974 | Whitham | |
| 4,042,552 A | 8/1977 | Grucza | |
| 4,045,547 A | 8/1977 | Le Boeuf | |
| 4,121,896 A | 10/1978 | Shepherd | |
| 4,209,289 A | 6/1980 | Davignon et al. | |
| 4,312,575 A | 1/1982 | Peyman et al. | |
| 4,347,198 A | 8/1982 | Ohkada | |
| 4,431,789 A * | 2/1984 | Okazaki | C08G 77/46 556/445 |
| 4,444,711 A | 4/1984 | Schad | |
| 4,460,534 A | 7/1984 | Boehm et al. | |
| 4,517,139 A | 5/1985 | Rawlings et al. | |
| 4,536,554 A | 8/1985 | Lim et al. | |
| 4,590,018 A | 5/1986 | Neefe | |
| 4,632,844 A | 12/1986 | Yanagihara et al. | |
| 4,924,739 A | 5/1990 | Ademovic | |
| 4,954,586 A | 9/1990 | Toyoshima et al. | |
| 4,983,702 A | 1/1991 | Mueller et al. | |
| 5,010,141 A | 4/1991 | Mueller | |
| 5,034,461 A | 7/1991 | Lai et al. | |
| 5,079,319 A | 1/1992 | Mueller | |
| 5,087,392 A | 2/1992 | Burke et al. | |
| 5,198,477 A | 3/1993 | Von Der Haegen et al. | |
| 5,219,965 A | 6/1993 | Valint, Jr. et al. | |
| 5,227,432 A | 7/1993 | Jung | |
| 5,244,981 A | 9/1993 | Seidner et al. | |
| 5,262,155 A * | 11/1993 | Vincent | C08G 77/38 424/78.02 |
| 5,271,874 A | 12/1993 | Osipo et al. | |
| 5,314,960 A | 5/1994 | Spinelli et al. | |
| 5,314,961 A | 5/1994 | Anton et al. | |
| 5,331,067 A | 7/1994 | Seidner et al. | |
| 5,347,896 A | 9/1994 | Jones | |
| 5,358,995 A | 10/1994 | Lai et al. | |
| 5,387,632 A | 2/1995 | Lai et al. | |
| 5,416,132 A | 5/1995 | Yokoyama et al. | |
| 5,656,210 A | 8/1997 | Hill et al. | |
| 5,760,100 A | 6/1998 | Nicolson et al. | |
| 5,776,381 A | 7/1998 | Haase | |
| 5,789,461 A | 8/1998 | Nicolson et al. | |
| 5,849,811 A | 12/1998 | Nicolson et al. | |
| 6,113,817 A | 9/2000 | Herbrechtsmeie et al. | |
| 6,193,369 B1 | 2/2001 | Valint, Jr. et al. | |
| 6,200,626 B1 | 3/2001 | Grobe, III et al. | |
| 6,213,604 B1 | 4/2001 | Valint, Jr. et al. | |
| 6,267,782 B1 | 7/2001 | Ogle et al. | |
| 6,312,713 B1 | 11/2001 | Korol et al. | |
| 6,318,549 B1 | 11/2001 | Bougamont et al. | |
| 6,348,507 B1 | 2/2002 | Heiler et al. | |
| 6,350,251 B1 | 2/2002 | Prosl et al. | |
| 6,367,929 B1 | 4/2002 | Maiden et al. | |
| 6,440,404 B1 | 8/2002 | Dupuis | |
| 6,440,405 B1 | 8/2002 | Cooper et al. | |
| 6,451,871 B1 | 9/2002 | Winterton et al. | |
| 6,717,929 B1 | 4/2004 | Ooba | |
| 6,793,973 B2 | 9/2004 | Winterton et al. | |
| 6,811,805 B2 | 11/2004 | Gilliard et al. | |
| 6,822,016 B2 | 11/2004 | McCabe et al. | |
| 6,843,784 B2 | 1/2005 | Modak et al. | |
| 6,884,457 B2 | 4/2005 | Gilliard et al. | |
| 6,896,926 B2 | 5/2005 | Qiu et al. | |
| 6,926,965 B2 | 8/2005 | Qiu | |
| 6,940,580 B2 | 9/2005 | Winterton et al. | |
| 7,213,918 B2 | 5/2007 | Phelan | |
| 7,279,507 B2 | 10/2007 | Hu et al. | |
| 7,655,744 B2 * | 2/2010 | Miyanaga | A61Q 19/00 556/445 |
| 7,976,863 B2 | 7/2011 | Wilcox et al. | |
| 8,048,968 B2 | 11/2011 | Phelan et al. | |
| 8,071,658 B2 | 12/2011 | Zhou et al. | |
| 8,227,017 B2 | 7/2012 | Leander et al. | |
| 8,231,218 B2 | 7/2012 | Hong et al. | |
| 8,383,744 B2 | 2/2013 | Justynska et al. | |
| 8,404,759 B2 | 3/2013 | Phelan | |
| 8,425,926 B2 | 4/2013 | Qiu et al. | |
| 8,491,824 B2 | 7/2013 | Goodenough et al. | |
| 8,552,085 B2 | 10/2013 | Hong et al. | |
| 9,804,417 B2 | 10/2017 | Hong et al. | |
| 2007/0195261 A1 | 8/2007 | Vogt et al. | |
| 2008/0181931 A1 | 7/2008 | Qiu et al. | |
| 2013/0109778 A1 | 5/2013 | Li et al. | |
| 2014/0364394 A1 * | 12/2014 | Tamura | A61Q 5/10 556/456 |
| 2019/0119514 A1 * | 4/2019 | Yudovin-Farber | B33Y 70/00 |

OTHER PUBLICATIONS

ASTM Designation: E1054-02, "Standard Test Methods for Evaluation of Inactivators of Antimicrobial Agents." Published Aug. 2002, pp. 1-8.

ASTM Designation: E2149-01, Standard Test Method for Determining the Antimicrobial Activity of Immobilized Antimicrobial Agents Under dynamic Contact Conditions, published Aug. 2001.

Atkinson, Jeffrey L., and Sergey Vyazovkin. "Non-oxidative Thermal Degradation of Poly (glycidol), Poly (glycidol)-g-L-lactide, and Poly (glycidol)-g-glycolide." Macromolecular Chemistry and Physics 212.19 (2011): 2103-2113.

De Paz Báñez, M. V., K. L. Robinson, and S. P. Armes. "Synthesis and solution properties of dimethylsiloxane-2-(dimethylamino) ethyl methacrylate block copolymers." Macromolecules 33.2 (2000): 451-456.

Brennan, N., Efron, N., Holden, B. A., 1986. "Oxygen Permeability of Hard Gas Permeable Contact Lens Materials", Clin. Exp. Optom., 69, 82-89.

Chalkley T et al. Evaluation of "Bacteriostatic" Contact Lenses, American Journal of Ophthalmology, 1966, 61(5), 866-869.

Compañ, V., Villar, M. A., Vallés, E. M., Riande, E., 1996. "Permeability and Diffusional Studies on Silicone Polymer Networks with Controlled Dangling Chains". Polymer, 37, 101-107.

Dakal, T. C., Kumar, A., Majumdar, R. S. & Yadav, V. *Mechanistic basis of antimicrobial actions of silver nanoparticles.* Front. Microbiol. 7, 1831. https://doi.org/10.3389/fmicb.2016.01831 (2016).

Davies, J. T. "A quantitative kinetic theory of emulsion type. I. Physical chemistry of the emulsifying agent." Gas/Liquid and Liquid/Liquid Interface. Proceedings of the International Congress of Surface Activity. vol. 1. 1957.pp. 426-3.

Evans, Richard A. "The rise of azide-alkyne 1, 3-dipolar 'click'cycloaddition and its application to polymer science and surface modification." Australian Journal of Chemistry 60.6 (2007): 384-395.

Fatt, I. "Oxygen transmissibility and permeability of gas permeable hard contact lenses and materials." Int Contact Lens Clin 11.3 (1984): 175-183.

Fritz, Jennifer L., and Michael J. Owen. "Hydrophobic recovery of plasma-treated polydimethylsiloxane." The Journal of adhesion 54.1-4 (1995): 33-45.

Gerba, Charles P. Quaternary ammonium biocides: efficacy in application Appl Environ Microbiol. Jan. 2015;81(2):464-9.

(56) References Cited

OTHER PUBLICATIONS

Griffin, William C. "Calculation of HLB values of non-ionic surfactants." J. Soc. Cosmet. Chem. 5 (1954): 249-256.
Hein, Christopher D., Xin-Ming Liu, and Dong Wang. "Click chemistry, a powerful tool for pharmaceutical sciences." Pharmaceutical research 25.10 (2008): 2216-2230.
Herold, David A., Katherine Keil, and David E. Bruns. "Oxidation of polyethylene glycols by alcohol dehydrogenase." Biochemical pharmacology 38.1 (1989): 73-76.
Ionescu, Mihail, S. Sinharoy, and Zoran S. Petrović. "Polyacetal polyols for polyurethanes." Journal of Polymers and the Environment 17.2 (2009): 123-130.
Jones, "Modern Contact Lens Materials: A Clinical Performance Update". Contact Lens Spectrum, Sep. 2002, 9 pages.
Kataoka et al. "Block copolymer micelles for drug delivery: design, characterization and biological significance." Adv. Drug Delivery. Rev 2001, 47:1, 113-31.
Khundkar R, Malic C, Burge T. *Use of Acticoat dressings in burns: What is the evidence?* Burns, journal of the International Society for Burn Injuries. 2010; 36:751-8.
Han, Seongok, Chongyoup Kim, and Dongsook Kwon. "Thermal degradation of polyethylene glycol." Polymer (1995): 203-208.
Henderson William A et al. The Nucleophilicity of Amines, J. Org. Chem. 1962, 27, 12, 4643-4646, Dec. 1, 1962.
Huang Y et al. *A randomized comparative trial between Acticoat and SD-Ag in the treatment of residual burn ocular environments, including safety analysis.* Burns, journal of the International Society for Burn Injuries. 2007; 33:161-6.
Knobloch et al. *Biofilm Formation by Staphylococcus epidermidis Depends on Functional RsbU, an Activator of the sigB Operon: Differential Activation Mechanisms Due to Ethanol and Salt Stress,* Journal of Bacteriology, vol. 183, No. 8, Apr. 2001, pp. 2624-2633.
Kolb, Hartmuth C., M. G. Finn, and K. Barry Sharpless. "Click chemistry: diverse chemical function from a few good reactions." Angewandte Chemie International Edition 40.11 (2001): 2004-2021.
Kolb, Hartmuth C., and K. Barry Sharpless. "The growing impact of click chemistry on drug discovery." Drug discovery today 8.24 (2003): 1128-1137.
Letchford, Kevin, and Helen Burt. "A review of the formation and classification of amphiphilic block copolymer nanoparticulate structures: micelles, nanospheres, nanocapsules and polymersomes." European journal of pharmaceutics and biopharmaceutics 65.3 (2007): 259-269.
Manke A et al. *Mechanisms of Nanoparticle-Induced Oxidative Stress And Toxicity.* Biomed. Res. Int. 2013, Article ID 942916 (15 pages).
Mantzavinos, Dionissios, et al. "Wet air oxidation of polyethylene glycols; mechanisms, intermediates and implications for integrated chemical-biological wastewater treatment." Chemical Engineering Science 51.18 (1996): 4219-4235.
McShan D et al. *Molecular Toxicity Mechanism of Nano Silver.* J. Food Drug Anal. 22, 116-127.
Merianos JJ. 2001. *Surface-active agents*, p. 283-320. *In Block SS (ed), Disinfection, sterilization, and preservation.* Lippincott Williams & Wilkins, Philadelphia, PA.
Mitra, Amitava, et al. "Nanocarriers for nuclear imaging and radiotherapy of cancer." Current pharmaceutical design 12.36 (2006): 4729-4749.
Moore LE et al. *In vitro study of the effect of cationic biocides on bacterial population dynamics and susceptibility.* Appl Environ Microbiol 2008, 74, 4825-4834.
Morgan, Philip B., and Nathan Efron. "The oxygen performance of contemporary hydrogel contact lenses." Contact Lens and Anterior Eye 21.1 (1998): 3-6.
O'Reilly, Rachel K., Craig J. Hawker, and Karen L. Wooley. "Cross-linked block copolymer micelles: functional nanostructures of great potential and versatility." Chemical Society Reviews 35.11 (2006): 1068-1083.

Owen, Michael J., and Patrick J. Smith. "Plasma treatment of polydimethylsiloxane." Journal of adhesion science and technology 8.10 (1994): 1063-1075.
Rostovtsev, Vsevolod V. "A Stepwise Huisgen Cycloaddition Process: Copper (I)—Catalyzed Regioselective." Ligation of Azides and Terminal Alkynes: 2596-2599.
Siegers, Conrad, Markus Biesalski, and Rainer Haag. "Self-assembled monolayers of dendritic polyglycerol derivatives on gold that resist the adsorption of proteins." Chemistry—A European Journal 10.11 (2004): 2831-2838.
Storm-Versloot MN et al. *Topical Silver for Preventing Wound Infection.* The Cochrane database of systematic reviews. 2010, 17(3), CD006478.
Sharma, Hari S et al. *Influence of Engineered Nanoparticles from Metals on the Blood-Brain Barrier Permeability, Cerebral Blood Flow, Brain Edema and Neurotoxicity. An Experimental Study in the Rat and Mice Using Biochemical and Morphological Approaches;* Journal of Nanoscience and Nanotechnology, vol. 9, No. 8, Aug. 2009, pp. 5055-5072(18).
Argrirova M et al. Application of the nanocrystalline silver in treatment of burn ocular environments in children. *Skin Grafts—Indications, Applications and Current Research.* Rijeka: 2011. pp. 237-264.
Sweeney, Deborah, Desmond Fonn, and K. Evans. "Silicone hydrogels: The evolution of a revolution." Contact Lens Spectrum Feb. 1, 2006.
Torchilin, Vladimir P. "Micellar nanocarriers: pharmaceutical perspectives." Pharmaceutical research 24.1 (2007): 1-16.
Trickler, William J. et al. *Silver Nanoparticle Induced Blood-Brain Barrier Inflammation and Increased Permeability in Primary Rat Brain Microvessel Endothelial Cells;* Toxicological Sciences, vol. 118, Issue 1, Nov. 2010, pp. 160-170.
Vlachou E et al. The safety of nanocrystalline silver dressing on burns: A study of systemic silver absorption. Burns, journal of the International Society for Burn Injuries. 2009; 35:306.
Tsujita, Y., et al. "Structure and gas permeability of siloxane-imide block copolymer membranes: 1. Effect of siloxane content." Polymer 34.12 (1993): 2597-2601.
Vaerewijck MJM et al. 2012. *Assessment of the efficacy of benzalkonium chloride and sodium hypochlorite against Acanthamoeba polyphaga and Tetahymena spp.* J Food Prot 76:541-546.
Vazquez-Munoz, R et al. *Toxicity of silver nanoparticles in biological systems: Does the complexity of biological systems matter?.* Toxicol. Lett. 276, 11-20. https://doi.org/10.1016/j.toxlet.2017.05.007 (2017).
Vimbela GV et al. *Antibacterial properties and toxicity from metallic nanomaterials.* Int. J. Nanomed. 12, 3941-3965. https://doi.org/10.2147/IJN.S134526 (2017).
Walker M et al. *The biological fate of silver ions following the use of silver-containing ocular environment care products—a review.* International ocular environment journal. 2012.
Weissman, Barry A., Steven D. Schwartz, and David A. Lee. "Oxygen transmissibility of disposable hydrogel contact lenses." The CLAO journal: official publication of the Contact Lens Association of Ophthalmologists, Inc 17.1 (1991): 62-64.
Turnbull, D. K., et al. "Oxygen flux through dry and wet hard gas-permeable contact lenses." Journal of the British Contact Lens Association 9.2 (1986): 75-84.
Zhang XF et al. *Silver nanoparticle-mediated cellular responses in various cell lines: An in vitro model.* Int. J. Mol. Sci. https://doi.org/10.3390/ijms17101603 (2016).
Zhu X et al. *Nanomedicine in the Management of Microbial Infection—Overview and Perspectives.* Nano Today 9, 478-498. https://doi.org/10.1016/j.nantod.2014.06.003 (2014).
Zinchenko AA et al. 2004. *DNA compaction by divalent cations: structural specificity revealed by the potentiality of designed quaternary diammonium salts.* Chembiochem 5:360-386.
International Search Report and Written Opinion issued for Application No. PCT/US2021/015036, dated Apr. 6, 2021, 8 pages.
Extended European Search Report mailed Dec. 12, 2023 in corresponding EP Application 21747973.2 (6 pages).

* cited by examiner

ANTIMICROBIAL OPHTHALMIC DEVICES COMPRISING POLYSILOXANE-POLYGLYCEROL BLOCK COPOLYMERS AND METHODS OF MAKING AND USE THEREOF

CROSS-REFERENCE TO RELATED APPLICATIONS

This application is a continuation of U.S. application Ser. No. 17/158,290 filed Jan. 26, 2021, which claims the benefit of priority to U.S. Provisional Application No. 62/966,233 filed Jan. 27, 2020, each of which is hereby incorporated herein by reference in its entirety.

BACKGROUND

Hydrogels have the ability to be shaped, as well as absorb and retain large amounts of water, which mimics natural tissues. Due to these distinctive characteristics, hydrogels have been recognized as important biomaterials in the fields of tissue engineering, regenerative medicine, medical device construction, coatings for medical devices, microfluidic devices, extracellular matrices for 3D cell cultures, and drug delivery applications. However, hydrogel biomaterials have relatively poor mechanical properties, which is a limiting factor associated with hydrogel biomaterials. Regulating the transport properties, hydrophilicity, and biomechanical properties of hydrogels is vital to product performance.

There remains a need in the art for cost effective and simplified methods for producing medical devices such as silicone hydrogel contact lenses having lubricious and wear resistance surfaces. In addition, the devices also need the combined characteristics of biocompatibility, low toxicity and low coefficient of friction in contact with body fluids, such as tears and blood.

Soft (hydrophilic) silicone hydrogel contact lenses provide improved oxygen permeability as compared to soft non-silicone hydrogel contact lenses such as cross-linked poly(2-Hydroxyethyl methacrylate) (Polymacon). Initial efforts to make silicone hydrogel contact lenses were plagued by substandard wettability, poor clarity, low water content and high modulus. In addition, early silicone hydrogel contact lenses were made from expensive custom-made raw materials. In order for first generation silicone hydrogel contact lenses to achieve acceptable hydrophilicity, surface treatment methods (such as plasma surface treatments) were utilized to improve wettability of these materials (U.S. Pat. Nos. 6,213,604, 6,348,507, 6,200,626, 5,760,100, 5,849, 811).

For example, commercial lenses such as Focus NIGHT & DAY™, AirOptix (Alcon), and PureVision™ (Bausch & Lomb) employ plasma surface treatments. Plasma surface treatments create a plasma coating at the treated surface. Advantages of a plasma coating include durability, relatively high hydrophilicity (or good wettability), and, in the case of plasma that produces non-ionic surfaces (Methane Plasma), low susceptibility to lipid and protein deposition and adsorption. However, plasma treatment of silicone hydrogel contact lenses may not be cost effective, especially in the case of single use contact lenses. One of the main reasons for this is high capital costs associated with high volume production lines equipped with plasma equipment. In addition to high capital investment, contact lenses can require extraction and drying prior to plasma treatment, thereby increasing complexity and cost to the manufacturing process.

Another method for modifying the hydrophilicity of a relatively hydrophobic contact lens material is a layer-by-layer (LBL) poly ionic material deposition technique (U.S. Pat. Nos. 6,451,871, 6,717,929, 6,793,973, 6,884,457, 6,896,926, 6,926,965, 6,940,580). Although LBL can provide a cost-effective process for rendering a silicone hydrogel material wettable, the dip coating baths employed in such processes are prone to cross contamination. Furthermore, LBL coatings are less durable than chemically bonded coatings.

In U.S. Pat. No. 6,367,929 B1, Johnson & Johnson Vision Care, Inc., describe producing wettable silicone hydrogel lenses by incorporating internal wetting agents into lens formulations. This patent states that a wettable silicone hydrogel is made by including a high molecular weight hydrophilic polymer into the silicone hydrogel monomer mix. The patent further states that the hydrophilic polymer is entrapped in the hydrogel matrix (little or no covalent bonding between internal wetting agent and the contact lens matrix). The use of internal wetting agents in lens formulations allows for a simpler manufacturing process compared to plasma treatment. However, there are some disadvantages to this approach. First, not all of the added wetting agent (PVP) is retained in the contact lens. Secondly, silicone hydrogel contact lenses typically require extraction with organic solvent. Since the internally wetting agent is not chemically bonded to the lens matrix, it can be removed or partially removed during extraction operations. Therefore, extraction of lenses containing non-chemically bound internal wetting agent (e.g., PVP) requires careful control of extraction operations to ensure the final product contains the desired loading of the internal wetting agent. Third, the internal wetting agent used was PVP, which is water soluble and therefore may continue to leach from the lens during use by customers. If too much PVP is lost due to leaching, contact lens lubricity may be compromised and contact lens dimensions may change thereby making it difficult to maintain product specifications and performance. Contact lens formulations described in U.S. Pat. No. 6,367,929 B1 contain two immiscible polymers (mono-methacrylated polydimethylsiloxane, and PVP). In order to achieve a homogeneous solution of the two immiscible polymers, the use of solvent(s) and/or compatibilizing agent(s) is necessary. Use of special compatibilizing agents, which may need to be custom manufactured, increases product cost. Combining two dissimilar polymers in a chemical mixture imposes considerable compositional limitations in achieving a homogenous clear solution. Furthermore, homogeneous clear contact lens formulations containing two or more dissimilar polymers or copolymers are susceptible to phase separation induced by changes in temperature, pressure, pH, ionic strength, and solvent quality. Phase separated formulations are inadequate for producing contact lenses since they would likely result in non-homogeneous contact lenses with variable composition and compromised optical transmittance. Therefore, a need remains for even simpler methods for producing silicone hydrogel contact lenses with hydrophilic surfaces.

U.S. Pat. No. 4,954,586 describes a process in which silicone hydrogel contact lenses are treated with alkali solution in a hydrolysis process in order to improve wettability. However, the hydrolysis process is non-selective and therefore may lead to undesirable degradation of certain monomer segments in the contact lens. The hydrolysis could, for example, lead to destruction of cross-links within the polymer network. For example, difunctional (meth) acrylate esters (e.g., ethylene glycol dimethacrylate, pentaerythritol trimethacrylate, pentaerythritol tetramethacrylate, ethylene glycol diacrylate, pentaerythritol triacrylate, pentaerythritol tetra-acrylate) are susceptible to hydrolysis in alkali solution. Loss of cross-linking can lead to poor mechanical properties, variation in contact lens water content, and contact lens parameters (diameter, base curve). (Meth)acrylate esters are one of the key building blocks employed in the production of silicone hydrogel contact lenses. Difunctional (meth)acrylate esters (e.g., ethylene glycol dimethacrylate, pentaerythritol trimethacrylate, pentaerythritol tetramethacrylate, ethylene glycol diacrylate, pentaerythritol triacrylate, pentaerythritol tetra-acrylate) are susceptible to hydrolysis in alkali solution. Hydrolysis of ester functionality in silicone hydrogel contact lenses can result in the formation of ionic methacrylic acid segments. The presence of ionic functionality in silicone hydrogel contact lenses is generally undesirable since such groups are known to increase the rate of contact lens fouling (e.g., from deposition of protein from tears).

In U.S. Pat. Nos. 8,231,218, 8,552,085, and 9,804,417, Cooper Vision discloses the use of hydrophilized poly (dimethyl siloxane) (PDMS) (e.g., PDMS-di-methacrylate having poly(ethylene glycol) (PEG) groups) as a means of obtaining silicone hydrogel contact lenses with good wettability. While this method is an improvement over plasma treatment of contact lenses, this method also has a number of limitations. PDMS-di-methacrylate having poly(ethylene glycol) (PEG) groups requires multiple synthetic sequences, thereby increasing product cost. In addition, PEG-containing polymers can be susceptible to degradation, which can cause changes in the properties of an article made from the poly(oxyalkylene)-containing polymers (US 2007/0195261 and Mantzavinos et al., *Chemical Engineering Science*, 1996, 51(18), 4219-4235). PEG segments are prone to oxidative degradation which results in the formation of ocular irritants such as formaldehyde, formic acid and other materials (US 2007/0195261). Air oxidation of PEG generates unstable peroxides, typical of the auto oxidation of ethers. The peroxides then react further, leading to cleavage of the PEG chain between oxygen and carbon atoms. Therefore, contact lenses containing PEG segments often need to be stabilized with antioxidants. However, many antioxidants (BHT, Hydroquinone, and MEHQ) are known ocular irritants and, while the antioxidants typically slow oxidation, they do not prevent it. A clear need remains for improved technologies to render silicone hydrogel contact lenses wettable.

The compositions, devices, and methods described herein address these and other needs.

SUMMARY

In accordance with the purposes of the disclosed compositions, devices, and methods, as embodied and broadly described herein, the disclosed subject matter relates to compositions comprising actinically-crosslinkable polysiloxane-polyglycerol block copolymers, methods of making and use thereof, and devices comprising the compositions described herein.

More specifically, disclosed herein are compositions comprising an actinically-crosslinkable polysiloxane-polyglycerol block copolymer derived from: a polysiloxane prepolymer comprising a polyglycerol side chain, the polyglycerol side chain comprising an ethylenically unsaturated group covalently linked thereto, wherein the ethylenically unsaturated group is actinically curable.

The block copolymers described herein comprise two or more polymeric chains (blocks), which are structurally different and chemically bonded to each other. Under certain conditions, these copolymers can segregate into a variety of ordered structures. In some examples, the ordered block copolymer structures can be substantially locked in place through chemical reactions such as cross-linking of actinically curable groups, substitution reactions, and addition reactions, "click" chemical reactions, polymerization reactions or any number of chemical reactions known in the art.

Also described herein are methods of use of the compositions described herein and articles of manufacture and devices of the compositions described herein. For example, also described herein are medical devices comprising of the compositions described herein and the use of such medical devices in ophthalmic applications such as contact lenses.

The compositions described herein can be used in the construction of medical devices, as coatings for medical devices, and any number of other biomedical applications. The compositions described herein can, in some examples, be used as hydrophilic coatings for any number of medical devices including, but not limited to catheters, contact lenses, endoscopes, cell growth platforms, microfluidic devices, body implants, coatings for implants that come into contact with tissue (e.g., epithelial tissue, connective tissue, muscle tissue, and nerve tissue) and biological fluids (e.g., blood, mucus, urine, tears, saliva, amniotic fluid, synovial fluid).

Also described herein are ophthalmic devices (e.g., contact lenses, intraocular lenses, corneal inlays, and corneal rings) obtained from the block copolymers described herein and optionally one or more hydrophilic and/or hydrophobic monomers. The block copolymers and compositions described herein can, for example, also be used in a range of cell culture applications for the expansion and directed differentiation of various cell types by acting as extracellular matrix mimics for 3D Cell Culture. The block copolymers and compositions described herein can, for example, be used as synthetic matrix metallo-proteinase-sensitive materials for the conduction of tissue regeneration. The block copolymers and compositions described herein can, for example, be used as micro-valves and micro-pumping devices due to the propensity of the copolymers and compositions described herein to absorb large volumes aqueous and non-aqueous fluids coupled with the response of the copolymers and compositions described herein to various forms of stimulation (examples: pH, electrical current, temperature, ionic strength).

Additional advantages of the disclosed compositions, devices, and methods will be set forth in part in the description which follows, and in part will be obvious from the description. The advantages of the disclosed compositions, devices, and methods will be realized and attained by means of the elements and combinations particularly pointed out in the appended claims. It is to be understood that both the foregoing general description and the following detailed description are exemplary and explanatory only and are not restrictive of the disclosed compositions and methods, as claimed.

The details of one of more embodiments of the invention are set forth in the accompanying drawings and description below. Other features, objects, and advantages of the invention will be apparent form the description and drawings, and from the claims.

BRIEF DESCRIPTION OF THE FIGURES

The accompanying figures, which are incorporated in and constitute a part of this specification, illustrate several aspects of the disclosure, and together with the description, serve to explain the principles of the disclosure.

DETAILED DESCRIPTION

Figure 1:
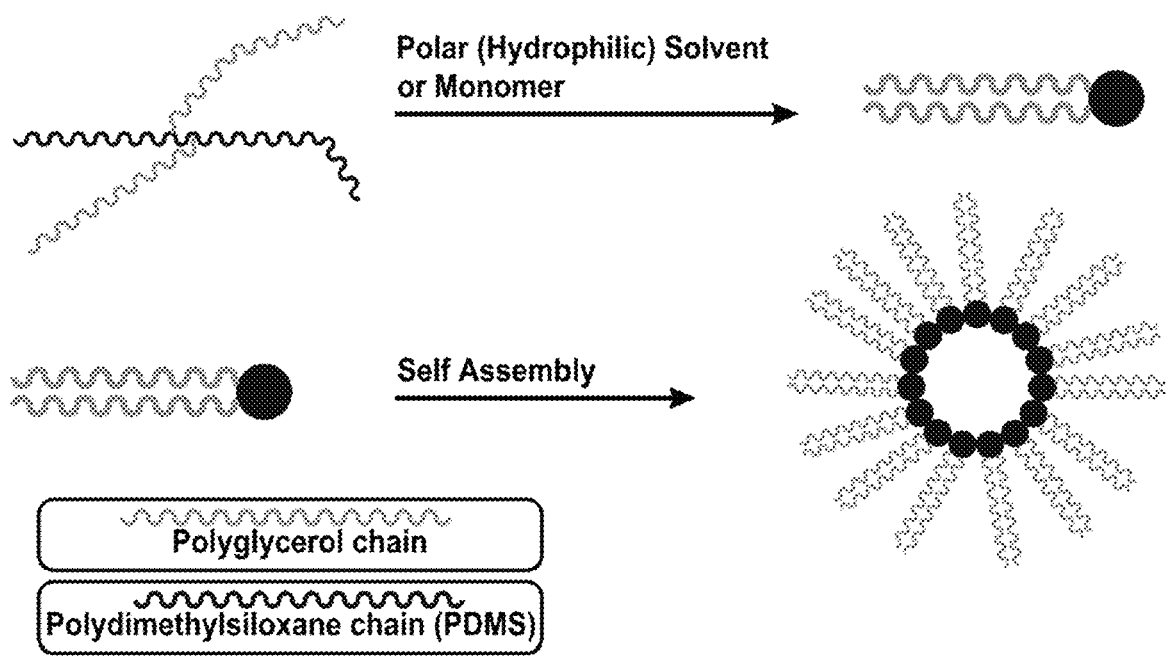
FIG. 1 illustrates the self-assembly of PDMS bearing polyglycerol chains.

The compositions, devices, and methods described herein may be understood more readily by reference to the following detailed description of specific aspects of the disclosed subject matter and the Examples included herein.

Before the present compositions, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed subject matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification, the word "comprise" and other forms of the word, such as "comprising" and "comprises," means including but not limited to, and are open, non-limiting terms that are not intended to exclude, for example, other additives, components, integers, or steps. Although the terms "comprising" and "including" have been used herein to describe various examples, the terms "consisting essentially of" and "consisting of" can be used in place of "comprising" and "including" to provide for more specific examples of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

"Exemplary" means "an example of" and is not intended to convey an indication of a preferred or ideal embodiment. "Such as" is not used in a restrictive sense, but for explanatory purposes.

As used in the description and the appended claims, the singular forms "a," "an," and "the" include plural referents unless the context clearly dictates otherwise. This, for example, reference to "a composition" includes mixtures of two or more such compositions, reference to "the compound" includes mixtures of two or more such compounds, reference to "an agent" includes mixtures of two or more such agents, and the like.

"Optional" or "optionally" means that the subsequently described event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

Unless otherwise defined, all technical and scientific terms used herein have the same meaning as commonly understood by one of ordinary skill in the art to which this invention belongs.

The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both at the same time within one molecule, cluster of molecules, molecular complex, or moiety (e.g., zwitterions)) or that can be made to contain a charge. Methods for producing a charge in a molecule, portion of a molecule, cluster of molecules, molecular complex, moiety, or atom are disclosed herein and can be accomplished by methods known in the art, e.g., protonation, deprotonation, oxidation, reduction, alkylation, acetylation, esterification, de-esterification, hydrolysis, etc.

The term "anion" is a type of ion and is included within the meaning of the term "ion." An "anion" is any molecule, portion of a molecule (e.g., zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion." A "cation" is any molecule, portion of a molecule (e.g., zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

As used herein, the term "alkyl" refers to saturated, straight-chained or branched saturated hydrocarbon moieties. Unless otherwise specified, $C_1$-$C_{24}$ (e.g., $C_1$-$C_{22}$, $C_1$-$C_{20}$, $C_1$-$C_{15}$, $C_1$-$C_{16}$, $C_1$-$C_{14}$, $C_1$-$C_{12}$, $C_1$-$C_{10}$, $C_1$-$C_8$, $C_1$-$C_6$, or $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, 1-ethyl-2-methyl-propyl, heptyl, octyl, nonyl, decyl, dodecyl, tetradecyl, hexadecyl, eicosyl, tetracosyl, and the like. Alkyl substituents may be unsubstituted or substituted with one or more chemical moieties. The alkyl group can be substituted with one or more groups including, but not limited to, hydroxyl, halogen, acyl, alkyl, alkoxy, alkenyl, alkynyl, aryl, heteroaryl, aldehyde, amino, cyano, carboxylic acid, ester, ether, ketone, nitro, phosphonyl, silyl, sulfo-oxo, sulfonyl, sulfone, sulfoxide, or thiol, as described below, provided that the substituents are sterically compatible and the rules of chemical bonding and strain energy are satisfied.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halides (halogens; e.g., fluorine, chlorine, bromine, or iodine). The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

As used herein, the term "alkenyl" refers to unsaturated, straight-chained, or branched hydrocarbon moieties containing a double bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, or $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure —CH=CH—CH$_3$; and 2-propenyl refers to a group with the structure —CH$_2$—CH=CH$_2$. Asymmetric structures such as (Z$^1$Z$^2$)C=C(Z$^3$Z$^4$) are intended to include both the E and Z isomers. This can be presumed in structural formulae herein wherein an asymmetric alkene is present, or it can be explicitly indicated by the bond symbol C=C. Alkenyl substituents may be unsubstituted or substituted with one or more chemical moieties. Examples of suitable substituents include, for example, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol, as described below, provided that the substituents are sterically compatible and the rules of chemical bonding and strain energy are satisfied.

As used herein, the term "alkynyl" represents straight-chained or branched hydrocarbon moieties containing a triple bond. Unless otherwise specified, C$_2$-C$_{24}$ (e.g., C$_2$-C$_{24}$, C$_2$-C$_{20}$, C$_2$-C$_{18}$, C$_2$-C$_{16}$, C$_2$-C$_{14}$, C$_2$-C$_{12}$, C$_2$-C$_{10}$, C$_2$-C$_8$, C$_2$-C$_6$, or C$_2$-C$_4$) alkynyl groups are intended. Alkynyl groups may contain more than one unsaturated bond. Examples include C$_2$-C$_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol, as described below.

As used herein, the term "aryl," as well as derivative terms such as aryloxy, refers to groups that include a monovalent aromatic carbocyclic group of from 3 to 50 carbon atoms. Aryl groups can include a single ring or multiple condensed rings. In some embodiments, aryl groups include C$_6$-C$_{10}$ aryl groups. Examples of aryl groups include, but are not limited to, benzene, phenyl, biphenyl, naphthyl, tetrahydronaphthyl, phenylcyclopropyl, phenoxybenzene, and indanyl. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is also included in the term "aryl," defines a group that contains an aromatic group that does not contain a heteroatom. The aryl substituents may be unsubstituted or substituted with one or more chemical moieties. Examples of suitable substituents include, for example, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, acyl, aldehyde, amino, cyano, carboxylic acid, ester, ether, halide, hydroxyl, ketone, nitro, phosphonyl, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "acyl" as used herein is represented by the formula —C(O)Z$^1$ where Z$^1$ can be a hydrogen, hydroxyl, alkoxy, alkyl, alkenyl, alkynyl, aryl, heteroaryl, cycloalkyl, cycloalkenyl, heterocycloalkyl, or heterocycloalkenyl group described above. As used herein, the term "acyl" can be used interchangeably with "carbonyl." Throughout this specification "C(O)" or "CO" is a shorthand notation for C=O.

The term "acetal" as used herein is represented by the formula (Z$^1$Z$^2$)C(=OZ$^3$)(=OZ$^4$), where Z$^1$, Z$^2$, Z$^3$, and Z$^4$ can be, independently, a hydrogen, halogen, hydroxyl, alkyl, alkenyl, alkynyl, aryl, heteroaryl, cycloalkyl, cycloalkenyl, heterocycloalkyl, or heterocycloalkenyl group described above.

The term "alkanol" as used herein is represented by the formula Z$^1$OH, where Z$^1$ can be an alkyl, alkenyl, alkynyl, aryl, heteroaryl, cycloalkyl, cycloalkenyl, heterocycloalkyl, or heterocycloalkenyl group described above.

As used herein, the term "alkoxy" as used herein is an alkyl group bound through a single, terminal ether linkage; that is, an "alkoxy" group can be defined as to a group of the formula Z$^1$—O—, where Z$^1$ is unsubstituted or substituted alkyl as defined above. Unless otherwise specified, alkoxy groups wherein Z$^1$ is a C$_1$-C$_{24}$ (e.g., C$_1$-C$_{22}$, C$_1$-C$_{20}$, C$_1$-C$_{18}$, $C_1$-$C_{16}$, $C_1$-$C_{14}$, $C_1$-$C_{12}$, $C_1$-$C_{10}$, $C_1$-$C_8$, $C_1$-$C_6$, or $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dim-ethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

The term "aldehyde" as used herein is represented by the formula —C(O)H. Throughout this specification "C(O)" is a shorthand notation for C=O.

The terms "amine" or "amino" as used herein are represented by the formula —NZ$^1$Z$^2$Z$^3$, where $Z^1$, $Z^2$, and $Z^3$ can each be substitution group as described herein, such as hydrogen, an alkyl, alkenyl, alkynyl, aryl, heteroaryl, cycloalkyl, cycloalkenyl, heterocycloalkyl, or heterocycloalkenyl group described above.

The terms "amide" or "amido" as used herein are represented by the formula —C(O)NZ$^1$Z$^2$, where $Z^1$ and $Z^2$ can each be substitution group as described herein, such as hydrogen, an alkyl, alkenyl, alkynyl, aryl, heteroaryl, cycloalkyl, cycloalkenyl, heterocycloalkyl, or heterocycloalkenyl group described above.

The term "anhydride" as used herein is represented by the formula Z$^1$C(O)OC(O)Z$^2$ where $Z^1$ and $Z^2$, independently, can be an alkyl, alkenyl, alkynyl, aryl, heteroaryl, cycloalkyl, cycloalkenyl, heterocycloalkyl, or heterocycloalkenyl group described above.

The term "cyclic anhydride" as used herein is represented by the formula:

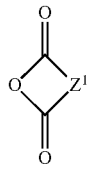

where $Z^1$ can be an alkyl, alkenyl, alkynyl, aryl, heteroaryl, cycloalkyl, cycloalkenyl, heterocycloalkyl, or heterocycloalkenyl group described above.

The term "azide" as used herein is represented by the formula —N=N=N.

The term "carboxylic acid" as used herein is represented by the formula —C(O)OH.

A "carboxylate" or "carboxyl" group as used herein is represented by the formula —C(O)O$^-$.

The term "cyano" as used herein is represented by the formula —CN.

The term "ester" as used herein is represented by the formula —OC(O)Z$^1$ or —C(O)OZ$^1$, where $Z^1$ can be an alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where $Z^1$ and $Z^2$ can be, independently, an alkyl, alkenyl, alkynyl, aryl, heteroaryl, cycloalkyl, cycloalkenyl, heterocycloalkyl, or heterocycloalkenyl group described above.

The term "epoxy" or "epoxide" as used herein refers to a cyclic ether with a three atom ring and can represented by the formula:

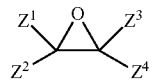

where $Z^1$, $Z^2$, $Z^3$, and $Z^4$ can be, independently, an alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where $Z^1$ and $Z^2$ can be, independently, an alkyl, alkenyl, alkynyl, aryl, heteroaryl, cycloalkyl, cycloalkenyl, heterocycloalkyl, or heterocycloalkenyl group described above.

The term "halide" or "halogen" or "halo" as used herein refers to fluorine, chlorine, bromine, and iodine.

The term "hydroxyl" as used herein is represented by the formula —OH.

The term "nitro" as used herein is represented by the formula —NO$_2$.

The term "perfluoro" is used herein as a prefix to indicate most or all C—H bonds in the compound following the prefix have been replaced by C—F bonds, as allowed under steric and stability constraints. For example, in the case of fluorinated (meth)acrylates, the compounds are not completely fluorinated due to instability. The —OCF$_2$— group in R—C(=CH$_2$)—C(=O)—OCF$_2$—(CF$_2$)$_n$—CF$_3$ is unstable, but R—C(=CH$_2$)—C(=O)—OCH$_2$—(CF$_2$)$_n$—CF$_3$ is stable (where R=H is an acrylate and R=CH$_3$ is a methacrylate). Similarly, the HOCF$_2$— group in HO—CF$_2$—(CF$_2$)$_n$—CF$_3$ is unstable, but HO—CH$_2$—(CF$_2$)$_n$—CF$_3$ is stable. Therefore the alcohols with the general structure HO—CH$_2$(CF$_2$)$_n$—CF$_3$ can be used in the synthesis of (meth)acrylates with highly fluorinated side chains. (Meth) acrylates with highly fluorinated side chains are available commercially. Examples of (meth)acrylates with highly fluorinated side chains include, but are not limited to 2,2,3,3,4,4,5,5,6,6,7,7-dodecafluoro-heptyl acrylate; 3,3,4,4,5,5,6,6,7,7,8,8,9,9,10,10,11,11,12,12,12-heneicosafluoro-dodecyl acrylate; 2,2,3,3,4,4,4-heptafluorobutyl (meth) acrylate; 1,1,1,3,3,3-hexafluoroisopropyl methacrylate; and 2,2,3,3,4,4,5,5-octafluoropentyl methacrylate. A perfluorinated polyether can be synthesized using a perfluorinated initiator M$^+$B$^-$, such as Na$^+$OCF$_3^-$, as shown below in Scheme 1.

Scheme 1. Ring opening synthesis of a perfluorinated polyether using a perfluorinated initiator M$^+$B$^-$.

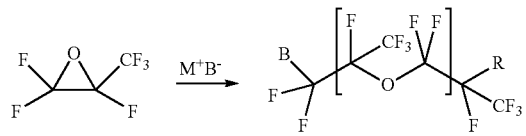

The term "phosphonyl" is used herein to refer to the phospho-oxo group represented by the formula —P(O) (OZ$^1$)$_2$, where $Z^1$ can be hydrogen, an alkyl, alkenyl, alkynyl, aryl, heteroaryl, cycloalkyl, cycloalkenyl, heterocycloalkyl, or heterocycloalkenyl group described above.

The term "silyl" as used herein is represented by the formula —SiZ$^1$Z$^2$Z$^3$, where Z$^1$, Z$^2$, and Z$^3$ can be, independently, hydrogen, alkyl, alkoxy, alkenyl, alkynyl, aryl, heteroaryl, cycloalkyl, cycloalkenyl, heterocycloalkyl, or heterocycloalkenyl group described above.

The term "sulfonyl" or "sulfone" is used herein to refer to the sulfo-oxo group represented by the formula —S(O)$_2$Z$^1$, where Z$^1$ can be hydrogen, an alkyl, alkenyl, alkynyl, aryl, heteroaryl, cycloalkyl, cycloalkenyl, heterocycloalkyl, or heterocycloalkenyl group described above.

The term "sulfide" as used herein is comprises the formula —S—.

The term "thiol" as used herein is represented by the formula —SH.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible stereoisomer or mixture of stereoisomer (e.g., each enantiomer, each diastereomer, each meso compound, a racemic mixture, or scalemic mixture).

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

An "ophthalmic device", as used herein, refers to any of the following: a contact lens (hard or soft), an intraocular lens, a corneal inlay, glaucoma shunt, or ophthalmic stent used on or about a subject's eye or ocular vicinity.

"Contact Lens" refers to a structure that can be placed on or within a subject's eye. A contact lens can correct, improve, or alter a subject's eyesight. However, a contact lens may also be used as an eye bandage, drug delivery device, and prosthetic device. In the case of color contact lenses, the device may be used to alter or enhance a subject's eye color, or to mask a subject's disfigured eyes. A contact lens can be of any appropriate material, and can be a soft lens, a hard lens, or a hybrid lens.

A "silicone hydrogel contact lens" refers to a contact lens comprising a silicone hydrogel material.

"Hydrophilic," as used herein, describes a material or portion thereof that has the characteristics of readily absorbing or dissolving in water, having polar groups (distribution of electrons is uneven, enabling it to take part in electrostatic interactions) that readily interact with water, and/or having an affinity for water.

As used herein, the term "hydrophobic" refers to the characteristics of not readily absorbing or dissolving in water, being adversely affected by water, and/or having little or no affinity for water.

As used herein, the term "amphiphilic" refers to the characteristics of having both hydrophilic and hydrophobic properties.

As used herein, the term "hydrophilic-lipophilic balance" (HLB) of a surfactant is a measure of the degree to which it is hydrophilic or lipophilic. The HLB for a substance is determined by calculating values for the different regions of the molecule, as described by Griffin (Griffin. *J Soc. Cosm. Chem.* 1954, 5, 249-256). Other methods for determining HLB have been suggested, notably in 1957 by Davies (Davies, Proceedings of the International Congress of Surface Activity, Gas/Liquid and Liquid/Liquid Interface, 1957, 426-3); HLB according to Davies is intended to mean the equilibrium between the size and the strength of the hydrophilic group and the size and the strength of the lipophilic group of the surfactant under consideration.

A "hydrogel" or "hydrogel material" refers to a polymeric material which can absorb 10% by weight of water or more when it is fully hydrated (e.g., 15% or more, 20% or more, 25% or more, 30% or more, 40% or more, 50% or more, 60% or more, 70% or more, 80% or more, or 90% or more).

A "silicone hydrogel" refers to a siloxane or silicone-containing hydrogel obtained by copolymerization of a polymerizable composition comprising at least one silicone-containing monomer, at least one silicone-containing macromer, or at least one crosslinkable silicone-containing prepolymer.

A "vinylic monomer" means a low molecular weight compound having one ethylenically unsaturated group. Low molecular weight typically means average molecular weights less than 600 Daltons. Vinyl group as described here includes, but is not limited to, the following functional groups: alkene, (meth)acrylate, (meth)acrylamide, and styrenic functionality.

A "silicone-containing vinylic monomer" refers to a vinylic monomer which contains silicone.

A "hydrophilic vinylic monomer" refers to a vinylic monomer which can be polymerized actinically to form a polymer that is water-soluble or can absorb 20% by weight of water or more (e.g., 30% or more, 40% or more, 50% or more, 60% or more, 70% or more, 80% or more, or 90% or more).

A "hydrophobic vinylic monomer" refers to a vinylic monomer which can be polymerized actinically (or thermally) to form a polymer that is insoluble in water and can absorb less than 20% by weight water (e.g., 15% or less, 10% or less, 5% or less, or 1% or less).

The term "olefinically unsaturated group" or "ethylenically unsaturated group" is employed herein in a broad sense and is intended to encompass any groups containing a carbon-carbon double bonded group (>C=C< group). Exemplary ethylenically unsaturated groups include, but are not limited to, (meth)acrylamide, (meth)acryloyl, allyl, vinyl, styrenyl, or other >C=C< containing groups.

"Polymer" means a material formed by polymerizing one or more monomers.

The term "(co)polymer" includes homopolymers, copolymers, or mixtures thereof.

The term "(meth)acryl . . . " includes "acryl . . . ," "methacryl . . . ," or mixtures thereof.

The term "block copolymer" as used herein is a copolymer comprised of two or more homopolymer subunits linked by covalent bonds. The joining of the homopolymer subunits may require an intermediate non-repeating subunit, known as a junction block. Block copolymers with two or three distinct blocks are called di-block copolymers and tri-block copolymers, respectively. A block is a portion of a macromolecule, comprising many constitutional units, that has at least one feature which is not present in the adjacent portions.

The term prepolymer is used herein to refer to a polymer that has reactive groups that are available for bond forming reactions that will crosslink (intermolecular and/or intramolecular crosslink). It is not meant to imply that the prepolymer is not yet a polymer (e.g., a monomer or polymer precursor). Rather, a "prepolymer" refers to a starting polymer which contains multiple actinically crosslinkable groups and can be cured (e.g., crosslinked) actinically to obtain a crosslinked polymer having a molecular weight higher than the starting polymer.

A "silicone-containing prepolymer" refers to a prepolymer which contains silicone and can be crosslinked actinically (or with heat) to obtain a crosslinked polymer having a molecular weight higher than the starting polymer.

"Molecular weight" of a polymeric material (including monomeric or macro-monomeric materials), as used herein, refers to the number-average molecular weight unless otherwise specifically noted or unless testing conditions indicate otherwise.

A "macromer" refers to a medium and high molecular weight compound which can be polymerized and/or cross-linked actinically. Medium and high molecular weight typically means average molecular weights greater than 600 Daltons. For example, a macromer can be a macromer with one or more ethylenically unsaturated groups. A "siloxane-containing macromer" is a macromer which contains silicone and can be crosslinked actinically or with heat.

The term "hyper-branched polyglycerol" as used herein refers to a branched aliphatic polyether with hydroxyl groups. It will be appreciated that the term also includes a branched polyether in which a proportion of the hydroxyl groups have been derivatized and/or replaced with a suitable group. Examples of hyper-branched polyglycerol structures are illustrated by Formula III, Formula IV, Formula V, Formula VI, Formula VII, Formula VIII, and Formula IX.

As used herein, the term "multiple" refers to at least two, preferably at least three.

As used herein, "actinically" in reference to curing, crosslinking, or polymerizing of a polymerizable composition, a prepolymer, or a material means that the curing (e.g., crosslinking and/or polymerizing) is performed by actinic irradiation, such as, for example, UV light, visible light, ionized radiation (e.g., gamma ray or X-ray irradiation), microwave radiation, and the like. Thermal curing or actinic curing methods are well-known in the art.

A "photo-initiator" refers to a chemical that initiates radical crosslinking/polymerizing reaction by the use of light.

A "thermal initiator" refers to a chemical that initiates free radical polymerization and/or cross-linking reactions using heat energy.

The term "fluid" as used herein indicates that a material is capable of flowing like a liquid. Fluids include, for example, liquids, gases, supercritical fluids, etc.

The term "genetic material" as used herein includes DNA, RNA, modified DNA and modified RNA.

The term "vesicle" as used herein refers to a synthetic or natural tube-like structure capable of being filled with a fluid. The vesicles may provide efficient mass transport for fluids by acting as conduits for the fluids. The vesicle tube walls may be hydrophilic or hydrophobic. Vesicles may coalesce with other vesicles to form more complex structures.

The term "chemical stability" as used herein is defined by substantial maintenance of chemical bonds in a particular structure.

The term "biological materials" includes, for example, cells, yeasts, bacteria, proteins, peptides, cytokines, and hormones. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Epithelial tissue covers or lines all body surfaces inside or outside the body of a subject. Examples of epithelial tissue include, but are not limited to, the skin, epithelium, dermis, and the mucosa and serosa that line the body cavity and internal organs (such as the heart, lung, liver, kidney, intestines, bladder, uterus, etc.).

Connective tissue is the most abundant and widely distributed of all tissues. Examples of connective tissue include, but are not limited to, vascular tissue (e.g., arteries, veins, and capillaries), blood (e.g., red blood cells, platelets, and white blood cells), lymph, fat, fibers, cartilage, ligaments, tendon, bone, teeth, omentum, peritoneum, mesentery, meniscus, conjunctiva, dura mater, umbilical cord, etc.

Muscle tissue accounts for nearly one-third of the total body weight of a human subject. There are three distinct subtypes of muscle tissue: striated (skeletal) muscle, smooth (visceral) muscle, and cardiac muscle. Examples of muscle tissue include, but are not limited to, myocardium (heart muscle), skeletal, intestinal wall, etc.

The fourth primary type of tissue is nerve tissue. Nerve tissue is found in the brain, spinal cord, and accompanying nerves. Nerve tissue is composed of specialized cells called neurons (nerve cells) and neuroglial or glial cells.

"Anti-thrombotic" as used herein refers to a medical device that has reduced ability to cause a blood clot and/or a reduced rated of clotting, as compared to an untreated medical device. It will be appreciated that the reduced clotting associated with the device is not to be limited to clots that form within the device, but also includes other clots associated with the use of the device.

The term "click chemistry" as used herein refers to a group of reactions that are versatile, fast, high yielding, highly selective (e.g. regio-selectivity and stereo selectivity) and allow targeted structures to be produced under conditions that allow for straightforward isolation and purification of reaction products. The term "click chemistry" was introduced by K. Barry Sharpless, Hartmuth Kolb, and M. G. Finn of The Scripps Research Institute in 2001 (Kolb et al. *Angewandte Chemie International Edition.* 2001, 40(11), 2004-2021; Evans. *Australian Journal of Chemistry.* 2007, 60(6), 384-395).

Examples of click chemical reactions include: Huisgen 1,3-dipolar cycloaddition of alkynes to azides to form 1,4-disubstituted-1,2,3-triazoles; thiol-ene reactions, (also alkene hydrothiolation)—an organic reaction between a thiol and an alkene to form an alkyl sulfide; nucleophilic ring-opening reactions, which refer to the openings of strained heterocyclic electrophiles, such as aziridines, epoxides, cyclic sulfates, aziridinium ions, and episulfonium ions; Thiol-Isocyanate reactions, such as base catalyzed thiol-isocyanate anionic reactions; and N-hydroxysuccinimide (NHS) activated ester reactions with amino groups.

Chain Extension reactions, as used herein in reference to polysiloxane-co-polyglycerol (branched) copolymers, is intended to describe a process in which one or more polydimethylsiloxane-polyglycerol (PDMS-PGLY) copolymer units are connected without formation of a cross-linked network.

The term "chain extender," as used herein in reference to polydimethylsiloxane-co-polyglycerol copolymers is intended to describe di-functional substances capable of connecting polydimethylsiloxane-co-polyglycerol copolymer units without formation of a cross-linked network.

Gelation as used herein refers to a stage in a chemical reaction at which a polymer is no longer able to flow. In a theoretical sense, gelation is characterized by interconnected polymers chains (Network Structure) forming an infinitely large molecule which is not able to flow. Cross-linking reactions can continue to occur beyond the point of gelation, thereby increasing the degree of rigidity of the polymer network.

Handling tint in reference to a contact lens means a lightly tinted contact lens. This is accomplished by dying (or coloring) of a lens to enable the subject to easily locate a contact lens in a clear solution within a lens storage container, disinfecting container, or cleaning container. A dye and/or a pigment can be used in visibility tinting of a contact lens.

"Dye" means a substance that is soluble in a solvent and that is used to impart color. Dyes are typically translucent and absorb but do not scatter light. Any suitable biocompatible dye can be used in the present invention.

A "pigment" refers to a powdered substance that is suspended in a liquid in which it is insoluble. A pigment can be a conventional pigment, fluorescent pigment, phosphorescent pigment, or pearlescent pigment. Any suitable pigment may be employed. In some examples, the pigment is heat resistant, non-toxic, and insoluble in aqueous solutions.

"Surface modification", as used herein, means that an article has been treated in a surface treatment process (or a surface modification process) prior to or posterior to the formation of the article, in which (1) a coating is applied to the surface of the article, (2) chemical species are adsorbed onto the surface of the article, (3) the chemical nature (e.g., electrostatic charge) of chemical groups on the surface of the article are altered, or (4) the surface properties of the article are otherwise modified. Exemplary surface treatment processes include, but are not limited to, corona, UV-ozone, and plasma processes in which an ionized gas is applied to the surface of an article (see, for example, U.S. Pat. Nos. 4,312,575 and 4,632,844); a surface treatment by energy other than plasma (e.g., a static electrical charge, irradiation, or other energy source); chemical treatments; the grafting of hydrophilic monomers or macromers onto the surface of an article; mold-transfer coating processes such as those described in U.S. Pat. No. 6,719,929; the incorporation of wetting agents into a lens formulation for making contact lenses (i.e., surface treatment prior to polymerization), such as those described in U.S. Pat. Nos. 4,045,547, 4,042,552, 5,198,477, 5,219,965, 6,367,929, 6,822,016, and 7,279,507; and layer-by-layer coating ("LBL coating") obtained, for example according to methods described in U.S. Pat. Nos. 6,451,871, 6,719,929, 6,793,973, 6,811,805, and 6,896,926.

"Post-curing surface treatment," as used herein in reference to a silicone hydrogel material or a soft contact lens, means a surface treatment process that is performed after the formation (curing) of the hydrogel material or the soft contact lens in a mold.

A "hydrophilic surface," as used herein in reference to a silicone hydrogel material or a contact lens, means that the silicone hydrogel material or the contact lens has a surface hydrophilicity characterized by an average water contact angle of 90 degrees or less (e.g., 80 degrees or less, 70 degrees or less, 60 degrees or less, 50 degrees or less, 40 degrees or less, 30 degrees or less, 20 degrees or less, or 10 degrees or less). Contact angle can be measured by a sessile drop method using advancing angle or using a captive bubble method. The average contact angle using sessile drop method refers to a water contact angle obtained by averaging the measurements of at least 3 individual contact lenses. The captive bubble (sessile bubble) method is a special arrangement for measuring the contact angle between a liquid and a solid using drop shape analysis. Instead of placing a drop on the solid as in the case of the sessile drop, a bubble of air is injected beneath a solid, the surface of which is located in the liquid. Unless otherwise noted, contact angles for materials of the present invention correspond to a captive bubble contact angle measurement.

An "antimicrobial agent", as used herein, refers to an agent that is capable of decreasing, eliminating, or inhibiting the growth of microorganisms.

"Antimicrobial compound" as used herein, refers to organic compounds with functional groups known for antimicrobial activity. Functional groups known for antimicrobial activity include, but are not limited to, quaternary ammonium, chalcones, quinolones, phenolics, polyphenols, phenolic acids, quinones, saponins, flavonoids, tannins, coumarins, terpenoids, alkaloids. Example antimicrobial compounds include, but are not limited to, substituted polycationic polysiloxane cationic anthraquinone-based dye and Poly(hexamethylenebiguanide) hydrochloride, "Antimicrobial metals" are metals whose ions have an antimicrobial effect and which are biocompatible. In some examples, the antimicrobial metal comprises Ag, Au, Pt, Pd, Ir, Sn, Cu, Sb, Bi, or Zn. In some examples, the antimicrobial metal comprises Ag.

"Antimicrobial metal-containing nanoparticles" refer to particles having a size of less than 1 micrometer and containing at least one antimicrobial metal present in one or more of its oxidation states. "Antimicrobial metal nanoparticles" refer to particles which consist essentially of an antimicrobial metal and have a size of less than 1 micrometer. The antimicrobial metal in the antimicrobial metal nanoparticles can be present in one or more of its oxidation states. For example, silver-containing nanoparticles can contain silver in one or more of its oxidation states, such as $Ag^0$, $Ag^{1+}$, and $Ag^{2+}$.

"Oxygen permeability" of a contact lens is abbreviated as Dk where "D" is diffusivity ($cm^2$/sec) and "k" is the solubility of oxygen in a given contact lens material (ml $O^2$/ml of material×mm Hg). Oxygen permeability, Dk, is conveniently expressed in units of barrers, where "barrer" is defined at standard temperature and pressure (STP) as: barrer=$10^{-11}$ ($mLO_2 \cdot cm$)/(sec·$cm^2$·mm Hg). Oxygen transmissibility (Dk/t) takes into account the thickness (t) of the contact lens and has the unit's mL $O_2$/(sec·$cm^2$·mm Hg).

The "oxygen transmissibility" of a contact lens, as used herein, is the rate at which oxygen will pass through a specific contact lens. Herein, a polarographic method was used to measures oxygen transmissibility (Dk/t) of contact lenses. In this method, Dk/t is measured by detecting the amount of electrical current produced between the two dissimilar metals of the polarographic cell (gold & silver) via an electrolyte (saline). Equation 1 below shows the chemical equation for the reduction of dissolved oxygen in water. Equation 1 shows that electrochemical reduction of one oxygen molecule in saline consumes 4 electrons and produces 4 hydroxide ions. In this process, hydroxide ions migrate through the electrolyte to the anode thereby generating an electric current. The amount of electrical current that is produced is proportional to the amount of oxygen available at the interface of the sample and polarographic cell.

$$O_2 + 2H_2O + 4e^- \rightarrow 4HO^- \quad (1)$$

The electric current associated with the electrochemical reduction of oxygen in saline can be represented by Equation 2.

$$\frac{Dk_{apparent}}{t_{ave}} = \frac{I}{nFA\Delta P} = BI \quad (2)$$

Equation 2 is the relationship between the Apparent Oxygen Transmissibility (AOT, $Dk_{apparent}/t_{ave}$), electric current (I), cell constant (B), and average lens thickness ($t_{ave}$), were n is the number of electrons generated at the electrode (4 in Equation 1), F is Faraday's Constant (96,487 Coulomb/mol Vol $O_2$ at STP), A is the area of the contact lens exposed to the gold cathode, and $\Delta P$ is the $O_2$ partial pressure difference across the lens at sea level pressure.

Apparent oxygen transmissibility (AOT) is obtained by multiplying measured electric current (I) by the instrument cell constant "B" as shown in Equation 3. The term "apparent oxygen transmissibility" is used since diffusion resistance of the solution layer between the sample and electrode (boundary layer) must be taken into account to obtain the true oxygen transmissibility.

$$Dk_{apparent} = BIt_{ave} \quad (3)$$

The cell constant, B, is defined by the equation below.

$$B = \frac{1}{nFA\Delta P}$$

The relationship between apparent oxygen transmissibility ($Dk_{apparent}/t_{ave}$) and true oxygen transmissibility ($Dk/t_{ave}$), is shown in Equation 4:

$$\frac{t_{ave}}{Dk_{apparent}} = \frac{t_{ave}}{Dk} + \frac{t_0}{Dk_0} \quad (4)$$

where $t_{ave}$ is the average thickness of the material [in units of cm] over the area being measured and $$\frac{t_0}{Dk_0}$$

is the boundary layer resistance.

Herein, the reciprocal of apparent oxygen transmissibility was plotted versus lens thickness and oxygen permeability was obtained from the inverse slope of this plot. Herein, thickness of lens material was varied by stacking contact lenses ("Stack Method"). Additional information concerning the stack method used herein to vary lens thickness is described in the literature (Fatt. *ICLC* 1984, 11, 175-187; Brennan et al. *Clin Exp Optm.* 1986, 37, 101-107; Weissman et al. *CLAO J* 1991, 17, 62-64).

Oxygen transmissibility, Dk/t, is conveniently expressed in units of barrers/mm, where "t" is the average thickness of the material [in units of cm] over the area being measured and "barrer/mm" is defined as: [($cm^3$ oxygen)/($cm^2$)(sec) (mm Hg)]$\times 10^{-9}$.

Oxygen transmissibility (Dk/t) takes into account the thickness (t) of the contact lens and has the unit's mL $O_2$/(sec·$cm^2$·mm Hg). Oxygen transmissibility, Dk/t, is conveniently expressed in units of barrers/mm. These are the units commonly used in the art. Thus, in order to be consistent with the use in the art, the unit "barrer" will have the same meanings as defined above. For example, a lens having a Dk of $120\times10^{-11}$ (m$LO_2$·cm)/(sec·$cm^2$·mm Hg) means the same as a contact lens having a Dk of 120 barrers. A contact lens with oxygen permeability 120 barrer and a thickness of 80 microns (0.8 mm, 0.08 cm) would have a Dk/t of $150\times10^{-9}$ mL $O_2$/(sec·$cm^2$·mm Hg).

"High oxygen permeability," as used herein in reference to a material or a contact lens, is characterized by an apparent oxygen permeability ($Dk_{apparent}$) of 40 barrers or more measured with a sample (film or lens) of 100 microns in thickness (e.g., 50 barrers or more, 60 barrers or more, 70 barrers or more, 80 barrers or more, 90 barrers or more, 100 barrers or more, 110 barrers or more, 120 barrers or more, 130 barrers or more, 140 barrers or more, or 150 barrers or more).

The "ion permeability" through a lens correlates with both the Ionoflux Diffusion Coefficient (D) and the Ionoton Ion Permeability Coefficient (P). The Ionoflux diffusion coefficient, D ($mm^2$/min), is determined by Fick's law of diffusion as follows:

$$D = -\frac{n'}{\left(A \times \frac{dc}{dx}\right)}$$

where n' is the rate of ion transport (mol/min), A is the area of ion transport ($mm^2$), dc is the concentration difference (mol/L), dx is the thickness of the lens (mm).

The Ionoton Ion Permeability Coefficient, P, is then determined in accordance with the following equation:

$$\ln(1 - 2C(t)/C(0)) = -\frac{2APt}{Vd}$$

where C(t) is the concentration of sodium ions at time t in the receiving cell, A is the membrane area (i.e., lens area exposed to cells), V is the volume of the cell compartment, d is the average lens thickness.

Abbreviations

| Abbreviation/ Acronym | Name/Meaning |
|---|---|
| PGLY or Gly | Polyglycerol or polyglycerol segment. Any of the possible isomers of polyglycerol are represented by PGLY or Gly. PGLY and Gly are used interchangeably herein |
| AC-PDMS-PGLY | Polydimethylsiloxane block copolymers containing actinically cross-linkable polyglycerol side branches. |
| UV-B locking AC-PDMS-PGLY | UV-Blocking Polydimethylsiloxane block copolymers containing actinically cross-linkable polyglycerol side branches. |
| BL-Blocking AC-PDMS-PGLY | Blue Light-Blocking Polydimethylsiloxane block copolymers containing actinically cross-linkable polyglycerol side branches. |

| Abbreviation/<br>Acronym | Name/Meaning |
| --- | --- |
| CE-(PDMS-PGLY) | Chain extended block copolymers of polydimethylsiloxane-polyglycerol |
| UV-Blocking CE-(PDMS-PGLY) | UV-Blocking Chain extended block copolymers of polydimethylsiloxane-polyglycerol |
| BL-Blocking CE-(PDMS-PGLY) | Blue Light-Blocking Chain extended block copolymers of polydimethylsiloxane-polyglycerol |
| AC-CE-(PDMS-PGLY) | Actinically curable chain extended block copolymers of polydimethylsiloxane-polyglycerol |
| UV-Blocking AC-CE-(PDMS-PGLY) | UV-Blocking Actinically curable chain extended block copolymers of polydimethylsiloxane-polyglycerol |
| BL-Blocking AC-CE-(PDMS-PGLY) | Blue Light-Blocking Actinically curable chain extended block copolymers of polydimethylsiloxane-polyglycerol |
| VAZO 52 | 2-2'-Azobis(2,4-dimethylvaleronitrile) |
| VAZO 67 (AMBN) | 2,2'-Azodi(2-methylbutyronitrile) |
| VAZO 88 (ACHN) | (1,1'-Azobis(cyanocyclohexane) |
| VAZO 56 WSP | 4,4'-Azobis(4-cyanovaleric Acid), 4,4'-Azobis(4-cyanopentanecarboxylic Acid) |
| VAZO 68 WSP | 4,4'-(1,2-Diazenediyl)bis[4-cyanopentanoic Acid; |
| >C=C< | Generic symbol for ethylenically unsaturated compound or group. Unsaturated monomers are those having carbon-carbon double bonds. Some examples of unsaturated monomers include: 2-Hydroxyethyl methacrylate, glyceryl monomethacrylate, acrylic acid, acrylamide, dimethyl acrylamide, acryloyl chloride, and methyl methacrylate. |
| GMMA | Glyceryl monomethacrylate, 2,3-Dihydroxypropyl methacrylate, 2-Propionic acid, 2-methyl-2,3-dihydroxypropyl ester |
| HEMA | 2-Hydroxyethyl methacrylate, 1,2-Ethanediol mono(2-methylpropenoate), Glycol methacrylate, |
| IPA | 2-propanol, isopropanol, isopropyl alcohol |
| NVP | 1-Vinyl-2-pyrrolidinone, N-Vinyl Pyrrolidone |
| EGDMA | Ethylene glycol di-methacrylate |
| TGDMA | Tetraethylene glycol dimethacrylate |
| PEG or PEO | Polyethylene glycol or polyethylene oxide (PEO) |
| SIGMA | 3-Methacryloxy-2-Hydroxypropoxy(propylbis (trimethylsilyloxy)-methylsilane |
| PDMS | Polydimethylsiloxane |
| TRIS | 3-methacryloxypropyl tris-(trimethylsiloxy) silane |
| PDMS-MA | Poly(dimethyl siloxane)-monomethacrylate |
| MA-PDMS-MA | Poly(dimethyl siloxane)-dimethacrylate |
| PDMS-DA | Polydimethylsiloxane-diacrylamide |
| DGE-PDMS-DGE | Poly(dimethyl siloxane), diglycidyl ether terminated |
| PDMS-DGE | Poly(dimethyl siloxane), mono-glycidyl ether terminated |
| BME | Benzoin methyl ether |
| IRGACURE 184 | 1-hydroxy-cyclohexyl-phenyl-ketone |
| IRGACURE 500 | 1-hydroxy-cyclohexyl-phenyl-ketone (50 wt. %), benzophenone (50 wt. %) |
| DARACURE 1173 (also known as Irgacure 1173) | Hydroxydimethylacetophenone |
| IRGACURE 2959 | 2-hydroxy-1-[4-(hydroxyethoxy)phenyl]-2-methyl-1-propanone |
| Irgacure 369 | 2-Benzyl-2-dimethylamino-1-(4-morpholinophenyl)-1-butanone |
| DAROCUR MBF | Methylbenzoylformate |
| IRGACURE 754 | oxy-phenyl-acetic acid 2-[2 oxo-2 phenyl-acetoxy-ethoxy]-ethyl ester and oxy-phenyl-acetic 2-[2-hydroxy-ethoxy]-ethyl ester |
| IRGACURE 651 | Alpha, alpha-dimethoxy-alpha-phenylacetophenone |
| Irgacure 369 | 2-Benzyl-2-(dimethylamino)-4-morpholino-butyrophenone |
| IRGACURE 907 | 2-Methyl-1-[4-(methylthio)phenyl]-2-(4-morpholinyl)-1-propanone |
| IRGACURE 1300 | IRGACURE 369 (30 wt. %) + IRGACURE 651 (70 wt. %) |
| DAROCUR TPO | Diphenyl (2,4,6-trimethylbenzoyl)-phosphine oxide |
| DAROCUR 4265 | DAROCUR TPO (50 wt. %) + DARACURE 1173 (50 wt. %) |
| DEAP | Diethoxyacetophenone |
| IRGACURE 651, BDK, DMPA, | Dimethoxyphenylacetophenone |
| IRGACURE 184 | Benzoylcyclohexanol |
| IRGACURE 819 | Phosphine oxide, phenyl bis (2,4,6-trimethyl benzoyl) |
| IRGACURE 2022 | IRGACURE 819 (20 wt. %) + DARACURE 1173 (80 wt. %) |
| IRGACURE 784 | Bis (eta 5-2,4-cyclopentadien-1-yl) Bis [2,6-difluoro-3-(1H-pyrrol-1-yl)phenyl]titanium |
| IRGACURE 250 | Iodonium, (4-methylphenyl) [4-(2-methylpropyl) phenyl]-, hexafluoro-phosphate(1-) |
| IRGACURE 379 | 2-(4-Methylbenzyl)-2-(dimethylamino)-4-morpholino-butyrophe-none |
| IRGACURE 651, | 2,2-Dimethoxy-1,2-diphenylethan-1-one |
| IEM | 2-isocyanatoethylmethacrylate |
| CQ | Camphor Quinone |
| DMBP | 4-(Dimethylamino)benzophenone |
| H-Nu Blue 640, H-Nu 660 | Cyanine borate Visible Light Photoinitiators available from Spectra Group Limited Inc, 27800 Lemoyne Road, Suite J, Millbury, OH, 43447, USA |
| H-Nu-IR 780, 815 | Infrared Light Photoinitiators available from Spectra Group Limited Inc, 27800 Lemoyne Road, Suite J, Millbury, OH, 43447, USA |
| MPPDASBD | N-[3-(4-methylpyridino)propyl]-2-(p-N,N-diethylaminostyryl)benzothiazolium dibromide |
| MPEA | 2-methylprop-2-enoic anhydride, methacrylic anhydride |
| MA | Maleic Anhydride |
| DMA | Dimethyl acrylamide |
| DBTDL | Dibutyltin dilaurate, [dibutyl(dodecanoyloxy) stannyl] dodecanoate |
| DMAP | N,N-Dimethylpyridin-4-amine; 4-Dimethylaminopyridine; N,N-Dimethylpyridin-4-amine |
| TETOHA | triethanolamine |
| TEA | Triethyl amine |
| Diopter (D)[a] | Diopter (D) is a unit of measure of the refractive power of a lens. One diopter is equal to the reciprocal of a focal length of one meter. |
| Dia[a] or Diameter | Dia is the contact lens diameter (chord diameter). Contact lens diameter is the greatest distance across the contact lens. Unless otherwise stated, contact lens diameter is reported in units of millimeters (mm). |
| BCR or BC | BCR (base curve radius) or base curve (BC) for a contact lens is the curvature of the back surface and is sometimes referred to as the back central optic radius (abbreviated BCOR). Unless otherwise stated, contact lens base curve radius is reported in units of millimeter (mm). |
| CT[a] | Axial or radial thickness of a contact lens along the lens axis at the geometric center. Center thickness of a contact lens. |
| Power, Lens Power or $F_v$[a] | Power, lens power or Front vertex power ($F_v$[a]): Negative reciprocal of the front vertex focal length in meters of the optic zone in air, expressed in diopters. The front vertex focal length is the distance from the front vertex to the primary focal point of the optic zone |
| Hydrogel[a] | A water absorbing (hydrophilic) material having an equilibrium water content greater than or equal to 10% in standard saline at room temperature. |
| Spherical Contact Lens[a] | A contact lens that brings a paraxial pencil of parallel rays to a single point of focus, and that has front and back optic zones consisting of spherical (non-toric) and non-aspheric) surfaces. |
| Toric Lens[a] | A toric lens is a contact lens with either front or back optic zone having a toric surface. |
| Toric Surface[a] | A toric surface is described by a circle rotating about an off center line in its own plane. Meridians of least and greatest curvature for these surfaces are perpendicular to each other. |
| Water Content[a] | Contact lens water content is the amount of water present in the lens expressed as a percentage of the total mass of the lens in its hydrated state under |

| Abbreviation/Acronym | Name/Meaning |
|---|---|
| | equilibrium conditions, when immersed in standard saline solution at a defined temperature. Contact lens water content may be measured gravimetrically, or by using a refractometer. |

[a]Description based on ANSI Z80.20-2010 (American National Standard) for Ophthalmic contact Lenses-Standard Terminology, Tolerances, Measurements and Physiochemical Properties.

Reference will now be made in detail to specific aspects of the disclosed materials, compounds, compositions, articles, and methods, examples of which are illustrated in the accompanying examples and figures.

Compositions

Described herein are compositions comprising an actinically cross-linkable block copolymer of polydimethyl-siloxane (PDMS) with one or more actinically curable polyglycerol branches. For example, the actinically cross-linkable block copolymers described herein comprise one or more actinically curable polyglycerol branches tethered to a PDMS main chain.

Described herein are actinically-crosslinkable polysiloxane-polyglycerol block copolymers comprising a polysiloxane prepolymer with one or more actinically curable polyglycerol branches, wherein the actinically curable polyglycerol branches include crosslinking sites that can be located near the junction of the polysiloxane prepolymer and the polyglycerol branches or at any location along the polyglycerol branches.

Described herein are compositions comprising an actinically-crosslinkable polysiloxane-polyglycerol block copolymer derived from: a polysiloxane prepolymer comprising a polyglycerol side chain, the polyglycerol side chain comprising an ethylenically unsaturated group covalently linked thereto, wherein the ethylenically unsaturated group is actinically curable. The term "derived from" in reference to polymeric units in the polymer chain means that the polymeric units are obtained from a specified monomer in a polymerization reaction. The polysiloxane prepolymer can comprise a linear or branched polysiloxane prepolymer, such that the actinically-crosslinkable polysiloxane-polyglycerol block copolymers can comprise actinically-crosslinkable linear or branched polysiloxane-polyglycerol block copolymers. In some examples, the polysiloxane prepolymer comprises polydimethyl siloxane (PDMS). The ethylenically unsaturated group can comprise any suitable actinically curable ethylenically unsaturated group. Exemplary ethylenically unsaturated groups include, but are not limited to, (meth)acryloyl, (meth)acrylamide, alkyl acrylamide, dialkyl acrylamide, allyl, vinyl, and styrenyl. In some examples, the ethylenically unsaturated group can be directly linked to the polyglycerol branches of PDMS-PGLY. In some examples, the ethylenically unsaturated group can be linked to the polyglycerol side chain through a linking group (e.g., connector group). Examples of linking groups include, but are not limited to, those provided in Table 1-Table 4. The * symbol is used in Table 1-Table 4 to represent a radical that forms (theoretically) upon homolytically separating linking groups from polyglycerol and cure groups.

TABLE 1

Bifunctional Monomers and linking groups.

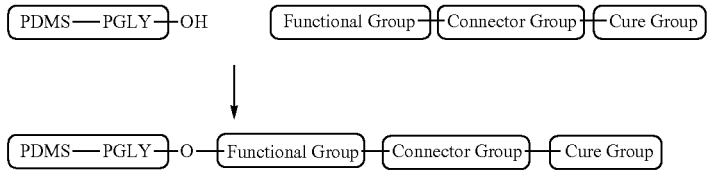

Functional Group can comprise a chemical group that reacts with OH groups present in PDMS-PGLY-OH (e.g., isocyanate, epoxy, anhydride, alkylhalide, etc.)

| Reactant (Species) that react with polyglycerol OH units. | Resulting Linking Group<br>Note: If one were to homolytically cleave the liking group at the cure group and polyglycerol junctions, the result is a di-radical species. |
|---|---|
| 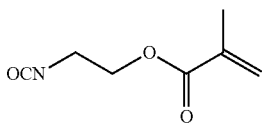 |  |
| 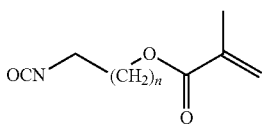 | 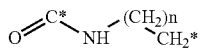 |

TABLE 1-continued

Bifunctional Monomers and linking groups.

[PDMS—PGLY]—OH   [Functional Group]—[Connector Group]—[Cure Group]

↓

[PDMS—PGLY]—O—[Functional Group]—[Connector Group]—[Cure Group]

Functional Group can comprise a chemical group that reacts with OH groups present in PDMS-PGLY-OH (e.g., isocyanate, epoxy, anhydride, alkylhalide, etc.)

| Reactant (Species) that react with polyglycerol OH units. | Resulting Linking Group<br>Note: If one were to homolytically cleave the liking group at the cure group and polyglycerol junctions, the result is a di-radical species. |
|---|---|
| OCN—R¹—R²—O—C(=O)—C(CH₃)=CH₂ | O=C*—NH—R²—R¹* |

TABLE 2

Bifunctional Monomers and linking groups.
Reaction of PDMS-PGLY with Glycidylmethacrylate

[polyglycerol structure with multiple OH groups attached to PDMS]

↓ (glycidyl methacrylate)

[product structure with methacrylate groups attached via polyglycerol to PDMS]

Reactant
One skilled in the art will recognized that reaction of polyglycerol units with certain reagents can lead to more than one isomer. For example, reaction of polyglycerol with epoxide derivatives can lead to two different isomers as shown below.

Linking Groups
Note: If one were to homolytically cleave the linking group at the cure group and polyglycerol junctions, the result is a di-racical species.

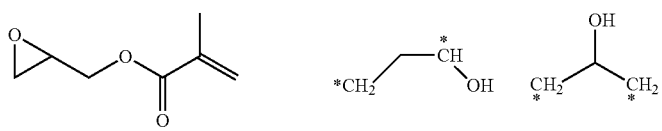

TABLE 2-continued
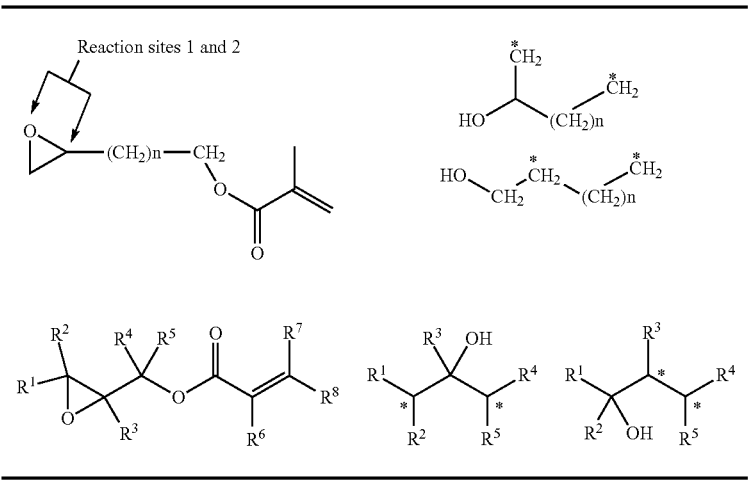
TABLE 3
Bifunctional Monomers and linking groups.
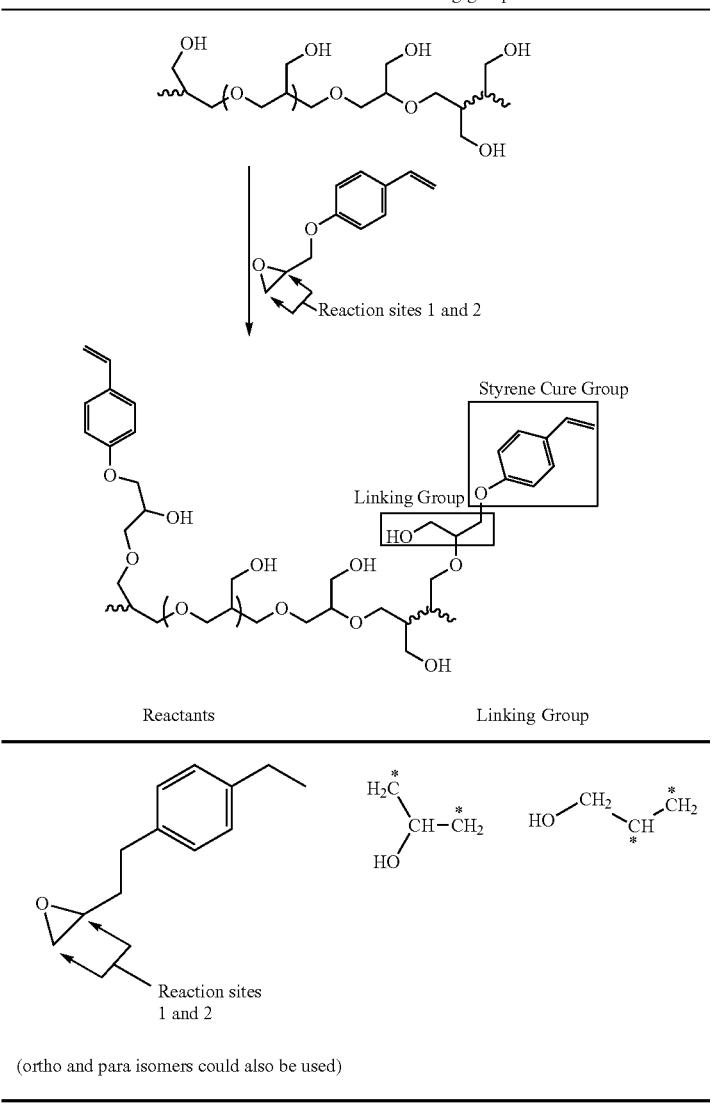
| Reactants | Linking Group |
(ortho and para isomers could also be used)

TABLE 4
Bifunctional Monomers and linking groups.
| Reactants | Linking Group<br>Note: If one were to homolytically cleave the liking group at the cure group and polyglycerol junctions, the result is a di-radical species. |
|---|---|
| 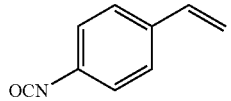 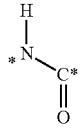 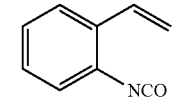 | 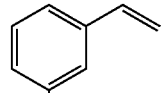 |
| 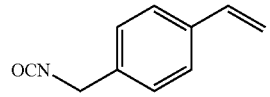 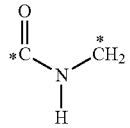 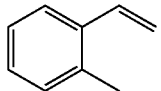 | 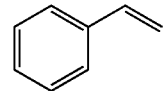 |
| 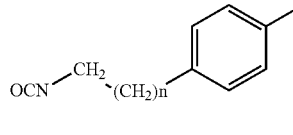 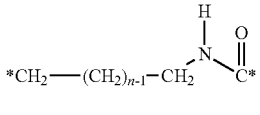 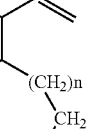 | 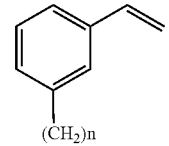 |
| 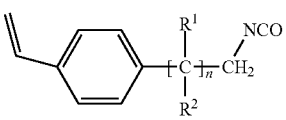<br>Plus ortho and meta isomers | 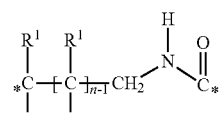 |
| 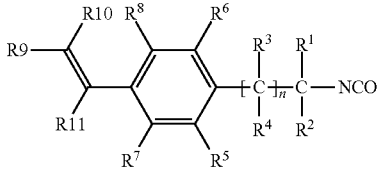<br>Plus ortho and meta isomers | 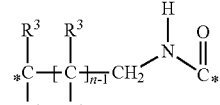 |

In some examples, the actinically-crosslinkable polysiloxane-polyglycerol block copolymers can be defined by Formula I:

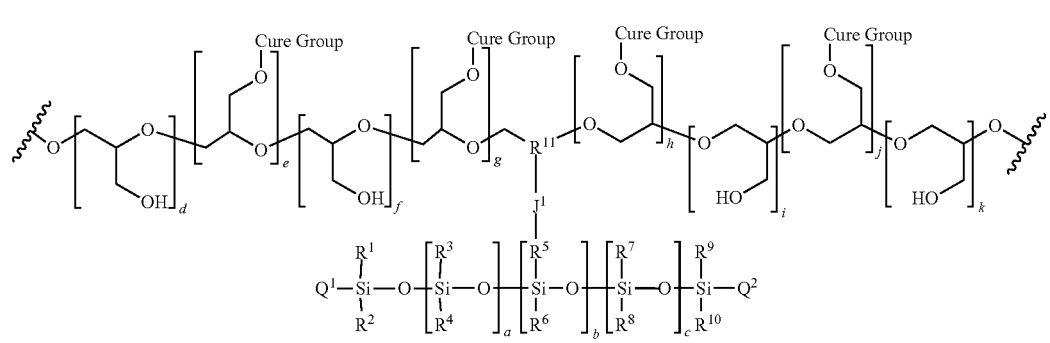

wherein $R^1$, $R^2$, $R^3$, $R^4$, $R^5$, $R^6$, $R^7$, $R^8$, $R^9$, $R^{10}$, $R^{11}$, and $J^1$ are, independently, alkyl, cycloalkyl, aryl, alkylpolyethylene oxide, or polyglycerol, any of which is optionally substituted with halide, hydroxy, thiol, carbonyl, alkoxy, alkylhydroxy, carboxyl, amino, amido, alkyl, alkenyl, alkynyl, aryl, —$NR^xR^y$, —$C(O)NR^xR^y$, azide, or a combination thereof;

$Q^1$ and $Q^2$ are independently H, OH, amino, alkyl, alkenyl, alkynyl, cycloalkyl, aryl, alkylaryl, or heteroaryl, any of which is optionally substituted with epoxy, hydroxy, thiol, carbonyl, alkoxy, alkylhydroxy, carboxyl, amino, amido, alkyl, alkenyl, alkynyl, aryl, —$NR^xR^y$, —$C(O)NR^xR^y$, azide, or a combination thereof;

$R^x$ and $R^y$ are independently H, OH, alkyl, alkenyl, alkynyl, cycloalkyl, aryl, alkylaryl, or heteroaryl;

Cure Group comprises the ethylenically unsaturated group;

a, c, d, e, f, g, h, i, j and k are, independently, an integer from 0 to 10,000;

with the proviso that:

at least one of e, g, h, and j is not 0; and at least one of d, f, i, and k is not 0; and b is an integer from 1 to 10,000.

Alkylpolyethylene oxide can comprise —$(CH_2CH_2O)_n$—$OR^{12}$, wherein n is an integer from 2 to 10,000 and $R^{12}$ is a substituted or unsubstituted alkyl group (e.g., a $C_1$-$C_{18}$ alkyl group).

Polyglycerol can comprise —$(C_3H_8O)_n$ wherein n is an integer from 2 to 10,000. Polyglycerol can comprise linear or branched polyglycerol. Exemplary structures of linear and branched polyglycerol are depicted in Formula II, Formula III, Formula IV, Formula V, Formula VI, Formula VII, and Formula VIII. The molecular weight of branched polyglycerol can, for example, be from 92 Daltons to 111,000 Daltons. Molecular weight of polyglycerol is determined by the number of repeat units and the molecular weight of the initiating species.

For example, the polyglycerol can comprise a linear polyglycerol defined by Formula II:

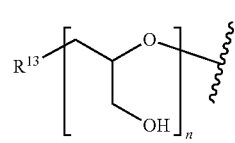

wherein $R^{13}$ is H, or an alkyl group or cycloalkyl group, either of which is optionally substituted with halide, alkylthio, carbonyl, alkoxy, carboxyl, amido, alkyl, cycloalkyl, alkenyl, cycloalkenyl, alkynyl, aryl, —$NR^xR^yR^z$, —$C(O)NR^xR^y$, or a combination thereof;

$R^x$, $R^y$, and $R^z$ are independently H, OH, alkyl, alkenyl, alkynyl, cycloalkyl, aryl, alkylaryl, or heteroaryl; and n is an integer from 2 to 1,000,000.

In some examples of Formula II, $R^{13}$ comprises a nucleophilic group capable of initiating ring opening polymerization of glycidol. Examples of such nucleophilic groups include, but are not limited to, OH, O-Alkyl, $NR^xR^yR^z$, S—H, S-Alkyl, etc. In some examples, $R^{13}$ can comprise an amide substituent.

In some examples of Formula II, $R^{13}$ can comprise $CH_3(CH_2)_mO^-$ $Na^+$ where m is an integer from 0 to 20; $(CH_3)_3CO^-$ $Na^+$; $NH_2$; a linear, branched, or cyclic alkylamino group (e.g., $CH_3(CH_2)_mNH$ where m is an integer from 0 to 20, $(CH_3)_2CHNH$, piperidinyl, cyclopentyl-NH, cyclohexyl-NH); a linear, branched, or cyclic dialkylamine (e.g., $(CH_3)_2N$, $CH_3(CH_3CH_2)N$, $(CH_3(CH_2)_z)_2N$ where z is an integer from 1 to 20, piperidinyl); a trialkylammonium groups (e.g., $(CH_3)_3N^+$, $(CH_3CH_2)_3N^+$, $(HOCH_2)_3N^+$, $(HOCH_2CH_3)_3N^+$); a linear, branched, or cyclic alkylthiol (e.g., $CH_3(CH_2)_mS$ where m is an integer from 0 to 20, $(CH_3)_2CHS$, $(CH_3)_3CS$, cyclohexyl-S).

In some examples of Formula II, $R^{13}$ can comprise X-Alkyl, where X=O, $NH_2$, S, $NHR^x$, $NR^xR^y$, $NR^xR^yR^{z+}$;

alkyl groups include linear, branched, or cyclic groups; and $R^x$, $R^y$, and $R^z$ are independently H, alkyl, alkenyl, alkynyl, cycloalkyl, aryl, alkylaryl, or heteroaryl. In some examples, of Formula II, $R^{13}$ can comprise a linear, branched or cyclic structure such as —X—$(CH_2)_mCH_3$ where X=O or S and m droxyethyl)-acetamide, N-(2-Hydroxyethyl)-formamide, N-(2-Hydroxyethyl)-propanamide, or N-(2-Mercaptoethyl)-acetamide.

In some examples, the polyglycerol comprises a branched polyglycerol defined by Formula III:

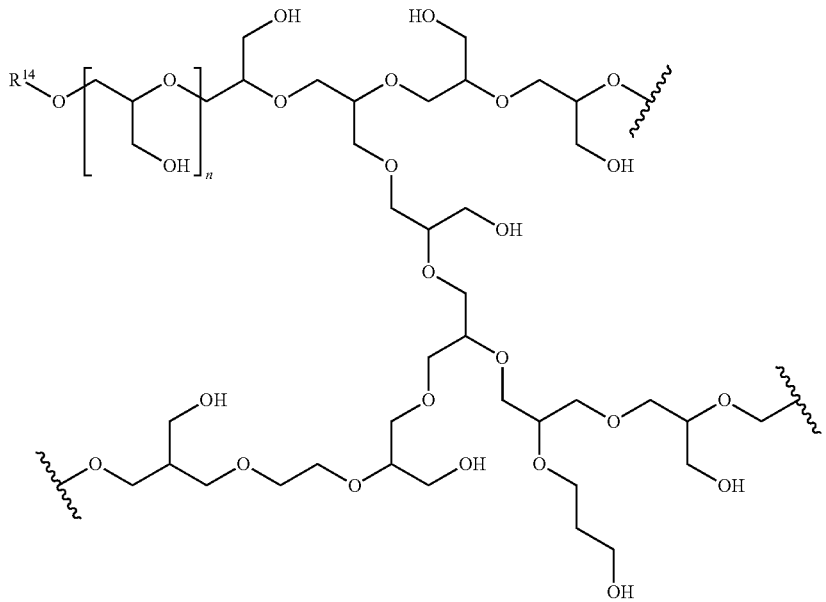

III is from 0 to 20, e.g., —X-Propyl, X-butyl, —X-secbutyl, —X-Pentyl, —X-isopentyl, —X-cyclopentyl, —X-cyclohexyl, —X-methylcyclopentyl, —X— methylcyclohexyl. The alkyl groups can optionally be substituted with various groups such as halide, alkoxy, thioether, carbonyl, carboxyl, amido, alkyl, cycloalkyl, alkenyl, cycloalkenyl, alkynyl, aryl, —C(O)NRxRy, or a combination thereof.

In some examples of Formula II, $R^{13}$ can comprise a linear, branched, or cyclic aminoalkyl structure, e.g., —NH$(CH_2)_mCH_3$ where m is from 0 to 20. For example, $R^{13}$ can comprise—NHAlkyl (e.g., —NHPropyl, —NHbutyl, —NHsecbutyl, —N-tbutyl, —NHPentyl, —NHisopentyl, —NHcyclopentyl, —NHcyclohexyl, —NHmethylcyclopently, —NH-methylcyclohexyl, etc.).

In some examples of Formula II, $R^{13}$ can comprise a linear, branched, or cyclic amino dialkyl structure, e.g., —N[$(CH_2)_nCH_3$]$_2$ where m is from 0 to 20. For example, $R^{13}$ can comprise —N(Alkyl)$_2$ (e.g., —N(propyl)$_2$, —N(butyl)$_2$, —N(secbutyl)$_2$, —N-(t-butyl)$_2$, —N(pentyl)$_2$, —N(isopentyl)$_2$, —N(cyclopentyl)$_2$, —N(cyclohexyl)$_2$, —N(methylcyclopentyl)$_2$, —N(methylcyclohexyl)$_2$, etc.).

In some examples of Formula II, $R^{13}$ can comprise a linear, branched, or cyclic amino trialkyl structure, e.g. —N[$(CH_2)_mCH_3$]$_3$ where m is from 0 to 20. For example, $R^{13}$ can comprise —N(Alkyl)$_3$, (e.g., —N(propyl)$_3$, —N(butyl)$_3$, —N(secbutyl)$_3$, —N(t-butyl)$_3$, —N(pentyl)$_3$, —N(isopentyl)$_3$, —N(cyclopentyl)$_3$, —N(cyclohexyl)$_3$, —N(methylcyclopentyl)$_3$, —N(methylcyclohexyl)$_3$, 1-Methylpiperidinyl, etc.).

In some examples of Formula II, $R^{13}$ can comprise 4-[1-(Aminomethyl)cyclopentanecarbonyl]-1-methylpiperazin-2-one, 2-Aminobutanamide, 3-Aminobutanamide, 4-Aminobutyramide, 5-aminopentanamide, N-(2-Aminoethyl)-acetamide, 2-Amino-N-methyl-acetamide, N-(2-Hywherein
$R^{14}$ is H, alkyl, or cycloalkyl, either of which is optionally substituted with halide, hydroxy, carbonyl, alkoxy, alkylhydroxy, carboxyl, amino, amido, alkyl, alkenyl, alkynyl, aryl, thioether, —NR$^x$R$^y$, —C(O)NR$^x$R$^y$, or a combination thereof;
$R^x$ and $R^y$ are independently H, OH, alkyl, alkenyl, alkynyl, cycloalkyl, aryl, alkylaryl, or heteroaryl; and
n is an integer from 1 to 10,000.

In some examples, the polyglycerol can comprise a branched polyglycerol defined by Formula IV:

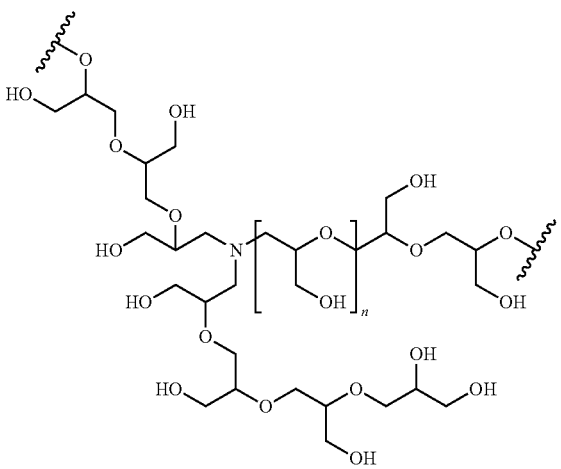

IV wherein n is an integer from 1 to 10,000.

In some examples, the polyglycerol can comprise a branched polyglycerol defined by Formula V:

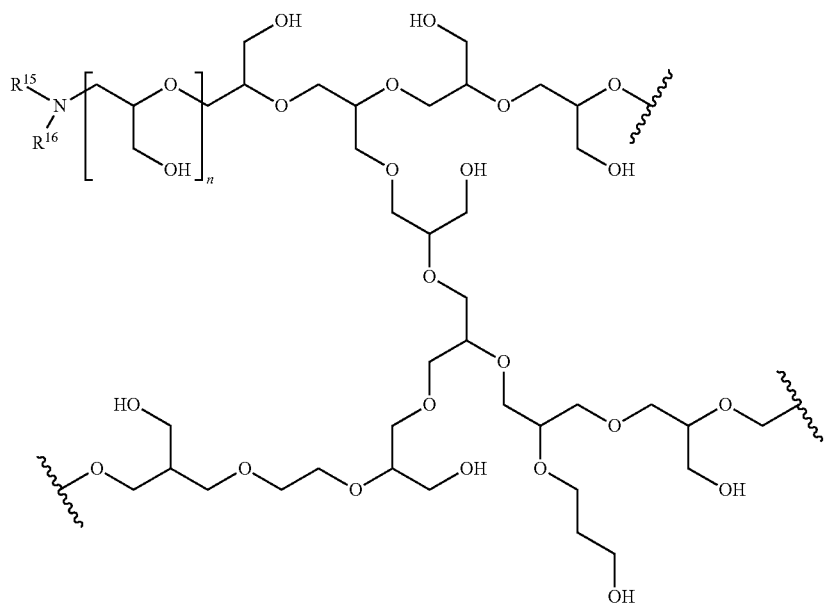

wherein

R$^{15}$ and R$^{16}$ are, independently, H, alkyl, or cycloalkyl, either of which is optionally substituted with halide, hydroxy, thioether, carbonyl, alkoxy, alkylhydroxy, carboxyl, amino, amido, alkyl, alkenyl, alkynyl, aryl, —NR$^x$R$^y$, —C(O)NR$^x$R$^y$, or a combination thereof, or R$^{15}$ and R$^{16}$, together with the atoms to which they are attached, form a 3-10 membered cyclic moiety, wherein any of the additional atoms are optionally heteroatoms and the 3-10 membered cyclic moiety is optionally substituted with halide, hydroxy, thiol, carbonyl, alkoxy, alkylhydroxy, carboxyl, amino, amido, alkyl, alkenyl, alkynyl, aryl, —NR$^x$R$^y$, —C(O)NR$^x$R$^y$, or a combination thereof, R$^x$ and R$^y$ are independently H, OH, alkyl, alkenyl, alkynyl, cycloalkyl, aryl, alkylaryl, or heteroaryl; and n is an integer from 1 to 10,000.

In some examples of Formula V, R$^{15}$ and R$^{16}$ are, independently, H, CH$_3$(CH$_2$)$_m$ where m is an integer from 1 to 20, cyclopentyl, or cyclohexyl. In some examples of Formula V, R$^{15}$ and R$^{16}$, together with which the atoms to which they are attached, comprise a piperidinyl group.

In some examples, the polyglycerol can comprise a branched polyglycerol defined by Formula VI:

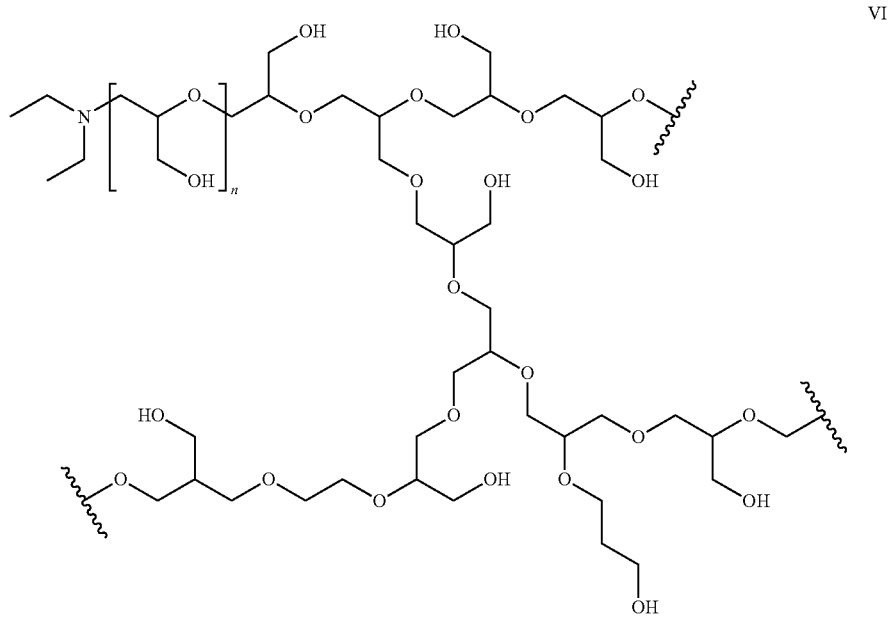

wherein n is an integer from 1 to 10,000.

In some examples, the polyglycerol can comprise a branched polyglycerol defined by Formula VII:

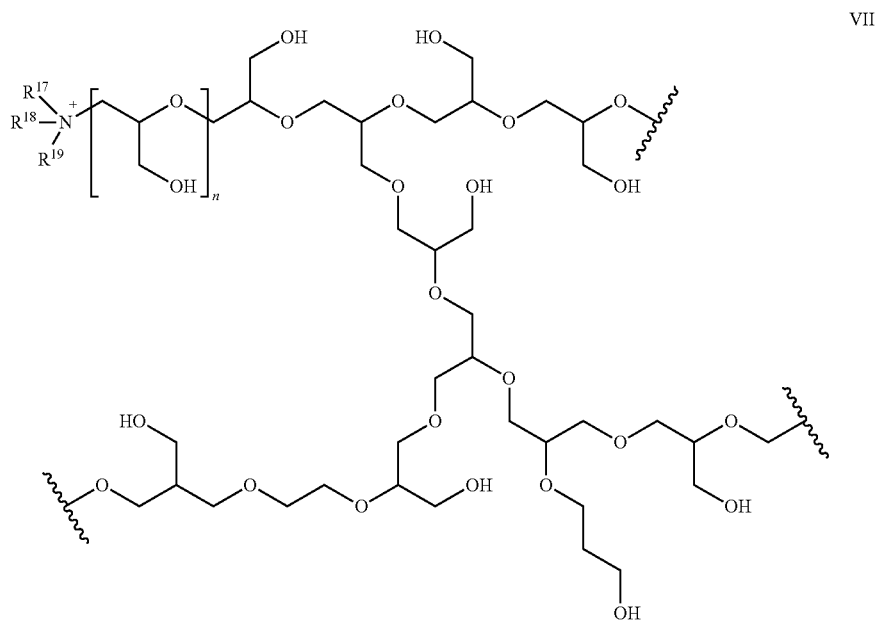

wherein

R$^{17}$, R$^{18}$, and R$^{19}$ are, independently, H, alkyl, or cycloalkyl, either of which is optionally substituted with halide, hydroxy, thioalkyl, carbonyl, alkoxy, alkylhydroxy, carboxyl, amino, amido, alkyl, alkenyl, alkynyl, aryl, —NR$^x$R$^y$, —C(O)NR$^x$R$^y$, or a combination thereof; or two or more of R$^{17}$, R$^{18}$, and R$^{19}$, together with the atoms to which they are attached, form a 3-10 membered cyclic moiety, wherein any of the additional atoms are optionally heteroatoms and the 3-10 membered cyclic moiety is optionally substituted with halide, hydroxy, thioether, carbonyl, alkoxy, alkylhydroxy, carboxyl, amino, amido, alkyl, alkenyl, alkynyl, aryl, —NR$^x$R$^y$, —C(O)NR$^x$R$^y$, or a combination thereof;

R$^x$ and R$^y$ are independently H, OH, alkyl, alkenyl, alkynyl, cycloalkyl, aryl, alkylaryl, or heteroaryl; and n is an integer from 1 to 10,000.

In some examples of Formula VII, $R^{17}$, $R^{18}$, and $R^{19}$ are, independently, H, $CH_3(CH_2)_m$ where m is an integer from 0 to 20, cyclopentyl, cyclohexyl, $CH_2OH$, or $OHCH_2CH_3$. In some examples of Formula VII, two of $R^{17}$, $R^{18}$, and $R^{19}$, together with which the atoms to which they are attached, comprise a piperidinyl group.

In some examples, the polyglycerol can comprise a branched polyglycerol defined by Formula VIII:

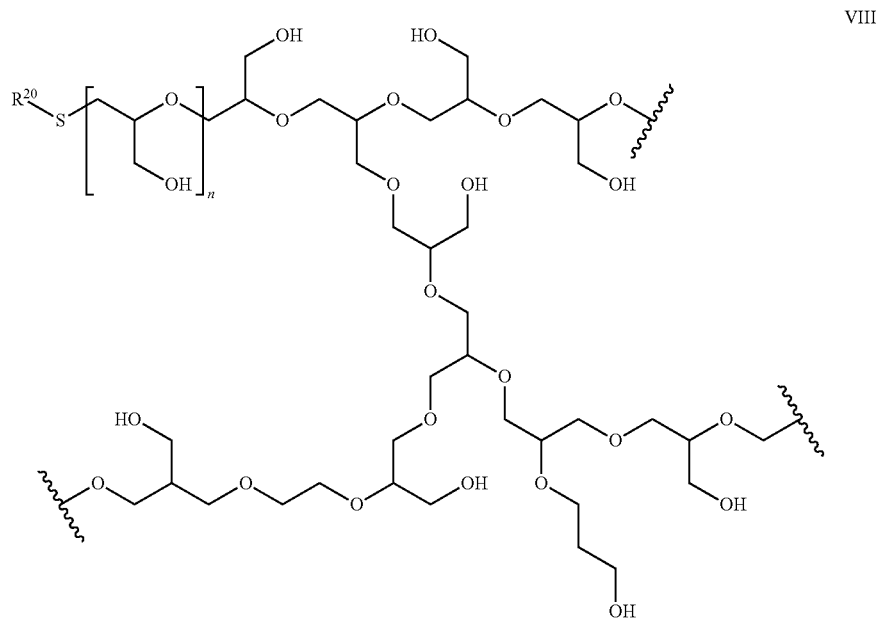

VIII wherein
$R^{20}$ is H, alkyl, or cycloalkyl, any of which is optionally substituted with halide, hydroxy, thioether, carbonyl, alkoxy, alkylhydroxy, carboxyl, amino, amido, alkyl, alkenyl, alkynyl, aryl, —$NR^xR^y$, —$C(O)NR^xR^y$, or a combination thereof;
$R^x$ and $R^y$ are independently H, OH, alkyl, alkenyl, alkynyl, cycloalkyl, aryl, alkylaryl, or heteroaryl; and
n is an integer from 1 to 10,000.

In some examples of Formula VIII, $R^{20}$ is $C_1$-$C_{12}$ alkyl, $C_3$-$C_{12}$ cycloalkyl, $C_1$-$C_{20}$ alkoxy, or $C_3$-$C_{20}$ cycloalkoxy, any of which is optionally substituted. In some examples of Formula VIII, $R^{20}$ is unsubstituted $C_1$-$C_{12}$ alkyl, unsubstituted $C_3$-$C_{12}$ cycloalkyl, unsubstituted $C_1$-$C_{20}$ alkoxy, or unsubstituted $C_3$-$C_{20}$ cycloalkoxy. In some examples of Formula VIII, $R^{20}$ is $CH_3(CH_2)_m$ where m is an integer from 0 to 20.

The polyglycerol and/or polyglycerol side chains present in the actinically-crosslinkable polysiloxane-polyglycerol block copolymers can be located at the termini of the polysiloxane prepolymer chains or at any location in between the termini. Furthermore, the length of the polysiloxane prepolymer and polyglycerol chains may vary.

In some examples of Formula I

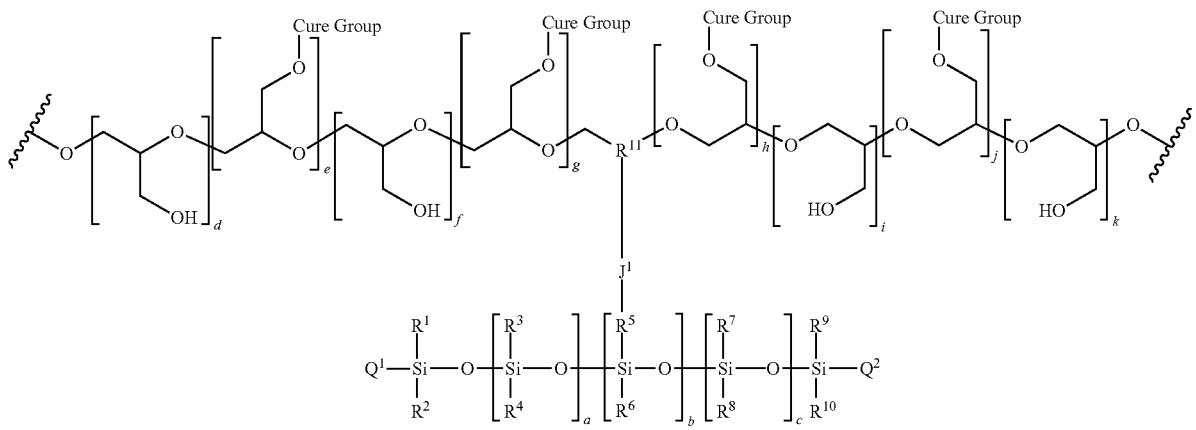

I $R^1$-$R^{11}$ and $J^1$ are, independently, $C_1$-$C_{18}$ alkyl, $C_3$-$C_{18}$ cycloalkyl, $C_3$-$C_{20}$ aryl, alkylpolyethylene oxide, or polyglycerol, any of which is optionally substituted with halide, hydroxy, thiol, carbonyl, alkoxy, alkylhydroxy, carboxyl, amino, amido, alkyl, alkenyl, alkynyl, aryl, —$NR^xR^y$, —$C(O)NR^xR^y$, azide, or a combination thereof.

In some examples of Formula I, $R^1$-$R^{11}$ and $J^1$ are, independently, linear $C_1$-$C_{18}$ alkyl, branched $C_2$-$C_{18}$ alkyl, cyclic $C_3$-$C_{18}$ alkyl, $C_3$-$C_{20}$ aryl, linear $C_1$-$C_{18}$ perfluoroalkyl, branched $C_2$-$C_{18}$ perfluoroalkyl, cyclic $C_3$-$C_{18}$ perfluoroalkyl, alkyl-polyethylene oxide, linear polyglycerol, or branched polyglycerol, any of which is optionally substituted.

In some examples of Formula I, $R^1$-$R^{11}$ and $J^1$ are, independently, linear $C_1$-$C_{18}$ alkyl, branched $C_2$-$C_{18}$ alkyl, cyclic $C_3$-$C_{18}$ alkyl, $C_3$-$C_{20}$ aryl, linear $C_1$-$C_{18}$ perfluoroalkyl, branched $C_2$-$C_{18}$ perfluoroalkyl, cyclic $C_3$-$C_{18}$ perfluoroalkyl, alkyl-polyethylene oxide, a linear polyglycerol of Formula III, or a branched polyglycerol of any of Formula IV-Formula VIII, any of which is optionally substituted.

In some examples of Formula I, $R_1$-$R_{10}$ are, independently, linear $C_1$-$C_{18}$ alkyl, any of which is optionally substituted. In some examples of Formula I, $R_1$-$R_{10}$ are, independently, unsubstituted linear $C_1$-$C_{18}$ alkyl. In some examples of Formula I, $R_1$-$R_{10}$ are, independently, linear $C_1$-$C_{12}$ alkyl, any of which is optionally substituted. In some examples of Formula I, $R_1$-$R_{10}$ are, independently, unsubstituted linear $C_1$-$C_{12}$ alkyl. In some examples of Formula I, $R_1$-$R_{10}$ are, independently, linear $C_1$-$C_8$ alkyl, any of which is optionally substituted. In some examples of Formula I, $R_1$-$R_{10}$ are, independently, unsubstituted linear $C_1$-$C_8$ alkyl. In some examples of Formula I, $R_1$-$R_{10}$ are, independently, linear $C_1$-$C_4$ alkyl, any of which is optionally substituted. In some examples of Formula I, $R_1$-$R_{10}$ are, independently, unsubstituted linear $C_1$-$C_4$ alkyl. In some examples of Formula I, $R^1$-$R^{10}$ are the same. In some examples of Formula I, $R^1$-$R^{10}$ are all methyl. In some examples, the polysiloxane prepolymer comprises polydimethyl siloxane.

In some examples of Formula I, $J^1$ is $C_1$-$C_{18}$ alkoxy which is optionally substituted. In some examples of Formula I, $J^1$ is unsubstituted $C_1$-$C_{18}$ alkoxy. In some examples of Formula I, $J^1$ is $C_1$-$C_{12}$ alkoxy which is optionally substituted. In some examples of Formula I, $J^1$ is unsubstituted $C_1$-$C_{12}$ alkoxy. In some examples of Formula I, $J^1$ is $C_1$-$C_8$ alkoxy which is optionally substituted. In some examples of Formula I, $J^1$ is unsubstituted $C_1$-$C_8$ alkoxy. In some examples of Formula I, $J^1$ is $C_1$-$C_4$ alkoxy which is optionally substituted. In some examples of Formula I, $J^1$ is unsubstituted $C_1$-$C_4$ alkoxy. In some examples of Formula I, $J^1$ is $OCH_2$.

In some examples of Formula I, $Q^1$ and $Q^2$ are independently H, OH, aryl, epoxide, alkanol, alkylthio, alkenylthio, arylthio, amine, alkylamine, dialkylamine, (meth)acrylate, (meth)acrylamide, dialkyl (meth)acrylamide, vinyl, ketone, aldehyde, carboxylic acid, anhydride, or azide, any of which is optionally substituted.

In some examples of Formula I, $Q^1$ and $Q^2$ are independently $C_1$-$C_{18}$ alkyl, $C_3$-$C_{20}$ aryl, $C_1$-$C_{18}$ perfluoroalkyl, $C_1$-$C_{18}$ alkanol (e.g., $C_nH_{2n}OH$, such as $CH_2OH$, $CH_2CH_2$—OH, $CH_2CH_2CH_2OH$, $CH_2CH_2CH_2CH_2OH$, $(CH_3)_2COH$, $CH_2CH_2OHCH_2CH_3$, $(CH_3)_3CCHOH$, $CH_2CHOHCH_2CH(CH_3)_2$, $CH_2CH_2CHOHCH(CH_3)_2$, $CH_2CH_2CH_2COH(CH_3)_2$, $CH_2CH_2CH_2CHCH_3CH_2OH$), $C_1$-$C_{18}$ alkylthiol (e.g., $C_nH_{2n}SH$, such as $CH_2SH$, $CH_2CH_2SH$, $CH_2CH_2CH_2SH$, $CH_2CH_2CH_2SH$), $C_1$-$C_{18}$ alkylamine (e.g., a primary alkyl amine $C_nH_{2n+1}NH_2$), $C_1$-$C_{18}$ dialkylamine (e.g., a secondary amine $C_nH_{2n+1}NHR'$, where R' is methyl, ethyl, propyl, isopropyl, butyl, sec butyl, t-butyl, pentyl, cyclopentyl, cyclohexyl, heptyl, etc.), or an ethylenically unsaturated group (e.g., acrylate, methacrylate, acrylamide, methacrylamide, allyl, and styryl), any of which is optionally substituted (e.g., with an epoxy group).

In some examples of Formula I, the Cure Group can be selected from the group consisting of:

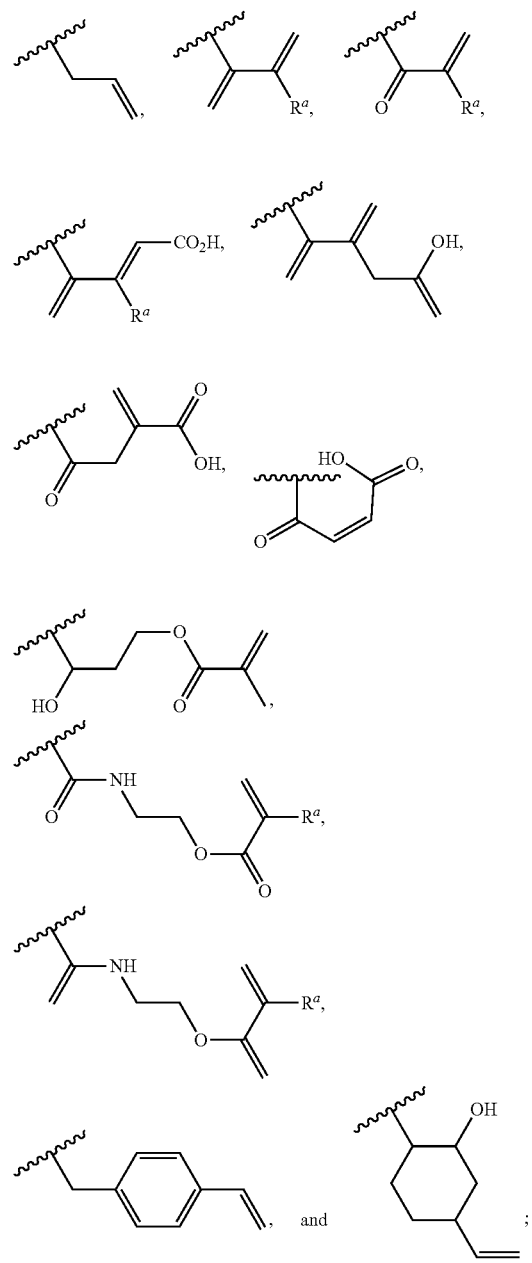

wherein $R^a$ is H, alkyl, or cycloalkyl, either of which is optionally substituted with halide, hydroxy, alkylthiol, carbonyl, alkoxy, alkylhydroxy, carboxyl, amino, amido, alkyl, alkenyl, alkynyl, aryl, —$NR^xR^y$, —$C(O)NR^xR^y$, or a combination thereof; and $R^x$ and $R^y$ are independently H, OH, alkyl, alkenyl, alkynyl, cycloalkyl, aryl, alkylaryl, or heteroaryl.

In some examples of Formula I, the cure group is

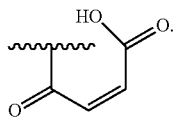

In some examples of Formula I, the cure group is

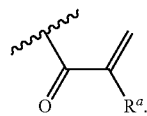

In some examples of Formula I, the cure group is

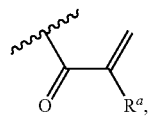

wherein $R^a$ is $C_1$-$C_{18}$ alkyl which is optionally substituted. In some examples of Formula I, the cure group is

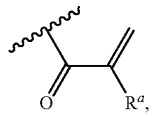

wherein $R^a$ is unsubstituted $C_1$-$C_{18}$ alkyl. In some examples of Formula I, the cure group is

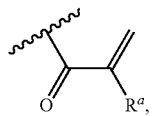

wherein $R^a$ is $C_1$-$C_{12}$ alkyl which is optionally substituted. In some examples of Formula I, the cure group is

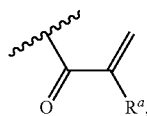

wherein $R^a$ is unsubstituted $C_1$-$C_{12}$ alkyl. In some examples of Formula I, the cure group is

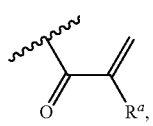

wherein $R^a$ is $C_1$-$C_8$ alkyl which is optionally substituted. In some examples of Formula I, the cure group is

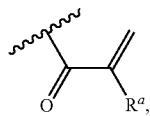

wherein $R^a$ is unsubstituted $C_1$-$C_8$ alkyl. In some examples of Formula I, the cure group is

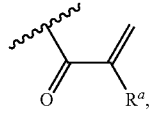

wherein $R^a$ is $C_1$-$C_4$ alkyl which is optionally substituted. In some examples of Formula I, the cure group is

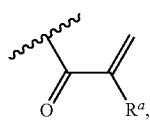

wherein $R^a$ is unsubstituted $C_1$-$C_4$ alkyl. In some examples of Formula I, the cure group is

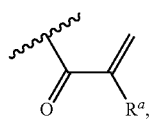

wherein $R^a$ is methyl.

In some examples of Formula I, the cure group is

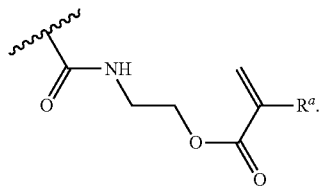

In some examples of Formula I, the cure group is

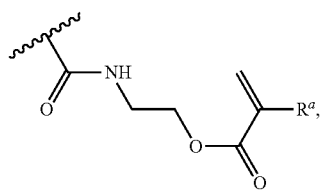

wherein $R^a$ is $C_1$-$C_{18}$ alkyl which is optionally substituted. In some examples of Formula I, the cure group is

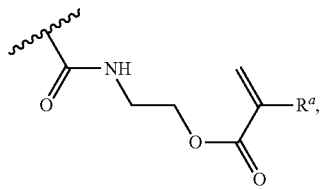

wherein $R^a$ is unsubstituted $C_1$-$C_{18}$ alkyl. In some examples of Formula I, the cure group is

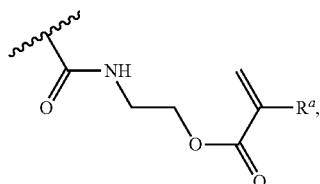

wherein $R^a$ is $C_1$-$C_{12}$ alkyl which is optionally substituted. In some examples of Formula I, the cure group is

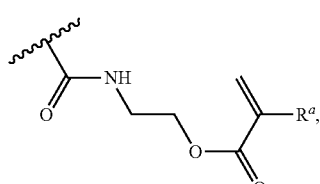

wherein $R^a$ is unsubstituted $C_1$-$C_{12}$ alkyl. In some examples of Formula I, the cure group is

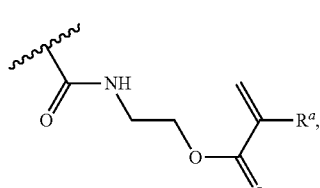

wherein $R^a$ is $C_1$-$C_8$ alkyl which is optionally substituted. In some examples of Formula I, the cure group is

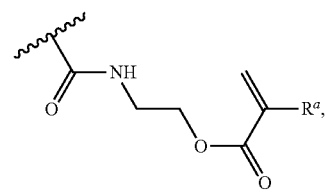

wherein $R^a$ is unsubstituted $C_1$-$C_8$ alkyl. In some examples of Formula I, the cure group is

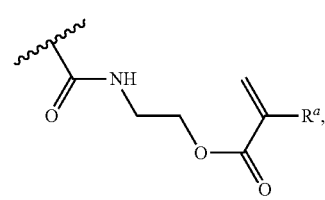

wherein $R^a$ is $C_1$-$C_4$ alkyl which is optionally substituted. In some examples of Formula I, the cure group is

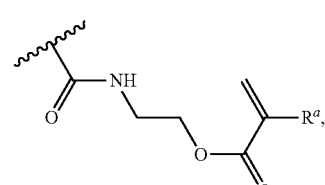

wherein $R^a$ is unsubstituted $C_1$-$C_4$ alkyl. In some examples of Formula I, the cure group is

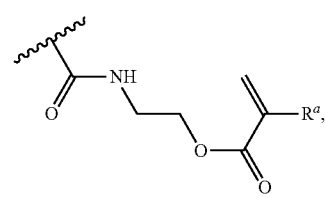

wherein $R^a$ is methyl.

In some examples, the actinically-crosslinkable polysiloxane-polyglycerol block copolymer is defined by Formula IX:

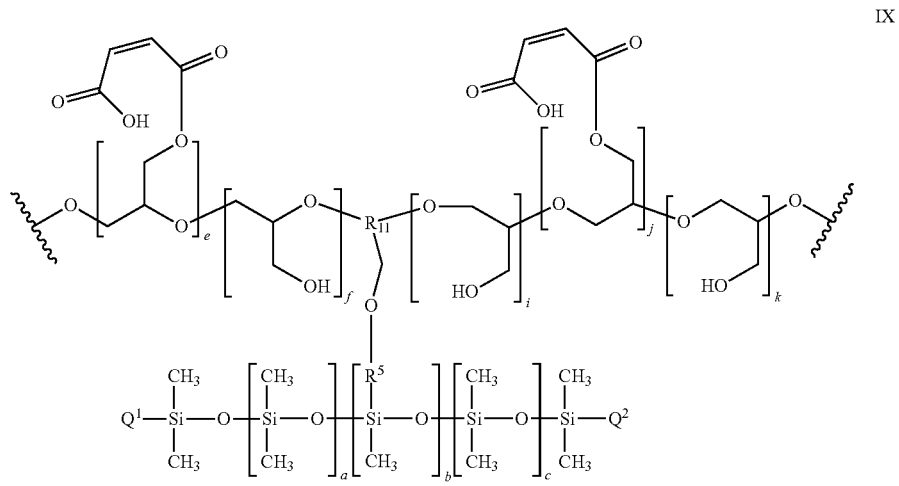

wherein
a, c, e, f, i, j and k are, independently, an integer from 0 to 10,000;
with the proviso that:
  at least one of e and j is not 0, and
  at least one of f, i, and k is not 0; and
b is an integer from 1 to 10,000.

In some examples, the actinically-crosslinkable polysiloxane-polyglycerol block copolymer is defined by Formula X:

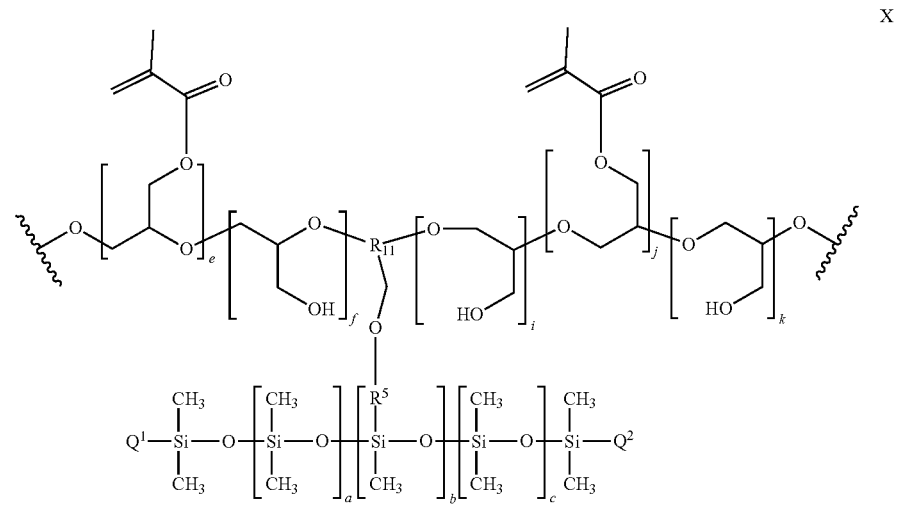

wherein
a, c, e, f, i, j and k are, independently, an integer from 0 to 10,000;
with the proviso that:
at least one of e and j is not 0, and
at least one of f, i, and k is not 0; and
b is an integer from 1 to 10,000.

In some examples, the actinically-crosslinkable polysiloxane-polyglycerol block copolymer is defined by Formula XI:

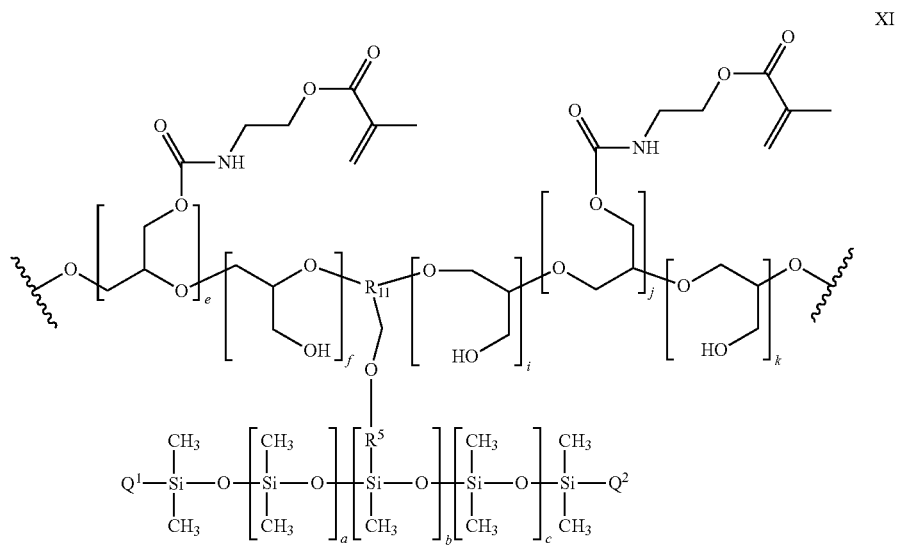

wherein
a, c, e, f, i, j and k are, independently, an integer from 0 to 10,000;
with the proviso that:
at least one of e and j is not 0, and
at least one of f, i, and k is not 0; and
b is an integer from 1 to 10,000.

In some examples, the actinically-crosslinkable polysiloxane-polyglycerol block copolymers are further derived from one or more monomer units selected from the group consisting of N-vinyl-2-pyrrolidone (NVP), N,N-dimethyl acrylamide (DMA), dimethylaminoethyl methacrylate, dimethylaminoethyl acrylate, vinyl acetate, 2-Hydroxyethyl methacrylate (HEMA), glycerol mono-methacrylate (GMMA), N-Hydroxyethyl acrylamide (NHA), N-(2,3-Dihydroxypropyl)acrylamide (NDHA), N-(hydroxyl methyl) acrylamide solution (NHMA), N-[3-(Dimethylamino)propyl]methacrylamide, a $C_1$-$C_4$-alkoxy polyethylene glycol (meth)acrylate having a weight average molecular weight of from 300 to 2000, N-vinyl-N-methyl isopropyl amide, N-vinyl-N-methyl acetamide, and mixtures thereof.

The actinically-crosslinkable polysiloxane-polyglycerol block copolymers described herein comprise two or more polymeric chains (blocks), which are structurally different and chemically bonded to each other. Under certain conditions, the actinically-crosslinkable polysiloxane-polyglycerol block copolymers can segregate into a variety of ordered structures.

In some examples, the actinically-crosslinkable polysiloxane-polyglycerol block copolymers can be subjected to chemical reactions such as cross-linking of actinically curable groups, substitution reactions, and addition reactions, "click" chemical reactions, polymerization reactions, or any number of chemical reactions known in the art to form ordered block copolymer structures that are substantially locked in place. In some examples, the actinically-crosslinkable polysiloxane-polyglycerol block copolymers can undergo cross-linking reactions.

Also disclosed herein are chain extended actinically-crosslinkable polysiloxane-polyglycerol block copolymers. Chain extended actinically-crosslinkable polysiloxane-polyglycerol block copolymers (CE-AC-(PDMS-PGLY) can be prepared through reaction of a polysiloxane-polyglycerol block copolymer with a difunctional reagent (e.g., diisocyanate, diepoxide, etc.) through a chain extension process, such as described herein below. Cure groups can be added to the polysiloxane-polyglycerol unit before or after chain extension. In some examples, it can be preferable to add cure groups after chain extension process, e.g., when the cure group(s) are heat sensitive.

In some examples, the chain extended actinically-crosslinkable polysiloxane-polyglycerol block copolymers can be defined by Formula XII:

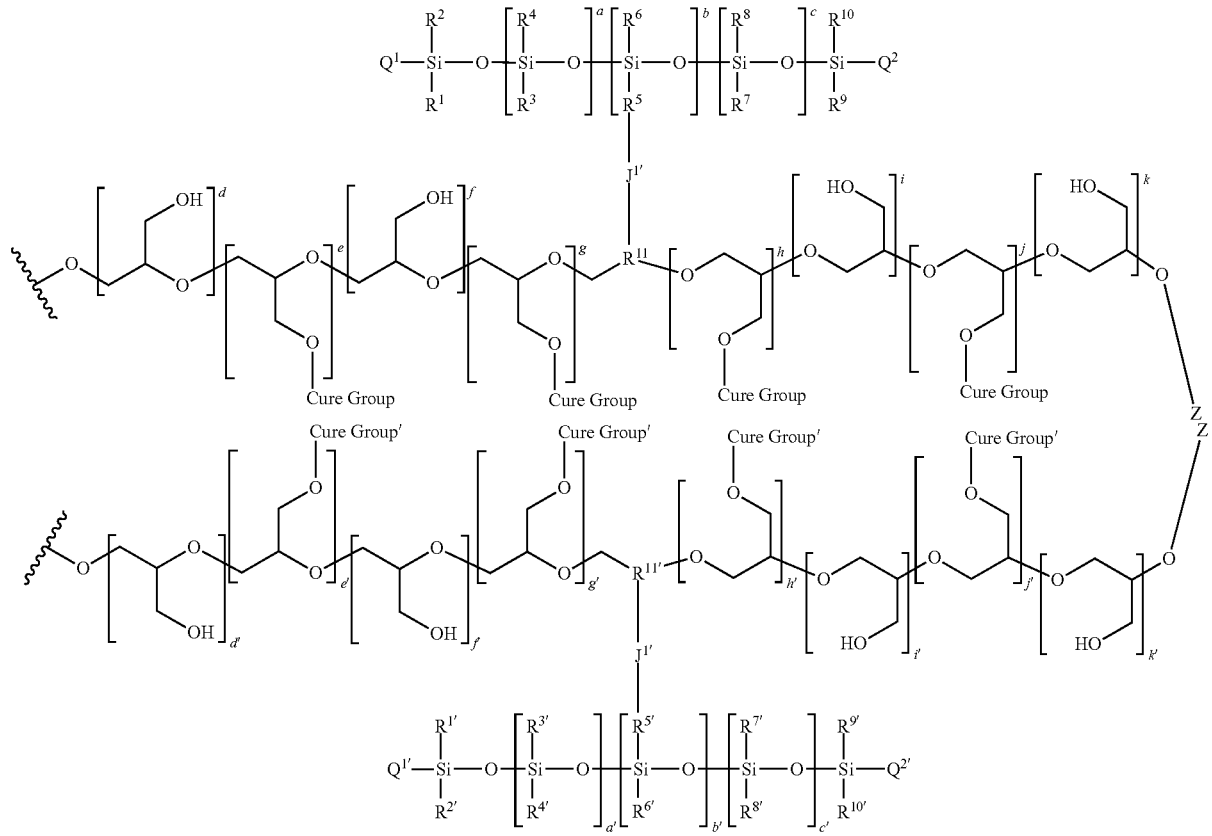

XII wherein
$R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$, $R^{7'}$, $R^8$, $R^{8'}$, $R^9$, $R^{9'}$, $R^{10}$, $R^{10'}$, $R^{11}$, $R^{11'}$, $J^1$, and $J^{1'}$ are, independently, alkyl, cycloalkyl, aryl, alkylpolyethylene oxide, or polyglycerol, any of which is optionally substituted with halide, hydroxy, thiol, carbonyl, alkoxy, alkylhydroxy, carboxyl, amino, amido, alkyl, alkenyl, alkynyl, aryl, —$NR^xR^y$, —$C(O)NR^xR^y$, azide, or a combination thereof;

$Q^1$, $Q^{1'}$, $Q^2$, and $Q^{2'}$ are independently H, OH, amino, alkyl, alkenyl, alkynyl, cycloalkyl, aryl, alkylaryl, or heteroaryl, any of which is optionally substituted with epoxy, hydroxy, thiol, carbonyl, alkoxy, alkylhydroxy, carboxyl, amino, amido, alkyl, alkenyl, alkynyl, aryl, —$NR^xR^y$, —$C(O)NR^xR^y$, azide, or a combination thereof;

$R^x$ and $R^y$ are independently H, OH, alkyl, alkenyl, alkynyl, cycloalkyl, aryl, alkylaryl, or heteroaryl;

Cure Group and Cure Group' independently comprise an ethylenically unsaturated group;

Z is a chain extension group;

a, a', c, c', d, d', e, e', f, f', g, g', h, h', i, i', j, j', k, and k' are, independently, an integer from 0 to 10,000, with the proviso that:
at least one of e, g, h, and j is not 0,
at least one of e', g', h', and j' is not 0,
at least one of d, f, i, and k is not 0, and
at least one of d', f', i', and k' is not 0; and
b and b' are independently an integer from 1 to 10,000.

In some examples of Formula XII, the chain extension group can comprise a linking group such as those described in Table 1-Table 4.

In some examples of Formula XII, $R^1$-$R^{11}$, $R^{1'}$-$R^{11'}$, $J^1$, and $J^{1'}$ are, independently, $C_1$-$C_{18}$ alkyl, $C_3$-$C_{18}$ cycloalkyl, $C_3$-$C_{20}$ aryl, alkylpolyethylene oxide, or polyglycerol, any of which is optionally substituted with halide, hydroxy, thiol, carbonyl, alkoxy, alkylhydroxy, carboxyl, amino, amido, alkyl, alkenyl, alkynyl, aryl, —$NR^xR^y$, —$C(O)NR^xR^y$, azide, or a combination thereof.

In some examples of Formula XII, $R^1$-$R^{11}$, $R^{1'}$-$R^{11'}$, $J^1$, and $J^{1'}$ are, independently, linear $C_1$-$C_{18}$ alkyl, branched $C_2$-$C_{18}$ alkyl, cyclic $C_3$-$C_{18}$ alkyl, $C_3$-$C_{20}$ aryl, linear $C_1$-$C_{18}$ perfluoroalkyl, branched $C_2$-$C_{18}$ perfluoroalkyl, cyclic $C_3$-$C_{18}$ perfluoroalkyl, alkyl-polyethylene oxide, linear polyglycerol, or branched polyglycerol, any of which is optionally substituted.

In some examples of Formula XII, $R^1$-$R^{11}$, $R^{1'}$-$R^{11'}$, $J^1$, and $J^{1'}$ are, independently, linear $C_1$-$C_{18}$ alkyl, branched $C_2$-$C_{18}$ alkyl, cyclic $C_3$-$C_{18}$ alkyl, $C_3$-$C_{20}$ aryl, linear $C_1$-$C_{18}$ perfluoroalkyl, branched $C_2$-$C_{18}$ perfluoroalkyl, cyclic $C_3$-$C_{18}$ perfluoroalkyl, alkyl-polyethylene oxide, a linear polyglycerol of Formula III, or a branched polyglycerol of any of Formula IV-Formula VIII, any of which is optionally substituted.

In some examples of Formula XII, $R^1$-$R^{10}$ and $R^{1'}$-$R^{10'}$ are, independently, linear $C_1$-$C_{18}$ alkyl, any of which is optionally substituted. In some examples of Formula XII, $R^1$-$R^{10}$ and $R^{1'}$-$R^{10'}$ are, independently, unsubstituted linear $C_1$-$C_{18}$ alkyl. In some examples of Formula XII, $R^1$-$R^{10}$ and $R^{1'}$-$R^{10'}$ are, independently, linear $C_1$-$C_{12}$ alkyl, any of which is optionally substituted. In some examples of Formula XII, $R^1$-$R^{10}$ and $R^{1'}$-$R^{10'}$ are, independently, unsubstituted linear $C_1$-$C_{12}$ alkyl. In some examples of Formula XII, $R^1$-$R^{10}$ and $R^{1'}$-$R^{10'}$ are, independently, linear $C_1$-$C_8$ alkyl, any of which is optionally substituted. In some examples of Formula XII, $R_1$-$R_{10}$ and $R^{1'}$-$R^{10'}$ are, independently, unsubstituted linear $C_1$-$C_8$ alkyl. In some examples of Formula XII, $R^1$-$R^{10}$ and $R^{1'}$-$R^{10'}$ are, independently, linear $C_1$-$C_4$ alkyl, any of which is optionally substituted. In some examples of Formula XII, $R^1$-$R^{10}$ and $R^{1'}$-$R^{10'}$ are, independently, unsubstituted linear $C_1$-$C_4$ alkyl. In some examples of Formula XII, $R^1$-$R^{10}$ and $R^{1'}$-$R^{10'}$ are the same. In some examples of Formula XII, $R^1$-$R^{10}$ and $R^{1'}$-$R^{10'}$ are all methyl. In some examples, the polysiloxane prepolymer comprises polydimethyl siloxane.

In some examples of Formula XII, $J^1$ and $J^{1'}$ are independently $C_1$-$C_{18}$ alkoxy which is optionally substituted. In some examples of Formula XII, $J^1$ and $J^{1'}$ are independently unsubstituted $C_1$-$C_{18}$ alkoxy. In some examples of Formula XII, $J^1$ and $J^{1'}$ are independently $C_1$-$C_{12}$ alkoxy which is optionally substituted. In some examples of Formula XII, $J^1$ and $J^{1'}$ are independently unsubstituted $C_1$-$C_{12}$ alkoxy. In some examples of Formula XII, $J^1$ and $J^{1'}$ are independently $C_1$-$C_8$ alkoxy which is optionally substituted. In some examples of Formula XII, $J^1$ and $J^{1'}$ are independently unsubstituted $C_1$-$C_8$ alkoxy. In some examples of Formula XII, $J^1$ and $J^{1'}$ are independently $C_1$-$C_4$ alkoxy which is optionally substituted. In some examples of Formula XII, $J^1$ and $J^{1'}$ are independently unsubstituted $C_1$-$C_4$ alkoxy. In some examples of Formula XII, $J^1$ and $J^{1'}$ are $OCH_2$.

In some examples of Formula XII, $Q^1$, $Q^{1'}$, $Q^2$, and $Q^{2'}$ are independently H, OH, aryl, epoxide, alkanol, alkylthio, alkenylthio, arylthio, amine, alkylamine, dialkylamine, (meth)acrylate, (meth)acrylamide, dialkyl (meth)acrylamide, vinyl, ketone, aldehyde, carboxylic acid, anhydride, or azide, any of which is optionally substituted.

In some examples of Formula XII, $Q^1$, $Q^{1'}$, $Q^2$, and $Q^{2'}$ are independently $C_1$-$C_{18}$ alkyl, $C_3$-$C_{20}$ aryl, $C_1$-$C_{18}$ perfluoroalkyl, $C_1$-$C_{18}$ alkanol (e.g., $C_nH_{2n}OH$, such as $CH_2OH$, $CH_2CH_2$—OH, $CH_2CH_2CH_2OH$, $CH_2CH_2CH_2CH_2OH$, $(CH_3)_2COH$, $CH_2CH_2OHCH_2CH_3$, $(CH_3)_3CCHOH$, $CH_2CHOHCH_2CH(CH_3)_2$, $CH_2CH_2CHOHCH(CH_3)_2$, $CH_2CH_2CH_2COH(CH_3)_2$, $CH_2CH_2CH_2CHCH_3CH_2OH$), $C_1$-$C_{18}$ alkylthiol (e.g., $C_nH_{2n}SH$, such as $CH_2SH$, $CH_2CH_2SH$, $CH_2CH_2CH_2SH$, $CH_2CH_2CH_2CH_2SH$), $C_1$-$C_{18}$ alkylamine (e.g., a primary alkyl amine $C_nH_{2n+1}NH_2$), $C_1$-$C_{18}$ dialkylamine (e.g., a secondary amine $C_nH_{2n+1}NHR'$, where R' is methyl, ethyl, propyl, isopropyl, butyl, sec butyl, t-butyl, pentyl, cyclopentyl, cyclohexyl, heptyl, etc.), or an ethylenically unsaturated group (e.g., acrylate, methacrylate, acrylamide, methacrylamide, allyl, and styryl), any of which is optionally substituted (e.g., with an epoxy group).

In some examples of Formula XII, Cure Group and cure Group' can independently be selected from the group consisting of.

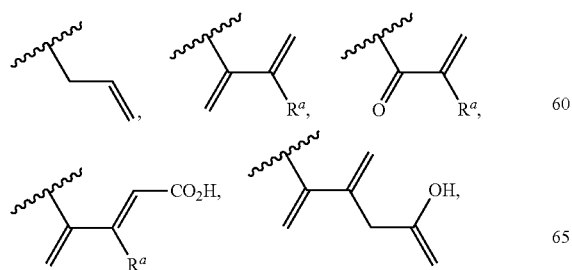

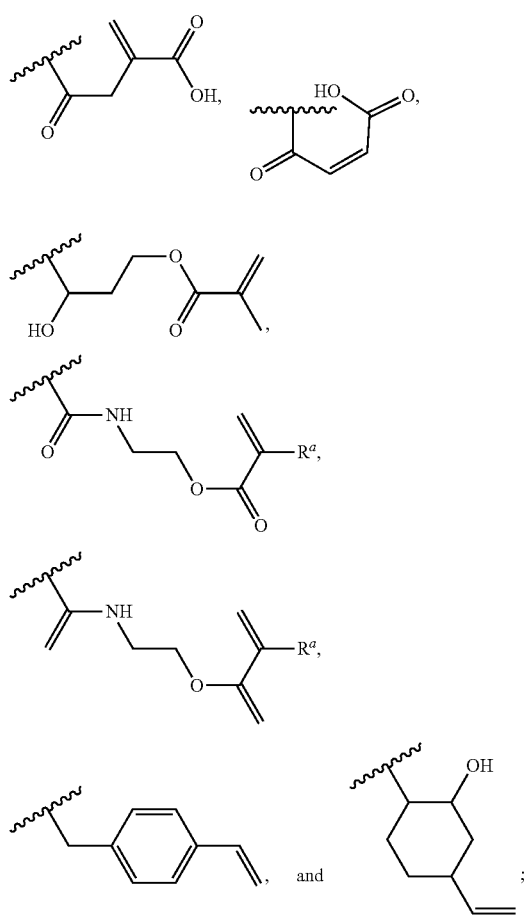

wherein $R^a$ is H, alkyl, or cycloalkyl, either of which is optionally substituted with halide, hydroxy, alkylthiol, carbonyl, alkoxy, alkylhydroxy, carboxyl, amino, amido, alkyl, alkenyl, alkynyl, aryl, —$NR^xR^y$, —$C(O)NR^xR^y$, or a combination thereof; and $R^x$ and $R^y$ are independently H, OH, alkyl, alkenyl, alkynyl, cycloalkyl, aryl, alkylaryl, or heteroaryl.

In some examples of Formula XII, Cure Group and Cure Group' are

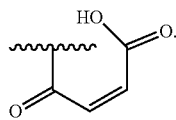 [SMILES: *C(=O)/C=C\C(=O)O]

In some examples of Formula XII, Cure Group and Cure Group' are independently

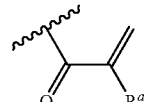

In some examples of Formula XII, Cure Group and Cure Group' are independently

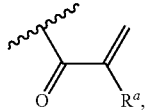

wherein $R^a$ is $C_1$-$C_{18}$ alkyl which is optionally substituted. In some examples of Formula XII, Cure Group and Cure Group' are independently

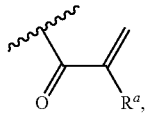

wherein $R^a$ is unsubstituted $C_1$-$C_{18}$ alkyl. In some examples of Formula XII, Cure Group and Cure Group' are independently

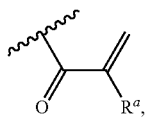

wherein $R^a$ is $C_1$-$C_{12}$ alkyl which is optionally substituted. In some examples of Formula XII, Cure Group and Cure Group' are independently

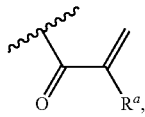

wherein $R^a$ is unsubstituted $C_1$-$C_{12}$ alkyl. In some examples of Formula XII, Cure Group and Cure Group' are independently

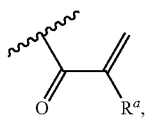

wherein $R^a$ is $C_1$-$C_8$ alkyl which is optionally substituted. In some examples of Formula XII, Cure Group and Cure Group' are independently

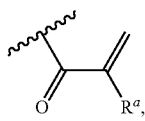

wherein $R^a$ is unsubstituted $C_1$-$C_8$ alkyl. In some examples of Formula XII, Cure Group and Cure Group' are independently

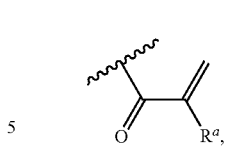

wherein $R^a$ is $C_1$-$C_4$ alkyl which is optionally substituted. In some examples of Formula XII, Cure Group and Cure Group' are independently

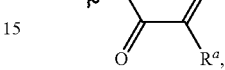

wherein $R^a$ is unsubstituted $C_1$-$C_4$ alkyl. In some examples of Formula XII, Cure Group and Cure Group' are

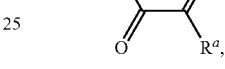

wherein $R^a$ is methyl.

In some examples of Formula XII, Cure Group and Cure Group' are independently

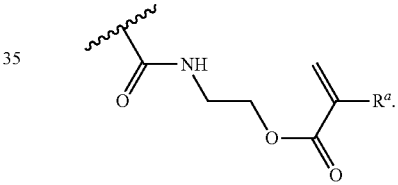

In some examples of Formula XII, Cure Group and Cure Group' are independently

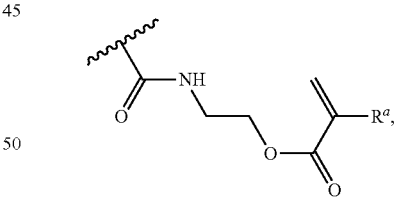

wherein $R^a$ is $C_1$-$C_{18}$ alkyl which is optionally substituted. In some examples of Formula XII, Cure Group and Cure Group' are independently

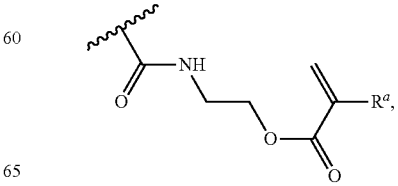

wherein $R^a$ is unsubstituted $C_1$-$C_{18}$ alkyl. In some examples of Formula XII, Cure Group and Cure Group' are independently

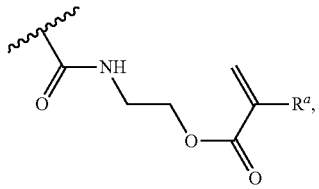

wherein $R^a$ is $C_1$-$C_{12}$ alkyl which is optionally substituted. In some examples of Formula XII, Cure Group and Cure Group' are independently

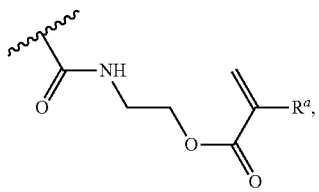

wherein $R^a$ is unsubstituted $C_1$-$C_{12}$ alkyl. In some examples of Formula XII, Cure Group and Cure Group' are independently

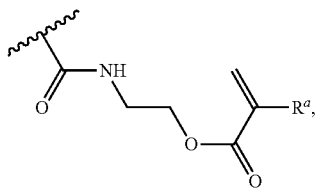

wherein $R^a$ is $C_1$-$C_8$ alkyl which is optionally substituted. In some examples of Formula XII, Cure Group and Cure Group' are independently

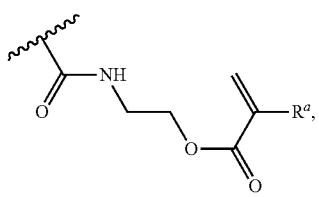

wherein $R^a$ is unsubstituted $C_1$-$C_8$ alkyl. In some examples of Formula XII, Cure Group and Cure Group' are independently

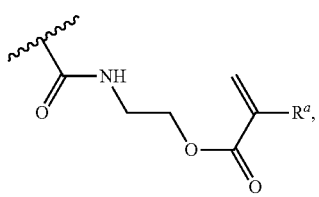

wherein $R^a$ is $C_1$-$C_4$ alkyl which is optionally substituted. In some examples of Formula XII, Cure Group and Cure Group' are independently

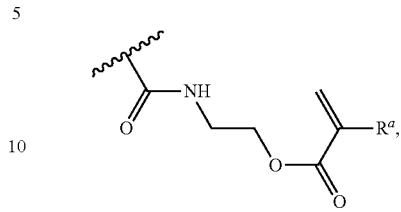

wherein $R^a$ is unsubstituted $C_1$-$C_4$ alkyl. In some examples of Formula XII, Cure Group and Cure Group' are

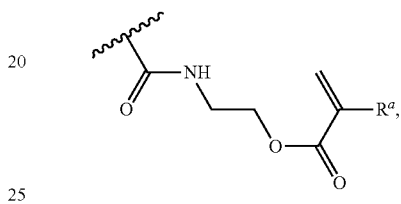

wherein $R^a$ is methyl.

Also disclosed herein are silicone hydrogel compositions comprising the actinically-crosslinkable polysiloxane-polyglycerol block copolymers crosslinked with a cross-linker. Cross-linkers include, for example, vinylic cross-linkers, difunctional isocyanate cross-linkers, difunctional epoxide cross-linkers, difunctional alkyl halides (e.g., difunctional acid halides), difunctional-anhydrides, bis-halo-alkyl derivatives, activated esters, or any number of difunctional reagents capable for forming chemical bonds with polyglycerol OH groups.

Examples of vinylic cross-linkers include but are not limited to: Ethylene glycol dimethacrylate; Triethylene glycol dimethacrylate; Diethyleneglycol Dimethacrylate; 1,3-Glycerol Dimethacrylate; 1,6-Hexanediol Dimethacrylate; 1,12-Dodecanediol Dimethacrylate; Trimethylolpropane Trimethacrylate; Poly (Ethyleneglycol) (400) Dimethacrylate; Isophorone Urethane Dimethacrylate; N,N'-Methylenebisacrylamide; 1,6-Hexamethylene bis-Methacrylamide; N,N'-Hexamethylenebismethacrylamide; N,N'-iso-Valerylidene bis-Methacrylamide; N,N'-Nonamethylenebisacrylamidem-Xylenebisacrylamide; 1,10-Decamethylene Glycol Diacrylate; 1,2-Propanediol Diacrylate; 1,3-Butanediol Diacrylate; 1,3-Propanediol Diacrylate; 1,4-Cyclohexanedimethyl Diacrylate; 1,5-Pentanediol Diacrylate; 1,9-Nonanediol Diacrylate; 2,2,3,3,4,4,5,5-Octafluoro-1,6-Hexanediol Diacrylate; 2,2,3,3-Tetrafluoro-1,4-Butanediol Diacrylate; 2-Butene-1,4-Diacrylate; Aliphatic Urethane Acrylate in Tripropylene Glycol Diacrylate; Diethylene Glycol Diacrylate; Ethylene Diacrylate; neo-Pentyl Glycol Diacrylate; Sorbitol Diacrylate; Hexamethylene Diacrylate; Thiol Diethylene Glycol Diacrylate; Tetraethylene Glycol Diacrylate; Triethylene Glycol Diacrylate; Bisphenol A Glycidyl Methacrylate; Pentaerythritol Tetramethacrylate; 1,3-Divinyltetramethyl-disiloxane; 3-Methacryloxypropyl Tris-(Vinyldimethylsiloxy) Silane; 1,1,5,5-Tetrahydroperfluoro-1,5-Pentanediol Dimethacrylate; 2,2,3,3,4,4,5,5-Octafluoro-1,6-Hexanediol Diacrylate; 2,2,3,3,4,4,5,5-Octafluoro-1,6-Hexanediol Dimethacrylate; divinylbenzene; diallylbutyl ether; and diallylbisphenol-A.

Examples of difunctional isocyanate cross-linkers include but are not limited to: Isophorone diisocyanate (IPDI), hexamethylene diisocyanate (HDI), methylene dicyclohexyl diisocyanate, toluene diisocyanate (TDI), Tolylene-2,4-diisocyanate, Tolylene-2,6-diisocyanate, trans-1,4-Cyclohexylene diisocyanate, Poly(propylene glycol), tolylene 2,4-diisocyanate terminated, 1,4-Diisocyanatobutane, 1,8-Diisocyanatooctane, 1,3-Bis(1-isocyanato-1-methylethyl) benzene, 2,2,4-Trimethylhexamethylene Diisocyanate, 2,4,4-Trimethylhexamethylene Diisocyanate, 1,4-Phenylene diisocyanate, 1,3-Phenylene diisocyanate, m-Xylylene diisocyanate, and methylenediphenyl diisocyanate (MDI). Depending on the ratio of diisocyanate to PDMS-PGLY, chain extension or crosslinking can occur.

Examples of difunctional epoxide cross-linkers include but are not limited to: diglycidyl ether, Bisphenol A diglycidyl ether, Glycerol diglycidyl ether, resorcinol diglycidyl ether, diglycidyl ether, bis(3,4-epoxycyclohexylmethyl) adipate, poly(ethylene glycol) diglycidyl ether, Bis[4-(glycidyloxy)phenyl]methane, 1,3-Butadiene diepoxide, 1,4-Butanediol diglycidyl ether, 1,4-Butanediol diglycidyl ether, 1,3-Butanediol diglycidyl ether, Bisphenol F diglycidyl ether, Bisphenol A propoxylate diglycidyl ether, neopentyl glycol diglycidyl ether, N,N-Diglycidyl-4-glycidyloxyaniline, 4,4'-Isopropylidenediphenol diglycidyl ether, Poly(propylene glycol) diglycidyl ether, Dicyclopentadiene dioxide, 1,2,5,6-Diepoxycyclooctane, 1,2,7,8-Diepoxyoctane, Diglycidyl 1,2-cyclohexanedicarboxylate, 3,4-Epoxycyclohexylmethyl 3,4-epoxy cyclohexanecarboxylate, 2,5-bis[(2-oxiranylmethoxy)-methyl]-furan (BOF) and 2,5-bis[(2-oxiranylmethoxy)methyl]-benzene, Poly(dimethyl siloxane), tetraglycidyl-4,4'-diaminodiphenylmethane (TGDDM), triglycidyl-aminophenol, e. 3-(3-glycidoxypropyl)-1,1,1,3,5,5,5-heptamethyltrisiloxane, 1-epoxyethyl-3,4-epoxycyclohexane, 1,3,5-Triglycidyl isocyanurate, PC-1000 Epoxy Siloxane Monomer (available from Polyset), PC-1035 Epoxy Siloxane Monomer (available from Polyset), Poly(dimethylsiloxane), diglycidyl ether terminated (average Mn ~800, available from SIGMA ALDRICH), epoxy terminated Poly(dimethylsiloxanes) available from Shin Etsu Silicone Company and sold under the trade names KF-105; X-22-163A; X-22-163B; X-22-163C; X-22-169AS; X-22-169B available from Shin Etsu Silicone Company; bis[2-(3,4-epoxycyclohexyl)-ethyl tetramethyldisiloxane, and 2,4,6,8-Tetramethyl-2,4,6,8-tetrakis(propyl glycidyl ether)cyclotetrasiloxane. Depending on the ratio of diepoxide to PDMS-PGLY, chain extension or crosslinking can occur.

Examples of difunctional alkyl halides include but are not limited to: 1,4-Dibromobutane, 1,5-Dibromopentane, 1,6-Dibromohexane, 1,8-Dibromooctane. Depending on the ratio of diepoxide to PDMS-PGLY, chain extension or crosslinking can occur.

Examples of difunctional acid chlorides include but are not limited to: malonyl chloride, isophthaloyl di-acid chloride, sebacoyl chloride, dodecanedioyl dichloride, octanedioic acid dichloride, fumaryl chloride, glutaryl chloride. Depending on the ratio of diacid chloride to PDMS-PGLY, chain extension or crosslinking can occur.

Examples of difunctional-anhydrides include but are not limited to: Diethylene-triaminepentaacetic dianhydride, 4,4'-(4,4'-Isopropylidenediphenoxy) bis(phthalic anhydride), 4,4'-(Hexafluoroisopropylidene)-diphthalic anhydride, bis(phthalic anhydride), 4,4'-Oxydiphthalic anhydride, 3,3',4,4'-Biphenyltetracarboxylic dianhydride, Benzophenone-3,3',4,4'-tetracarboxylic dianhydride, and Pyromellitic di-anhydride. Silicones containing two or more anhydride groups per polymer chain many also be used as cross-linkers. The dual end anhydride terminated Poly(dimethylsiloxanes) available from Shin Etsu Silicone Company and sold under the trade name X-22-2290AS may also be used as a cross-linking agent. Depending on the ratio of dianhydride to PDMS-PGLY, chain extension or crosslinking can occur.

Examples of Bis-haloalkylether-derivatives include: Bis (chloromethyl) ether, Bis(bromomethyl) ether, bis(iodomethyl) ether, bis(chloroethyl) ether, bis(bromoethyl) ether, bis(iodoethyl) ether.

Activated Esters such as: 3,3'-Dithiodipropionic acid di(N-hydroxysuccinimide ester) may also be used.

Dual end reactive silicones may also be used as cross-linking agents or chain extenders. Examples reactive silicones bearing dual end methacrylate functionality sold under the trade names X-22-164A; X-22-164B area available from Shin Estu Silicone Company.

In some examples, the silicone hydrogel compositions further comprise a hydrophilic monomer, a hydrophobic monomer, an amphiphilic monomer, a zwitterionic monomer, an antimicrobial monomer, a UV-blocker, a blue light blocker, a dye, a pigment, a solvent, or a combination thereof.

Suitable hydrophilic monomers comprise, for example, hydroxyl-substituted lower alkyl ($C_1$ to $C_8$) (meth)acrylates, (meth)acrylamide, (lower allyl) (meth)acrylamides, ethoxylated (meth)acrylates, hydroxyl-substituted (lower alkyl) (meth)acrylamides, hydroxyl-substituted lower alkyl vinyl ethers, sodium vinyl sulfonate, sodium styrene sulfonate, 2-acrylamido-2-methylpropanesulfonic acid, methyl vinyl ether, vinyl acetate, and methacrylated glyco-monomers. Examples of hydrophilic monomers include but are not limited to N-Hydroxyethyl acrylamide; N,N-dimethyl acrylamide (DMA); N-Ethyl acrylamide; N-(3-Methoxypropyl) acrylamide; 2-hydroxyethylmethacrylate (HEMA); 2-hydroxyethyl acrylate (HEA); hydroxypropyl acrylate; hydroxypropyl methacrylate (HPMA); N-[Tris(hydroxymethyl)methyl]acrylamide; trimethylammonium 2-hydroxy propylmethacrylate hydrochloride; dimethylaminoethyl methacrylate (DMAEMA); glycerol methacrylate (GMA); N-vinyl-2-pyrrolidone (NVP); dimethylaminoethyl methacrylamide; (meth)acrylamide; allyl alcohol; vinyl pyridine; N-(1,1-dimethyl-3-oxobutyl)acrylamide; acrylic acid (AA); methacrylic acid (MAA); N-(2-methacryloyloxy)ethyl-N,N-dimethylamino propane sulfonate; N-(3-methacryloylimino) propyl-N,N-dimethylammino propane sulfonate; N-(3-methacryloylimino)propyl-N,N-dimethylammino propane sulfonate; 2-(methacryloyloxy)ethyl phosphatidylcholine and 3-(2'-vinyl-pyridinio) propane sulfonate, 6-O-vinylsebacyl-D-glucose, fructose methacrylate, glucose methacrylate, ribose methacrylate, mannitol methacrylate, sorbitol methacrylate, methacrylated oligosaccharides, methacrylated oligo-fructose, 2-Acetoacetoxy-ethyl Methacrylates, Tetrahydrofurfuryl Methacrylates; 2-Hydroxyethyl Methacrylates/Succinates; 2-Hydroxyethyl Methacrylate Phosphates; Hepta-O-benzyl monomethacryloyl sucrose.

Examples of hydrophobic monomers include but are not limited to Methyl methacrylate; glycidyl methacrylate; ethyl methacrylate; butyl methacrylate; hexyl methacrylate; tert-butyl methacrylate; cyclohexyl methacrylate; Isobornyl Methacrylates; 2-ethylhexyl methacrylate; heptyl methacrylate; octal methacrylate; Lauryl methacrylate; 2,2,2-trifluoroethyl methacrylate; 1,1-dihydroperfluoroethylacrylate; 1H,1H,7H-dodecafluoroheptyl acrylate; hexafluoroisopropyl acrylate; 1H,1H,2H,2H-heptadecafluorodecyl acrylate; pentafluorostyrene; trifluoromethyl styrene; pentafluoroethyl acrylate; pentafluoroethyl methacrylate; hexafluoroisopropyl acrylate; hexafluoroisopropyl methacrylate (HFIPMA); methacrylate-functionalized fluorinated polyethylene oxides; 3-Methacryloxypropyl Tris-(Trimethylsiloxy) Silane; 3-Methacryloxypropyl Tris-(Trimethylsiloxy) Silane; Methacryloxyethoxytris-(Trimethylsiloxy) Silane; Trimethylsilylmethyl Methacrylate; 1H,1H,11H-Eicosafluoroundecyl Methacrylate; 1H,1H,9H-Hexadecafluorononyl Acrylate; 4-Vinylbenzyl Hexafluoroisopropyl Ether; Pentafluorobenzyl Acrylate; Pentafluorobenzyl Methacrylate; Perfluorocyclohexyl Methyl Acrylate; Perfluorocyclohexylmethyl Methacrylate; m-Fluorostyrene; and the like.

Examples of Amphiphilic Monomers include but are not limited to 2-Methoxyethoxyethyl Methacrylates; Ethoxyethyl Methacrylates; 2-(dimethylamino)ethyl methacrylate; 2-(diethylamino)ethyl methacrylate; N-[3-(Dimethylamino)-propyl] acrylamide; N-[3-(Dimethylamino)propyl] meth-acrylamide; Hydroxy oligo(ethylene glycol)$_6$ methacrylate; Methoxy oligo(ethylene glycol)s methacrylate; N-(1,1-di(O—B-D-glucorpyranosyloxymethyl)-1-(undecyl carbamoyloxymethyl) methyl)acrylamide; 5-acrylamido-5-undecylcarbamoyloxymethyl-2.2-dimethyl-cyclol, 3 dioxahexane; N-(1,1-(2',3',4'6"tetra-O-acetyl-B-D-glucopyranosyloxy-methyl)-1-(undecylcarbamoyl oxymethyl)-methyl)-acryl-amide; N-1,1-di(hydroxymethylmethyl)-1 (undecylcarbamoyl Oxymethyl)-methyl)acrylamide; N-(1, 1-(2, 3, 4, 6-"tetra-O-acetyl-ft-D-glucopyranosyloxy-methyl)-1-(undecyl carbamoyloxymethyl)-methyl)-acryl-amide; (2-Hydroxy-3-Methacryloxypropyl) Trimethylammonium Chloride; acrylamide functionalized Polyetheramine such as Acrylamide derivatives of polyether amines.

Polyetheramines are available from Huntsman Chemical and sold under the trade name "Jeffamine" (examples of polyether amines include Jeffamine M-(600, 1000, 2005, 2070) Acrylamide derivatives of polyether amines may be formed through reaction of a polyetheramine with reagents such as methacrylic anhydride or acryloyl chloride as shown in Scheme 2, where hydrophilic/lipophilic balance (HLB) depends on values of X and Y and where X and Y are whole numbers.

Scheme 2. Functionalization of Polyether amine (e.g. Jeffamine) with methacrylic anhydride to form amphiphilic macromer.

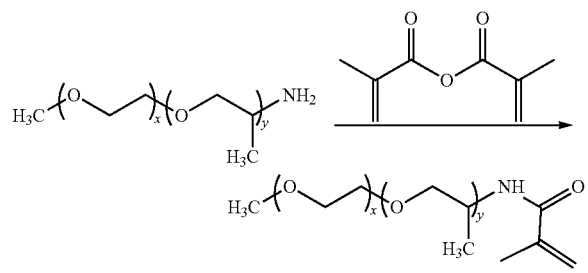

Zwitterionic Monomers include, but are not limited to, 1-(3-Sulfopropyl)-2-Vinylpyridinium Betaine; N-(3-Sulfopropyl)-N-Methacryloxyethyl-N,N-Dimethylammonium Betaine; and N-(3-Sulfopropyl)-N-Methacryloylamidopropyl-N,N-Dimethylammonium Betaine.

Examples of antimicrobial monomers include but are not limited to 2 (Methacryloyloxy)-ethyl]-trimethylammonium chloride; 2-(methacryloxy)ethyl]dimethyl dodecyl ammonium chloride; 2-(methacryloxy)ethyl]-dimethyl hexadecyl ammonium chloride; 2-(methacryloxy)decyl]dimethyl hexadecyl ammonium chloride; 2-(methacryloxy)-dodecyl]dimethyl hexadecyl ammonium chloride; 2-(methacryloxy) hexadecyl]dimethyl hexadecyl ammonium chloride; [2-(methacryloxyethyl]azabicyclo[2.2.2]ammonium chloride; 1-{2-[(2-methylprop-2-enoyl)oxy]ethyl}pyridin-1-ium chloride; 1-{2-[(2-methylprop-2enoyl)oxy]decyl}pyridin-1-ium chloride; 1-{2-[(2-methylprop-2-enoyl)oxy] dodecyl}pyridin-1-ium chloride; 1-{2-[(2-methylprop-2-enoyl)oxy]hexadecyl}pyridin-1-ium chloride.

Examples of UV-Blockers include: 2-[3-(2H-Benzotriazol-2-yl)-4-hydroxyphenyl]ethyl methacrylate; 2-{2'-Hydroxy-5'-(γ-propoxy)-3'-t-butylphenyl}-5-methoxy-2H-benzotriazole, 2-(2H-Benzotriazol-2-yl)-4-methyl-6-(2-propenyl)phenol; and 1-(2-METHYL-ALLYL)-1H-BENZOTRIAZOLE; 2-hydroxy-4-Acryloyloxybenzophenone).

Examples of Blue Light Blockers include, but are not limited to, various yellow and/or orange dyes. Examples of yellow dyes include but are not limited to: N,N-bis-(2-allylcarbomatoethyl)-(4'-phenylazo) aniline; N,N-bis-(2-hydroxyethyl)-(4-phenylazo) aniline; N,N-bis-(2-vinylacetoxyethyl)-(4'-phenylazo)aniline; and N-2-[3'-2"-methylphenylazo)-4'-hydroxyphenyl]ethylvinylacetamide. Examples of orange dyes include but are not limited to: Reactive Orange 16, Reactive Orange 13 (PROCION ORANGE H-2R), disperse orange 3 acrylamide, disperse orange 3 meth-acrylamide, disperse orange 3 acrylate, disperse orange 3 methacrylate, disperse orange 25 acrylamide, disperse orange 25 methacrylamide, disperse orange 25 acrylate, and disperse orange 25 methacrylate, Reactive orange dye containing vinyl sulfone.

Solvents include, but are not limited to: alcohols such as methanol, ethanol, isopropanol, 1-propanol, n-butanol, ter-tbutyl alcohol, t-amyl alcohol; Isoamyl alcohol; Benzyl alcohol; 2-Ethylhexanolethyleneglycol, propylene glycol; ethyl lactate, cyclopentanone, 2-ethoxyethanol, glycerin, 2-Butoxyethanol; Propylene Glycol Monomethyl Ether; Decyl Alcohol; Cyclohexanol; Diethylene glycol monobutyl ether; Glymes such as Ethylene glycol dimethyl ether; Ethylene glycol diethyl ether; Diethylene glycol dimethyl ether; Dipropylene glycol dimethyl ether; Diethylene glycol dibutyl ether; Poly(ethylene glycol) dimethyl ether; Tetraethylene glycol dimethyl ether; Ethyl Acetate; Propyl Acetate; n-Butyl Acetate; t-Butyl Acetate; Propylene carbonate; Dimethyl carbonate; Diethyl carbonate; 2 Ethylhexyl Acetate; Butyrolactone; Acetone, methyl ethyl ketone, cyclopentanone; cyclohexanone; 2-heptanone, -methyl-2-hexanone; Acetyl acetone; Ethyl propionate; Methyl isobutyl ketone; 2-Butoxyethanol acetate; Bis(2-ethylhexyl) adipate; Methyl phenyl acetate; Methyl lactate; Hexyl acetate; Dimethyl form amide, N-methylpyrolidone, 2-Methyl-tetrahydrofuran; N,N-dimethyl lactamide, Tetrahydrothiophene (Sulfolane), acetamide, dimethyl acetamide. Mixtures formed by combining two or more of the solvents can also be used.

Also disclosed herein are UV-blocking actinically-crosslinkable polysiloxane-polyglycerol block copolymers comprising any of the actinically-crosslinkable polysiloxane-polyglycerol block copolymers disclosed herein and a UV-blocker.

Also disclosed herein are blue-light blocking actinically-crosslinkable polysiloxane-polyglycerol block copolymers comprising any of the actinically-crosslinkable polysiloxane-polyglycerol block copolymers described herein and a blue light blocker.

Also disclosed herein are interpenetrating polymer networks. An "interpenetrating polymer network" (IPN) as used herein refers broadly to an intimate network of two or more polymers at least one of which is either synthesized and/or crosslinked in the presence of the other(s). Techniques for preparing IPN are known to one skilled in the art. For a general procedure, see U.S. Pat. Nos. 4,536,554; 4,983,702; 5,087,392; and 5,656,210, the contents of which are all incorporated herein by reference.

In some examples, the interpenetrating polymer networks comprise the actinically-crosslinkable polysiloxane-polyglycerol block copolymers described herein crosslinked with a crosslinker in the presence of an initiator (e.g., a photo-initiator, a thermal initiator), a hydrophilic monomer, a hydrophobic monomer, an amphiphilic monomer, a zwitterionic monomer, a UV-blocker, a blue light blocker, an antimicrobial monomer, a dye, a pigment, a solvent, or a combination thereof.

Suitable photo-initiators include, but are not limited to, acetophenone; anisoin; anthraquinone; benzoin; benzoin methyl ether; benzoin ethyl ether; benzoin isobutyl ether; diethoxyacetophenone; benzoylphosphine oxide; 1-hydroxycyclohexyl phenyl ketone; 50/50 blend of Benzophenone/1-Hydroxycyclohexyl phenylketone; 2,2-Diethoxyacetophenone; 4,4'-Dihydroxybenzophenone; 2,2-Dimethoxy-2-phenylacetophenone; 4-(Dimethylamino)-benzophenone; 4,4'-Dimethyl-benzyl; 2,5-Dimethylbenzophenone; 3,4-Dimethylbenzophenone; Diphenyl(2,4,6-trimethylbenzoyl) phosphine oxide/2-Hydroxy-2-methylpropiophenone; 50/50 blend; 4'-Ethoxyacetophenone; 3'-Hydroxyacetophenone; 4'-Hydroxyacetophenone, 3-Hydroxybenzophenone; 4-Hydroxybenzophenone; 1-Hydroxycyclohexyl phenyl ketone; 2-Methyl-4'-(methylthio)-2-morpholinopropiophenone; Phenanthrenequinone, 4'-Phenoxy-acetophenone; Thioxanthen-9-one; DARACURE® types (e.g., DARACURE® 1173); Irgacure® types (e.g., Irgacure 1173 and Irgacure® 2959); and UV/visible light photo initiators (Available from Spectra Group and sold under the trade names H-Nu 470, H-Nu 535, H-Nu 635).

Examples of thermal initiators include, but are not limited to, azo type initiators such as: 2,2'-azobis(2,4-dimethylpentanenitrile), 2,2'-azobis(2-methylpropanenitrile), 2,2'-azobis (2-methylbutanenitrile), Azobisisobutyronitrile (trade name VAZO 64); 2,2'-Azodi(2-methylbutyronitrile) (trade name VAZO 67); 2-2'-Azobis(2,4-dimethylvaleronitrile) (trade name VAZO 52); and 1,1'-Azobis(cyanocyclohexane) (trade name VAZO 88). In some examples, the thermal initiator is 2,2'-Azobis-(isobutyronitrile) (AIBN). One skilled in the art will recognize that polymerization and curing of formulations containing azo type initiators can also be triggered with UV-light.

Other types of initiators include organic peroxy compounds such as: benzoyl peroxide; tert-Butyl hydro peroxide; tert-Butyl per acetate, t-butyl peroxyneodecanoate; t-butyl peroxypivalate; tertiary-butyl peroxyisopropyl carbonate; cumene hydro peroxide; 2,5-Di(tert-butylperoxy)-2, 5-dimethyl-3-hexyne; Dicumyl peroxide; 2,5-Bis(tert-butylperoxy)-2,5-dimethylhexane; 2,5-Bis(tert-butylperoxy)-2,5-dimethylhexane; 1,1-Bis(tert-butylperoxy)-3,3,5-trimethylcyclohexane; 1,1-Bis(tert-butylperoxy)cyclohexane; tert-Butyl peroxide; Lauryl peroxide and the like. Many peroxy based initiators are sold under the trade name Luperox and are available from ARKEMA.

In some examples, two or more of the various types of initiators can be combined in the compositions described herein. For example, the compositions can comprise a combination of one or more thermal initiator and one or more photo-initiator. Compositions comprising both a thermal initiator and a photo-initiator can be subjected to both photocuring (e.g., with UV light) and thermal curing. For example, the composition can be partially cured with UV light followed by thermal curing and post curing.

In some examples, the silicone hydrogel compositions described herein comprise the crosslinked polysiloxane-polyglycerol block copolymers and optionally one or more monomers, polymers, or macromers. The choice of monomer, polymer, or macromer depends, in part, on the desired structure of the polymer network. Therefore, one might select hydrophilic monomers, hydrophobic monomers, amphiphilic monomers, or combinations thereof in view of the desired structure. The actinically cross-linkable polysiloxane-polyglycerol block copolymers with actinically curable polyglycerol branches can increasing the compatibility of the silicone hydrogel compositions prepared therefrom with various hydrophobic monomers and hydrophilic monomers.

In some examples, the silicone hydrogel compositions described herein can further comprise one or more monomer units selected from the group consisting of N-vinyl-2-pyrrolidone (NVP), N,N-dimethyl acrylamide (DMA), dimethylaminoethyl methacrylate, dimethylaminoethyl acrylate, vinyl acetate, 2-Hydroxyethyl methacrylate (HEMA), glycerol mono-methacrylate (GMMA), N-Hydroxyethyl acrylamide (NHA), N-(2,3-Dihydroxypropyl)acrylamide (NDHA), N-(hydroxyl methyl)acrylamide solution (NHMA), N-[3-(Dimethylamino)propyl]methacrylamide, a $C_1$-$C_4$-alkoxy polyethylene glycol (meth)acrylate having a weight average molecular weight of from 300 to 2000, N-vinyl-N-methyl isopropyl amide, N-vinyl-N-methyl acetamide, and mixtures thereof.

The silicone hydrogel compositions described herein comprising the actinically-crosslinkable polysiloxane-polyglycerol block copolymers described herein crosslinked with a crosslinker can exhibit improved properties. For example, the silicone hydrogel compositions can provide an improvement over hydrogels in which the hydrophilicity of polydimethylsiloxane copolymers was improved by attaching PEG chains to PDMS (e.g., as described by U.S. Pat. Nos. 8,231,218, 8,552,085, and 9,804,417). The use of polysiloxane prepolymers, such as polydimethyl siloxane, with polyglycerol branches described herein provides the following advantages over PDMS-PEG: The polyglycerol repeat units are more hydrophilic than PEG due to the presence of one OH group per repeat unit in the polyglycerol. The OH rich polyglycerol chains are more readily functionalized than PEG chains, which allows for the polyglycerol units to be substituted with actinically curable groups, therefore allowing for UV cure in the production of contact lenses prepared from the actinically-crosslinkable polysiloxane-polyglycerol block copolymers described herein. The OH functionality in polyglycerol repeat units also allows such copolymers to be cross-linked with a variety of crosslinkers, such as difunctional isocyanates, epoxies, alkyl halides, and aldehydes. Another potential advantage of materials described in this invention is improved thermal oxidative stability as compared to PDMS-PEG (Siegers et al. *Chemistry A European Journal,* 2004, 10(11), 2831-2838). Thermal oxidative stability of polyglycerol units is relatively high compared to PEG. Thermal degradation of linear polyglycerol starts at 250° C. (Atkinson et al. *Macromol. Chem. Phys.* 2011, 212(19), 2103-2113), while heating PEG at 80° C. in air results in degradation reactions which produce esters and formic esters (Chongyoup et al. *Polymer,* 1997, 38(2), 317-323). In some examples, the polyglycerol is useful as an internal wetting agent for contact lenses comprising the silicone hydrogel compositions, such that the contact lenses derived from the silicone hydrogel compositions exhibit hydrophilic surfaces without the need for post-curing surface treatment due to the presence of the polyglycerol side chains in the polysiloxane-polyglycerol block copolymers.

Devices and Methods of Use

Also disclosed herein are methods of use of any of the actinically-crosslinkable polysiloxane-polyglycerol block copolymers and silicone hydrogels described herein.

For example, also described herein are methods of use of any of the actinically-crosslinkable polysiloxane-polyglycerol block copolymers and silicone hydrogels described herein in medical devices and ophthalmic applications such as contact lenses.

In some examples, the actinically-crosslinkable polysiloxane-polyglycerol block copolymers and silicone hydrogels described herein can be used in the construction of co-continuous biphasic or multiphasic materials.

The methods of use can, for example, comprise using the actinically-crosslinkable polysiloxane-polyglycerol block copolymers and/or the silicone hydrogel compositions described herein in the construction of medical devices, coatings for medical devices and a variety of biomedical applications. For example, the methods of use can comprise using the actinically-crosslinkable polysiloxane-polyglycerol block copolymers, the silicone hydrogel compositions, and/or the interpenetrating polymer networks described herein as hydrophilic coatings for any number of medical devices including, but not limited to catheters, contact lenses, endoscopes, cell growth platforms, microfluidic devices, body implants, coatings for implants that come into contact with tissue (e.g., epithelial tissue, connective tissue, muscle tissue, and nerve tissue) and biological fluids (e.g., blood, mucus, urine, tears, saliva, amniotic fluid, synovial fluid). The methods of use can, in some examples, comprise applying the actinically-crosslinkable polysiloxane-polyglycerol block copolymers and/or the silicone hydrogel compositions described herein to any lens material including hydrogels and silicone hydrogels and rigid gas permeable lenses (RGP's) to thereby render the lens material hydrophilic.

Examples of lens materials that can be rendered hydrophilic include, but are not limited to, avefilcon A, acofilcon A, acofilcon B, acquafilcon A, alofilcon A, alphafilcon A, amfilcon A (reclassified to ocufilcon series), astifilcon A, atlafilcon A, balafilcon A, bisfilcon A, bufilcon A, comfilcon A, crofilcon A, cyclofilcon A, darfilcon A, delefilcon A, deltafilcon A, deltafilcon B, dimefilcon A, droxifilcon A, efrofilcon A, elastofilcon A, enfilcon A, epsificon A, esterifilcon A, etafilcon A, galyfilcon A, genfilcon A, govafilcon A, hefilcon A, hefilcon B, hefilcon C, hefilcon D, hilafilcon A, hilafilcon B, hioxifilcon A, hioxifilcon B, hioxifilcon C, hioxifilcon D, hydrofilcon A, iberfilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, narafilcon A, narafilcon B, nelfilcon A, nesofilcon A, netrafilcon A, ocufilcon A, ocufilcon B, ocufilcon C, ocufilcon D, ocufilcon E, ocufilcon F, ofilcon A, omafilcon A, oxyfilcon A, pentafilcon, perfilcon A, petrafocon A-hem-larafilcon A, pevafilcon A, phemfilcon A, phemfilcon B, polymacon A, senofilcon A, shofilcon A, sifilcon A, silafilcon, siloxyfilcon A, surfilcon, tasfilcon, tefilcon, tetrafilcon A, trifilcon, uvifilcon, vasurfilcon A, vifilcon A, vifilcon B, and xylofilcon A.

In some examples, the methods of use can comprise using the actinically-crosslinkable polysiloxane-polyglycerol block copolymers, the silicone hydrogel compositions, and/or the interpenetrating polymer networks described herein in a range of cell culture applications for the expansion and directed differentiation of various cell types by acting as extracellular matrix mimics for 3D Cell Culture.

The methods of use can, for example, comprise using the actinically-crosslinkable polysiloxane-polyglycerol block copolymers, the silicone hydrogel compositions, and/or the interpenetrating polymer networks described herein as synthetic matrix metallo-proteinase-sensitive materials for the conduction of tissue regeneration.

In some examples, the methods of use can comprise using the actinically-crosslinkable polysiloxane-polyglycerol block copolymers, the silicone hydrogel compositions, and/or the interpenetrating polymer networks described herein as micro-valves and/or micro-pumping devices due to the propensity of the actinically-crosslinkable polysiloxane-polyglycerol block copolymers, the silicone hydrogel compositions, and/or the interpenetrating polymer networks to absorb large volumes aqueous and/or non-aqueous fluids coupled with the response of the actinically-crosslinkable polysiloxane-polyglycerol block copolymers, the silicone hydrogel compositions, and/or the interpenetrating polymer networks to various forms of stimulation (e.g., pH, electrical current, temperature, ionic strength).

The actinically-crosslinkable polysiloxane-polyglycerol block copolymers described herein can, for example, be used to make soft (hydrophilic) contact lenses with or without decorative print patterns (e.g., soft contact lenses that are optionally cosmetically tinted). For example, soft contact lenses that are cosmetically tinted can be prepared from formulations comprising the actinically-crosslinkable polysiloxane-polyglycerol block copolymers described herein and a dye and/or a pigment.

In some examples, the actinically-crosslinkable polysiloxane-polyglycerol block copolymers and silicone hydrogels described herein can be used as a contact lens, wherein the actinically-crosslinkable polysiloxane-polyglycerol block copolymers are derived from a polysiloxane prepolymer comprising a polyglycerol side chain and the polyglycerol is useful as an internal wetting agent for contact lenses comprising the silicone hydrogel compositions, such that the contact lenses derived from the silicone hydrogel compositions exhibit hydrophilic surfaces without the need for post-curing surface treatment due to the presence of the polyglycerol side chains in the polysiloxane-polyglycerol block copolymers.

Also disclosed herein are articles of manufacture and devices comprising any of the actinically-crosslinkable polysiloxane-polyglycerol block copolymers, silicone hydrogels, and/or interpenetrating polymer networks described herein. The article of manufacture can, for example, comprise an ophthalmic device (e.g., contact lens, intraocular lens, corneal inlay, corneal ring) or membrane. Such articles of manufacture and devices can be fabricated by methods known in the art.

In some examples, the article of manufacture can comprise a membrane prepared from the silicone hydrogel compositions described herein. The membrane can, for example, allow for efficient permeation of small molecules and ions. In some examples, the contact lens or membrane can allow for efficient transport of water, ions, oxygen, and nutrients and are therefore well suited for use as ophthalmic devices such as contact lenses. In some examples, the article of manufacture can comprise an ophthalmic device (e.g., contact lens, intraocular lens, corneal inlay, corneal ring) obtained from a lens-forming material including the actinically-crosslinkable polysiloxane-polyglycerol block copolymers and optionally a hydrophilic monomer and/or hydrophobic monomer.

In some examples, the article of manufacture can comprise a contact lens comprising the silicone hydrogel compositions described herein, wherein the contact lens can exhibit an improved lubricous surface having wear permanence, combined with the characteristics of biocompatibility and a low coefficient of friction in contact with tear fluid.

Also described herein are silicone hydrogel contact lenses obtained by actinically cross-linking the actinically-crosslinkable polysiloxane-polyglycerol block copolymer, wherein the actinically-crosslinkable polysiloxane-polyglycerol block copolymer comprises a methacrylated polydimethylsiloxane-polyglycerol block copolymer. The silicone hydrogel contact lens can comprises: a silicone hydrogel material and hydrophilic polymer branches which are covalently anchored to the polymer matrix of the silicone hydrogel material, wherein the silicone hydrogel material is obtained by polymerizing a lens-forming material including the actinically-crosslinkable polysiloxane-polyglycerol block copolymers described herein, wherein the polyglycerol side chains in the silicone hydrogel material are capable of imparting the silicone hydrogel contact lens with a hydrophilic surface without post-curing surface treatment. This contrasts with silicone hydrogel materials other than those described herein and contact lenses prepared therefrom, which typically require a post-curing surface treatment to render the surface hydrophilic.

For example, silicone hydrogel materials other than those described herein typically have a surface or at least a portion of its surface which is hydrophobic (non-wettable). Hydrophobic surfaces or portions of surfaces that are hydrophobic will up-take lipids or proteins. In the case where the silicone hydrogel materials are used as contact lenses, such hydrophobic surfaces or portions of surfaces that are hydrophobic will up-take lipids or proteins from the ocular environment and can adhere to the eye. Thus, a silicone hydrogel contact lens will generally require a surface modification which is typically carried out after cast-molding of the lens.

On the other hand, when a liquid lens forming material including the actinically-crosslinkable polysiloxane-polyglycerol block copolymers described herein is introduced in a mold for making a contact lens, the actinically curable groups linked to the polysiloxane prepolymer are hydrophilic (e.g., they comprise actinically curable hydrophilic polymer chains) and can be adsorbed at the interface between the mold and the lens forming material. When the actinically curable hydrophilic polymer chains are present in a sufficient amount, interfacial films comprising the hydrophilic polymer chains can be formed with an adequate thickness at the mold-liquid interface prior to curing (polymerization), and the interfacial films can be subsequently preserved after curing.

The silicone hydrogel contact lenses prepared from the compositions described herein can, for example, have an Ionoflux Diffusion Coefficient, D, of $2.0 \times 10^{-6}$ mm$^2$/min or more (e.g., $4.0 \times 10^{-6}$ mm$^2$/min or more, $9.0 \times 10^{-6}$ mm$^2$/min or more, $1 \times 10^{-5}$ mm$^2$/min or more, or $5 \times 10^{-5}$ mm$^2$/min or more).

The silicone hydrogel contact lenses prepared from the compositions described herein can, for example, have a high oxygen permeability. For example, the silicone hydrogel contact lenses prepared from the compositions described herein can have an apparent oxygen permeability of 35 barrers or more (e.g., 40 barrers or more, 50 barrers or more, 60 barrers or more, 70 barrers or more, or 80 barrers or more).

The silicone hydrogel contact lenses prepared from the compositions described herein can, for example have an elastic modulus of 0.25 MPa or more (e.g., 0.3 MPa or more, 0.4 MPa or more, 0.5 MPa or more, 0.6 MPa or more, 0.7 MPa or more, 0.8 MPa or more, 0.9 MPa or more, 1 MPa or more, 1.1 MPa or more, 1.2 MPa or more, 1.3 MPa or more, 1.4 MPa or more, 1.5 MPa or more, or 1.6 MPa or more). In some examples, the silicone hydrogel contact lenses prepared from the compositions described herein can have an elastic modulus of 1.75 MPa or less (e.g., 1.7 MPa or less, 1.6 MPa or less, 1.5 MPa or less, 1.4 MPa or less, 1.3 MPa or less, 1.2 MPa or less, 1.1 MPa or less, 1 MPa or less, 0.9 MPa or less, 0.8 MPa or less, 0.7 MPa or less, 0.6 MPa or less, or 0.5 MPa or less). The elastic modulus of the silicone hydrogel contact lenses prepared from the compositions described herein can range from any of the minimum values described above to any of the maximum values described above. For example, the silicone hydrogel contact lenses prepared from the compositions described herein can have an elastic modulus of from 0.25 MPa to 1.75 MPa (e.g., from 0.25 MPa to 1 MPa, from 1 MPa to 1.75 MPa, from 0.25 MPa to 0.75 MPa, from 0.75 MPa to 1.25 MPa, from 1.25 MPa to 1.75 MPa, from 0.5 MPa to 1.25 MPa, or from 0.75 MPa to 1 MPa).

The silicone hydrogel contact lenses prepared from the compositions described herein can, for example, have a water content of 15% or more (e.g., 20% or more, 25% or more, 30% or more, 35% or more, 40% or more, 45% or more, 50% or more, 55% or more, 60% or more, 65% or more, or 70% or more). In some examples, the silicone hydrogel contact lenses prepared from the compositions described herein can have a water content of 80% or less (e.g., 75% or less, 70% or less, 65% or less, 60% or less, 55% or less, 50% or less, 45% or less, 40% or less, 35% or less, 30% or less, or 25% or less). The water content of the silicone hydrogel contact lenses prepared from the compositions described herein can range from any of the minimum values described above to any of the maximum values described above. For example, the silicone hydrogel contact lenses prepared form the compositions described herein can have a water content of from 15% to 80% (e.g., from 15% to 45% from 45% to 80%, from 15% to 30%, from 30% to 45%, from 45% to 60%, from 60% to 80%, from 25% to 8%, from 15% to 60%, or from 25% to 70%).

The silicone hydrogel contact lenses prepared from the compositions described herein can, for example, have an averaged water contact angle of 70 degrees or less (e.g., 65 degrees or less, 60 degrees or less, 55 degrees or less, 50 degrees or less, 45 degrees or less, 40 degrees or less, 35 degrees or less, 30 degrees or less, 25 degrees or less, 20 degrees or less, 15 degrees or less, or 10 degrees or less).

The silicone hydrogel contact lenses prepared from the compositions described herein can, in some examples, further comprise a silicone-containing vinylic monomer, a silicone-containing macromer, a silicone-containing prepolymer, a hydrophilic vinylic monomer, a hydrophobic vinylic monomer, a hydrophilic prepolymer, a cross-linking agents, an antimicrobial agent, a chain transfer agent, radical initiator, a UV-absorber, an inhibitor, a filler, a visibility tinting agent, a bioactive agent, a leachable lubricant, or a combination thereof.

In some examples, the actinically-crosslinkable polysiloxane-polyglycerol block copolymers described herein comprise two or more polymeric chains (blocks), which are structurally different and chemically bonded to each other. Under certain conditions, the actinically-crosslinkable polysiloxane-polyglycerol block copolymers can segregate into a variety of ordered structures.

In some examples, ordered block copolymer structures are substantially locked in place through chemical reactions such as cross-linking of actinically curable groups (FIG. 3), substitution reactions, addition reactions, "click reactions", polymerization reactions or any number of chemical reactions known in the art. In one some examples, block copolymers comprising PDMS with cross-linkable polyglycerol branches are self-assembled in polar solvent and/or polar monomer(s) to form vesicles having bi-continuous or multiphasic structures. In certain examples, polymerization induced self-assembly (PISA) is achieved by polymerization of monomer solutions containing the actinically-crosslinkable polysiloxane-polyglycerol block copolymers described herein.

These ordered structures with bi-continuous phases are particularly well suited to uses and devices when two fundamentally different properties are required from the same material. For example, bi-continuous materials can be used in the area of polymer electrolyte membranes which require efficient transport of ions and simultaneously resilient mechanical properties. In the case of polyelectrolytes, the presence of a continuous phase suitable for uninterrupted ion-conducting pathways while also having a second phase that can provide mechanical strength is desirable. Bi-continuous materials can also be used in cases requiring mass transfer of chemical species having significantly different physical or chemical properties (e.g., solubility, polarity, non-polar, acidity, basicity, pharmacologically activity, molecular size/MW, boiling physical state (gas, liquid, solid)). For example, it can be desirable to have one phase that is suitable for mass transfer of hydrophilic species while having a second phase that is suitable for mass transfer of lipophilic species. In certain applications, it is desirable to have materials that are capable of efficient mass transfer of gaseous substances, liquid substances, and solid substances. For example, a wound dressing capable of efficient mass transfer of oxygen, antimicrobial agents, antifungal agents, and antiviral agents, fluid (e.g. liquor puris), and gases (oxygen, $CO_2$) would be highly effective in facilitating wound healing.

Examples of antimicrobial agents include but are not limited to (neomycin, bacitracin, Penicillin, Penicillin G, Amoxicillin, Ampicillin, Cloxacillin, Methicillin, Amoxicillin+Clavulanate (Augmentin), Ticarcillin+Clavulanate, Nafcillin, Cefuroxime, Lacking Urine, Cefotaxime, Cefoperazone, Cephtriaxone, Cefepime, Tetracycline, Minocycline, Doxycycline, Azithromycin, Erythromycin, Clarithromycin, Clindamycin, Sulfamethoxazole-Trimethoprim, Ciprofloxacin (Cipro), Norfloxacin, Ofloxacin, Levofloxacin, Streptomycin, Tobramycin, Gentamycin, Amikacin). Examples of antifungal agents include but are not limited to (Amphotericin B, Candicidin, Bifonazole, Albaconazole, Amantadine, Amprenavir, Atazanavir, Efavirenz, Ibacitabine, Umifenovir, Abafungin, Ciclopirox, Norvir, Peramivir, Podophyllotoxin, Saquinavir, Sofosbuvir). Examples of antiviral agents include but are not limited to (Acyclovir, Trifluridine, Zanamivir, Ribavirin, Tenofovir, Tromantadine).

Bi-continuous or multi-continuous multiphasic materials can also be used in cases that require mass transfer of one or more of the following types of species: ionic species, gases, oxygen, pharmacologically active substances, biomolecular species, and fluids. Examples of ionic species include but are not limited to potassium salts, sodium salts, calcium salts, magnesium salts, silver salts, copper salts, iron salts, aluminum salts, chloride salts, bromide salts, fluoride salts, iodide salts, Sulphur salts, phosphate salts, and borate salts. Examples of gases include but are not limited to $CO_2$, NO (nitric oxide), $N_2O$ (nitrous oxide), $NO_2$ (nitrogen dioxide), water vapor, $O_2$, $O_3$, $NH_3$, boron tri-fluoride ($BF_3$), sulfur hexafluoride ($SF_6$), silane ($SiH_4$), silicon tetrachloride ($SiCl_4$), silicon tetrafluoride ($SiF_4$), $PH_3$, phosgene ($COCl_2$), carbon monoxide (CO), sulfur dioxide ($SO_2$), methane ($CH_4$), ethane ($C_2H_6$), propane ($C_3H_8$), cyclopropane ($C_3H_6$), butane ($C_4H_{10}$), cyclobutane ($C_4H_8$), acetylene, chlorine, fluorine, argon, neon, krypton, radon, xenon, hydrogen cyanide, hydrogen sulfide, HCl, HF, HBr, nitrogen ($N_2$), hydrogen ($H_2$), chlorofluorocarbons (CFCs), and hydro-chlorofluorocarbons (HCFCs), The actinically-crosslinkable polysiloxane-polyglycerol block copolymers described herein comprise one or more polyglycerol branches tethered to a polysiloxane (e.g., PDMS) main chain. Because the hydrophilic polyglycerol branches are chemically anchored to the polysiloxane chains, contact lenses and membranes produced from these materials have lubricity that is more resistant to failure or variation in lubricity during use than contact lenses prepared from other silicone hydrogel materials.

For example, contact lenses and membranes prepared from the actinically-crosslinkable polysiloxane-polyglycerol block copolymers described herein can exhibit improved properties over contact lenses and membranes wherein surface lubricity was improved using PDMS bearing PEG chains (e.g., as described in U.S. Pat. Nos. 8,231, 218, 8,552,085, and 9,804,417), because PEG is prone to oxidative degradation as discussed above. Contact lenses and membranes produced from the actinically-crosslinkable polysiloxane-polyglycerol block copolymers described herein are also an improvement over contact lenses and membranes prepared using PDMS bearing PVP chains (e.g., as described in U.S. Pat. No. 6,367,929), because PVP can leach from those silicone hydrogel lenses.

Furthermore, the actinically-crosslinkable polysiloxane-polyglycerol block copolymers described herein can have an amphiphilic nature due to the polysiloxane prepolymer which can be hydrophobic and the polyglycerol side chains which can be hydrophilic. The amphiphilic nature of the actinically-crosslinkable polysiloxane-polyglycerol block copolymers described herein can facilitate microscopic phase separation in a silicone hydrogel material prepared therefrom into a silicone-rich microscopic phase and a hydrophilic microscopic phase. With the existence of a co-continuous bi-phase structure (in microscopic scale), the silicone hydrogel material can have relatively high oxygen and ion permeability's.

The actinically-crosslinkable polysiloxane-polyglycerol block copolymers described herein comprising actinically cross-linkable groups located on the polyglycerol grafts can be used to prepare silicone hydrogels with excellent wettability. In addition, it was long thought that oxygen permeability, Dk, of a silicone hydrogel contact lens and a non-silicone hydrogel contact lens would be approximately the same if both types of lenses had a water content of ≥70% (Morgan et al. *Cont. Lens Anterior Eye* 1998, 21, 3-6; Sweeney et al. *Contact Lens Spectrum*, Feb. 1, 2006; Jones, *Contact Lens Spectrum*, September 2002). Further, it was previously thought that in order for a silicone hydrogel contact lens to have a Dk of ≥60 barrer, the silicone hydrogel lens would need to have a water content of 45% or less or 80% or more. However, certain silicone hydrogel compositions described herein have a Dk of 90 barrer and water content of 66%, showing that previous notions regarding silicone hydrogel Dk and water content were incomplete.

Methods of Making

Also described herein are methods of making the actinically-crosslinkable polysiloxane-polyglycerol block copolymers, the silicone hydrogel compositions, and/or the interpenetrating polymer networks described herein, and the devices comprising the actinically-crosslinkable polysiloxane-polyglycerol block copolymers, the silicone hydrogel compositions, and/or the interpenetrating polymer networks described herein.

For example, the actinically-crosslinkable polysiloxane-polyglycerol block copolymers can be prepared by contacting a polysiloxane polymer comprising a polyglycerol side chain with a catalyst and a cure group precursor (e.g., an ethylenically unsaturated reagent).

a catalyst. The advantage of a polymer supported catalyst is the ease of separation from reaction products.

Any number of other ethylenically unsaturated reagents may be used as a cure group precursor to produce the actinically-crosslinkable polysiloxane-polyglycerol block copolymers. For example, the cure group precursor can comprise maelic anhydride, methacrylic anhydride, 2-isocyanatoethylmethacrylate (IEM), acryloyl chloride, allylbromide, allylchloride, vinylbenzylchloride, or ethylenically activated esters (e.g., N-Acryloxy succinimide, N-(Methacryloxy)succinimide).

In some examples, actinically-crosslinkable polysiloxane-polyglycerol block copolymers defined by Formula I can be prepared using the method illustrated in Scheme 3 by contacting a polysiloxane polymer comprising a polyglycerol side chain with a cure group precursor and optionally a catalyst.

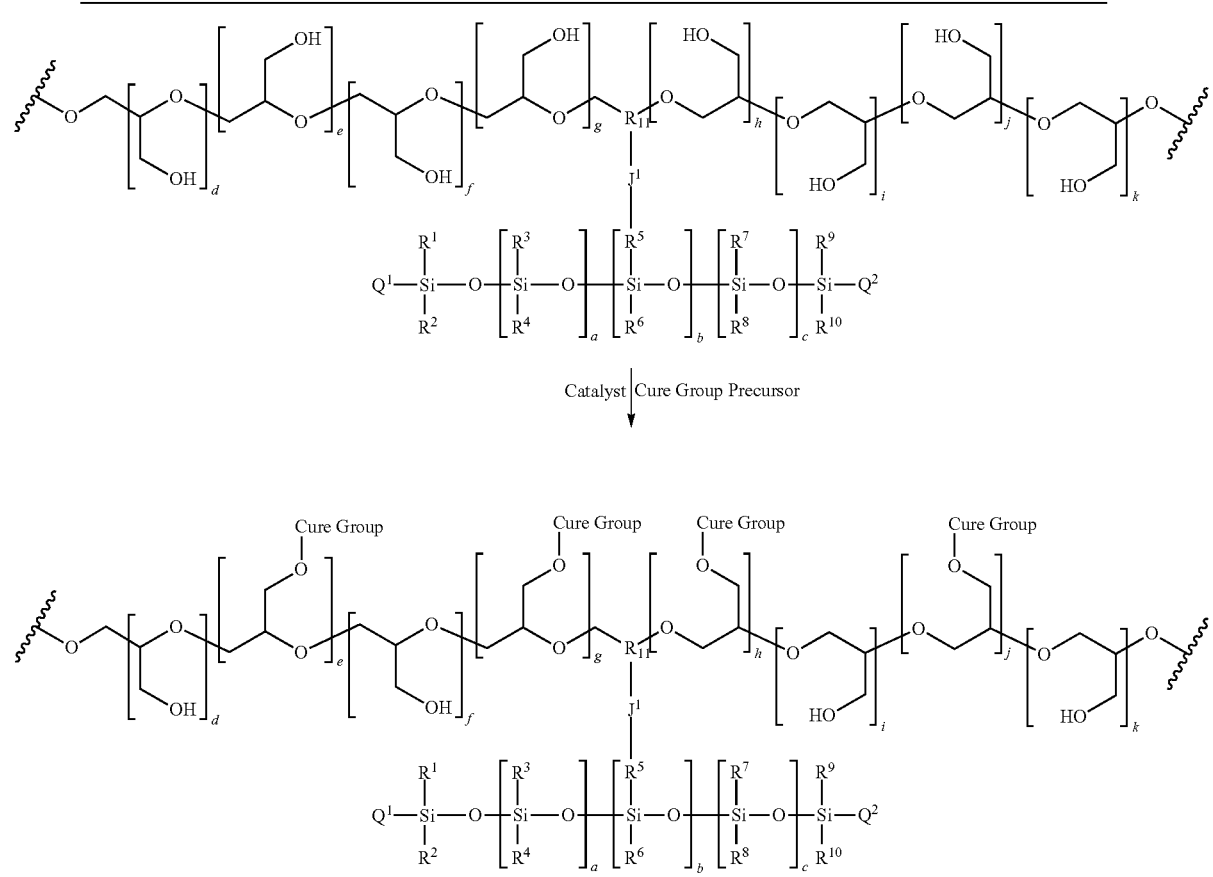

Scheme 3. Formation of the actinically crosslinkable polysiloxane-polyglycerol block copolymers by contacting a polysiloxane polymer comprising a polyglycerol side chain with a catalyst and a cure group precursor.

Any suitable catalyst can be used to facilitate reactions of PDMS-PGLY with the cure group precursor (e.g., anhydrides and other functionalizing agents). For example, small molecule catalysts such as triethyl amine, pyridine, dimethylaminopyridine (DMAP), and dibutyltindilaurate (DBTDL) can be used. In some examples, small molecule catalysts can be replaced by polymer supported catalysts. For example, polystyrene supported DMAP can be used as In some examples, actinically-crosslinkable polysiloxane-polyglycerol block copolymers defined by Formula IX can be prepared using the method illustrated in Scheme 4 by contacting a polysiloxane polymer comprising a polyglycerol side chain with a dimethylaminopyridine (DMAP) catalyst and maelic anhydride as the cure group precursor. Use of maleic anhydride provides an added advantage of not producing a small molecule bi-product as is the case with linear anhydrides.

Scheme 4. Synthesis of the actinically-crosslinkable polysiloxane-polyglycerol block copolymer defined by Formula IX by contacting a polysiloxane polymer comprising a polyglycerol side chain with a 4-Dimethylaminopyridine (DMAP) catalyst and maelic anhydride as the cure group precursor.

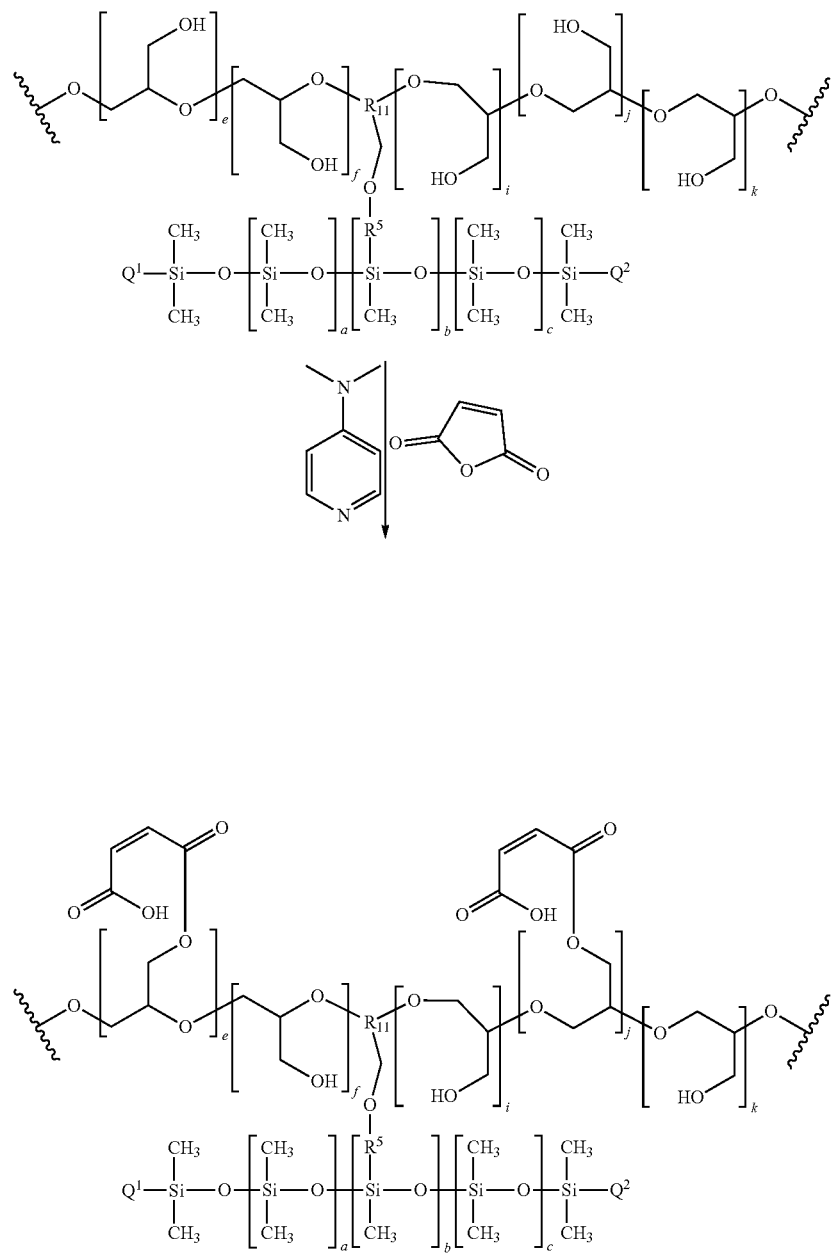

In some examples, actinically-crosslinkable polysiloxane-polyglycerol block copolymers defined by Formula X can be prepared using the method illustrated in Scheme 5 by contacting a polysiloxane polymer comprising a polyglycerol side chain with a DMAP catalyst and methacrylic anhydride as a cure group precursor.

Scheme 5. Synthesis of the actinically-crosslinkable polysiloxane-polyglycerol block copolymer defined by Formula X by contacting a polysiloxane polymer comprising a polyglycerol side chain with a DMAP catalyst and methacrylic anhydride as a cure group precursor.

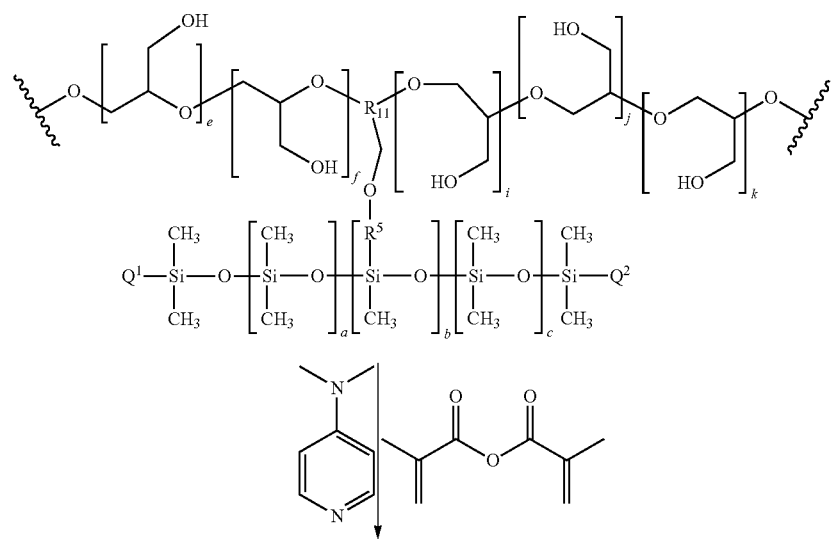

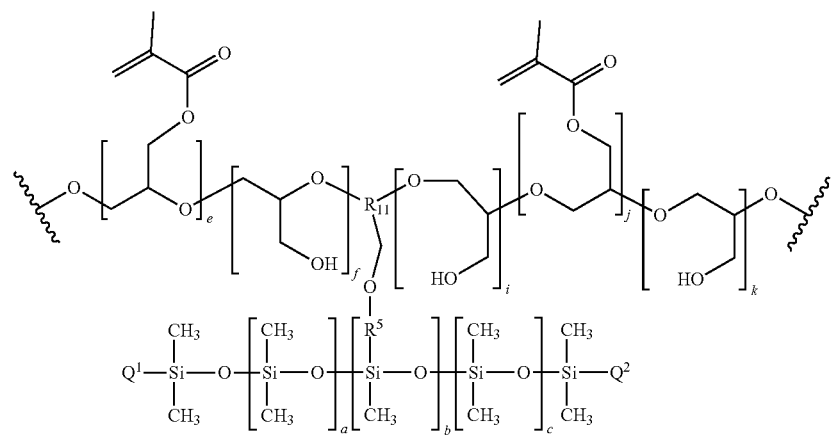

In some examples, actinically-crosslinkable polysiloxane-polyglycerol block copolymers defined by Formula XI can be prepared using the method illustrated in Scheme 6 by contacting a polysiloxane polymer comprising a polyglycerol side chain with dibutyltindilaurate (DBTDL) or other suitable catalyst and 2-isocyanatoethylmethacrylate (IEM) as a cure group precursor.

Scheme 6. Synthesis of the actinically-crosslinkable polysiloxane-polyglycerol block copolymer defined by Formula IX by contacting a polysiloxane polymer comprising a polyglycerol side chain with dibutyltindilaurate or other suitable catalyst and 2-isocyanatoethylmethacrylate (IEM) as a cure group precursor.

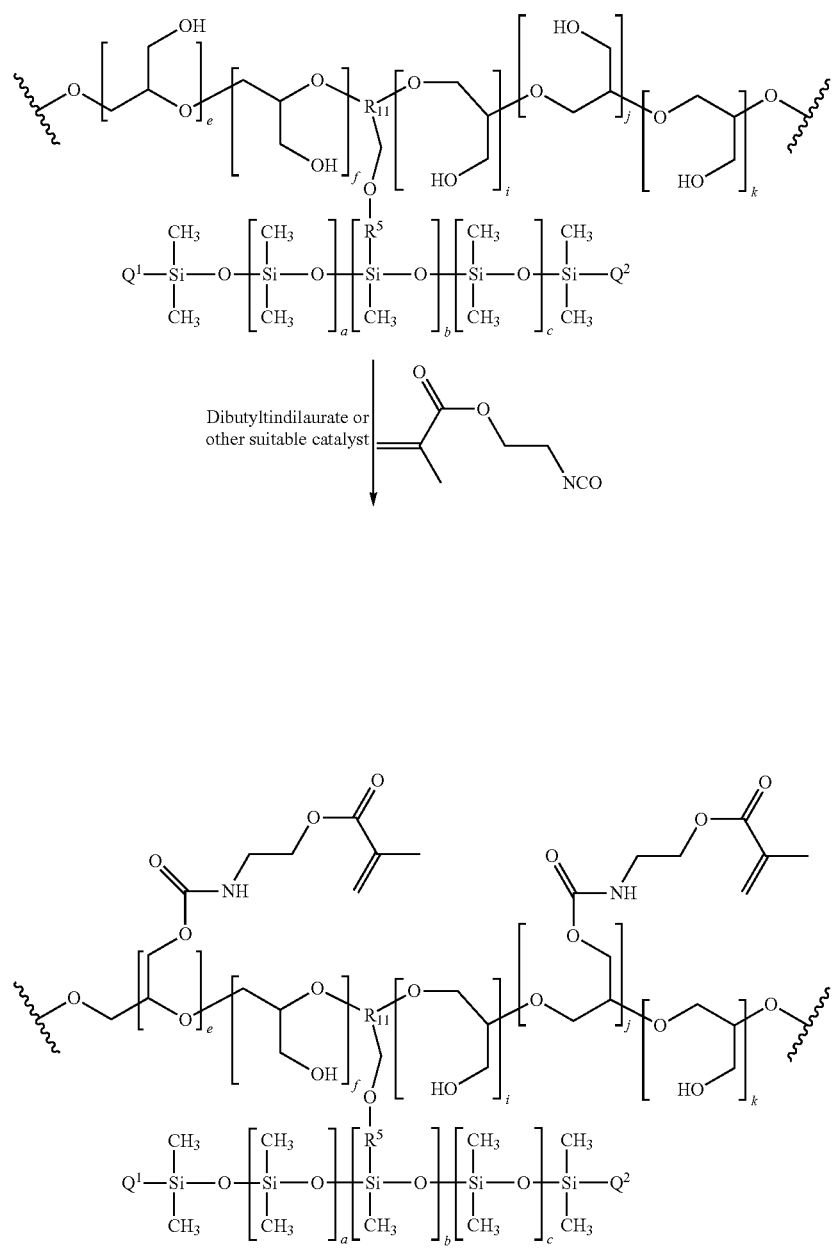

In some examples, the methods of making the actinically-crosslinkable polysiloxane-polyglycerol block copolymers can further comprise preparing the polysiloxane polymer comprising a polyglycerol side chain. For example, a polysiloxane polymer comprising a polyglycerol side chain can be prepared using the method illustrated in Scheme 7 by coupling a thiol functionalized polydimethylsiloxane with an allyl substituted polyglycerol.

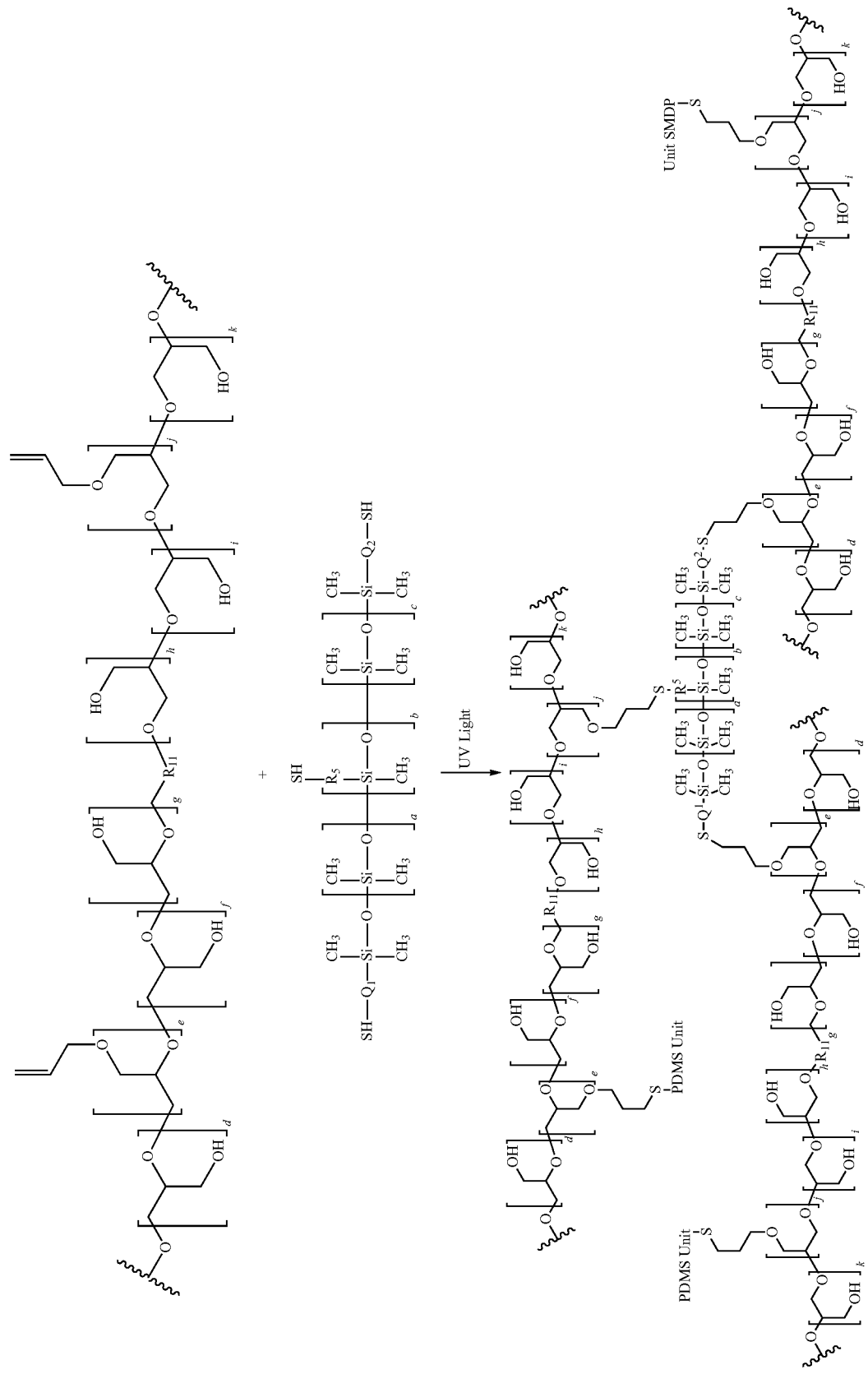
Scheme 7: Coupling of Thiol functionalized Polydimethylsiloxane with allyl substituted polyglycerol.

In some examples, the methods can further comprise preparing the allyl substituted polyglycerol, for example through reaction of polyglycerol and allyl bromide with added catalyst (e.g., triethyl amine, pyridine, Pt, or DMAP) or without added catalyst. For example, the allyl substituted polyglycerol can be prepared using the method illustrated in Scheme 8.

Scheme 8: Synthesis of allyl-substituted polyglycerol.

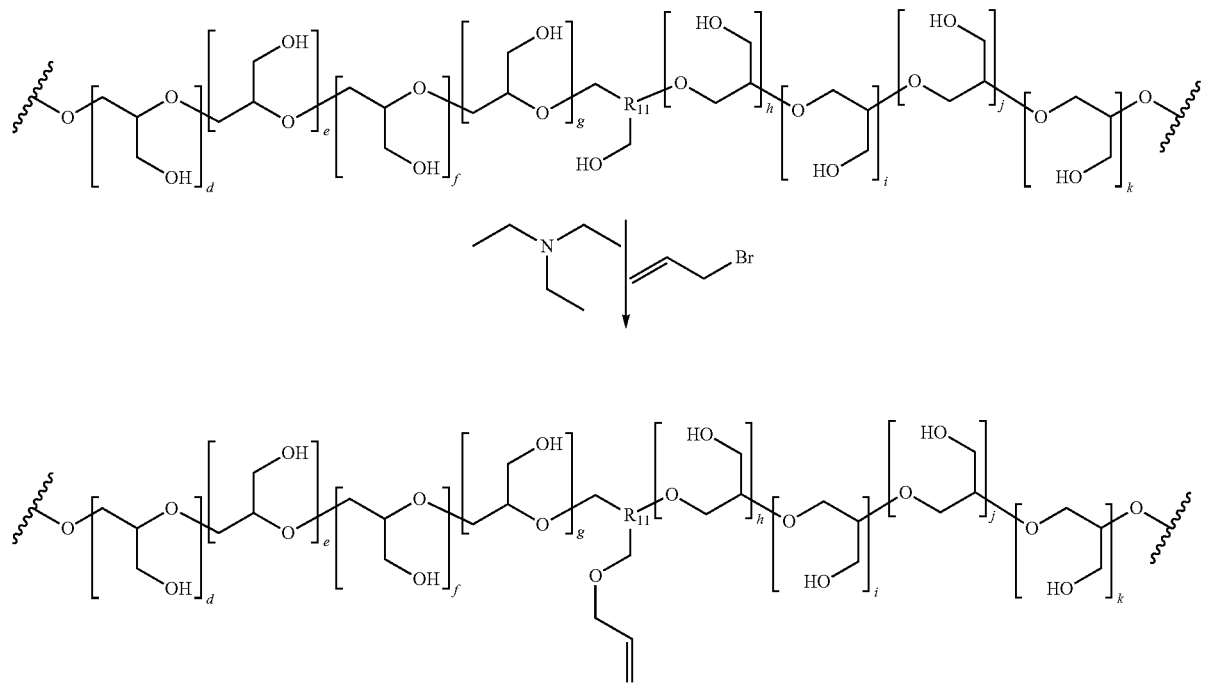

In some examples, the methods of making the actinically-crosslinkable polysiloxane-polyglycerol block copolymers can further comprise preparing the polysiloxane polymer comprising a polyglycerol side chain. For example, a polysiloxane polymer comprising a polyglycerol side chain can be prepared using the method illustrated in Scheme 9 by coupling a thiol functionalized polydimethylsiloxane with an allyl substituted polyglycerol (which can be prepared as illustrated in Scheme 8), where the catalyst can, for example, comprise Pt.

Scheme 9: Synthesis of PDMS-PGL from allyl-substituted polyglycerol and PDMS with a methylhydrosiloxane unit.

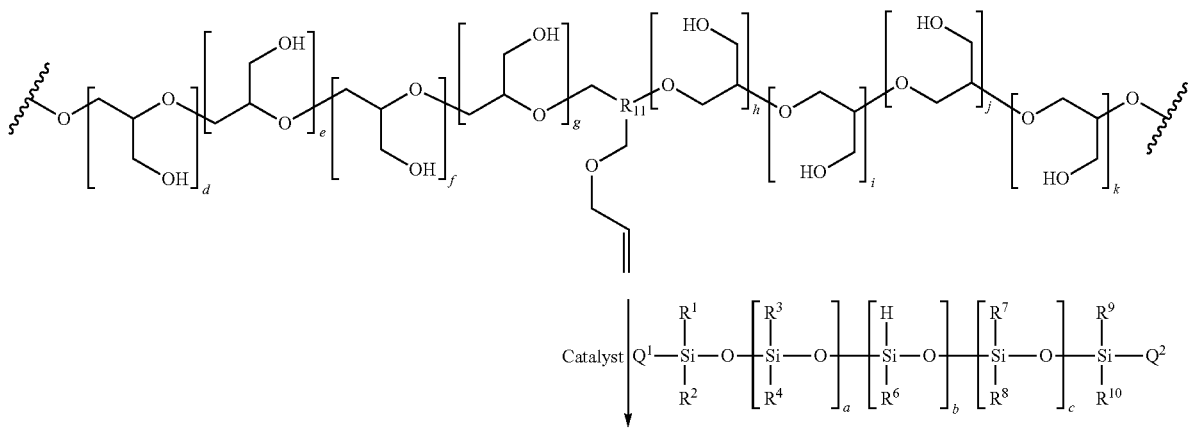

-continued

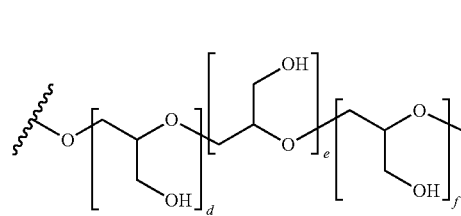

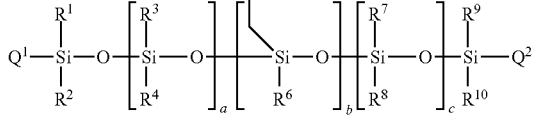

Figure 2:
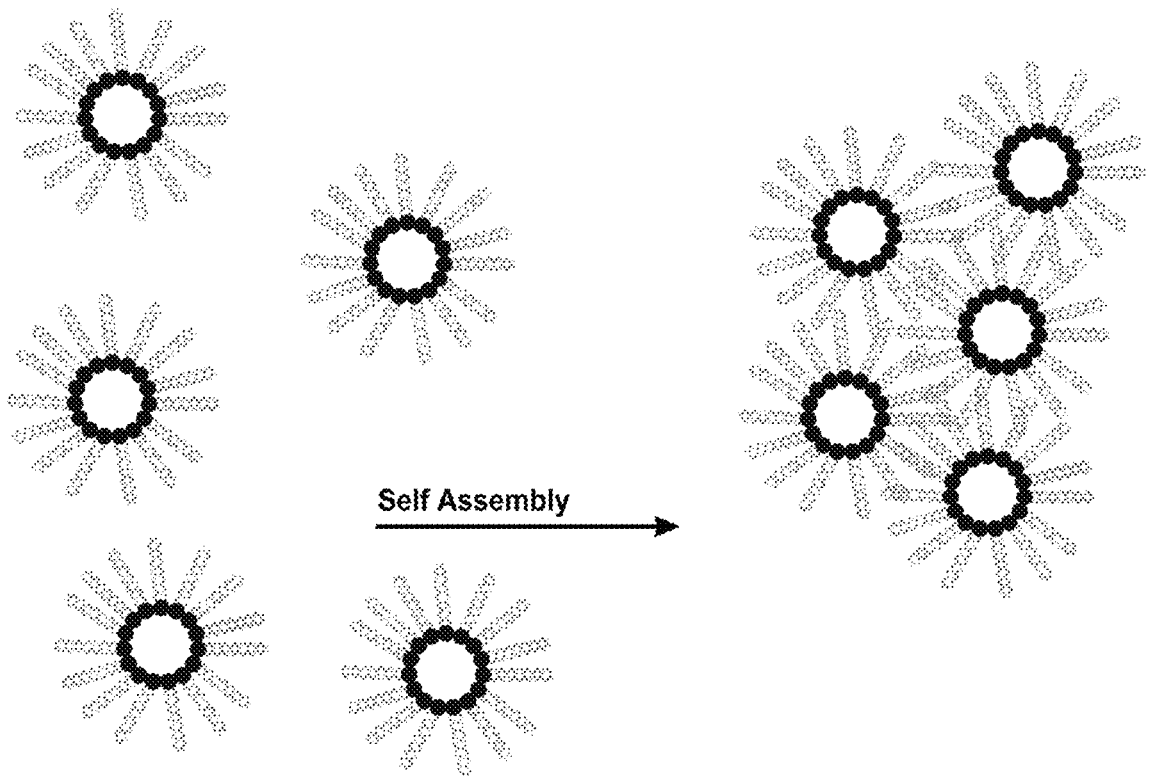
FIG. 2 illustrates the self-assembly of uni-lamellar AC-PDMS-PGLY vesicles to form a multi-lamellar vesicle.
Figure 3:
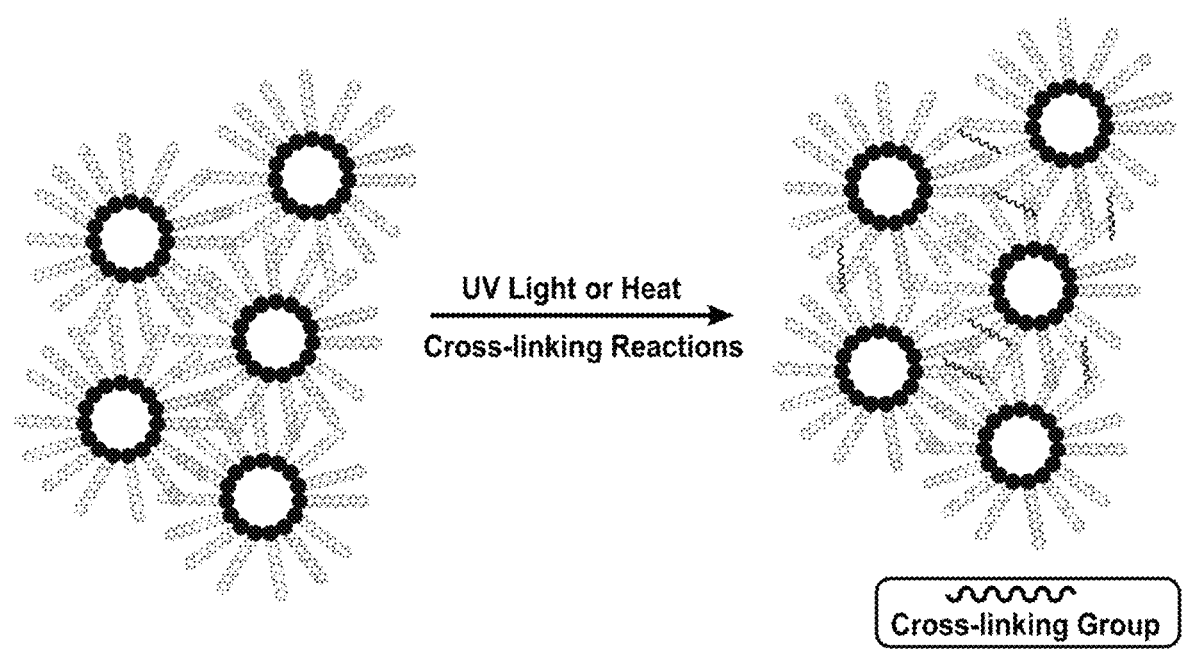
FIG. 3 illustrates cross-linking of multilamellar AC-PDMS-PGLY.

Under certain conditions, polysiloxane block copolymers bearing polyglycerol side chains (or substituted polyglycerol side chains) can segregate into a variety of ordered structures by the repulsion of the immiscible blocks as shown in FIG. 1-FIG. 3.

In some examples, the ordered block copolymer structures can be substantially locked in place through chemical reactions such as cross-linking of actinically curable groups (FIG. 3), substitution reactions, addition reactions, "click reactions", polymerization reactions, or any number of chemical reactions known in the art. In some examples, the actinically-crosslinkable polysiloxane-polyglycerol block copolymers comprising a polysiloxane (e.g., PDMS) with actinically cross-linkable polyglycerol branches can self-assemble in a polar solvent and/or in the presence of a polar monomer to form vesicles having bi-continuous or multiphasic structures. For example, polymerization induced self-assembly (PISA) can be achieved by polymerization of monomer solutions containing the actinically-crosslinkable polysiloxane-polyglycerol block copolymers described herein.

Also disclosed herein are methods for making heat stable bi-continuous phase membranes from the actinically-cross-linkable polysiloxane-polyglycerol block copolymers described herein, wherein the heat stable bi-continuous phase membranes have substantially uninterrupted ion-conducting conduits and uninterrupted oxygen transport channels. The bi-continuous membrane structure can be locked in place or substantially locked in place through cross-linking reactions and/or polymerization. The resulting materials can form vesicles in which the outer shell is comprised of polyglycerol chains while the inner core is comprised of polysiloxane (e.g., polydimethylsiloxane) chains. The vesicles can form aggregates which can then be cross-linked/polymerized to yield stabilized structures suitable for use as contact lenses and various biomedical applications. The extent of self-assembly can be varied by the addition of materials such as monomers, solvents, and polymers. The extent of self-assembly can also be varied by the addition of various chemicals, changing pH, changing ionic strength, changing temperature, and/or changing pressure. In some examples, the vesicles can be inverted, disrupted, or damaged by a number of factors (e.g., thermal stress, chemical stress, electrical stress, mechanical stress such as pressure, etc.). Vesicle stability can be influenced by environmental factors such as temperature and pressure, as well as by chemical composition (e.g., salts, solvents, monomers, buffers, polymers, bio-molecules). Therefore, such factors can increase or decrease vesicle stability. The stability of the vesicles can be increased or made substantially permanent by cross-linking reactions. In hydrophilic solvents (e.g., polar solvents), the inner core of the vesicles will comprise hydrophobic domains (e.g., polysiloxane such as PDMS) while the outer shell will comprise hydrophilic domains (e.g., polyglycerol). Decreasing the polarity of the chemical environment through addition of substances that are more hydrophobic than hydrophilic can lead to vesicles in which the outer shell comprises hydrophobic domains (e.g., polysiloxane such as PDMS) while the inner core comprises hydrophilic domains (e.g., polyglycerol). Upon cross-linking the outer shell, the inner core becomes trapped and does not migrate to the surface of the vesicle under contact lens use conditions. The cross-linking/polymerization can be achieved by a number of means, such as photo-polymerization, typically in the presence of a photo-initiator.

Also disclosed herein are methods of making silicone hydrogel compositions, for example by crosslinking the actinically-crosslinkable polysiloxane-polyglycerol block copolymers described herein. In some examples, the method of making the silicone hydrogel compositions can comprise mixing an initiator (e.g., photo-initiator, thermal initiator, or other suitable initiator) and a crosslinker with any of the actinically-crosslinkable polysiloxane-polyglycerol block copolymers to form a mixture and crosslinking the mixture to form the (cross-linked) silicone hydrogel composition. The crosslinking can, for example, be performed with the aid of any number of energy forms (e.g., thermal energy, visible light energy, X-Rays, gamma rays, microwaves, ultrasonic energy). In some examples, the crosslinking can comprise UV-curing (e.g., by UV irradiating the mixture) and the initiator can comprise a photo-initiator. In the case of UV-curing, the use of the photo-initiator is optional, however UV-curing in the absence of an added photo-initiator is generally slow and inefficient.

Suitable photo-initiators include, but are not limited to, acetophenone; anisoin; anthraquinone; benzoin; benzoin methyl ether; benzoin ethyl ether; benzoin isobutyl ether; diethoxyacetophenone; benzoylphosphine oxide; 1-hydroxycyclohexyl phenyl ketone; 50/50 blend of Benzophenone/1-Hydroxycyclohexyl phenylketone; 2,2-Diethoxyacetophenone; 4,4'-Dihydroxybenzophenone; 2,2-Dimethoxy-2-phenylacetophenone; 4-(Dimethylamino)-benzophenone; 4,4'-Dimethyl-benzyl; 2,5-Dimethylbenzophenone; 3,4-Dimethylbenzophenone; Diphenyl(2,4,6-trimethylbenzoyl) phosphine oxide/2-Hydroxy-2-methylpropiophenone; 50/50 blend; 4'-Ethoxyacetophenone; 3'-Hydroxyacetophenone; 4'-Hydroxyacetophenone, 3-Hydroxybenzophenone; 4-Hydroxybenzophenone; 1-Hydroxycyclohexyl phenyl ketone; 2-Methyl-4'-(methylthio)-2-morpholinopropiophenone; Phenanthrenequinone, 4'-Phenoxy-acetophenone; Thioxanthen-9-one; DARACURE® types (e.g., DARACURE® 1173); Irgacure® types (e.g., Irgacure 1173 and Irgacure® 2959); and UV/visible light photo initiators (Available from Spectra Group and sold under the trade names H-Nu 470, H-Nu 535, H-Nu 635).

Examples of thermal initiators include, but are not limited to, azo type initiators such as: 2,2'-azobis(2,4-dimethylpentanenitrile), 2,2'-azobis(2-methylpropanenitrile), 2,2'-azobis(2-methylbutanenitrile), Azobisisobutyronitrile (trade name VAZO 64); 2,2'-Azodi(2-methylbutyronitrile) (trade name VAZO 67); 2-2'-Azobis(2,4-dimethylvaleronitrile) (trade name VAZO 52); and 1,1'-Azobis(cyanocyclohexane) (trade name VAZO 88). In some examples, the thermal initiator is 2,2'-Azobis-(isobutyronitrile) (AIBN).

Other types of initiators include organic peroxy compounds such as: benzoyl peroxide; Luperox tert-Butyl hydro peroxide; tert-Butyl per acetate, t-butyl peroxyneodecanoate; t-butyl peroxypivalate; tertiary-butyl peroxyisopropyl carbonate; cumene hydro peroxide; 2,5-Di(tert-butylperoxy)-2,5-dimethyl-3-hexyne; Dicumyl peroxide; 2,5-Bis(tert-butylperoxy)-2,5-dimethylhexane; 2,5-Bis(tert-butylperoxy)-2,5-dimethylhexane; 1,1-Bis(tert-butylperoxy)-3,3,5-trimethylcyclohexane; 1,1-Bis(tert-butylperoxy)cyclohexane; tert-Butyl peroxide; Lauryl peroxide and the like. Many peroxy based initiators are sold under the trade name Luperox and are available from ARKEMA.

Cross-linkers include, for example, vinylic cross-linkers, difunctional isocyanate cross-linkers, difunctional epoxide cross-linkers, difunctional alkyl halides (e.g., difunctional acid halides), difunctional-anhydrides, bis-halo-alky derivatives, activated esters, or any number of difunctional reagents capable for forming chemical bonds with polyglycerol OH groups.

Examples of vinylic cross-linkers include but are not limited to: Ethylene glycol dimethacrylate; Triethylene glycol dimethacrylate; Diethyleneglycol Dimethacrylate; 1,3-Glycerol Dimethacrylate; 1,6-Hexanediol Dimethacrylate; 1,12-Dodecanediol Dimethacrylate; Trimethylolpropane Trimethacrylate; Poly (Ethyleneglycol) (400) Dimethacrylate; Isophorone Urethane Dimethacrylate; N,N'-Methylenebisacrylamide; 1,6-Hexamethylene bis-Methacrylamide; N,N'-Hexamethylenebismethacrylamide; N,N'-iso-Valerylidene bis-Methacrylamide; N,N'-Nonamethylenebisacrylamidem-Xylenebisacrylamide; 1,10-Decamethylene Glycol Diacrylate; 1,2-Propanediol Diacrylate; 1,3-Butanediol Diacrylate; 1,3-Propanediol Diacrylate; 1,4-Cyclohexanedimethyl Diacrylate; 1,5-Pentanediol Diacrylate; 1,9-Nonanediol Diacrylate; 2,2,3,3,4,4,5,5-Octafluoro-1,6-Hexanediol Diacrylate; 2,2,3,3-Tetrafluoro-1,4-Butanediol Diacrylate; 2-Butene-1,4-Diacrylate; Aliphatic Urethane Acrylate in Tripropylene Glycol Diacrylate; Diethylene Glycol Diacrylate; Ethylene Diacrylate; neo-Pentyl Glycol Diacrylate; Sorbitol Diacrylate; Hexamethylene Diacrylate; Thiol Diethylene Glycol Diacrylate; Tetraethylene Glycol Diacrylate; Triethylene Glycol Diacrylate; Bisphenol A Glycidyl Methacrylate; Pentaerythritol Tetramethacrylate; 1,3-Divinyltetramethyl-disiloxane; 3-Methacryloxypropyl Tris-(Vinyldimethylsiloxy) Silane; 1,1,5,5-Tetrahydroperfluoro-1,5-Pentanediol Dimethacrylate; 2,2,3,3,4,4,5,5-Octafluoro-1,6-Hexanediol Diacrylate; 2,2,3,3,4,4,5,5-Octafluoro-1,6-Hexanediol Dimethacrylate.

Examples of difunctional isocyanate cross-linkers include but are not limited to: Isophorone diisocyanate (IPDI), hexamethylene diisocyanate (HDI), methylene dicyclohexyl diisocyanate, toluene diisocyanate (TDI), Tolylene-2,4-diisocyanate, Tolylene-2,6-diisocyanate, trans-1,4-Cyclohexylene diisocyanate, Poly(propylene glycol), tolylene 2,4-diisocyanate terminated, 1,4-Diisocyanatobutane, 1,8-Diisocyanatooctane, 1,3-Bis(1-isocyanato-1-methylethyl) benzene, 2,2,4-Trimethylhexamethylene Diisocyanate, 2,4, 4-Trimethylhexamethylene Diisocyanate, 1,4-Phenylene diisocyanate, 1,3-Phenylene diisocyanate, m-Xylylene diisocyanate, and methylenediphenyl diisocyanate (MDI).

Examples of difunctional epoxide cross-linkers include but are not limited to: Bisphenol A diglycidyl ether, Glycerol diglycidyl ether, resorcinol diglycidyl ether, diglycidyl ether, bis(3,4-epoxycyclohexylmethyl) adipate, poly(ethylene glycol) diglycidyl ether, Bis[4-(glycidyloxy)phenyl]methane, 1,3-Butadiene diepoxide, 1,4-Butanediol diglycidyl ether, 1,4-Butanediol diglycidyl ether, 1,3-Butanediol diglycidyl ether, Bisphenol F diglycidyl ether, Bisphenol A propoxylate diglycidyl ether, neopentyl glycol diglycidyl ether, N,N-Diglycidyl-4-glycidyloxyaniline, 4,4'-Isopropylidenediphenol diglycidyl ether, Poly(propylene glycol) diglycidyl ether, Dicyclopentadiene dioxide, 1,2,5,6-Diepoxycyclooctane, 1,2,7,8-Diepoxyoctane, Diglycidyl 1,2-cyclohexanedicarboxylate, 3,4-Epoxycyclohexylmethyl 3,4-epoxy cyclohexanecarboxylate, 2,5-bis[(2-oxiranylmethoxy)-methyl]-furan (BOF) and 2,5-bis[(2-oxiranylmethoxy)methyl]-benzene, Poly(dimethyl siloxane), tetraglycidyl-4,4'-diaminodiphenylmethane (TGDDM), tri-glycidyl-aminophenol, e. 3-(3-glycidoxypropyl)-1,1,1,3,5,5,5-heptamethyltrisiloxane, 1-epoxyethyl-3,4-epoxycyclohexane, 1,3,5-Triglycidyl isocyanurate, PC-1000 Epoxy Siloxane Monomer (available from Polyset), PC-1035 Epoxy Siloxane Monomer (available from Polyset), Poly(dimethylsiloxane), diglycidyl ether terminated (average Mn ~800, available from SIGMA ALDRICH), epoxy terminated Poly(dimethylsiloxanes) available from Shin Etsu Silicone Company and sold under the trade names KF-105; X-22-163A; X-22-163B; X-22-163C; X-22-169AS; X-22-169B available from Shin Etsu Silicone Company; BIS[2-(3,4-EPOXYCYCLOHEXYL)-ETHYL 2,4,6, 8-Tetramethyl-2,4,6,8-tetrakis(propyl glycidyl ether) cyclotetrasiloxane.

Examples of difunctional alkyl halides include but are not limited to: 1,4-Dibromobutane, 1,5-Dibromopentane, 1,6-Dibromohexane, 1,8-Dibromooctane.

Examples of difunctional acid chlorides include but are not limited to: malonyl chloride, isophthaloyl di-acid chloride, sebacoyl chloride, dodecanedioyl dichloride, octanedioic acid dichloride, fumaryl chloride, glutaryl chloride.

Examples of difunctional-anhydrides include but are not limited to: Diethylene-triaminepentaacetic dianhydride, 4,4'-(4,4'-Isopropylidenediphenoxy) bis(phthalic anhydride), 4,4'-(Hexafluoroisopropylidene)-diphthalic anhydride, bis(phthalic anhydride), 4,4'-Oxydiphthalic anhydride, 3,3',4,4'-Biphenyltetracarboxylic dianhydride, Benzophenone-3,3',4,4'-tetracarboxylic dianhydride, and Pyromellitic di-anhydride. Silicones containing two or more anhydride groups per polymer chain many also be used as cross-linkers. The dual end anhydride terminated Poly(dimethylsiloxanes) available from Shin Etsu Silicone Company and sold under the trade name X-22-2290AS may also be used as a cross-linking agent.

Examples of Bis-haloalkylether-derivatives include: Bis (chloromethyl) ether, Bis(bromomethyl) ether, bis(iodomethyl) ether, bis(chloroethyl) ether, bis(bromoethyl) ether, bis(iodoethyl) ether.

Activated Esters such as: 3,3'-Dithiodipropionic acid di(N-hydroxysuccinimide ester) may also be used.

Dual end reactive silicones may also be used as cross-linking agents. Examples of reactive silicones bearing dual end methacrylate functionality sold under the trade names X-22-164A; X-22-164B area available from Shin Estu Silicone company.

Also disclosed herein are methods for making the silicone hydrogel compositions disclosed herein by actinically-crosslinking the actinically-crosslinkable polysiloxane-polyglycerol block copolymers described herein (AC-PDMS-PGLY), the method comprising: mixing any of the actinically-crosslinkable polysiloxane-polyglycerol block copolymers described herein with an initiator and optionally a hydrophilic monomer (e.g., an ethylenically unsaturated hydrophilic monomer), a hydrophobic monomer (e.g., an ethylenically unsaturated hydrophobic monomer), an amphiphilic monomer (e.g., an ethylenically unsaturated amphiphilic monomer), a zwitterionic monomer, an antimicrobial monomer, a UV-blocker, a blue light blocker, a dye, a pigment, a solvent, or a combination thereof, thereby forming a mixture and crosslinking the mixture to form a cross-linked silicone hydrogel composition.

Nearly any hydrophilic vinylic monomer can be used. Suitable hydrophilic monomers comprise, for example, hydroxyl-substituted lower alkyl ($C_1$ to $C_8$) (meth)acrylates, (meth)acrylamide, (lower allyl) (meth)acrylamides, ethoxylated (meth)acrylates, hydroxyl-substituted (lower alkyl) (meth)acrylamides, hydroxyl-substituted lower alkyl vinyl ethers, sodium vinyl sulfonate, sodium styrene sulfonate, 2-acrylamido-2-methylpropanesulfonic acid, methyl vinyl ether, vinyl acetate, and methacrylated glyco-monomers. Examples of hydrophilic monomers include but are not limited to N-Hydroxyethyl acrylamide; N,N-dimethyl acrylamide (DMA); N-Ethyl acrylamide; N-(3-Methoxypropyl) acrylamide; 2-hydroxyethylmethacrylate (HEMA); 2-hydroxyethyl acrylate (HEA); hydroxypropyl acrylate; hydroxypropyl methacrylate (HPMA); N-[Tris(hydroxymethyl)methyl]acrylamide; trimethylammonium 2-hydroxy propylmethacrylate hydrochloride; dimethylaminoethyl methacrylate (DMAEMA); glycerol methacrylate (GMA); N-vinyl-2-pyrrolidone (NVP); dimethylaminoethyl methacrylamide; (meth)acrylamide; allyl alcohol; vinyl pyridine; N-(1,1dimethyl-3-oxobutyl)acrylamide; acrylic acid (AA); methacrylic acid (MAA); N-(2-methacryloyloxy)ethyl-N,N-dimethylammino propane sulfonate; N-(3-methacryloylimino)propyl-N,N-dimethylammino propane sulfonate; N-(3-methacryloylimino)propyl-N,N-dimethylammino propane sulfonate; 2-(methacryloyloxy)ethyl phosphatidylcholine and 3-(2'-vinyl-pyridinio) propane sulfonate, 6-O-vinylsebacyl-D-glucose, fructose methacrylate, glucose methacrylate, ribose methacrylate, mannitol methacrylate, sorbitol methacrylate, methacrylated oligosaccharides, methacrylated oligo-fructose, 2-Acetoacetoxy-ethyl Methacrylates, Tetrahydrofurfuryl Methacrylates; 2-Hydroxyethyl Methacrylates/Succinates; 2-Hydroxyethyl Methacrylate Phosphates; Hepta-O-benzyl monomethacryloyl sucrose. In some examples, the methods can further comprise forming the hydrophilic monomer. In some examples, copolymers containing vinyl acetate units can be rendered hydrophilic through hydrolysis of acetate groups (vinyl alcohol units are formed). For example, poly(vinyl acetate) upon hydrolysis becomes hydrophilic and water soluble.

Examples of hydrophobic monomers include but are not limited to Methyl methacrylate; ethyl methacrylate; butyl methacrylate; hexyl methacrylate; tert-butyl methacrylate; cyclohexyl methacrylate; Isobornyl Methacrylates; and 2-ethylhexyl methacrylate; heptyl methacrylate; octal methacrylate; Lauryl methacrylate; 2,2,2-trifluoroethyl methacrylate, 1,1-dihydroperfluoroethylacrylate, 1H,1H,7H-dodecafluoroheptyl acrylate; hexafluoroisopropyl acrylate, 1H,1H,2H,2H-heptadecafluorodecyl acrylate, pentafluorostyrene, trifluoromethyl styrene, pentafluoroethyl acrylate, pentafluoroethyl methacrylate, hexafluoroisopropyl acrylate, hexafluoroisopropyl methacrylate (HFIPMA), methacrylate-functionalized fluorinated polyethylene oxides; 3-Methacryloxypropyl Tris-(Trimethylsiloxy) Silane, 3-Methacryloxypropyl Tris-(Trimethylsiloxy) Silane; Methacryloxyethoxytris-(Trimethylsiloxy) Silane; Trimethylsilylmethyl Methacrylate; 1H,1H,11H-Eicosafluoroundecyl Methacrylate; a 1H,1H,9H-Hexadecafluorononyl Acrylate; 4-Vinylbenzyl Hexafluoroisopropyl Ether; Pentafluorobenzyl Acrylate; Pentafluorobenzyl Methacrylate; Perfluorocyclohexyl Methyl Acrylate, Perfluorocyclohexylmethyl Methacrylate; m-Fluorostyrene and the like.

Examples of Amphiphilic Monomers include but are not limited to 2-Methoxyethoxyethyl Methacrylates; Ethoxyethyl Methacrylates; 2-(dimethylamino)ethyl methacrylate; 2-(diethylamino)ethyl methacrylate; N-[3-(Dimethylamino)-propyl] acrylamide; N-[3-(Dimethylamino)propyl] meth-acrylamide; Hydroxy oligo(ethylene glycol)$_6$ methacrylate; Methoxy oligo(ethylene glycol)s methacrylate; N-(1.1-di(O—B-D-glucorpyranosyloxymethyl)-1-(undecyl carbamoyloxymethyl) methyl)acrylamide; 5-acrylamido-5-undecylcarbamoyloxymethyl-2.2-dimethyl-cyclol, 3 dioxahexane; N-(1,1-(2',3',4'6"tetra-O-acetyl-B-D-glucopyranosyloxy-methyl)-1-(undecylcarbamoyl oxymethyl)-methyl)-acryl-amide; N-1,1-di(hydroxymethylmethyl)-1 (undecylcarbamoyl Oxymethyl)-methyl)acrylamide; N-(1, 1-(2, 3, 4, 6-"tetra-O-acetyl-ft-D-glucopyranosyloxy-methyl)-1-(undecyl carbamoyloxymethyl)-methyl)-acryl-amide; (2-Hydroxy-3-Methacryloxypropyl) Trimethylammonium Chloride; acrylamide functionalized Polyetheramine such as Acrylamide derivatives of polyether amines. Polyetheramines are available from Huntsman Chemical and sold under the trade name "Jeffamine" (examples of polyether amines include Jeffamine M-(600, 1000, 2005, 2070)

Zwitterionic Monomers include, but are not limited to, 1-(3-Sulfopropyl)-2-Vinylpyridinium Betaine; N-(3-Sulfopropyl)-N-Methacryloxyethyl-N,N-Dimethylammonium Betaine; and N-(3-Sulfopropyl)-N-Methacryloylamidopropyl-N,N-Dimethylammonium Betaine.

Examples of antimicrobial monomers include but are not limited to 2 (Methacryloyloxy)-ethyl]-trimethylammonium chloride; 2-(methacryloxy)ethyl]dimethyl dodecyl ammonium chloride; 2-(methacryloxy)ethyl]-dimethyl hexadecyl ammonium chloride; 2-(methacryloxy)decyl]dimethyl hexadecyl ammonium chloride; 2-(methacryloxy)-dodecyl]dimethyl hexadecyl ammonium chloride; 2-(methacryloxy) hexadecyl]dimethyl hexadecyl ammonium chloride; [2-(methacryloxyethyl]azabicyclo[2.2.2]ammonium chloride; 1-{2-[(2-methylprop-2-enoyl)oxy]ethyl}pyridin-1-ium chloride; 1-{2-[(2-methylprop-2enoyl)oxy]decyl}pyridin-1-ium chloride; 1-{2-[(2-methylprop-2-enoyl)oxy] dodecyl}pyridin-1-ium chloride; 1-{2-[(2-methylprop-2-enoyl)oxy]hexadecyl}pyridin-1-ium chloride.

Examples of UV-Blockers include: 2-[3-(2H-Benzotriazol-2-yl)-4-hydroxyphenyl]ethyl methacrylate; 2-{2'-Hydroxy-5'-(γ-propoxy)-3'-t-butylphenyl}-5-methoxy-2H-benzotriazole, 2-(2H-Benzotriazol-2-yl)-4-methyl-6-(2-propenyl)phenol; and 1-(2-METHYL-ALLYL)-1H-BENZOTRIAZOLE; 2-hydroxy-4-Acryloyloxybenzophenone).

Examples of Blue Light Blockers include various yellow and or orange dyes. Examples of yellow dyes include but are not limited to: N,N-bis-(2-allylcarbomatoethyl)-(4'-phenylazo) aniline, N,N-bis-(2-hydroxyethyl)-(4-phenylazo)

aniline; N,N-bis-(2-vinylacetoxyethyl)-(4'-phenylazo)aniline; and N-2-[3'-2"-methylphenylazo)-4'-hydroxyphenyl] ethylvinylacetamide. Examples of orange dyes include but are not limited to: Reactive Orange 16 (Reactive Orange 13 (PROCION ORANGE H-2R), disperse orange 3 acrylamide, disperse orange 3 meth-acrylamide, disperse orange 3 acrylate, disperse orange 3 methacrylate, disperse orange 25 acrylamide, disperse orange 25 methacrylamide, disperse orange 25 acrylate, and disperse orange 25 methacrylate, Reactive orange dye containing vinyl sulfone.

Solvents include, but are not limited to: alcohols such as methanol, ethanol, isopropanol, 1-propanol, n-butanol, ter-tbutyl alcohol, t-amyl alcohol; Isoamyl alcohol; Benzyl alcohol; 2-Ethylhexanolethyleneglycol, propylene glycol; ethyl lactate, cyclopentanone, 2-ethoxyethanol, glycerin, 2-Butoxyethanol; Propylene Glycol Monomethyl Ether; Decyl Alcohol; Cyclohexanol; Diethylene glycol monobutyl ether; Glymes such as Ethylene glycol dimethyl ether; Ethylene glycol diethyl ether; Diethylene glycol dimethyl ether; Dipropylene glycol dimethyl ether; Diethylene glycol dibutyl ether; Poly(ethylene glycol) dimethyl ether; Tetraethylene glycol dimethyl ether; Ethyl Acetate; Propyl Acetate; n-Butyl Acetate; t-Butyl Acetate; Propylene carbonate; Dimethyl carbonate; Diethyl carbonate; 2 Ethylhexyl Acetate; Butyrolactone; Acetone, methyl ethyl ketone, cyclopentanone; cyclohexanone; 2-heptanone, -methyl-2-hexanone; Acetyl acetone; Ethyl propionate; Methyl isobutyl ketone; 2-Butoxyethanol acetate; Bis(2-ethylhexyl) adipate; Methyl phenyl acetate; Methyl lactate; Hexyl acetate; Dimethyl form amide, N-methylpyrolidone, 2-Methyl-tetrahydrofuran; N,N-dimethyl lactamide, Tetrahydrothiophene (Sulfolane), acetamide, dimethyl acetamide. Mixtures of one or more solvents can also be used.

Also disclosed herein are methods of making the UV-Blocking actinically-crosslinkable polysiloxane-polyglycerol block copolymers described herein, the methods comprising mixing any of the actinically-crosslinkable polysiloxane-polyglycerol block copolymers described herein with a UV-blocker. Also disclosed herein are methods of making UV-blocking silicone hydrogel compositions, the methods comprising crosslinking any of the UV-Blocking actinically-crosslinkable polysiloxane-polyglycerol block copolymers described herein.

Also disclosed herein are methods of making the blue light-blocking actinically-crosslinkable polysiloxane-polyglycerol block copolymers described herein, the methods comprising mixing any of the actinically-crosslinkable polysiloxane-polyglycerol block copolymers described herein with a blue light-blocker. Also disclosed herein are methods of making blue light-blocking silicone hydrogel compositions, the methods comprising crosslinking any of the blue light-blocking actinically-crosslinkable polysiloxane-polyglycerol block copolymers described herein.

Also disclosed herein are methods of making the interpenetrating polymer networks described herein. The methods of, making the interpenetrating polymer networks can comprise polymerization any of the actinically-crosslinkable polysiloxane-polyglycerol block copolymers described herein in the presence of a hydrophilic monomer, a hydrophobic monomer, an amphiphilic monomer, an initiator, a solvent, or a combination thereof. An "interpenetrating polymer network" (IPN) as used herein refers broadly to an intimate network of two or more polymers at least one of which is either synthesized and/or crosslinked in the presence of the other(s). Techniques for preparing IPN are known to one skilled in the art (see, for example, U.S. Pat. Nos. 4,536,554; 4,983,702; 5,087,392; and 5,656,210).

Also disclosed herein are methods of forming a cross-linked network from a polysiloxane-polyglycerol copolymer (PDMS-PGLY) through addition reactions of OH groups (OH from PDMS-PGLY) to suitable bi-functional or difunctional reagents. This type of reaction is illustrated below. Depending on the ratio of difunctional reagent (X—R—X, X—R—Y) relative to PDMS-PGLY, a cross-linked network can form or molecular weight may increase without resulting in the formation of a cross-linked network. An increase in molecular weight without forming a cross-linked network is defined as chain extension, which is discussed further below. Gelation is the stage in a chemical reaction at which a polymer is no longer able to flow due to the formation of a cross-linked network. In a theoretical sense, gelation is characterized by interconnected polymers chains (Network Structure) forming an infinitely large molecule which is not able to flow. Cross-linking reactions can continue to occur beyond the point of gelation thereby increasing the degree of rigidity of the polymer network. Scheme 10 is an illustration showing gelation/Cross-linking/formation of a cross-linked network formation from reaction of PDMS-PGLY or AC-(PDMS-PGLY) with X—R—X. Gelation occurs if.

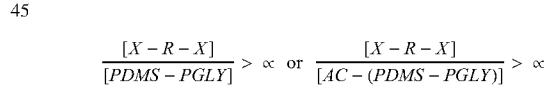

$$\frac{[X-R-X]}{[PDMS-PGLY]} > \propto \quad \text{or} \quad \frac{[X-R-X]}{[AC-(PDMS-PGLY)]} > \propto$$

where $\propto$ is defined as the critical value for gelation to occur.

Scheme 10. Formation of Cross-Linked Network from PDMS-PGLY and difunctionaol reagent X—R—X.

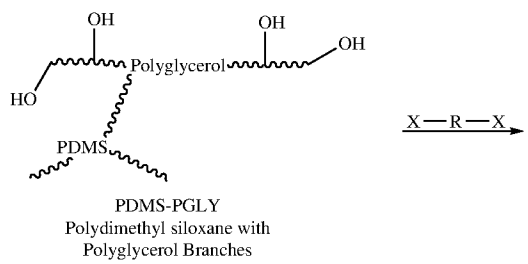

PDMS-PGLY
Polydimethyl siloxane with
Polyglycerol Branches

X—R—X

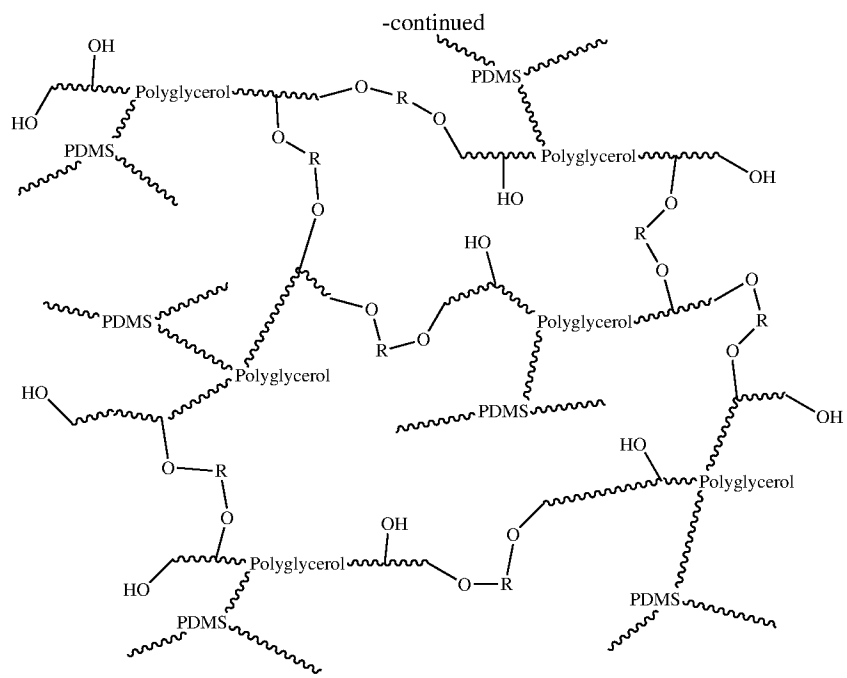

Chain extension of PDMS-PGLY or AC-(PDMS-PGLY) through reaction with bifunctional agent X—R—X is illustrated in Scheme 11. Chain extension occurs if:

$$\frac{[X-R-X]}{[PDMS-PGLY]} < \alpha \quad \text{or} \quad \frac{[X-R-X]}{[AC-(PDMS-PGLY)]} < \alpha$$

where $\alpha$ is defined as the critical value for gelation to occur.

Scheme 11. Chain extension reaction of PDMS-PGLY through reaction with difunctional reagent X—R—X.

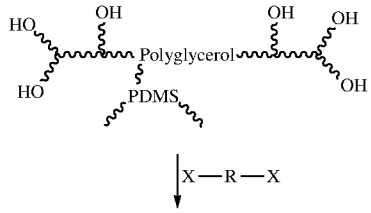

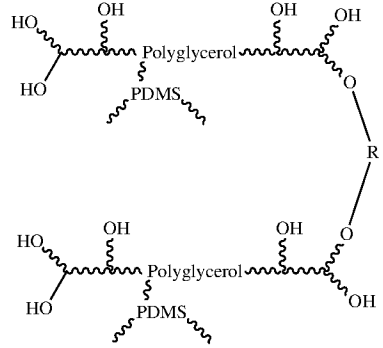

Chain extension of PDMS-PGLY through reaction with a chain extender is illustrated in Scheme 12.

Scheme 12. Synthesis of actinically curable chain extended polydimethylsiloxane-polyglycerol (AC-CE-(PDMS-PGLY)).

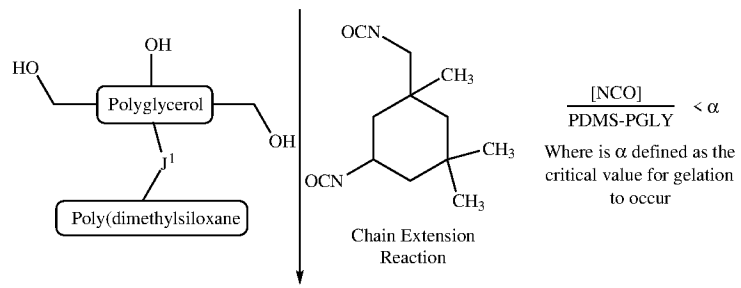

$$\frac{[NCO]}{PDMS\text{-}PGLY} < \alpha$$

Where is $\alpha$ defined as the critical value for gelation to occur

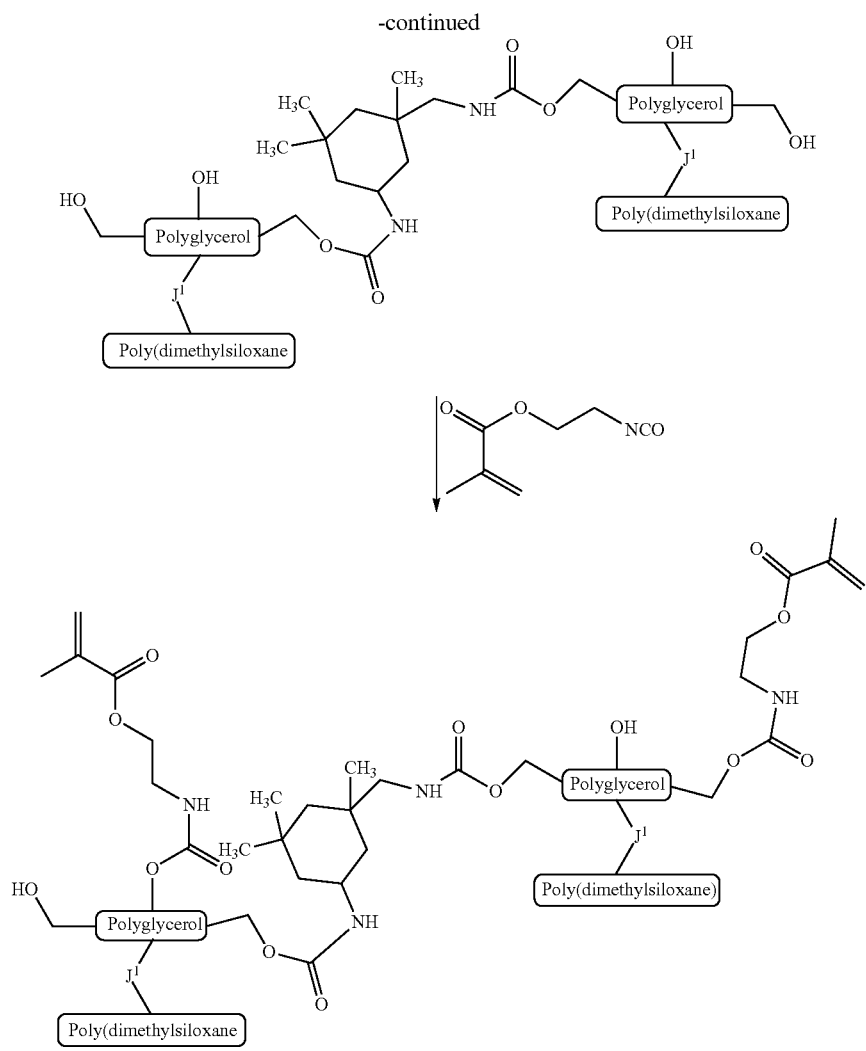

Use of IPDI as a chain extender to produce AC-CE-(PDMS-PGLY) is illustrated in Scheme 13. Other diisocyanates such as HDI, MDI, etc. can also be used as chain extending reagents. Scheme 13 illustrates the preparation of CE-PDMS followed by conversion to AC-CE-PDMS-PGLY. Alternatively, AC-PDMS-PGLY can be formed in step one of a two-step reaction sequence and then AC-PDMS-PGLY can be converted to AC-CE-PDMS-PGLY in a second step.

Chain extended PDMS-PGLY copolymers described herein are hereby referred to as "CE-PDMS-PGLY". Copolymers of the present invention can be joined together by mixing PDMS-PGLY with a di-functional monomer (X—R—Y) and optionally solvent and catalyst to promote addition reactions between OH groups from polyglycerol segments and the difunctional monomer, and allowing the reaction to proceed until the difunctional-monomer is substantially consumed. In order to obtain chain extended PDMS-PGLY, the ratio of difunctional monomer relative to PDMS-PGLY must be sufficiently low so as to prevent gelation, as discussed above.

Actinically curable chain extended copolymers described herein are hereby referred to as "AC-CE(PDMS-PGLY)". These copolymers can be joined together by mixing AC-(PDMS-PGLY) with a di-functional monomer (X—R—Y) and optionally solvent and catalyst to promote addition reactions between OH groups from polyglycerol segments and the difunctional monomer, and allowing the reaction to proceed until the difunctional-monomer is substantially consumed. In order to obtain chain extended AC-(PDMS-PGLY), the ratio of difunctional monomer relative to AC-(PDMS-PGLY) must be sufficiently low so as to prevent gelation, as discussed above.

At a sufficiently high ratio of difunctional (X—R—Y) monomer to PDMS-PGLY a cross linked polymer network will form. The "R" group of the difunctional monomer can comprise alkyl, aryl, and siloxanes of various lengths. X and Y can be the same or different and can comprise any of the following functional groups: epoxy, isocyanate, ester, activated ester, carboxylic acid, Br, Cl, I, anhydride, and acylhalide. Chain extended block copolymers of polydimethylsiloxane-polyglycerol can be further converted to actinically curable materials (hereby known as AC-CE-PDMS-PGLY) through reaction with any number of reagents such as 2-isocyanatoethylmethacrylate (IEM), methacrylic anhydride, acryloyl chloride, 4-vinylbenzyl chloride, or Glycidyl (meth)acrylate.

Examples of difunctional reagents for chain extension include, but are not limited to, difunctional vinylic compounds, difunctional isocyanates, difunctional epoxides, difunctional alkyl halides (e.g., difunctional acid halides), difunctional-anhydrides, bis-halo-alkyl derivatives, activated esters, or any number of difunctional reagents capable for forming chemical bonds with polyglycerol OH groups.

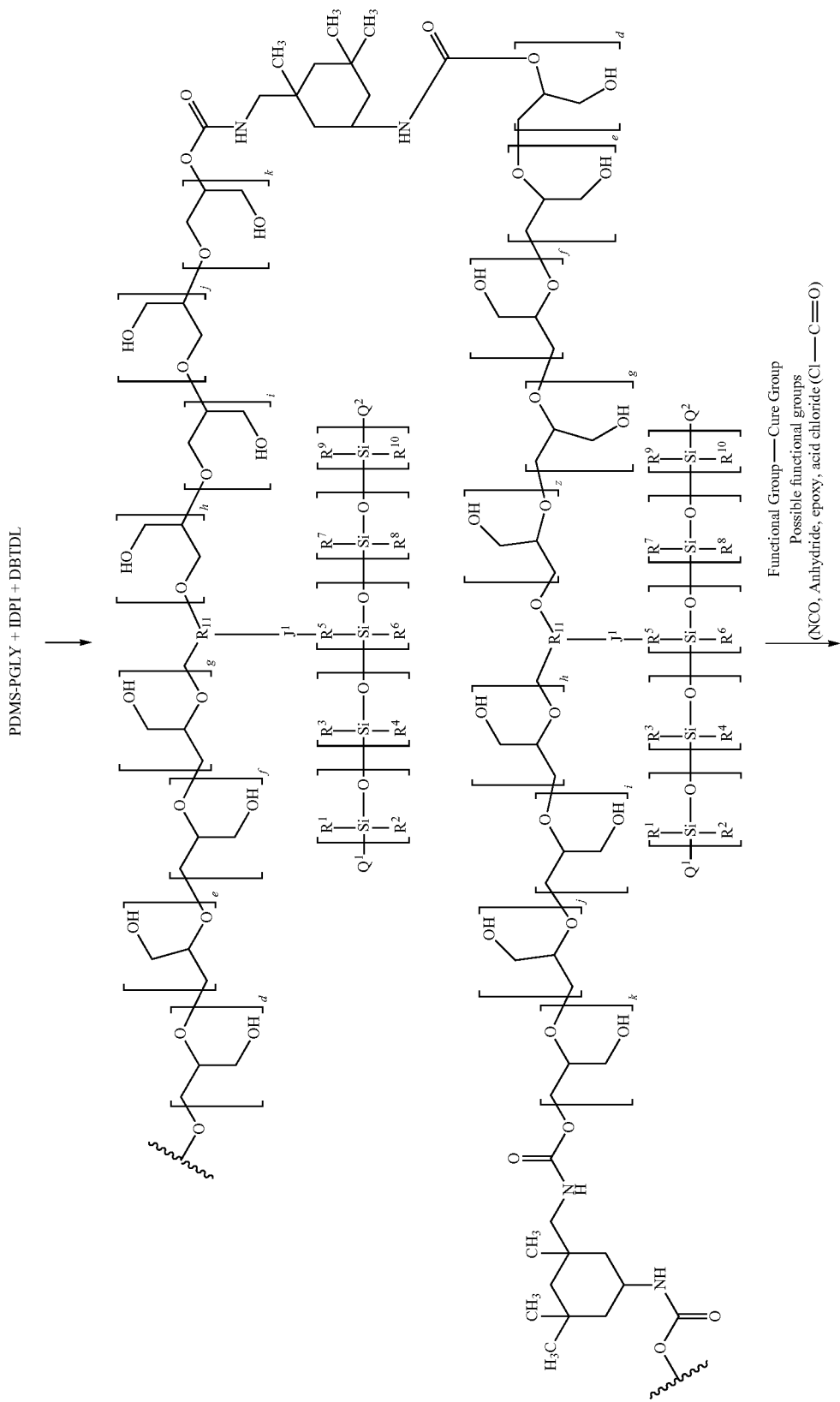
Scheme 13. Use of IPDI as a chian extender to produce CE-PDMS followed by conversion to AC-CE-PDMS-PGLY.

-continued
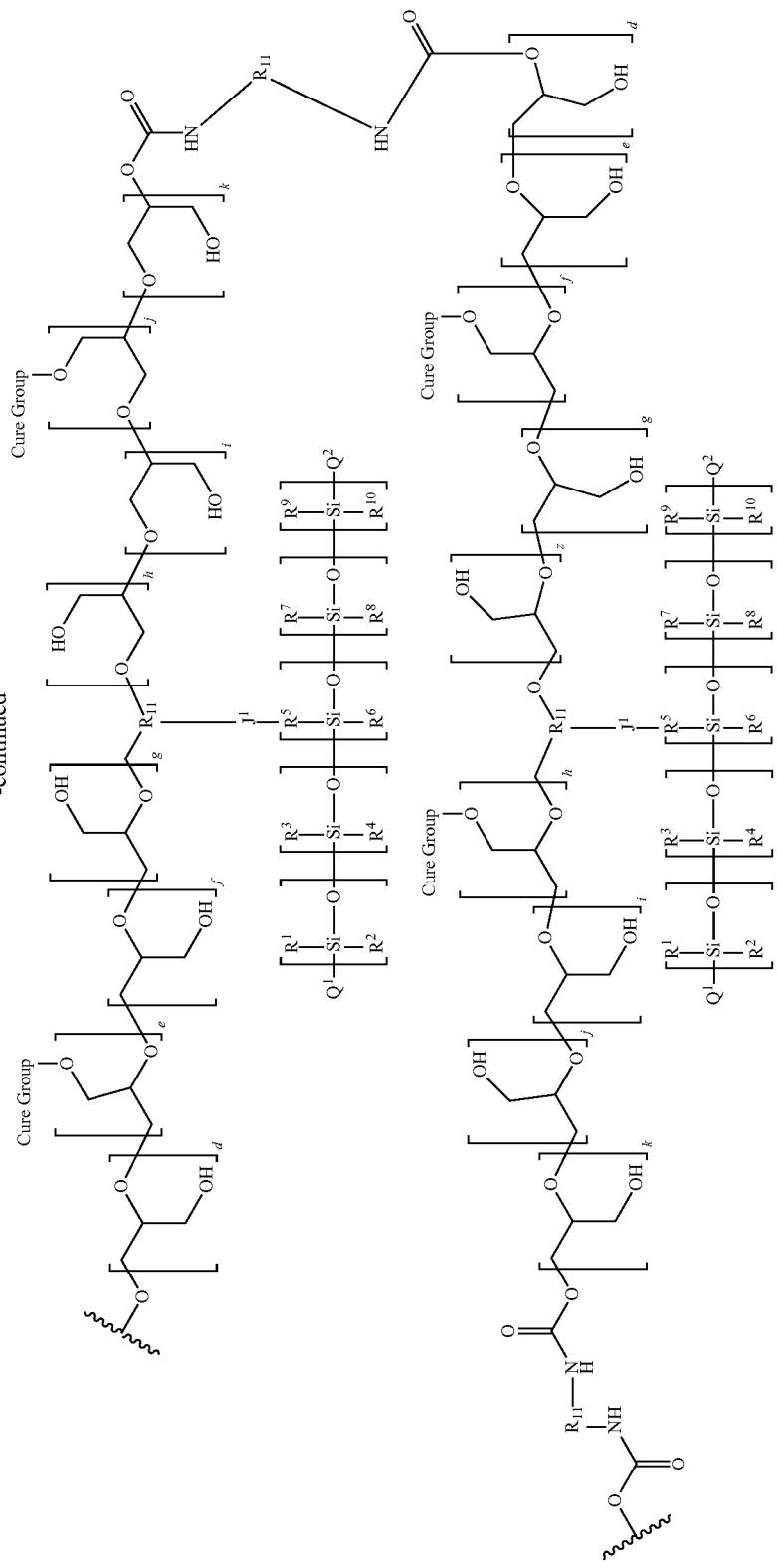

Examples of difunctional reagents known to react with hydroxyl groups include, but are not limited to, divinylethers (*J Polym Environ*, 2009, 17, 123-130).

Examples of difunctional vinyl ether chain extenders include, but are not limited to: ethylene glycol divinyl ether; 1-butanedio divinyl ether; triethyleneglycol divinyl ether; and 1,4-cyclohexane dimethanol divinyl ether.

Examples of difunctional isocyanate chain extenders include but are not limited to: Isophorone diisocyanate (IPDI), hexamethylene diisocyanate (HDI), methylene dicyclohexyl diisocyanate, toluene diisocyanate (TDI), Tolylene-2,4-diisocyanate, Tolylene-2,6-diisocyanate, trans-1,4-Cyclohexylene diisocyanate, Poly(propylene glycol), tolylene 2,4-diisocyanate terminated, 1,4-Diisocyanatobutane, 1,8-Diisocyanatooctane, 1,3-Bis(1-isocyanato-1-methylethyl)benzene, 2,2,4-Trimethylhexamethylene Diisocyanate, 2,4,4-Trimethylhexamethylene Diisocyanate, 1,4-Phenylene diisocyanate, 1,3-Phenylene diisocyanate, m-Xylylene diisocyanate, and methylenediphenyl diisocyanate (MDI).

Examples of difunctional epoxide chain extenders include but are not limited to: diglycidyl ether, Bisphenol A diglycidyl ether, Glycerol diglycidyl ether, resorcinol diglycidyl ether, diglycidyl ether, bis(3,4-epoxycyclohexylmethyl) adipate, poly(ethylene glycol) diglycidyl ether, Bis[4-(glycidyloxy)phenyl]methane, 1,3-Butadiene diepoxide, 1,4-Butanediol diglycidyl ether, 1,3-Butanediol diglycidyl ether, Bisphenol F diglycidyl ether, Bisphenol A propoxylate diglycidyl ether, neopentyl glycol diglycidyl ether, N,N-Diglycidyl-4-glycidyloxyaniline, 4,4'-Isopropylidenediphenol diglycidyl ether, Poly(propylene glycol) diglycidyl ether, Dicyclopentadiene dioxide, 1,2,5,6-Diepoxycyclooctane, 1,2,7,8-Diepoxyoctane, Diglycidyl 1,2-cyclohexanedicarboxylate, 3,4-Epoxycyclohexylmethyl 3,4-epoxy cyclohexanecarboxylate, 2,5-bis[(2-oxiranylmethoxy)-methyl]-furan (BOF) and 2,5-bis[(2-oxiranylmethoxy)methyl]-benzene, Poly(dimethyl siloxane), tetraglycidyl-4,4'-diaminodiphenylmethane (TGDDM), tri-glycidyl-aminophenol, e. 3-(3-glycidoxypropyl)-1,1,1,3,5,5,5-heptamethyltrisiloxsane, 1-epoxyethyl-3,4-epoxycyclohexane, 1,3,5-Triglycidyl isocyanurate, PC-1000 Epoxy Siloxane Monomer (available from Polyset), PC-1035 Epoxy Siloxane Monomer (available from Polyset), Poly(dimethylsiloxane), diglycidyl ether terminated (average Mn ~800, available from SIGMA ALDRICH), epoxy terminated Poly(dimethylsiloxanes) available from Shin Etsu Silicone Company and sold under the trade names KF-105; X-22-163A; X-22-163B; X-22-163C; X-22-169AS; X-22-169B available from Shin Etsu Silicone Company; BIS[2-(3,4-EPOXYCYCLOHEXYL)-ETHYL TETRAMETHYLDISILOXANE, and 2,4,6,8-Tetramethyl-2,4,6,8-tetrakis(propyl glycidyl ether)cyclotetrasiloxane.

Examples of difunctional alkyl halides include but are not limited to: 1,4-Dibromobutane, 1,5-Dibromopentane, 1,6-Dibromohexane, 1,8-Dibromooctane.

Examples of difunctional acid chlorides include but are not limited to: malonyl chloride, isophthaloyl di-acid chloride, sebacoyl chloride, dodecanedioyl dichloride, octanedioic acid dichloride, fumaryl chloride, glutaryl chloride.

Examples of difunctional-anhydrides include but are not limited to: Diethylene-triaminepentaacetic dianhydride, 4,4'-(4,4'-Isopropylidenediphenoxy) bis(phthalic anhydride), 4,4'-(Hexafluoroisopropylidene)-diphthalic anhydride, bis(phthalic anhydride), 4,4'-Oxydiphthalic anhydride, 3,3',4,4'-Biphenyltetracarboxylic dianhydride, Benzophenone-3,3',4,4'-tetracarboxylic dianhydride, and Pyromellitic di-anhydride. Silicones containing two or more anhydride groups per polymer chain many also be used as cross-linkers. The dual end anhydride terminated Poly(dimethylsiloxanes) available from Shin Etsu Silicone Company and sold under the trade name X-22-2290AS may also be used as a cross-linking agent.

Examples of Bis-haloalkylether derivatives include: Bis (chloromethyl) ether, Bis(bromomethyl) ether, bis(iodomethyl) ether, bis(chloroethyl) ether, bis(bromoethyl) ether, bis(iodoethyl) ether.

Activated Esters such as: 3,3'-Dithiodipropionic acid di(N-hydroxysuccinimide ester) may also be used.

Dual end reactive silicones may also be used as chain extending agents. Reactive end groups for silicones include, but are not limited to, epoxy, carboxylic anhydride, reactive esters, and alkyl halides. Examples reactive silicones bearing dual end epoxy functionality sold under the trade names X-22-163; KF-105, X-22-163A; X-22-163B; and X-22-163C available from Shin Estu Silicone Company. Examples of reactive silicones bearing dual end carboxylic acid anhydrides include: X-22-168AS, X22-168A, and X-22-168-P5B available from Shin Etsu Silicone Company.

Chain extenders (CE) as defined herein are difunctional reactive compounds (X—R—Y) that are capable of reacting with OH groups (e.g., OH groups from polyglycerol segments). The R group in the chain extender can comprise a low molecular weight species or a polymeric species. Chain extenders can be used to join units of PDMS-PGLY or AC-PDMS-PGLY together, for example as shown in Scheme 14 and Scheme 15, respectively.

PDMS-PGLY-OH+X—R—Y+OH-PGLY-PDMS→PDMS-PGLY—O—R—O-PGLY-PDMS Scheme 14. Use of chain extender X—R—Y to join units of PDMS-PGLY together.

AC-PDMS-PGLY-OH+X—R—Y+OH-PGLY-PDMS-AC→AC-PDMS-PGLY—O—R—O-PGLY-PDMS-AC
Scheme 15. Use of chain extender X—R—Y to join units of AC-PDMS-PGLY together.

Reaction of PDMS-PGLY with diisocyanate followed by functionalization with methacryloyl chloride to form Chain extended actinically polymerizable poly(dimethyl siloxane) bearing polyglycerol branches(AC-CE-PDMS-PGLY) is shown in Scheme 16. Any number of diisocyanates may be used in the chain extension process. Likewise, any number of bi-functional vinylic monomers may be used to render the copolymer actinically curable. As previously noted, any number of reagents may be used to chain extend PDMS-PGLY while any number of reagents may be used to render the copolymer actinically curable.

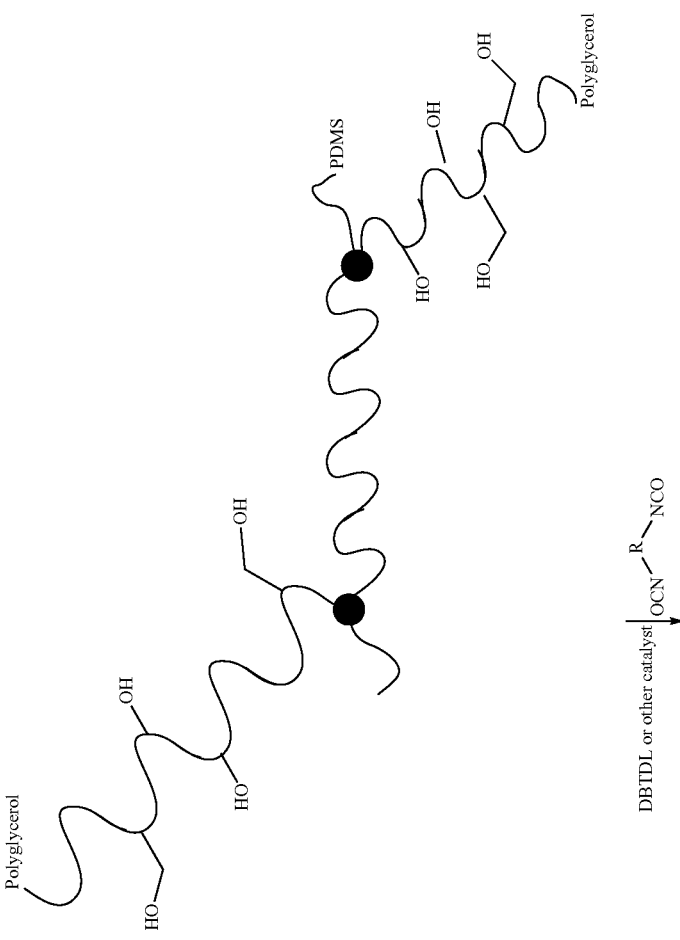
Scheme 16: Reaction of PDMS-PGLY with diisocyanate followed by functionalization with methacryloyl chloride to form Chain extended actinically polymerizable poly(dimethyl siloxane) bearing polyglycerol branches (AC-CE-PDMS-PGLY).

-continued

-continued
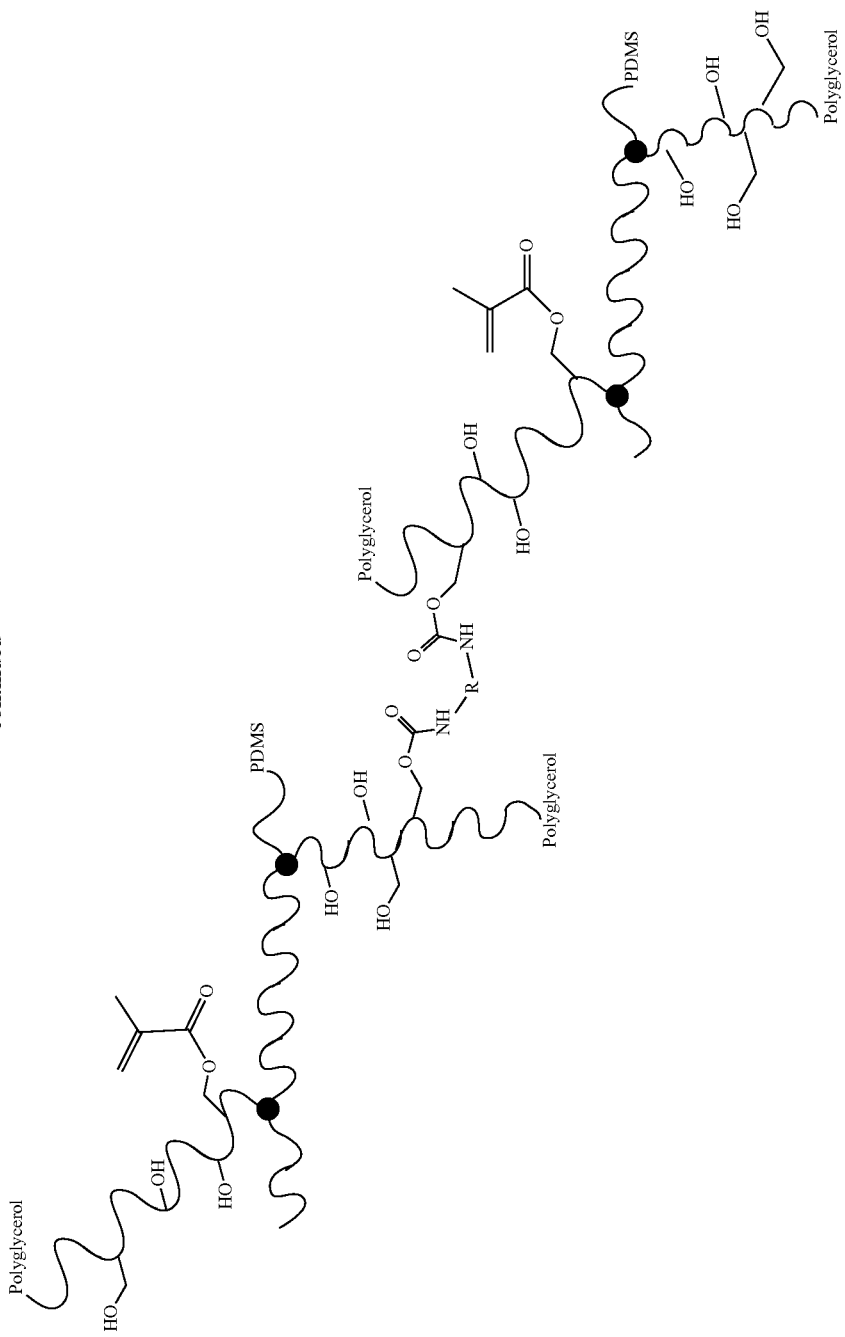

Also described herein are actinically curable silicone hydrogels (AC-CE-PDMS-PGLY) produced in accordance with the following steps of: (a) mixing PDMS-PGLY with a difunctional monomer (X—R—Y), optionally solvent and optionally catalyst to promote the formation of chemical linkages between polyglycerol OH segments, (b) allowing reaction to proceed until difunctional-monomer is substantially consumed, followed by (c) functionalization of CE-PDMS with bi-functional reagents such as (CH2=CR—Z). Some examples of functionalization reagents include: acryloyl chloride, methacryloyl chloride, Glycidyl methacrylate, methacrylic anhydride allyl chloride, vinyl-benzyl chloride, methacrylic acid, acrylic acid, or 2-bromo-methacrylate.

Also described herein are methods of making contact lenses using chain extended or non-chain extended polydimethylsiloxane-polyglycerol copolymers containing actinically cross-linkable polyglycerol side branches described herein, the method comprising the steps of: mixing a polymerization initiator with the AC-PDMS-Polyglycerol and optionally one or more hydrophilic monomers, one or more hydrophobic monomers, one or more amphiphilic monomers, one or more zwitterionic monomers; one or more antimicrobial monomers, one or more UV-blocking monomers, one or more blue light blocking monomers, and one or more cross-linking agents. Cross-linking reactions can occur through reactions of difunctional vinylic monomers, difunctional isocyanates, difunctional epoxides, difunctional anhydrides, difunctional alkyl halides, or difunctional activated esters.

Also described herein are methods for producing hydrogel membranes with ordered structures for use as medical devices or components of medical devices. Also disclosed herein are methods of controlling the degree of ordering by addition or removal of various monomers and/or solvents. Furthermore, the degree of ordering can also be altered by increasing or decreasing temperature.

Also described herein are methods of increasing or decreasing the degree of self-assembly of the silicone hydrogels formulations described herein by increasing or decreasing temperature or by adding or removing various monomers, or solvent.

In some examples, the methods can further comprise making polyglycerol, such as linear or branched polyglycerol. In some examples, the polyglycerol can be made via a ring opening polymerization by contacting a reagent suitable for initiating a ring opening polymerization with glycidol. Reagents suitable for initiating ring opening polymerizations are known in the art and, for example, include, but are not limited to, bases (e.g., alkali metal alkoxides, alkali metal hydroxides, amines). Examples of alkali metal alkoxides include, but are not limited to, $NaOCH_3$, $NaOCH_2CH_3$, $KOCH_3$, $KOCH_2CH_3$, and $KOC(CH_3)_3$. Examples of alkali metal hydroxides, $R^{14}OM$ where $R^{14}$ is H, include NaOH, KOH, LiOH, RbOH, and CsOH.

Branched polyglycerol can be formed through reaction of glycidol with any number of linear, branched or cyclic primary amines or secondary amines. Examples of amino epoxy ring opening polymerization initiators suitable for producing polyglycerol include, but are not limited to, $NH_3$, $CH_3(CH_2)_mNH_2$ where m=0-20, $(CH_3)_2CHNH_2$, cyclopentyl-NH, cyclohexyl-NH, linear branched or cyclic dialkylamines (e.g., $(CH_3(CH_2)_m)_2NH$ where m=1-20, piperidinyl), and trialkyl ammonium groups (e.g., $(CH_3)_3N$, $(CH_3CH_2)_3N$, $(HOCH_2)_3N$, $(HOCH_2CH_3)_3N$). Reagents other than bases which are nucleophilic may also be used to initiate epoxy ring opening polymerization of glycidol. Thiols and thiol salts are known to initiate ring opening polymerization of glycidol. Examples of such thiols include but are not limited to linear, branched or cyclic alkyl-substituted thiol (e.g., HSH, $CH_3$—SH, $CH_3(CH_2)_mS$,j $(CH_3)_2CHS$, $(CH_3)_3CS$, cyclohexyl-SH). The molecular weight of branched polyglycerol may vary from 92 Daltons to 1,11000 Daltons. Molecular weight of polyglycerol is determined by the number of repeat units and the molecular weight of the initiating species.

In some examples, the polyglycerol can comprise a branched polyglycerol defined by Formula (III), which can be made using a ring opening polymerization as shown in Scheme 17, wherein $R^{14}OM$ is an alkali metal alkoxide or alkali metal hydroxide reagent suitable for initiating the ring opening polymerization. $R^{14}$ can comprise, for example, H, alkyl, or cycloalkyl, either of which is optionally substituted with halide, hydroxy, thioether, carbonyl, alkoxy, alkylhydroxy, carboxyl, amido, alkyl, alkenyl, alkynyl, aryl, —C(O)$NR^xR^y$, or a combination thereof, and $R^x$ and $R^y$ are independently H, OH, alkyl, alkenyl, alkynyl, cycloalkyl, aryl, alkylaryl, or heteroaryl. In some examples, $R^{14}$ can comprise H, methyl, ethyl, propyl, isopropyl, butyl, sec-butyl, or tert-butyl. M comprises an alkali metal, e.g., Li, Na, K, Rb, or Cs.

Scheme 17. Formation of branched polyglycerol of Formula (III) via ring opening polymerization.

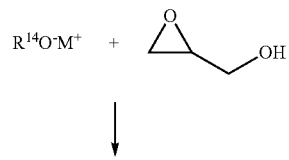

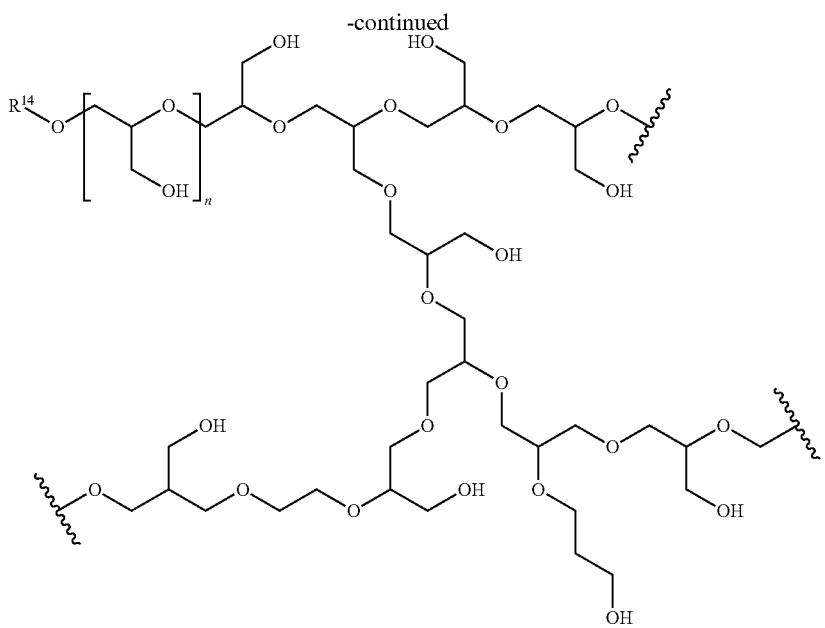
-continued

In some examples, the polyglycerol can comprise a branched polyglycerol defined by Formula (IV), which can be made using a ring opening polymerization as shown in Scheme 18.

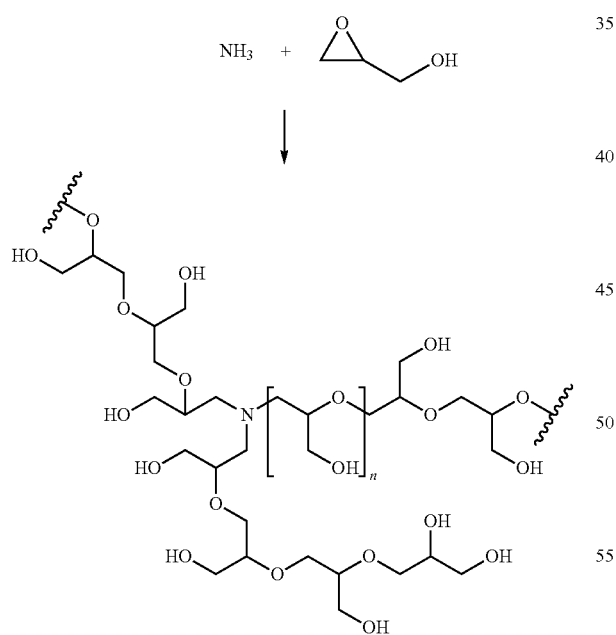

Scheme 18. Formation of branched polyglycerol of Formula (IV) via ring opening polymerization.

In some examples, the polyglycerol can comprise a branched polyglycerol defined by Formula (V), which can be made using a ring opening polymerization as shown in Scheme 19, where $R^{15}$ and $R^{16}$ are, independently, H, alkyl, or cycloalkyl, either of which is optionally substituted with halide, hydroxy, thioether, carbonyl, alkoxy, alkylhydroxy, carboxyl, amino, amido, alkyl, alkenyl, alkynyl, aryl, —C(O)NR$^x$R$^y$, or a combination thereof; or $R^{15}$ and $R^{16}$, together with the atoms to which they are attached, form a 3-10 membered cyclic moiety, wherein any of the additional atoms are optionally heteroatoms and the 3-10 membered cyclic moiety is optionally substituted with halide, hydroxy, thiol, carbonyl, alkoxy, alkylhydroxy, carboxyl, amido, alkyl, alkenyl, alkynyl, aryl, —C(O)NR$^x$R$^y$, or a combination thereof; and $R^x$ and $R^y$ are independently H, OH, alkyl, alkenyl, alkynyl, cycloalkyl, aryl, alkylaryl, or heteroaryl. In some examples, $R^{15}$ and $R^{16}$ are, independently, H, CH$_3$, CH$_3$CH$_2$, CH$_3$(CH$_2$)$_n$ where n=1-20, cyclopentyl, cyclohexyl, piperidinyl, (CH$_3$)$_3$, (CH$_3$CH$_2$)$_3$, (HOCH$_2$)$_3$, or (HOCH$_2$CH$_3$)$_3$.

Scheme 19. Formation of branched polyglycerol of Formula (V) via ring opening polymerization.

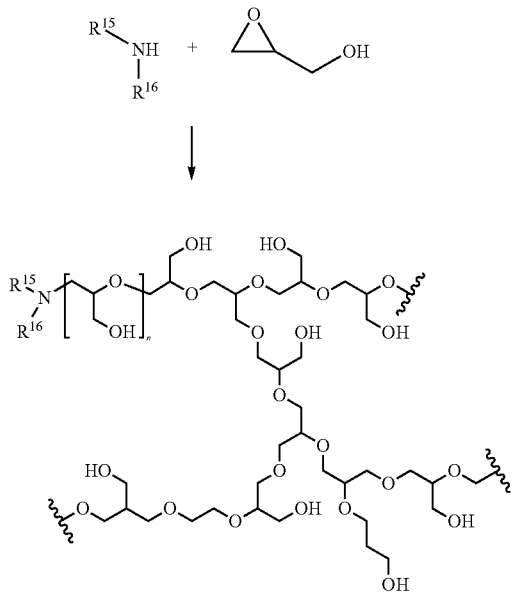

In some examples, the polyglycerol can comprise a branched polyglycerol defined by Formula (VI), which can be made using a ring opening polymerization as shown in Scheme 20.

Scheme 20. Formation of branched polyglycerol of Formula (VI) via ring opening polymerization.

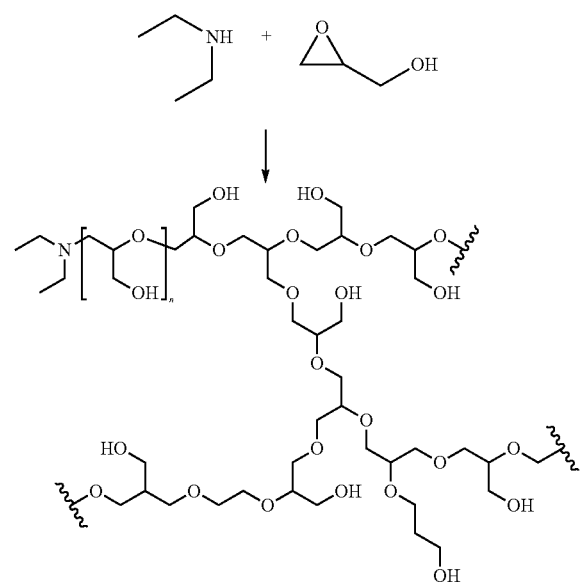

In some examples, the polyglycerol can comprise a branched polyglycerol defined by Formula (VII), which can be made using a ring opening polymerization as shown in Scheme 21.

Scheme 21. Formation of branched polyglycerol of Formula (VII) via ring opening polymerization.

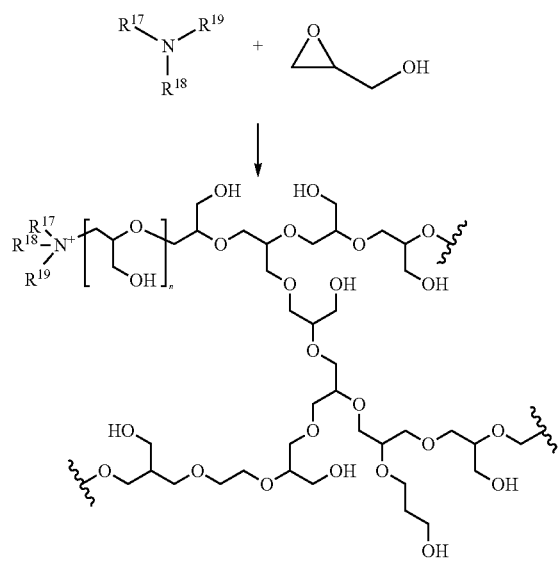

In some examples, the polyglycerol can comprise a branched polyglycerol defined by Formula (VIII), which can be made using a ring opening polymerization as shown in Scheme 22.

Scheme 22. Formation of branched polyglycerol of Formula (VIII) via ring opening polymerization.

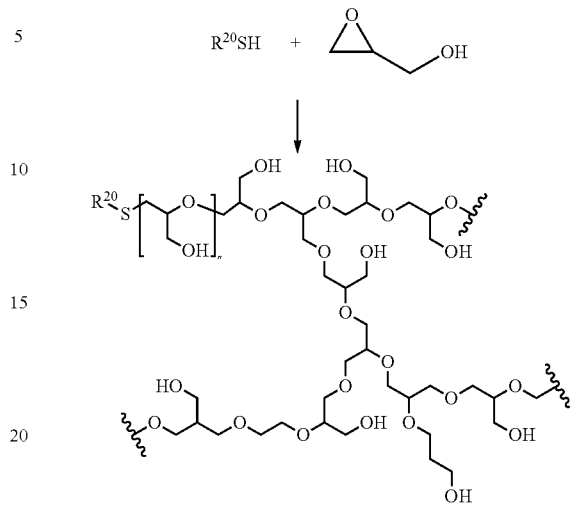

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

The examples below are intended to further illustrate certain aspects of the compositions and methods described herein and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Polydimethylsiloxane bearing polyglycerol branches (PDMS-PGLY) can be synthesized as illustrated in Scheme 9. Alternatively, PDMS-PGLY is available from Shin Etsu Chemical Co., Ltd and sold under the trade names of KF6100 (visocosity ~40,000 mPa*sec) and KF6104 (viscosity ~4,000 mPa*sec).

2-Hydroxy-2-methylpropiophenone (Daracure 1173), 2-Hydroxy-4'-(2-hydroxyethoxy)-2-methylpropiophenone (Irgacure 2959), Dibutyltin dilaurate (DBTDL), 2-Isocyanatoethyl methacrylate (IEM), Isophorone diisocyanate (IPDI), diethylene glycol, were obtained from SIGMA-ALDRICH. NVP was obtained from Shijiazhuang Aopharm Import & Export Trading Co., Ltd. Glyceryl monomethacrylate (GMMA) Methyl di(trimethylsiloxy) silylpropylglyceryl methacrylate (SIGMA) and was obtained from Bimax Chemicals Ltd.

Larger or smaller batch sizes as described herein can be employed to produce AC-(PDMS-PGLY), AC-CE-(PDMS-PGLY), or CE-(PDMS-PGLY). A solvent can be used in the synthesis operations to improve mixing, reduce viscosity, and/or improve control of reaction temperature. Equipment specifically designed for the mixing of viscous materials can be used as a means of improving mixing and control of reaction temperature. Increasing the ratio of diisocyanate relative to PDMS-PGLY (KF6100) can result in an increase in molecular weight while increasing the ratio of IEM relative to PDMS-PGLY and or diisocyanate can yield copolymers capable of forming more highly cross-linked networks.

Measurement of Contact Lens Water Content

The refractive index of a hydrogel is dependent on water content of the material. The water content of contact lenses described herein were measured based on this principle using an ATAGO handheld refractometer. ATAGO corporation sells handheld refractometers that are calibrated in % Solids (BRIX) or % Water depending on the model. If one uses a handheld refractometer calibrated in BRIX, then the water content of the contact lens=100−BRIX reading.

Measurement of Oxygen Permeability (Dk)

Oxygen permeability was determined using a polarographic measurement method. Rheders O2 Measurements were performed using Permeometer model 201T. Details for measuring oxygen permeability are available in ANSI Z80.20-2010.

Methods of Manufacturing Contact Lenses

Lathe cut contact lenses can be produced by using a lathe (example, use of ophthalmic lathe manufactured Sterling Ultra Precision Optiform 40, Optiform 60 or Optiform 80) to shape one surface of a singled sided molded part or by lathe shaping both the front and back surface of a contact lens material. Cured contact lens material in the form of blanks, bonnets, disks or buttons can be produced in plastic molds, glass molds, or metal molds. Alternatively, contact lens disks can be formed by filing a cylindrical tube with contact lens fluid material, curing the material, removing the resulting rod, cutting the rod into disks and forming a contact lens by double sided lathing (DSL). If the contact lens formulation is cured in a mold that imparts an optical quality anterior or posterior surface, only one side the resulting bonnet (blank) requires lathe cutting. For example, a contact lens can be produced by filling a bonnet shaped mold with a lens-forming fluid material, curing the lens formulation in the bonnet shaped mold, wherein the bonnet shaped mold includes a molding surface with optical quality, wherein the molding surface defines one of the posterior and anterior surface of the contact lens. Then the bonnet is removed from the mold and the anterior or posterior surface is formed by direct lathing of the bonnet on the side opposite to the molded surface (methods of producing lathe cut contact lenses are described in U.S. Pat. Nos. 3,835,588; 4,924,739; 5,347,896; and 7,213,918).

Contact lenses can be manufactured by a process known as double sided molding (DSM). This method comprises the steps of providing a mold for making a soft contact lens, wherein the mold has a one mold half with molding surface defining the anterior surface of a contact lens and a second mold half with a second molding surface defining the posterior surface of the contact lens. Typically, in the DSM process, a liquid contact lens formulation is dispensed into the female mold half, the male mold half is affixed to the female mold half and the fluid is converted to a solid in a polymerization reaction. Polymerization and cross-linking reactions (curing) are typically triggered by applying thermal energy or actinic radiation (e.g., visible light, UVA, UVB, UVC) thereby converting the liquid formulation into a solid contact lens. Contact lens formulations cured with actinic radiation can contain a photo-initiator suitable for use with the radiation source. For example, if one desires to cure contact lens formulation with visible light, the lens formulation can contain a visible light photo-initiator. If one desires to cure a contact lens formulation using UV radiation, the lens formulation can contain a UV photo-initiator. If one desires to cure a contact lens formulation using thermal energy, the formulation can contain a thermal initiator.

In a process known as double sided molding, contact lenses may be formed by molding the front surface and back surface of the lens. Materials used to make contact lens molds may be suitable for single use or repeated use. Double sided molding technology used in the production of contact lenses is described in a number of patents (e.g., U.S. Pat. Nos. 4,209,289; 4,347,198; 4,121,896; 5,271,874; 5,776,381; 8,491,824; EP0802852A2; U.S. Pat. No. 6,113,817). Contact lens molds are typically made from polypropylene or polystyrene. However, the mold can be made from any number of other materials including: nylon, glass, quartz glass, and metal. Single use contact lens molds are generally made from inexpensive plastics such as polypropylene, polystyrene, and polymethyl methacrylate. The contact lens mold materials should be chemically compatible (non-damaging) with the contact lens formulations. Re-usable molds can be made from glass/quartz, metals (e.g., stainless steel, tungsten carbide, titanium alloys, cobalt alloys, nickel alloys, copper alloys), ceramic materials, or suitable engineering resins. Engineering resins include but are not limited to composite materials which can contain glass fibers ("fiber glass"), carbon fibers, or boron fibers, Common engineering resins include materials such as polycarbonate, polyetheretherketone, polyetherimide (PEI), Topas (cyclic-olefin polymer, COC resin), nylon (Nylon 6; Nylon 12; Nylon 6,6; glass filled Nylons), polyphenylenesulfide, glass filled epoxy resin, polyphenyleneoxides (Noryl), polyesters (polybutylene terephthalate, Delrin (DuPont), glass filled polyesters (glass filled unsaturated polyester resins), polycarbonate-acrylic alloy, polyamide-imide, polyether sulphone, polytetrafluoroethylene and perfluoroalkylvinyl ether copolymer, polyvinylidene fluoride, perfluoroalkoxy alkane, and tetrafluoroethylene hexafluoropropylene vinylidene copolymer.

Contact lenses described herein were prepared in polypropylene contact lens molds using spin cast manufacturing technology. Spin cast manufacturing of contact lenses is described in a number of patents (e.g., U.S. Pat. Nos. 3,660,545; 3,408,429; 3,699,089; 4,517,139; 4,590,018). In spin cast manufacturing of contact lenses, molds are dosed with a formulation and rotated at a defined speed (in the absence of externally applied UV light) and then polymerization is triggered by UV light, thermal energy, or both. The centrifugal forces resulting from rotational motion helps spread (wet) the contact lens formulation across the mold and provides the concave lens curvature. Wetting of the contact lens molds by the lens formulation can be facilitated by surface treatment of the molds (e.g., corona or plasma treatment) and/or spinning at high speed (often at a speed higher than that which is used to obtain a specific lens power). Once molds containing the contact lens formulation are sufficiently wetted, the rotational speed is adjusted to achieve a targeted lens power. In the case of high speed spinning (higher than that desired for a particular lens power), rotational speed is decreased and the liquid monomer moves inward and a receding contact angle will be present at the lens edge. UV irradiation of the lens formulation triggers polymerization of the liquid lens monomer and provides a solid lens having a smooth edge. The resulting lens is characterized by a convex optical surface which corresponds to the concave surface of the mold and a concave optical surface whose geometry has been created, mainly by the centrifugal force. Polymerization of the lens formulation is typically conducted in a low oxygen environment. A low oxygen environment can be achieved by displacing air in a cure chamber with a gas such as nitrogen, argon, $CO_2$, or any number of gases that do not interfere with free radical polymerization.

Procedure for Preparation of Contact Lenses

The contact lenses can be produced using variety methods known in the art, such as double sided molding (DSM), spin casting, single sided molding single with single sided lathing (SSM-SSL), and double sided lathing (DSL).

Contact lenses described herein were prepared using spin cast technology. Briefly, about 14 to 20 microliters of lens formulation was dosed into corona treated polypropylene molds (the amount of contact lens formulation dosed into the molds varied depending on targeted optical power and thickness profile). The molds containing the contact lens formulation were rotated in the absence of externally applied UV light at a speed above that used during the polymerization process to aid in the wetting of the molds and spreading the contact lens formulation. Rotational speed of the molds containing lens formulation was then decreased sufficiently to achieve a targeted lens power. After a defined amount of time in a nitrogen flushed chamber, polymerization (cure) was triggered by irradiating the spinning molds containing the lens formulation with UV light. The spinning molds containing the contact lens formulation were irradiated from about 5 minutes to 45 minutes with UVA radiation (Intensity was from about 3 $mW/cm^2$ to 6 $mW/cm^2$) while nitrogen was continuously flushed through the curing chamber. The time needed for sufficient polymerization/cure depends, in part, on UV intensity, initiator concentration, volume of contact lens formulation, and the concentration of oxygen in the lens formulation and curing chamber. Although the contact lenses herein were UV cured in a nitrogen atmosphere, other types of atmospheres can be used. The curing of the contact lenses can be conducted under nitrogen, argon, $CO_2$, or in air atmospheres. Since oxygen is known to interfere with free radical polymerization of contact lens formulations, curing/polymerization is ideally conducted in an atmosphere with a low percentage of oxygen. If one desires to cure the lens formulations described herein in air, photo-initiator concentration can be increased to overcome polymerization inhibition and retardation caused by oxygen. If desired, cured or partially cured contact lenses can be subjected to post curing using thermal energy in order to minimize residual monomer content. Inclusion of both a UV and thermal polymerization initiator(s) in a contact lens formulation is preferable for processes that involve initial cure by UV light followed by thermal post cure. Contact lens formulation can also be cured in a heated UV chamber.

BSA Protocol

For the BSA assay, 0.1 mL of each standard and unknown sample replicate were pipetted into an appropriate labeled test tube. Next, 2.0 mL of the working reagent (WR) was added to each tube and the mixture was mixed well (sample to WR ratio=1:20). The tubes are then covered and incubated at a selected temperature for a selected time.

For a standard protocol, the tubes were incubated at 37° C. for 30 minutes (working range=20-2,000 µg/mL). For a room temperature (RT) protocol, the tubes were incubated at room temperature for 2 hours (working range=20-2,000 µg/mL). For an enhanced protocol, the tubes were incubated at 60° C. for 30 minutes (working range=5-250 µg/mL). Increasing the incubation time or temperature increases the net 562 nm absorbance for each test and decreases both the minimum detection level of the reagent and the working range of the protocol. A water bath is used to heat the tubes for either the Standard (37° C. incubation) or Enhanced (60° C. incubation) Protocol. Using a forced-air incubator can introduce significant error in color development because of uneven heat transfer.

Following incubation at the selected temperature for the selected time, all tubes were cooled to room temperature. With the spectrophotometer set to 562 nm, the instrument was zeroed on a cuvette filled only with water. Subsequently, the absorbance for all samples was measured within 10 minutes. Because the BSA assay does not reach a true end point, color development will continue even after cooling to room temperature. However, because the rate of color development is low at room temperature, no significant error will be introduced if the 562 nm absorbance measurements of all tubes are made within 10 minutes of each other. The average 562 nm absorbance of the blank standard replicates is subtracted from the 562 nm absorbance measurement of all other individual standard and unknown sample replicates. A standard curve is prepared by plotting the average blank-corrected 562 nm measurement for each BSA standard vs. its concentration in µg/mL. The standard curve can then be used to determine the protein concentration of each unknown sample.

Preparation of Actinically Curable Copolymers Comprised of a Polydimethylsiloxane Main Chain with Polyglycerol Branches (AC-(PDMS-PGLY)) Bearing an Ethylenically Unsaturated Functionality (Examples 1-7)

Example 1 (1002-138-1), Macromer-1

AC-PDMS-PGLY: An actinically curable copolymer comprised of a polydimethylsiloxane main chain with polyglycerol branches bearing ethylenically unsaturated functionality (AC-PDMS-PGLY) was prepared as follows: A reaction vessel was charged with of KF6100 (40.94 grams), IEM (1.283 grams), and DBTDL (0.046). The components were mixed until homogenous and the reaction was allowed to proceed at 35-40° C. until the isocyanate group (NCO) from IEM was no longer visible by FT-IR.

Example 2 (1002-138-2), Macromer-2

An actinically curable copolymer comprised of a polydimethylsiloxane main chain with polyglycerol branches bearing ethylenically unsaturated functionality (AC-PDMS-PGLY) was prepared as follows: KF61004 (40.10 grams), methacrylic anhydride (2.55 grams), Aberlyst 15 (0.48 grams) and ethyl acetate (100 mL). The components were mixed until homogenous and the reaction was allowed to proceed at 35-40° C.

Example 3 (1002-138-3), Macromer-3

An actinically curable copolymer comprised of a polydimethylsiloxane main chain with polyglycerol branches bearing ethylenically unsaturated functionality (AC-PDMS-PGLY) was prepared as follows: A reaction vessel was charged with KF6104 (40.44 grams), IEM (1.29 grams) and DBTDL (0.05 grams). The components were mixed until homogenous and the reaction was allowed to proceed at 35-40° C. until the NCO group from IEM was no longer visible by FT-IR.

Example 4 (1002-152-1), Macromer-4

An actinically curable copolymer comprised of a polydimethylsiloxane main chain with polyglycerol branches bearing ethylenically unsaturated functionality (AC-PDMS-PGLY) was prepared as follows: A reaction vessel was charged with KF6100 (40.69 grams), IEM (0.65 grams) and DBTDL (0.029 grams). The components were mixed until homogenous and the reaction was allowed to proceed at 35-40° C. until the NCO group from IEM was no longer visible by FT-IR.

Example 5 (1002-152-2), Macromer-5

An actinically curable copolymer comprised of a polydimethylsiloxane main chain with polyglycerol branches bearing ethylenically unsaturated functionality (AC-PDMS-PGLY) was prepared as follows: A reaction vessel was charged with KF6104 (42.30 grams), IEM (0.64 grams) and DBTDL (0.033 grams). The components were mixed until homogenous and the reaction was allowed to proceed at 35-40° C. until the NCO group from IEM was no longer visible by FT-IR.

Example 6 (1002-152-3), Macromer-6

An actinically curable copolymer comprised of a polydimethylsiloxane main chain with polyglycerol branches bearing ethylenically unsaturated functionality (AC-PDMS-PGLY) was prepared as follows: A reaction vessel was charged with KF6104 (30.23 grams), IEM (1.48 grams) and DBTDL (0.025 grams). The components were mixed until homogenous and the reaction was allowed to proceed at 35-40° C. until the NCO group from IEM was no longer visible by FT-IR.

Example 7 (1002-152-7), Macromer-7

A reaction vessel was charged with 23.54 grams of Polyglycerol branched Polydimethylsiloxane (KF6100), 1.446 grams of IEM and 0.036 grams of DBTDL. The components were mixed until homogenous and the reaction was allowed to proceed at 35-40° C. until the isocyanate group from IEM was no longer visible by FT-IR.

Chain Extension and/or Cross-Linking of PDMS-PGLY Using Isophorone Diisocyanate

Example 8-13

Example 8 AC-CE-(PDMS-PGLY) (1002-156-1), Macromer-8

A reaction vessel was charged with KF6100 (18.80 grams), IPDI (1.20 grams, 5.398 mmol) and DBTDL (0.04 grams). The contents of the reaction vessel were mixed until homogenous and then heated at 35-40° C. until NCO functionality was no longer visible by FT-IR. The resulting copolymer was noticeably more viscous, but it remained fluid. IEM (0.65 grams) was then added to the reaction vessel allowed react until all NCO from the IEM was no longer visible by FT-IR. This example demonstrates under the conditions of 0.287 mmol diisocyanate (IPDI) per gram of KF6100 chain extension may be accomplished without causing gelation (i.e.; cross-linked network).

Example 9 CE-(PDMS-PGLY) (1002-154-4)

A plastic centrifuge tube was charged with KF6100 (5.30 grams) IPDI (0.51 grams, 2.29 mmol) and DBTDL (0.5 mg). The resulting fluid was mixed and allowed to react for 12 hours at room temperature. After heating for several hours at 70° C., the sample remained fluid. This example demonstrates that KF6100 may be chain extended under the conditions of 0.97 mmol IPDI per gram of KF6100.

Example 10 [CE-(PDMS-PGLY)] (1002-154-5)

A plastic centrifuge tube was charged with KF6100 (5.01 grams) IPDI (1.08 grams, 4.86 mmol), diethylene glycol (1.10 grams) and DBTDL (3 drops). Upon mixing the resulting solution became warm to the touch and its viscosity increased. After the solution was no longer warm to the touch, it was spread over a 6 inch×4 inch sheet of polyethylene which was then placed in an oven preheated to 70° C. After 30 minutes at 70° C., the sample remained fluid. Isophorone diisocyanate (IPDI) used in this experiment was doped with 0.1 mg of DBTDL per mL.

Example 11 [CE-(PDMS-PGLY)] (1002-154-6)

A plastic centrifuge tube was charged with KF6100 (5.35 grams) IPDI (21.54 grams, 96.9 mmol), and diethylene glycol (2.01 grams). Upon mixing the resulting solution became warm to the touch and viscosity increased noticeably. After the solution was no longer warm to the touch, it was spread over a 6 inch×4 inch sheet of polyethylene which was then placed in an oven preheated to 70° C. After curing for 30 minutes at 70° C., the sample remained fluid (not cross-linked). Isophorone diisocyanate (IPDI) used in this experiment was doped with 0.1 mg of DBTDL per mL.

Example 12 [CE-(PDMS-PGLY)]

A plastic centrifuge tube was charged with KF6104 (2.56 grams) IPDI (1.96 grams, 8.82 mol), 1.93 grams of diethylene glycol and 3 drops of DBTDL. Upon mixing the resulting solution became warm to the touch and viscosity increased noticeably. After the solution was no longer warm to the touch, it was spread over a 6 inch×4 inch sheet of polyethylene which was then placed in an oven preheated to 70° C. oven for 30 minutes, removed and examined. It was noted that the sample remained fluid.

Example 13 (1002-154-8)

A blend comprising two different PDMS-PGLY copolymers was prepared. A plastic centrifuge tube was charged with KF6100 (25.03 parts by weight) and KF6104 (14.24 parts by weight). Components were mixed to yield a cloudy solution. No further experimentation was performed with this sample.

Evaluation of Formulations Containing Modified PDMS-PGLY (Examples 14-23)

Example 14 (1002-138-F-01)

A formulation containing copolymer prepared in example 1 (1.024 grams of) was combined with DARACURE 1173 (0.016 grams), of isopropanol (0.501 grams) and mixed until homogenous. 0.25 grams of the formulation was placed in a polyethylene plastic mold (diameter ~30 mm) and then exposed to UVA (~3 mW/cm$^2$) for 10 minutes after which a clear tacky gel was obtained.

Example 15 (1002-138-F-02)

Formulation prepared in Example 11 (~0.75 grams) was combined with GMMA (~0.25 grams). Approximately 0.25 grams of the formulation was placed in a polyethylene plastic cap (diameter ~30 mm) and then exposed to UVA (~3 mW/cm$^2$) for 10 minutes after which a clear gel was obtained.

Example 16 (1002-138-F-03)

A formulation containing 7.5 grams sample prepared in example 1 was combined with NVP (3.675 grams), SIGMA (3.675 grams), AMA (0.075 grams), and Daracure 1173 (0.078 grams) and mixed until homogenous. The formulation was subjected to a UV cure test and mechanical performance testing as follows: a portion of the formulation was spread in a plastic cap (diameter ~30 mm) and then exposed to UVA light (~3 mW/cm$^2$) for 15 minutes after which a clear gel was obtained. The gel was allowed to hydrate in water for 20 minutes after which a clear hydrogel was obtained. The elastic properties of the gel were evaluated by gripping the hydrated sample between forefinger and thumb and then gently stretching it until it broke. The gel evaluated in this example was stretched to ~50-75% of its original length before breaking.

Example 17 (1002-138-3-F-01)

A formulation containing 1.024 grams copolymer from Example 3 was combined with, and 0.016 grams Daracure 1173 (0.05 grams) and isopropanol (0.38 grams). After mixing a slightly cloudy fluid was obtained. A portion of the formulation was spread in a plastic cap (~30 mm diameter) and then exposed to UVA light (~3 mW/cm2) for 10 minutes to yield a tacky material.

Example 18 (1002-138-1-F02)

A formulation containing 0.75 grams of formulation from Example 13 was combined with, GMMA (0.25 grams), Daracure 1173 (0.05 gram) and isopropanol 0.38 grams) and mixed. formulation was spread in plastic cap and irradiated with UVA (about 3 mW/cm2) for about 10 minutes to yield a gel.

Example 19 (1002-138-1-F03)

A formulation was prepared by combining 7.516 grams of macromer (prepared as described in example 1) with SIGMA (3.726 grams), GMMA (3.717 grams) and Daracure 1173 (0.062 grams).

Example 20 (1002-138-1-F04)

A formulation was prepared by combining about a 15 grams of formulation from Example 16 (1002-138-1-F03) with AMA (0.005 grams), IPA (21 grams), and Daracure 1173 (0.005 grams). About 3 mL of the mixture was placed in a plastic beaker and exposed with UVA (about 3.5 mW/cm2) for about 30 minutes. The formulation remained fluid and did not form a gel.

Example 21 (1002-138-1-FO5)

A formulation was prepared by combining 7.601 grams of copolymer (prepared as described in example 1) with 3.705 grams of NVP, 3.774 grams of SIGMA, and 0.077 grams of allyl methacrylate (AMA). After mixing a clear solution was obtained. A plastic mold (~30 mm diameter) was dosed with formulation and then placed under UVA (3.5 mW/cm2) for 15 minutes to yield a clear gel. The gel was extracted in 5 mL of isopropanol for 15 minutes and then soaked in 10 mL of purified water. The resulting gel was clear, lubricous and displayed good elasticity. The gel could be stretched to 100% its original length before breaking.

Example 22 (1002-154-1)

A formulation was prepared by combining 3.63 grams of copolymer (prepared as described in example 1) with 2.50 grams of isopropanol. 1 gram of sample was placed in a plastic mold (~30 mm) and then exposed to UVA (~3.5 mW/cm2) for ~20 minutes. The sample did not gel under these conditions.

Example 23 (1002-154-2)

A formulation was prepared by combining 3.54 copolymer prepared in example 7 with 1.51 grams IPA solution containing 3.33 mg/mL of IRGACURE 2951. The resulting formulation was spread on polyethylene sheet to give a sample thickness of ~0.2 cm. The sample was exposed to UVA (~3.5 mW/cm$^2$) for 30 minutes to yield a gel. The resulting gel was hydrated in water to yield a lubricous silicone hydrogel film.

Formulation of Cross-Linked Network from Polydimethylsiloxane-co-polyglycerol (KF6104) and diisocyanate (IPDI) (Example 24-25)

Example 24 (1002-153-1)

A formulation was prepared by combining 5.142 grams of KF6104, 0.186 grams of IPDI, and 0.022 grams DBTDL, as shown in Table 5. The formulation was mixed for 30 seconds and then poured into circular molds (diameter ~30 mm) and sonicated for 2 minutes and allowed to cure at room temperature for 10 minutes. After 15 minutes at room temperature, the samples were placed in an oven pre-heated to 70° C. to yield clear gels (cross-linked).

Example 25 (1002-153-2)

A formulation was prepared by combining 5.303 grams of KF6104, 0.396 grams of IPDI, and 0.04 grams DBTDL, as shown in Table 5. The formulation was mixed for 30 seconds and then poured into circular molds (diameter ~30 mm) and sonicated for 2 minutes and allowed to cure at room temperature for 10 minutes. After 15 minutes at room temperature, the samples were placed in an oven pre-heated to 70° C. to yield clear (cross-linked) gels.

TABLE 5

Cross-linking of PDMS-Polyglycerol with
Diisocyanate (isophoronediisocyanate)

| Macromers | Example 24 (1002-153-1) | | Example 25 (1002-153-2) | |
|---|---|---|---|---|
| | Grams/ Parts | Percent by Weight | Grams/ Parts | Percent by Weight |
| KF6104 | 5.142 | 96.11 | 5.303 | 92.40 |
| IPDI | 0.186 | 3.48 | 0.396 | 6.90 |
| DBTDL | 0.022 | 0.41 | 0.04 | 0.70 |
| Total | 5.35 | 100.0 | 5.739 | 100.0 |
| Comment | Formed Clear Gel | | Formed Clear Gel | |

Preparation of Modified
PDMS-Polyglycerolformulations

Example 26 AC-CE-(PDMS-PGL1) (1002-156-1),
Macromer-26

A reaction vessel was charged with branched 18.8 grams of PDMS-PGLY (KF6100, Viscosity ~40,000 cps), 1.20 grams of IPDI and 2 drops (0.02 grams) of DBTDL. The components were mixed until homogenous and the reaction was allowed to proceed at 35-40° C. until the isocyanate group (NCO) from IPDI was no longer visible by FT-IR. The viscosity of the mixture was noticeably higher after reaction with IPDI. The resulting copolymer was then allowed to react with IEM (0.65 grams) at 35-40° C. until the isocyanate group from IEM was no longer visible by FT-IR. This copolymer (Macromer-26) was used to prepare additional formulations and contact lenses therefrom (described below).

Example 27 (PDMS-PGLY-01)

A formulation (PDMS-PGLY-01) was prepared by combining AC-CE-(PDMS-PGLY) (prepared according to procedure described in Example 26), glycerol methacrylate (GMMA), and Daracure 1173 (photoinitiator) as shown in Table 6. Before curing, the formulation was clear. Contact lenses were then prepared from the formulation. Contact lenses were then prepared from the formulation using spin cast technology with UV curing, as described further below. The prepared contact lenses exhibited phase separation and a cloudy ring, and had a clarity rank of 7. The prepared contact lenses had an average diameter of 13.8 mm.

Example 28 (PDMS-PGLY-02)

A formulation (PDMS-PGLY-02) was prepared by combining AC-CE-(PDMS-PGLY) (prepared according to procedure described in Example 26), GMMA, 2-hydroxyethylmethacrylate (HEMA), and Daracure 1173 as shown in Table 6. Before curing, the formulation was clear. Contact lenses were then prepared from the formulation using spin cast technology with UV cure in a nitrogen flushed UV light chamber, as described above. The prepared contact lenses exhibited phase separation and had a clarity rank of 7. The prepared contact lenses had an average diameter of 14 mm.

Example 29 (PDMS-PGLY-03)

A formulation (PDMS-PGLY-03) was prepared by combining AC-CE-(PDMS-PGLY) (prepared according to procedure described in Example 26), GMMA, HEMA, and Daracure 1173 as shown in Table 6. Before curing, the formulation was clear. Contact lenses were then prepared from the formulation using spin cast technology with UV cure in a nitrogen flushed UV light chamber, as described above. The prepared contact lenses exhibited phase separation and had a clarity rank of 7. The prepared contact lens had an average diameter of 14 mm.

Example 30 (PDMS-PGLY-04)

A formulation (PDMS-PGLY-04) was prepared by combining AC-CE-(PDMS-PGLY) (prepared according to procedure described in Example 26), GMMA, HEMA, Daracure 1173, and water as shown in Table 6. Before curing, the formulation was clear. Contact lenses were then prepared from the formulation using spin cast technology with UV cure in a nitrogen flushed UV light chamber, as described above. The prepared contact lenses exhibited phase separation and had a clarity rank of 6. The prepared contact lenses had an average diameter of 14.1 mm. The prepared contact lenses had an oxygen permeability ($D_k$) of 66.

Example 31 (PDMS-PGLY-05)

A formulation (PDMS-PGLY-05) was prepared by combining AC-CE-(PDMS-PGLY) (prepared according to procedure described in Example 26), GMMA, HEMA, and Daracure 1173 as shown in Table 6. Before curing, the formulation was clear. Contact lenses were then prepared from the formulation using spin cast technology with UV cure in a nitrogen flushed UV light chamber, as described above. The prepared contact lens exhibited phase separation and had a clarity rank of 5. The prepared contact lenses had an average diameter of 15.8 mm. The prepared contact lenses had an oxygen permeability ($D_k$) of 66.

TABLE 6

Formulations containing modified PDMS-Polyglycerol.

| Materials | Example 27 (PDMS-PGLY-01) Percent | Example 28 (PDMS-PGLY-02) Percent | Example 29 (PDMS-PGLY-03) Percent | Example 30 (PDMS-PGLY-04) Percent | Example 31 (PDMS-PGLY-05) Percent |
|---|---|---|---|---|---|
| AC-CE-(PDMS-PGLY)* | 49.25 | 49.25 | 39.42 | 35.49 | 19.70 |
| GMMA | 49.25 | 36.94 | 44.34 | 39.92 | 59.11 |
| HEMA | 0.00 | 12.31 | 14.78 | 13.30 | 19.70 |
| Initiator (Daracure 1173) | 1.50 | 1.50 | 1.47 | 1.32 | 1.48 |
| water | 0.00 | 0.00 | 0.00 | 9.97 | 0.00 |
| Total | 100 | 100 | 100 | 100 | 100 |
| Formulation Before Cure | clear | clear | clear | clear | clear |
| Lens Appearance | Phase separation Cloudy ring | Phase separation | Phase separation | Phase separation | Phase separation |
| Lens Clarity Rank | 7 | 7 | 7 | 6 | 5 |
| Lens Diameter (mm) | ~13.8 | ~14.0 | 14 | 14.0-14.20 | 15.8 |

TABLE 6-continued

Formulations containing modified PDMS-Polyglycerol.

| Materials | Example 27 (PDMS-PGLY-01) Percent | Example 28 (PDMS-PGLY-02) Percent | Example 29 (PDMS-PGLY-03) Percent | Example 30 (PDMS-PGLY-04) Percent | Example 31 (PDMS-PGLY-05) Percent |
|---|---|---|---|---|---|
| Average Diameter (mm) | 13.8 | 14 | 14 | 14.1 | 15.8 |
| Dk | — | — | — | 66 | 110 |

*AC-CE-(PDMS-PGLY) was prepared according to procedure described in Example 26; Lens Clarity Rank is from 1 to 10, with 1 being the worst (completely opaque);
Dk = Oxygen permeability of a contact lens is abbreviated, where "D" is diffusivity $(cm^2/sec)$ and "k" is the solubility of oxygen in a given contact lens material (ml $O^2$/ml of material × mm Hg);
Contact lenses were prepared by UV curing in a nitrogen flushed chamber using spin cast technology as described above.

Example 32 (PDMS-PGL Y-06)

A contact lens formulation (PDMS-PGLY-06) was prepared by combining AC-CE-(PDMS-PGLY) (prepared according to the procedure described in Example 26), GMMA, N-vinyl-2-pyrrolidone (NVP), and Daracure 1173 as shown in Table 7. Before curing, the formulation was clear. Contact lenses were then prepared from the formulation using spin cast technology with UV cure in a nitrogen flushed UV light chamber, as described above. The prepared contact lenses had a diameter of ~15 mm.

Example 33 (PDMS-PGLY-07)

A formulation (PDMS-PGLY-07) was prepared by combining AC-CE-(PDMS-PGLY) (prepared according to the procedure described in Example 26), GMMA, NVP, Daracure 1173, and water as shown in Table 7. Before curing, the formulation was clear. Contact lenses were then prepared from the formulation using spin cast technology with UV cure in a nitrogen flushed UV light chamber, as described above. The prepared contact lens exhibited phase separation and had a clarity rank of 8. The prepared contact lenses had an average diameter of 14.1 mm.

Example 34 (PDMS-PGLY-08)

A formulation (PDMS-PGLY-08) was prepared by combining AC-CE-(PDMS-PGLY) (prepared according to the procedure described in Example 26), GMMA, NVP, Daracure 1173, and water as shown in Table 7. Before curing, the formulation was clear. Contact lenses were then prepared from the formulation using spin cast technology with UV cure in a nitrogen flushed UV light chamber, as described above. The prepared contact lens exhibited phase separation and had a clarity rank of 6. The prepared contact lenses had an average diameter of 14.1 mm. The prepared contact lenses had an oxygen permeability $(D_k)$ of 64.

Example 35 (PDMS-PGLY-09)

A formulation (PDMS-PGLY-09) was prepared by combining AC-CE-(PDMS-PGLY) (prepared according to the procedure described in Example 26), GMMA, HEMA, Daracure 1173, and water as shown in Table 7. Before curing, the formulation was clear. Contact lenses were then prepared from the formulation using spin cast technology with UV cure in a nitrogen flushed UV light chamber, as described above. The prepared contact lens exhibited phase separation and had a clarity rank of 7. The prepared contact lenses had an average diameter of 15.45 mm. The prepared contact lenses had an oxygen permeability $(D_k)$ of 63.

Example 36 (PDMS-PGLY-10)

A formulation (PDMS-PGLY-10) was prepared by combining AC-CE-(PDMS-PGLY) (prepared according to the procedure described in Example 26), GMMA, NVP, and Daracure 1173 as shown in Table 7. Before curing, the formulation was clear. Contact lenses were then prepared from the formulation using spin cast technology with UV cure in a nitrogen flushed UV light chamber, as described above. The prepared contact lens had a clarity rank of 5. The prepared contact lenses had an average diameter of 18 mm.

TABLE 7

Formulations containing modified PDMS-Polyglycerol.

| Materials | Example 32 (PDMS-PGLY-06) Percent | Example 33 (PDMS-PGLY-07) Percent | Example 34 (PDMS-PGLY-08) Percent | Example 35 (PDMS-PGLY-09) Percent | Example 36 (PDMS-PGLY-10) Percent |
|---|---|---|---|---|---|
| AC-CE-(PDMS-PGLY) (Macromer-26) | 39.40 | 35.48 | 31.52 | 14.79 | 19.70 |
| GMMA | 39.40 | 35.48 | 31.52 | 44.37 | 59.11 |
| HEMA | 0.00 | 0.00 | 0.00 | 14.79 | 0.00 |
| NVP | 19.70 | 17.74 | 15.76 | 0.00 | 19.70 |
| Initiator (Daracure 1173) | 1.50 | 1.35 | 1.20 | 1.11 | 1.48 |
| water | 0.00 | 10.00 | 20.00 | 24.94 | 0.00 |
| Total | 100 | 100 | 100 | 100 | 100 |
| Formulation Before Cure | clear | clear | clear | clear | clear |
| Lens Appearance | Phase separation | Phase separation | Phase separation | Phase separation | — |
| Lens Clarity Rank | — | 8 | 6 | 7 | 5 |
| Lens Diameter (mm) | ~15 | 14-14.2 | 14.0-14.20 | 15.40-15.50 | 17.50-18.50 |
| Average Diameter | — | 14.1 | 14.1 | 15.45 | 18 |
| Dk | — | — | 64 | 63 | — |

AC-CE-(PDMS-PGLY) was prepared according to procedure described in Example 26; Lens Clarity Rank is from 1 to 10, with 1 being the worst (completely opaque);
Dk = Oxygen permeability of a contact lens is abbreviated, where "D" is diffusivity $(cm^2/sec)$ and "k" is the solubility of oxygen in a given contact lens material (ml $O^2$/ml of material × mm Hg);
Contact lenses were prepared by UV curing in a nitrogen flushed chamber using spin cast technology as described above.

Example 37 (PDMS-PGLY-11)

A formulation (PDMS-PGLY-11) was prepared by combining AC-CE-PDMS-PGLY (prepared according to the procedure described in Example 26), GMMA, NVP, and Daracure 1173 as shown in Table 8. Before curing, the formulation was clear. Contact lenses were then prepared from the formulation using spin cast technology with UV cure in a nitrogen flushed UV light chamber, as described above. The prepared contact lens had a clarity rank of 6. The prepared contact lenses had an average diameter of 15.45 mm.

Example 38 (PDMS-PGLY-12)

A formulation (PDMS-PGLY-12) was prepared by combining AC-CE-(PDMS-PGLY) (prepared according to the procedure described in Example 26), GMMA, NVP, and Daracure 1173 as shown in Table 8. Before curing, the formulation was clear. Contact lenses were then prepared from the formulation using spin cast technology with UV cure in a nitrogen flushed UV light chamber, as described above. The prepared contact lens had a clarity rank of 10. The prepared contact lenses had an average diameter of 15.55 mm.

Example 39 (PDMS-PGLY-13)

A formulation (PDMS-PGLY-13) was prepared by combining AC-CE-(PDMS-PGLY) (prepared according to the procedure described in Example 26), GMMA, NVP, and Daracure 1173 as shown in Table 8. Before curing, the formulation was clear. Contact lenses were then prepared from the formulation using spin cast technology with UV cure in a nitrogen flushed UV light chamber, as described above. The prepared contact lens had a clarity rank of 10. The prepared contact lenses had an average diameter of 13.45 mm.

Example 40 (PDMS-PGLY-14)

A formulation (PDMS-PGLY-14) was prepared by combining AC-CE-PDMS-PGLY (prepared according to the procedure described in Example 26), GMMA, NVP, and Daracure 1173 as shown in Table 8. Before curing, the formulation was clear. Contact lenses were then prepared from the formulation using spin cast technology with UV cure in a nitrogen flushed UV light chamber, as described above. The prepared contact lens had a clarity rank of 9. The prepared contact lenses had an average diameter of 16.75 mm.

Example 41 (PDMS-Gly-22)

A formulation (PDMS-Gly-22) was prepared by combining AC-CE-(PDMS-PGLY) (prepared according to the procedure described in Example 26), NVP, and Daracure 1173 as shown in Table 9. Contact lenses were then prepared from the formulation using spin cast technology with UV cure in a nitrogen flushed UV light chamber, as described above. The prepared contact lenses were clear with no phase separation. The prepared contact lenses had a diameter of 14.6 mm. The prepared contact lenses were too fragile to measure the oxygen permeability (Dk). The prepared contact lenses had a water percentage of 67%.

TABLE 8

Formulations containing modified PDMS-Polyglycerol.

| Materials | Example 37 (PDMS-PGLY-11) Percent | Example 38 (PDMS-PGLY-12) Percent | Example 39 (PDMS-PGLY-13) Percent | Example 40 (PDMS-PGLY-14) Percent |
|---|---|---|---|---|
| AC-CE-PDMS-PGLY (Macromer-26) | 28.15 | 24.63 | 39.53 | 16.42 |
| GMMA | 42.22 | 24.63 | 19.76 | 49.26 |
| NVP | 28.15 | 49.26 | 39.53 | 32.84 |
| Initiator (Daracure 1173) | 1.48 | 1.48 | 1.19 | 1.48 |
| Total | 100 | 100 | 100 | 100 |

TABLE 8-continued

Formulations containing modified PDMS-Polyglycerol.

| Materials | Example 37 (PDMS-PGLY-11) Percent | Example 38 (PDMS-PGLY-12) Percent | Example 39 (PDMS-PGLY-13) Percent | Example 40 (PDMS-PGLY-14) Percent |
|---|---|---|---|---|
| Formulation Before Cure | clear | clear | clear | clear |
| Lens Clarity Rank | 6 | 10 | 10 | 9 |
| Lens Diameter (mm) | 15.40 to 15.50 mm | 15.50 to 15.60 mm | 13.40 to 13.50 mm | 16.50 to 17 mm |
| Average Diameter | 15.45 | 15.55 | 13.45 | 16.75 |

AC-CE-PDMS-PGLY used in the above formulations was prepared according to the procedure described in Example 26
Lens Clarity Rank is from 1 to 10, with 1 being the worst (completely opaque)
Contact lenses were prepared by UV curing in a nitrogen flushed chamber using spin cast technology as described above Example 42 (PDMS-Gly-23)

A formulation (PDMS-Gly-23) was prepared by combining AC-CE-(PDMS-PGLY) (prepared according to the procedure described in Example 26), NVP, 3-Methacryloxy-2-Hydroxypropoxy(propylbis(trimethylsilyloxy)-methylsilane (SIGMA), GMMA, polyvinylpyrrolidone (PVP), and Daracure 1173 as shown in Table 9. Contact lenses was then prepared from the formulation using spin cast technology with UV cure in a nitrogen flushed UV light chamber, as described above. The prepared contact lenses exhibited a slight phase separation. The prepared contact lenses had a diameter of 14.6 mm. The prepared contact lenses had an oxygen permeability (Dk) of $62.13 \times 10^{-11}$ and a water percentage of 66.3%.

Example 43 (PDMS-PGLY-24)

A formulation (PDMS-PGLY-24) was prepared by combining AC-CE-(PDMS-PGLY) (prepared according to the procedure described in Example 26), NVP, SIGMA, GMMA, PVP, and Daracure 1173 as shown in Table 9. Contact lenses were then prepared from the formulation using spin cast technology with UV cure in a nitrogen flushed UV light chamber, as described above. The prepared contact lenses were clear with no phase separation. The prepared contact lenses had a diameter of 14.2-14.3 mm. The prepared contact lenses had an oxygen permeability (Dk) of $101.43 \times 10^{-11}$ and a water percentage of 65.4%.

Example 44 (PDMS-PGLY-25)

A formulation (PDMS-PGLY-25) was prepared by combining AC-CE-(PDMS-PGLY) (prepared according to the procedure described in Example 26), NVP, 3-Methacryloxy-2-Hydroxypropoxy(propylbis(trimethylsilyloxy)-methylsilane (SIGMA), GMMA, polyvinylpyrrolidone (PVP), and Daracure 1173 as shown in Table 9. Contact lenses were then prepared from the formulation using spin cast technology with UV cure in a nitrogen flushed UV light chamber, as described above. The prepared contact lenses were clear with no phase separation. The prepared contact lenses had a diameter of 13.3-13.4 mm. The prepared contact lenses had an oxygen permeability (Dk) of $78.35 \times 10^{-11}$ and a water percentage of 56.5%.

Example 45 (PDMS-Gly-25A)

A formulation (PDMS-Gly-25A) was prepared by combining AC-CE-(PDMS-PGLY) (prepared according to the procedure described in Example 26), NVP, SIGMA, GMMA, PVP, and Daracure 1173 as shown in Table 10. Contact lenses were then prepared from the formulation using spin cast technology with UV cure in a nitrogen flushed UV light chamber, as described above. The prepared contact lenses had slight phase separation but were less cloudy than Example 42 (PDMS-Gly-23). The prepared contact lenses had a diameter of 13.30 mm. The prepared contact lenses had an oxygen permeability (Dk) of $80.04 \times 10^{-11}$ and a water percentage of 57.3%.

Example 46 (PDMS-PGLY-28)

A formulation (PDMS-PGLY-28) was prepared by combining AC-CE-(PDMS-PGLY) (prepared according to the procedure described in Example 26), NVP, SIGMA, and Daracure 1173 as shown in Table 10. Contact lenses were then prepared from the formulation using spin cast technology with UV cure in a nitrogen flushed UV light chamber, as described above. The prepared contact lenses were opaque. The prepared contact lenses had a diameter of 13.8-13.85 mm. The prepared contact lenses had an oxygen permeability (Dk) of $92.59 \times 10^{-11}$ and a water percentage of 64%.

TABLE 9

Formulations containing modified PDMS-Polyglycerol.

| Materials | Example 41 (PDMS-Gly-22) Percent | Example 42 (PDMS-Gly-23) Percent | Example 43 (PDMS-PGLY-24) Percent | Example 44 (PDMS-PGLY-25) Percent |
|---|---|---|---|---|
| AC-CE-(PDMS-PGLY) (Macromer-26) | 59.17 | 24.44 | 22.22 | 24.66 |
| NVP | 39.45 | 36.66 | 44.44 | 24.66 |
| SIGMA | 0.00 | 12.22 | 22.22 | 24.66 |
| GMMA | 0.00 | 24.44 | 1.42 | 24.66 |
| PVP | 0.00 | 0.88 | 8.33 | 0.00 |
| Initiator (Daracure 1173) | 1.38 | 1.37 | 1.38 | 1.35 |
| Total | 100.0 | 100.0 | 100.0 | 100.0 |
| Lens Clarity | Clear Lens No Phase Separation | Slight phase separation | Clear lens No phase separation | Clear lens No phase separation |
| Lens Diameter (mm) | 14.6 | 14.6 | 14.20-14.30 | 13.3-13.40 |
| Dk | Too fragile to measure | $62.13 \times 10^{-11}$ | $101.43 \times 10^{-11}$ | $78.35 \times 10^{-11}$ |
| % Water | 67 | 66.3 | 65.4 | 56.5 |

AC-CE-(PDMS-PGLY) used in the above formulations was prepared according to procedure described in Example 26;
Lens Clarity Rank is from 1 to 10, with 1 being the worst (completely opaque);
Dk = Oxygen permeability of a contact lens is abbreviated, where "D" is diffusivity ($cm^2$/sec) and "k" is the solubility of oxygen in a given contact lens material (ml $O_2$/ml of material × mm Hg);
Contact lenses were prepared by UV curing in a nitrogen flushed chamber using spin cast technology as described above.

Example 47 (PDMS-PGL Y-29)

A formulation (PDMS-PGLY-29) was prepared by combining AC-CE-(PDMS-PGLY) (prepared according to the procedure described in Example 26), NVP, SIGMA, PVP, and Daracure 1173 as shown in Table 10. Contact lenses were then prepared from the formulation using spin cast technology with UV cure in a nitrogen flushed UV light chamber, as described above. The prepared contact lenses were opaque. The prepared contact lenses had a diameter of 14.40-14.45 mm. The prepared contact lenses had an oxygen permeability (Dk) of $127.01 \times 10^{-11}$ and a water percentage of 64.7%.

Example 48 (PDMS-Gly-30)

A formulation (PDMS-Gly-30) was prepared by combining AC-CE-(PDMS-PGLY) (prepared according to the procedure described in Example 26), NVP, SIGMA, PVP, and Daracure 1173 as shown in Table 10. Contact lenses were then prepared from the formulation using spin cast technology with UV cure in a nitrogen flushed UV light chamber, as described above. The prepared contact lenses were opaque. The prepared contact lenses had a diameter of 15.20-15.25 mm. The prepared contact lenses had an oxygen permeability (Dk) of $109.36 \times 10^{-11}$ and a water percentage of 68.7%.

Example 49 (PDMS-PGLY-31)

A formulation (PDMS-PGLY-31) was prepared by combining AC-CE-(PDMS-PGLY) (prepared according to the procedure described in Example 26), NVP, SIGMA, PVP, and Daracure 1173 as shown in Table 11. Contact lenses were then prepared from the formulation using spin cast technology with UV cure in a nitrogen flushed UV light chamber, as described above. The prepared contact lenses were opaque.

Example 50 (PDMS-PGLY-32)

A formulation (PDMS-PGLY-32) was prepared by combining AC-CE-(PDMS-PGLY) (prepared according to the procedure described in Example 26), NVP, SIGMA, PVP, and Daracure 1173 as shown in Table 11. Contact lenses were then prepared from the formulation using spin cast technology with UV cure in a nitrogen flushed UV light chamber, as described above. The prepared contact lenses were opaque.

Example 51 (PDMS-PGLY-33)

A formulation (PDMS-PGLY-33) was prepared by combining AC-CE-(PDMS-PGLY) (prepared according to the procedure described in Example 26), NVP, SIGMA, PVP, and Daracure 1173 as shown in Table 11. Contact lenses were then prepared from the formulation using spin cast technology with UV cure in a nitrogen flushed UV light chamber, as described above. The prepared contact lenses were opaque.

Example 52 (PDMS-PGLY-34)

A formulation (PDMS-PGLY-34) was prepared by combining AC-CE-(PDMS-PGLY) (prepared according to the procedure described in Example 26), NVP, SIGMA, GMMA, PVP, and Daracure 1173 as shown in Table 11. Contact lenses were then prepared from the formulation using spin cast technology with UV cure in a nitrogen flushed UV light chamber, as described above. The prepared contact lenses were clear and exhibited no phase separation. The prepared contact lenses had a diameter of 14.7 mm. The prepared contact lenses had an oxygen permeability (Dk) of $94.64 \times 10^{-11}$ and a water percentage of 69.9%.

TABLE 10

Formulations containing modified PDMS-Polyglycerol.

| Materials | Example 45 (PDMS-Gly-25A) Percent | Example 46 (PDMS-PGLY-28) Percent | Example 47 (PDMS-PGLY-29) Percent | Example 48 (PDMS-Gly-30) Percent |
|---|---|---|---|---|
| AC-CE-(PDMS-PGLY) (Macromer-26) | 24.45 | 24.66 | 24.44 | 24.45 |
| NVP | 24.45 | 49.32 | 48.88 | 48.90 |
| SIGMA | 24.45 | 24.66 | 24.44 | 24.45 |
| GMMA | 24.45 | 0.00 | 0.00 | 0.00 |
| PVP | 0.88 | 0.00 | 0.88 | 0.88 |
| Initiator (Daracure 1173) | 1.34 | 1.35 | 1.34 | 1.34 |
| Total | 100.0 | 100.0 | 100.0 | 100.0 |
| Lens Clarity | Slight Phase separation, but less cloudy than PDMS-Gly-23 | Opaque lens | Opaque lens | Opaque lens |
| Lens Diameter (mm) | 13.30 | 13.80-13.85 | 14.40-14.45 | 15.20-15.25 |
| Dk | $80.04 \times 10^{-11}$ | $92.59 \times 10^{-11}$ | $127.01 \times 10^{-11}$ | $109.36 \times 10^{-11}$ |
| % Water | 57.3 | 64 | 64.7 | 68.7 |

AC-CE-(PDMS-PGLY) used in the above formulations was prepared according to procedure described in Example 26;
Lens Clarity Rank is from 1 to 10, with 1 being the worst (completely opaque);
Dk = Oxygen permeability of a contact lens is abbreviated, where "D" is diffusivity ($cm^2$/sec) and "k" is the solubility of oxygen in a given contact lens material (ml $O_2$/ml of material × mm Hg);
Contact lenses were prepared by UV curing in a nitrogen flushed chamber using spin cast technology as described above.

TABLE 11

Formulations containing modified PDMS-Polyglycerol.

| Materials | Example 49 (PDMS-PGLY-31) Percent | Example 50 (PDMS-PGLY-32) Percent | Example 51 (PDMS-PGLY-33) Percent | Example 52 (PDMS-PGLY-34) Percent |
|---|---|---|---|---|
| AC-CE-(PDMS-PGLY) (Macromer-26) | 24.45 | 24.45 | 24.45 | 22.37 |
| NVP | 48.89 | 48.89 | 48.89 | 44.74 |
| SIGMA | 24.45 | 24.45 | 24.45 | 22.37 |
| GMMA | 0.00 | 0.00 | 0.00 | 8.39 |
| PVP | 0.88 | 0.88 | 0.88 | 0.78 |
| Initiator (Daracure 1173) | 1.34 | 1.34 | 1.35 | 1.35 |
| Total | 100.0 | 100.0 | 100.0 | 100.0 |
| Lens Clarity | Opaque lens | Opaque lens | Opaque lens | Clear lens-No phase separation |
| Lens Diameter (mm) | — | — | — | 14.7 |
| Dk | — | — | — | $94.64 \times 10^{-11}$ |
| % Water | — | — | — | 69.9 |

AC-CE-(PDMS-PGLY) used in the above formulations was prepared according to procedure described in Example 26;
Lens Clarity Rank is from 1 to 10, with 1 being the worst (completely opaque);
Dk = Oxygen permeability of a contact lens is abbreviated, where "D" is diffusivity ($cm^2$/sec) and "k" is the solubility of oxygen in a given contact lens material (ml $O_2$/ml of material × mm Hg);
Contact lenses were prepared by UV curing in a nitrogen flushed chamber using spin cast technology as described above.

Example 53 (PDMS-PGL Y-35)

A formulation (PDMS-PGLY-35) was prepared by combining AC-CE-(PDMS-PGLY) (prepared according to the procedure described in Example 26), NVP, SIGMA, GMMA, PVP, and Daracure 1173 as shown in Table 12. Contact lenses were then prepared from the formulation using spin cast technology with UV cure in a nitrogen flushed UV light chamber, as described above. The prepared contact lenses were clear and exhibited no phase separation. The prepared contact lenses had a diameter of 13.80-13.85 mm. The prepared contact lenses had an oxygen permeability (Dk) of $84.26 \times 10^{-11}$ and a water percentage of 66.1%.

Example 54 (PDMS-PGLY-36)

A formulation (PDMS-PGLY-36) was prepared by combining AC-CE-(PDMS-PGLY) (prepared according to the procedure described in Example 26), NVP, SIGMA, GMMA, PVP, and Daracure 1173 as shown in Table 12. Contact lenses were then prepared from the formulation using spin cast technology with UV cure in a nitrogen flushed UV light chamber, as described above. The prepared contact lenses were clear and exhibited no phase separation. The prepared contact lenses had a diameter of 13.8 mm. The prepared contact lenses had an oxygen permeability (Dk) of $72.94 \times 10^{-11}$ and a water percentage of 66.9%.

Example 55 (PDMS-PGLY-37)

A formulation (PDMS-PGLY-37) was prepared by combining AC-CE-(PDMS-PGLY) (prepared according to the procedure described in Example 26), NVP, SIGMA, GMMA, PVP, and Daracure 1173 as shown in Table 12. Contact lenses were then prepared from the formulation using spin cast technology with UV cure in a nitrogen flushed UV light chamber, as described above. The prepared contact lenses were clear and exhibited no phase separation. The prepared contact lenses had a diameter of 14.00-14.10 mm and a base curve of 8.65 to 8.80 mm. The prepared contact lenses had an oxygen permeability (Dk) of $90 \times 10^{-11}$ barrer and a water content percentage of 66%.

Example 56 (PDMS-PGLY-38)

A formulation (PDMS-PGLY-38) was prepared by combining AC-CE-(PDMS-PGLY) (prepared according to the procedure described in Example 26), NVP, SIGMA, GMMA, PVP, and Daracure 1173 as shown in Table 12. Contact lenses were then prepared from the formulation using spin cast technology with UV cure in a nitrogen flushed UV light chamber, as described above. The prepared contact lenses were clear and exhibited no visible indications of phase separation.

Example 57 (PDMS-PGLY-39)

A formulation (PDMS-PGLY-39) was prepared by combining AC-CE-(PDMS-PGLY) (prepared according to the procedure described in Example 26), NVP, SIGMA, GMMA, PVP, and Daracure 1173 as shown in Table 13.

Example 58 (PDMS-PGLY-40)

A formulation (PDMS-PGLY-40) was prepared by combining AC-CE-(PDMS-PGLY) (prepared according to the procedure described in Example 26), NVP, SIGMA, GMMA, PVP, and Daracure 1173 as shown in Table 13.

TABLE 12

Formulations containing modified PDMS-Polyglycerol.

| Materials | Example 53 (PDMS-PGLY-35) Percent | Example 54 (PDMS-PGLY-36) Percent | Example 55 (PDMS-PGLY-37) Percent | Example 56 (PDMS-PGLY-38) Percent |
|---|---|---|---|---|
| AC-CE-(PDMS-PGLY) (Macromer-26) | 31.32 | 35.79 | 22.37 | 22.37 |
| NVP | 35.79 | 35.79 | 40.26 | 35.79 |
| SIGMA | 22.37 | 17.90 | 26.84 | 31.32 |
| GMMA | 8.39 | 8.39 | 8.39 | 8.39 |
| PVP | 0.78 | 0.78 | 0.78 | 0.78 |
| Initiator (Daracure 1173) | 1.35 | 1.35 | 1.35 | 1.36 |
| Total | 100.0 | 100.0 | 100.0 | 100.0 |
| Lens Clarity | Clear lens- No phase separation | Clear lens- No phase separation | Clear lens- No phase separation; | Clear lens- No phase separation |
| Lens Diameter (mm) | 13.80-13.85 | 13.8 | 14.00-14.10 | — |
| Dk | $84.26 \times 10^{-11}$ | $72.94 \times 10^{-11}$ | $90 \times 10^{-11}$; | — |
| % Water | 66.1 | 66.9 | 66 | — |

AC-CE-(PDMS-PGLY) used in the above formulations was prepared according to procedure described in Example 26;
Lens Clarity Rank is from 1 to 10, with 1 being the worst (completely opaque);
Dk = Oxygen permeability of a contact lens is abbreviated, where "D" is diffusivity ($cm^2$/sec) and "k" is the solubility of oxygen in a given contact lens material (ml $O_2$/ml of material × mm Hg);
Contact lenses were prepared by UV curing in a nitrogen flushed chamber using spin cast technology as described above.

Example 59 (PDMS-PGLY-41)

A formulation (PDMS-PGLY-41) was prepared by combining AC-CE-(PDMS-PGLY) (prepared according to the procedure described in Example 26), NVP, SIGMA, GMMA, PVP, and Daracure 1173 as shown in Table 13.

Example 60 (PDMS-Gly-42)

A formulation (PDMS-Gly-42) was prepared by combining AC-CE-(PDMS-PGLY) (prepared according to the procedure described in Example 26), NVP, SIGMA, GMMA, PVP, and Daracure 1173 as shown in Table 13. Contact lenses were then prepared from the formulation using spin cast technology with a UV cure in a nitrogen flushed UV light chamber, as described above. The prepared contact lenses were clear and exhibited no phase separation. The prepared contact lenses had a diameter of 13.90-13.95 mm. The prepared contact lenses had an oxygen permeability (Dk) of $61.55 \times 10^{-11}$ and a water percentage of 62%.

Example 61 (PDMS-PGLY-44)

A formulation (PDMS-PGLY-44) was prepared by combining AC-CE-(PDMS-PGLY) (prepared according to the procedure described in Example 26), NVP, SIGMA, GMMA, PVP, and Daracure 1173 as shown in Table 14. Contact lenses were then prepared from the formulation using spin cast technology with UV cure in a nitrogen flushed UV light chamber, as described above. The prepared contact lenses were clear and exhibited no phase separation. The prepared contact lenses had a diameter of 14.30-14.35 mm. The prepared contact lenses had an oxygen permeability (Dk) of $85.59 \times 10^{-11}$ and a water percentage of 67.5%.

Example 62 (PDMS-PGLY-45)

A formulation (PDMS-PGLY-45) was prepared by combining AC-CE-(PDMS-PGLY) (prepared according to the procedure described in Example 26), NVP, SIGMA, GMMA, PVP, and Daracure 1173 as shown in Table 14. Contact lenses were then prepared from the formulation using spin cast technology with UV cure in a nitrogen flushed UV light chamber, as described above. The prepared contact lenses were clear and exhibited no phase separation. The prepared contact lenses had a diameter of 14.40-14.45 mm. The prepared contact lenses had an oxygen permeability (Dk) of $100.32 \times 10^{-11}$ and a water percentage of 68%.

Example 63 (PDMS-PGLY-46)

A formulation (PDMS-PGLY-46) was prepared by combining AC-CE-(PDMS-PGLY) (prepared according to the procedure described in Example 26), NVP, SIGMA, GMMA, PVP, and Daracure 1173 as shown in Table 14. Contact lenses were then prepared from the formulation using spin cast technology with a UV cure in a nitrogen flushed UV light chamber, as described above. The prepared contact lenses were clear and exhibited no phase separation. The prepared contact lenses had a diameter of 14.20-14.25 mm. The prepared contact lenses had an oxygen permeability (Dk) of $85.05 \times 10^{-11}$ and a water percentage of 67%.

TABLE 13

Formulations containing modified PDMS-Polyglycerol.

| Materials | Example 57 (PDMS-PGLY-39) Percent | Example 58 (PDMS-PGLY-40) Percent | Example 59 (PDMS-PGLY-41) Percent | Example 60 (PDMS-Gly-42) Percent |
|---|---|---|---|---|
| AC-CE-(PDMS-PGLY) (Macromer-26) | 22.37 | 26.85 | 31.31 | 22.37 |
| NVP | 35.79 | 31.32 | 31.31 | 33.55 |
| SIGMA | 31.32 | 31.32 | 26.84 | 26.84 |
| GMMA | 8.39 | 8.39 | 8.39 | 15.10 |
| PVP | 0.78 | 0.78 | 0.78 | 0.78 |
| Initiator (Daracure 1173) | 1.35 | 1.35 | 1.35 | 1.36 |
| Total | 100.0 | 100.0 | 100.00 | 100.0 |
| Lens Clarity | — | — | — | Clear lens- No Phase Separation |
| Lens Diameter (mm) | — | — | — | 13.90-13.95 |

TABLE 13-continued

Formulations containing modified PDMS-Polyglycerol.

| Materials | Example 57 (PDMS-PGLY-39) Percent | Example 58 (PDMS-PGLY-40) Percent | Example 59 (PDMS-PGLY-41) Percent | Example 60 (PDMS-Gly-42) Percent |
|---|---|---|---|---|
| Dk | — | — | — | $61.55 \times 10^{-11}$ |
| % Water | — | — | — | 62 |

AC-CE-(PDMS-PGLY) used in the above formulations was prepared according to procedure described in Example 26;
Lens Clarity Rank is from 1 to 10, with 1 being the worst (completely opaque);
Dk = Oxygen permeability of a contact lens is abbreviated, where "D" is diffusivity ($cm^2$/sec) and "k" is the solubility of oxygen in a given contact lens material (ml $O_2$/ml of material x mm Hg);
Contact lenses were prepared by UV curing in a nitrogen flushed chamber using spin cast technology as described above.

TABLE 14

Formulations containing modified PDMS-Polyglycerol.

| Materials | Example 61 (PDMS-PGLY-44) Percent | Example 62 (PDMS-PGLY-45) Percent | Example 63 (PDMS-PGLY-46) Percent |
|---|---|---|---|
| AC-CE-(PDMS-PGLY) (Macromer-26) | 22.68 | 22.37 | 22.32 |
| NVP | 40.82 | 40.27 | 40.17 |
| SIGMA | 24.94 | 22.37 | 24.55 |
| GMMA | 10.77 | 12.86 | 10.60 |
| PVP | 0.79 | 0.78 | 1.00 |
| Initiator (Daracure 1173) | 1.38 | 1.36 | 1.35 |
| Total | 100.0 | 100.0 | 100.0 |
| Lens Clarity | Clear lens-No Phase Separation | Clear lens-No Phase Separation | Clear lens-No Phase Separation |
| Lens Diameter (mm) | 14.30-14.35 | 14.40-14.45 | 14.20-14.25 |
| Dk | $85.59 \times 10^{-11}$ | $100.32 \times 10^{-11}$ | $85.05 \times 10^{-11}$ |
| % Water | 67.5 | 68 | 67 |

AC-CE-(PDMS-PGLY) used in the above formulations was prepared according to procedure described in Example 26;
Lens Clarity Rank is from 1 to 10, with 1 being the worst (completely opaque);
Dk = Oxygen permeability of a contact lens is abbreviated, where "D" is diffusivity ($cm^2$/sec) and "k" is the solubility of oxygen in a given contact lens material (ml $O_2$/ml of material x mm Hg);
Contact lenses were prepared by UV curing in a nitrogen flushed chamber using spin cast technology as described above.

Example 64 (PDMS-PGLY-48)

A small scale amount (<1 gram) of a formulation (PDMS-PGLY-48) was prepared by combining AC-CE-(PDMS-PGLY) (prepared according to the procedure described in Example 26), NVP, SIGMA, GMMA, PVP, and Daracure 1173 as shown in Table 15. Contact lenses were then prepared from the formulation using spin cast technology with UV cure in a nitrogen flushed UV light chamber, as described above. The prepared contact lenses were clear and exhibited no phase separation. The prepared contact lenses had a diameter of 14.15-14.20 mm. The prepared contact lenses had an oxygen permeability (Dk) of $91.02 \times 10^{-11}$ and a water percentage of 66.7%.

Example 65 (PDMS-PGLY-48A)

A formulation was prepared by combining 25 grams of macromer, AC-CE-(PDMS-PGLY) (prepared according to the procedure described in Example 26), NVP, SIGMA, GMMA, PVP, and Daracure 1173 as shown in Table 15. Contact lenses were then prepared from the formulation using spin cast technology with UV cure in a nitrogen flushed UV light chamber, as described above. The prepared contact lenses were clear and exhibited no phase separation. The prepared contact lenses had a diameter of 14.15-14.20 mm.

TABLE 15

Formulations containing modified PDMS-Polyglycerol.

| | Example 64 (PDMS-PGLY-48) Percent | Example 65 (PDMS-PGLY-48A) Percent |
|---|---|---|
| AC-CE-(PDMS-PGLY) (Macromer-26) | 22.62 | 22.62 |
| NVP | 37.33 | 37.33 |
| SIGMA | 24.89 | 24.89 |
| GMMA | 13.01 | 13.01 |
| PVP | 0.79 | 0.79 |
| Initiator (Daracure 1173) | 1.37 | 1.37 |
| Total | 100.0 | 100.0 |
| Lens Clarity | Clear lens-No Phase Separation | Clear lens-No Phase Separation |
| Lens Diameter (mm) | 14.15-14.20 | 14.15-14.20 |
| Dk | $97.02 \times 10^{-11}$ | — |
| % Water | 66.7 | — |

AC-CE-(PDMS-PGLY) used in the above formulations was prepared according to procedure described in Example 26;
Lens Clarity Rank is from 1 to 10, with 1 being the worst (completely opaque);
Dk = Oxygen permeability of a contact lens is abbreviated, where "D" is diffusivity ($cm^2$/sec) and "k" is the solubility of oxygen in a given contact lens material (ml $O_2$/ml of material x mm Hg);
Contact lenses were prepared by UV curing in a nitrogen flushed chamber using spin cast technology as described above.

Example 66

A formulation (1002-138-1F-1) was prepared by combining macromer AC-(PDMS-PGLY) (prepared according to procedure given in example 1) with various monomers, as shown in Table 16. A portion of the sample was placed in a plastic cap (~30 mm diameter) and exposed to UVA (3 mW/cm²) for about 10-15 minutes. The viscosity of this formulation increased after exposure to UVA, but it did not form a discernable gel under these conditions.

Example 67

A formulation (1002-138-1-F-2) was prepared by combining macromer AC-(PDMS-PGLY) (prepared according to procedure given in example 1) with various monomers, as shown in Table 16. A portion of the sample was placed in a plastic cap (~30 mm diameter) and exposed to UVA (3 mW/cm²) for about 10-15 minutes to yield a clear gel.

Example 68

Formulation 1002-138-1-F-4 was prepared by combining 15.02 grams of formulation 1002-138-1-F-3 with 0.005 grams of AMA, 0.005 grams of Daracure 1173, and 21.15 grams of isopropanol. Mass of individual components in listed in formulation 1002-138-1-F-4 shown in Table 16 were calculated. A portion of the sample was placed in a plastic cap (~30 mm diameter) and exposed to UVA (3.5 mW/cm²) for about 30 minutes. A discernable cross-linked gel did not form under these conditions.

Example 69

A formulation (1002-138-1-F-5) was prepared by combining macromer AC-(PDMS-PGLY) (prepared according to procedure given in example 1) with various monomers, as shown in Table 17. A portion of the formulation was placed in a plastic cap (~30 mm diameter) and exposed to UVA (3 mW/cm$^2$) for about 15 minutes to yield a clear gel. The gel was soaked in about 5 mL isopropyl alcohol for about 15 minutes and then equilibrated in purified water. The gel remained clear in its hydrated state and was noted to be lubricious and good elasticity. The gel was stretched to about double its original length before breaking.

Example 70

A formulation (1002-142-1-F-1) was prepared by combining macromer AC-(PDMS-PGLY) (prepared according to procedure given in example 1) with various monomers, as shown in Table 17. About 0.3 mL portion of the formulation was placed in a plastic cap (~30 mm diameter) and exposed to UVA (3 mW/cm$^2$) for about 10 minutes to yield a clear gel. The gel was further exposed to UVA for about 10 more minutes. The gel was soaked in about 10 mL of isopropanol for about 10 minutes. The isopropanol was drained from the gel and replaced with fresh isopropanol. The gel was further extracted by heating the isopropanol to about 60° C. for about 15 minutes. The gel was then placed in purified water. The gel was noted to be opaque (white) and brittle.

TABLE 16

Evaluation of formulations containing actinically cross-linkable polydimethylsiloxane-polyglycerol {AC-(PDMS-PGLY)}

| Materials | Example 66 (1002-138-1-F-1) Grams | Percent | Example 67 (1002-138-1-F-2) Grams | Percent | Example 68 (1002-138-1-F-4) Grams (calculated) | Percent |
|---|---|---|---|---|---|---|
| AC-(PDMS-PGLY) (Macromer-1) | 1.024 | 66.45 | 0.498 | 49.84 | 7.516 | 20.8 |
| SIGMA | — | — | — | — | 3.726 | 10.3 |
| GMMA | — | — | 0.250 | 25.00 | 3.717 | 10.3 |
| NVP | — | — | — | — | — | — |
| AMA | — | — | — | — | 0.005 | — |
| Daracure 1173 | 0.016 | 1.04 | 0.008 | 0.78 | 0.067 | 0.2 |
| IPA | 0.501 | 32.51 | 0.244 | 24.38 | 21.15 | 58.5 |
| Total | 1.541 | 100 | 1.000 | 100 | 36.181 | 100 |

AC-(PDMS-PGLY) (1002-138-1) used in the above formulations was prepared as described in example 1.

Example 71

A formulation (1002-142-1-F-2) was prepared by combining 7.506 grams of formulation 1002-142-1-F-1 with 1.104 grams of NVP. Mass of individual components in listed in formulation 1002-142-1-F-2 shown in Table 17 were calculated. About 0.3 mL portion of the above formulation was placed in a plastic cap (~30 mm diameter) and exposed to UVA (3 mW/cm$^2$) for about 10 minutes to yield a clear and tacky gel. Additional curing for 20 minutes (total cure time of 30 minutes) yielded a semiflexible gel. The gel was hydrated in purified water and was noted to be brittle and opaque (white).

Example 72 (1002-138-3-F1)

A formulation was prepared by combining 1.048 grams of macromer-2 (prepared according to procedure given in example 2) with 0.046 grams of Daracure 1173 and 0.375 grams of isopropyl alcohol. The resulting formulation was noted to be cloudy and was not subjected to cure testing.

TABLE 17

Evaluation of formulations containing actinically cross-linkable polydimethylsiloxane-polyglycerol {AC-(PDMS-PGLY)}

| Materials | Example 69 (1002-138-1-F-5) Grams | Percent | Example 70 (1002-142-1-F-1) Grams | Percent | Example 71 (1002-142-1-F-2) Grams (calculated) | Percent |
|---|---|---|---|---|---|---|
| AC-(PDMS-PGLY) (Macromer-1) | 7.60 | 21.0 | 7.63 | 46.8 | 3.513 | 46.8 |
| SIGMA | 3.77 | 10.4 | 4.61 | 28.3 | 2.124 | 28.3 |
| GMMA | 0.00 | 0.0 | 0.00 | 0.0 | 0.000 | 0 |
| NVP | 3.71 | 10.2 | 3.92 | 24.0 | 2.905 | 24 |
| AMA | 0.08 | 0.2 | 0.08 | 0.5 | 0.038 | 0.5 |
| Daracure 1173 | 0.08 | 0.2 | 0.08 | 0.5 | 0.038 | 0.5 |
| Total | 36.181 | 100 | 16.30 | 100.0 | 7.506 | 100 |

AC-(PDMS-PGLY) (1002-138-1) used in the above formulations was prepared as described in example 1.

Example 73 (1002-156-2)

A formulation (1002-156-2) was prepared by combining 1.520 grams of Macromer-26 (macromer prepared as described in Example 26), 1.051 grams of macromer-5 (macromer prepared as described in example 5), 0.058 grams AMA, and about 10 microliters (calculated 0.011 grams) of Daracure 1173, as shown in Table 18, to yield a hazy fluid. Upon addition of 6.5 grams t-amyl alcohol (tAA), the formulation became clear. This formulation formed a gel when exposed to UVA. Hydration of the UV cured sample in purified water, yielded a lubricous gel with a hazy appearance.

Example 74 (1002-156-3)

A formulation (1002-156-3) was prepared by combining 1.252 grams of Macromer-26 (prepared as described in Example 26), 1.253 grams of macromer-4 (prepared as described in Example 4), and about 10 microliters (calculated 0.011 grams) of Daracure 1173 as shown in Table 18. The prepared formulation was hazy. Upon addition of 8.5 grams t-amyl alcohol (tAA), the formulation became clear. To further test the formulation, a cure test was performed as described for Example 73. After hydration, a hazy, lubricous gel was obtained.

Example 75 (1002-156-4)

A formulation (1002-156-4) was prepared by combining 1.251 grams of macromer-26 (prepared as described in Example 26), 1.254 grams of macromer-4 (prepared as described in Example 4), 0.015 grams AMA, and about 10 microliters (calculated 0.011 grams) of Daracure 1173 as shown in Table 18 to yield a hazy fluid. Addition of SIGMA monomer (14.5 grams) did not improve miscibility. No further tests were performed on this formulation.

TABLE 18

Evaluation of actinically cross-linkable formulations containing allyl methacrylate, SIGMA and chain extended PDMS-Polyglycerol Modified PDMS-Polyglycerol

| Formulation Components | Example 73 (1002-156-2) | | Example 74 (1002-156-3) | | Example 75 (1002-156-4) | |
|---|---|---|---|---|---|---|
| | Grams | Percent by Weight | Grams | Percent by Weight | Grams | Percent by Weight |
| Macromer-26 | 1.520 | 16.63 | 1.252 | 11.48 | 1.251 | 7.35 |
| Macromer-4 | 0 | 0 | 1.253 | 11.48 | 1.254 | 7.36 |
| Macromer-5 | 1.051 | 11.5 | 0 | 0 | 0 | 0 |
| Macromer-6 | 0 | 0 | 0 | 0 | 0 | 0 |
| Macromer-7 | 0 | 0 | 0 | 0 | 0 | 0 |
| AMA | 0.058 | 0.63 | 0 | 0 | 0.015 | 0.09 |
| SIGMA | 0 | 0 | 0 | 0 | 14.501 | 85.14 |
| t-amyl alcohol | 6.5 | 71.12 | 8.5 | 76.94 | 0 | 0 |
| Daracure 1173 | 0.011 | 0.12 | 0.011 | 0.1 | 0.011 | 0.06 |
| Total | 9.140 | 100.00 | 10.917 | 100.00 | 17.032 | 100.00 |
| Appearance of formulation | hazy before addition of tAA | | hazy before addition of tAA | | Cloudy before addition of SIGMA | |
| Clarity of Formulation after addition of tAA or SIGMA | clear after addition of tAA | | clear after addition of tAA | | Cloudy after addition of SIGMA | |

Example 76 (1002-156-5)

A formulation (1002-156-5) was prepared by combining 1.029 grams of macromer-5 (prepared as described in Example 5), 1.114 grams of macromer-4 (prepared as described in Example 4), 0.059 grams AMA, and about 10 microliters (calculated 0.011 grams) of Daracure 1173 as shown in Table 19 to yield a clear fluid. Upon addition of 7.5 grams t-amyl alcohol (tAA) the formulation remained clear. This formulation was then exposed to UVA. Hydration of the UV cured sample in purified water yielded a lubricous gel with a hazy appearance.

Example 77 (1002-156-6)

A formulation (1002-156-6) was prepared by combining 1.252 grams of Macromer-26 (prepared as described in Example 26), with 1.250 grams of macromer-6 (prepared as described in Example 6), 0.065 grams AMA, and about 10 microliters (calculated 0.011 grams) of Daracure 1173 as shown in Table 19 to yield a clear fluid. The formulation formed a gel when exposed to UVA. Hydration of the UV cured sample in purified water yielded a lubricous gel with a partly hazy appearance.

Example 78 (1002-156-7)

A formulation (1002-156-7) was prepared by combining 1.253 grams of Macromer-26 (prepared as described in Example 26), 1.258 grams of macromer-7 (prepared as described in Example 7), and about 10 microliters (calculated 0.011 grams) of Daracure 1173 as shown in Table 19 to yield a clear fluid. The formulation formed a gel when exposed to UVA. Hydration of the UV cured sample in purified water yielded a clear lubricous gel with a white outer ring.

Example 79 (1002-154-4)

A formulation (1002-154-4) was prepared by combining polydimethylsiloxane (KF6100, Viscosity ~40,000 cps), and isophorone diisocyanate (IPDI) containing 0.1 mg DBTDL/mL as shown in Table 20.

Example 80 (1002-154-5)

A formulation (1002-154-5) was prepared by combining polydimethylsiloxane (KF6100, Viscosity ~40,000 cps), isophorone diisocyanate (IPDI) containing 0.1 mg DBTDL/mL, and diethylene glycol as shown in Table 20.

Example 81 (1002-154-6)

A formulation (1002-154-6) was prepared by combining polydimethylsiloxane (KF6100, Viscosity ~40,000 cps), isophorone diisocyanate (IPDI) containing 0.1 mg DBTDL/mL, and diethylene glycol as shown in Table 20.

Example 82 (1002-154-3)

A formulation (1002-154-3) was prepared by combining macromer-4 (prepared as described in Example 4) and IPA containing 3.33 mg IRGACURE as shown in Table 21. The sample was spread on a polyethylene sheet and exposed to UV irradiation (3.5 mW/cm$^2$) for 30 minutes. Upon UV exposure, the sample thickened but did not gel.

TABLE 19

Evaluation of actinically cross-linkable formulations containing allyl methacrylate, SIGMA and chain extended PDMS-Polyglycerol Modified PDMS-Polyglycerol

| Formulation Components | Example 76 (1002-156-5) Grams | Percent by Weight | Example 77 (1002-156-6) Grams | Percent by Weight | Example 78 (1002-156-7) Grams | Percent by Weight |
|---|---|---|---|---|---|---|
| Macromer-26 | 0 | 0 | 1.252 | 48.56 | 1.253 | 49.69 |
| Macromer-4 | 1.114 | 11.47 | 0 | 0 | 0 | 0 |
| Macromer-5 | 1.029 | 10.59 | 0 | 0 | 0 | 0 |
| Macromer-6 | 0 | 0 | 1.250 | 48.49 | 0 | 0 |
| Macromer-7 | 0 | 0 | 0 | 0 | 1.258 | 49.89 |
| AMA | 0.059 | 0.61 | 0.065 | 2.52 | 0 | 0 |
| SIGMA | 0 | 0 | 0 | 0 | 0 | 0 |
| t-amyl alcohol | 7.5 | 77.22 | 0 | 0 | 0 | 0 |
| Daracure 1173 | 0.011 | 0.11 | 0.011 | 0.42 | 0.011 | 0.43 |
| Total | 9.713 | 100.00 | 2.578 | 99.99 | 2.522 | 100.00 |
| Appearance of formulation | clear | | clear | | clear | |
| Clarity of Formulation after addition of tAA or SIGMA | N/A | | N/A | | N/A | |

TABLE 20

PDMS-Polyglycerol Copolymerized with diisocyanate and diethyleneglycol.

| Materials | Example 79 (1002-154-4) Grams | Percent | Example 80 (1002-154-5) Grams | Percent | Example 81 (1002-154-6) Grams | Percent |
|---|---|---|---|---|---|---|
| KF6100 | 5.3 | 91.22 | 5.01 | 69.68 | 5.35 | 57.04 |
| IPDI containing 0.1 mg DBTDL/mL | 0.51 | 8.78 | 1.08 | 15.02 | 2.02 | 21.54 |
| Diethylene glycol | 0.00 | 0.00 | 1.10 | 15.30 | 2.01 | 21.43 |
| Total | 5.81 | 100 | 7.19 | 100 | 9.38 | 100 |

TABLE 21

Evaluation of actinically curable formulation containing PDMS-Polyglycerol copolymer dissolved in IPA.

| Materials | Example 82 (1002-154-3) Actual Grams | Percent |
|---|---|---|
| 1002-152-1 (98.43% KF6100-1.58% IEM) | 3.5 | 70.1 |
| IPA containing 3.33 mg Irgacure 2951/ml | 1.49 | 29.9 |
| Total | 4.99 | 100 |

TABLE 22

Diameter of contact lenses after repeated autoclave sterilization at 121° C. using +3.00 diopter contact lenses.

| | Test | Autoclaved 1× | Autoclaved 2× | Autoclaved 3× | Autoclaved 4× | Autoclaved 5× |
|---|---|---|---|---|---|---|
| Diameter (mm) | Mean | 14.32 | 14.32 | 14.33 | 14.38 | 14.39 |
| | Maximum | 14.40 | 14.35 | 14.35 | 14.40 | 14.40 |
| | Minimum | 14.30 | 14.30 | 14.30 | 14.35 | 14.35 |
| | Range (Max − Min) | 0.10 | 0.05 | 0.05 | 0.05 | 0.05 |
| | Standard Deviation | 0.03 | 0.02 | 0.03 | 0.03 | 0.02 |
| Power (D) | Average | +3.00 | +3.00 | +3.00 | +3.00 | +3.00 |
| | Maximum | +3.00 | +3.00 | +3.00 | +3.00 | +3.00 |
| | Minimum | +3.00 | +3.00 | +3.00 | +3.00 | +3.00 |

TABLE 22-continued

Diameter of contact lenses after repeated autoclave sterilization at 121° C. using +3.00 diopter contact lenses.

| Test | Autoclaved 1× | Autoclaved 2× | Autoclaved 3× | Autoclaved 4× | Autoclaved 5× |
|---|---|---|---|---|---|
| Range (Max − Min) | 0.00 | 0.00 | 0.00 | 0.00 | 0.00 |
| Standard Deviation | 0.00 | 0.00 | 0.00 | 0.00 | 0.00 |

Heat Stability of Contact Lenses (Example 83)

A formulation with about the same composition as described in Example 64 was used to produce contact lenses. Contact lenses with different powers were prepared using polypropylene molds and a spin cast UV-Cure process as described above. Contact lenses were removed from molds, extracted in an aqueous-ethanol solution, extracted in purified water, and placed in polypropylene blisters containing buffered saline. The blisters containing the contact lenses immersed in buffered saline were heat sealed with foil lidding and subjected to repeated (1×, 2×, 3×, 4×, 5×) autoclave sterilization at about 121° C. Results from these tests (Table 22-Table 25) show the contact lenses were stable to repeated autoclave sterilization.

TABLE 23

Contact lens diameter repeated autoclave sterilization at 121° C. using −3.25 diopter contact lenses.

| | Test | Autoclaved 1× | Autoclaved 2× | Autoclaved 3× | Autoclaved 4× | Autoclaved 5× |
|---|---|---|---|---|---|---|
| Diameter (mm) | Mean | 14.51 | 14.51 | 14.54 | 14.55 | 14.55 |
| | Maximum | 14.55 | 14.55 | 14.55 | 14.60 | 14.60 |
| | Minimum | 14.40 | 14.40 | 14.50 | 14.50 | 14.50 |
| | Range (Max − Min) | 0.15 | 0.15 | 0.05 | 0.10 | 0.10 |
| | Standard Deviation | 0.04 | 0.04 | 0.02 | 0.03 | 0.03 |
| Power (D) | Mean | −3.25 | −3.25 | −3.25 | −3.25 | −3.25 |
| | Maximum | −3.25 | −3.25 | −3.25 | −3.25 | −3.25 |
| | Minimum | −3.25 | −3.25 | −3.25 | −3.25 | −3.25 |
| | Range (Max − Min) | 0.00 | 0.00 | 0.00 | 0.00 | 0.00 |
| | Standard Deviation | 0.00 | 0.00 | 0.00 | 0.00 | 0.00 |

TABLE 24

Base curve of contact lenses in Table 23 after repeated autoclave sterilization.

| | Test | Autoclaved 1× | Autoclaved 2× | Autoclaved 3× | Autoclaved 4× | Autoclaved 5× |
|---|---|---|---|---|---|---|
| Base Curve (mm) | Mean | 8.94 | 8.99 | 9.00 | 9.00 | 8.99 |
| | Maximum | 9.00 | 9.00 | 9.05 | 9.05 | 9.00 |
| | Minimum | 8.90 | 8.95 | 8.95 | 8.95 | 8.90 |
| | Range (Max − Min) | 0.10 | 0.05 | 0.10 | 0.10 | 0.10 |
| | Standard Deviation | 0.05 | 0.02 | 0.03 | 0.03 | 0.03 |

TABLE 24-continued

Base curve of contact lenses in Table 23 after repeated autoclave sterilization.

| | Test | Autoclaved 1× | Autoclaved 2× | Autoclaved 3× | Autoclaved 4× | Autoclaved 5× |
|---|---|---|---|---|---|---|
| Power (D) | Mean | −3.25 | −3.25 | −3.25 | −3.25 | −3.25 |
| | Maximum | −3.25 | −3.25 | −3.25 | −3.25 | −3.25 |
| | Minimum | −3.25 | −3.25 | −3.25 | −3.25 | −3.25 |
| | Range (Max − Min) | 0.00 | 0.00 | 0.00 | 0.00 | 0.00 |
| | Standard Deviation | 0.00 | 0.00 | 0.00 | 0.00 | 0.00 |

TABLE 25

Diameter of contact lenses after repeated autoclave sterilization at 121° C. using −8.25 diopter contact lenses.

| | Test | Autoclaved 1× | Autoclaved 2× | Autoclaved 3× | Autoclaved 4× | Autoclaved 5× |
|---|---|---|---|---|---|---|
| Diameter (mm) | Mean | 14.46 | 14.48 | 14.49 | 14.50 | 14.48 |
| | Maximum | 14.55 | 14.55 | 14.55 | 14.60 | 14.55 |
| | Minimum | 14.30 | 14.25 | 14.25 | 14.25 | 14.25 |
| | Range (Max − Min) | 0.25 | 0.30 | 0.30 | 0.35 | 0.30 |
| | Standard Deviation | 0.09 | 0.09 | 0.10 | 0.11 | 0.09 |
| Power (D) | Mean | −8.25 | −8.25 | −8.25 | −8.25 | −8.25 |
| | Maximum | −8.25 | −8.25 | −8.25 | −8.25 | −8.25 |
| | Minimum | −8.25 | −8.25 | −8.25 | −8.25 | −8.25 |
| | Range (Max − Min) | 0.00 | 0.00 | 0.00 | 0.00 | 0.00 |
| | Standard Deviation | 0.00 | 0.00 | 0.00 | 0.00 | 0.00 |

Evaluation of Antifouling Properties (Example 84)

This example demonstrates that the materials described herein show good resistance to fouling by protein. Contact lenses were prepared as described in Example 28 and evaluated for Lysozyme deposition propensity. For comparison, ionic contact lenses (etafilcon A) were also evaluated for Lysozyme deposition propensity. Three lenses were soaked separately in ISO PBS and the ISO PBS was changed per hour (×3 times) to wash away any surfactant. Before placing the lens in the respective deposition solution, the lens was wiped to remove any excess ISO PBS on the lens. Each contact lens was then placed separately in 3×1.5 mL of the respective deposition solution in a glass vial. All the glass vials containing the lenses in deposition solution were incubated at 37° C. for 48 hours in water bath. After 48 hours, the vials were cooled to room temperature and analyzed via the Bovine serum albumin assay (BSA). A standard BSA assay protocol is provided above. As a control, two glass vials containing the deposition solution without a contact lens were also incubated using the same conditions above. The original deposition solution and the solution after incubation in glass vial were analyzed via BSA assay to ensure that there was no uptake of the protein solution by the vial.

Using the BSA assay, a protein uptake of 1701 μg/mL was observed on Clear58 contact lens and 413 μg/mL for Acuvue Moist contact lenses. Both Clear58 and Acuvue Moist comprise etafilcon-A, which is an ionic high water contact lenses (FDA group IV) material. Meanwhile, protein uptake for a silicone hydrogel contact lens described herein was 3.78 μg/mL.

Example 85

Figure 4:
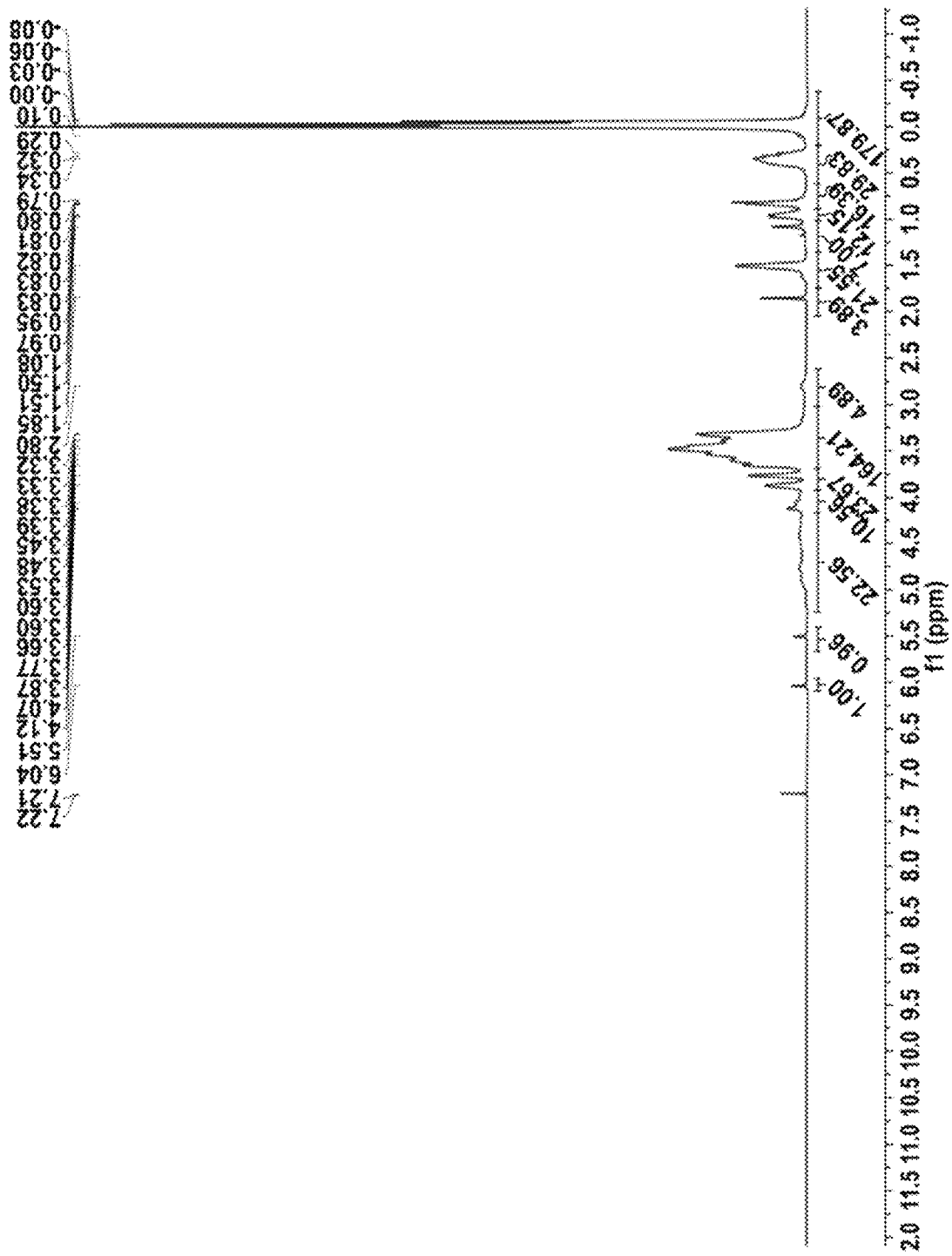
FIG. 4 is a proton NMR spectrum of a cross-linkable polysiloxane-polyglycerol block copolymer.

A proton NMR spectrum of a cross-linkable polysiloxane-polyglycerol block copolymer is shown in FIG. 4.

An example crosslinkable polysiloxane-polyglycerol block copolymer as disclosed herein is shown in Scheme 23.

Example 86—Stability Testing

The purpose of this example is to summarize the testing results for lenses at 15 months incubation. This example will discuss the results obtained at 15 month for lenses aged under accelerated aging conditions at 45° C.

The scope of the report is limited to the 15 months incubation of the stability study of the soft silicone (Polyglyceryl-siloxane) hydrogel contact lens. This report documents the results and analyses of tests executed in accordance with stability protocol S-STB-PTC-18-014.

Details of lenses which were used in the stability study are shown in Table 26.

Scheme 23 An example crosslinkable polysiloxane-polyglycerol block copolymer.
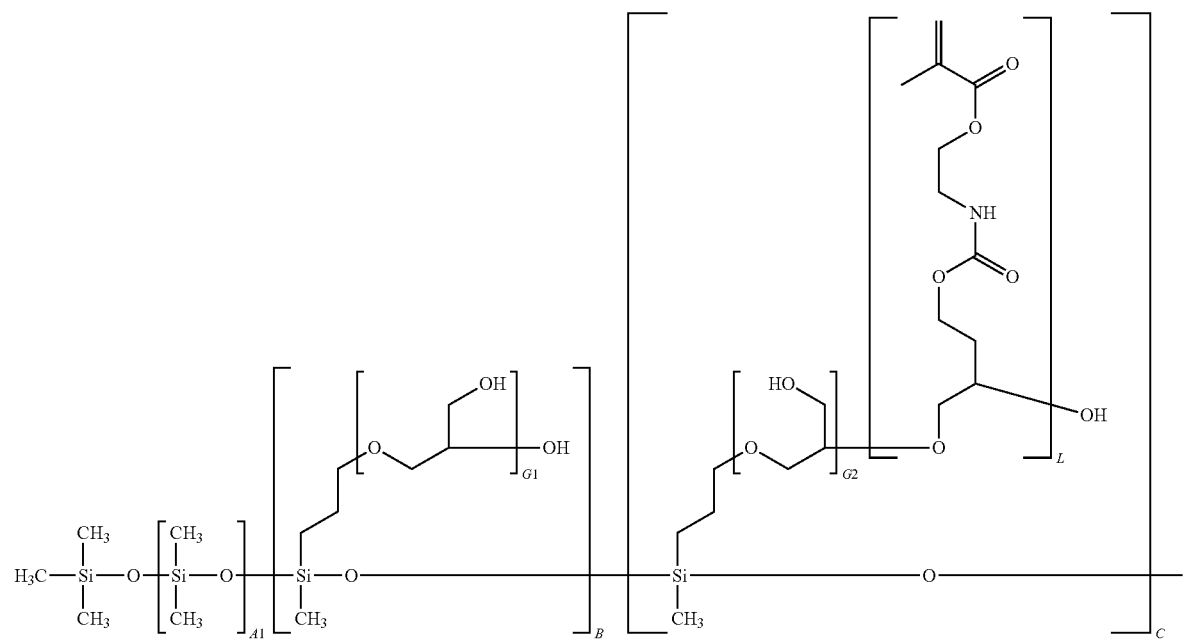
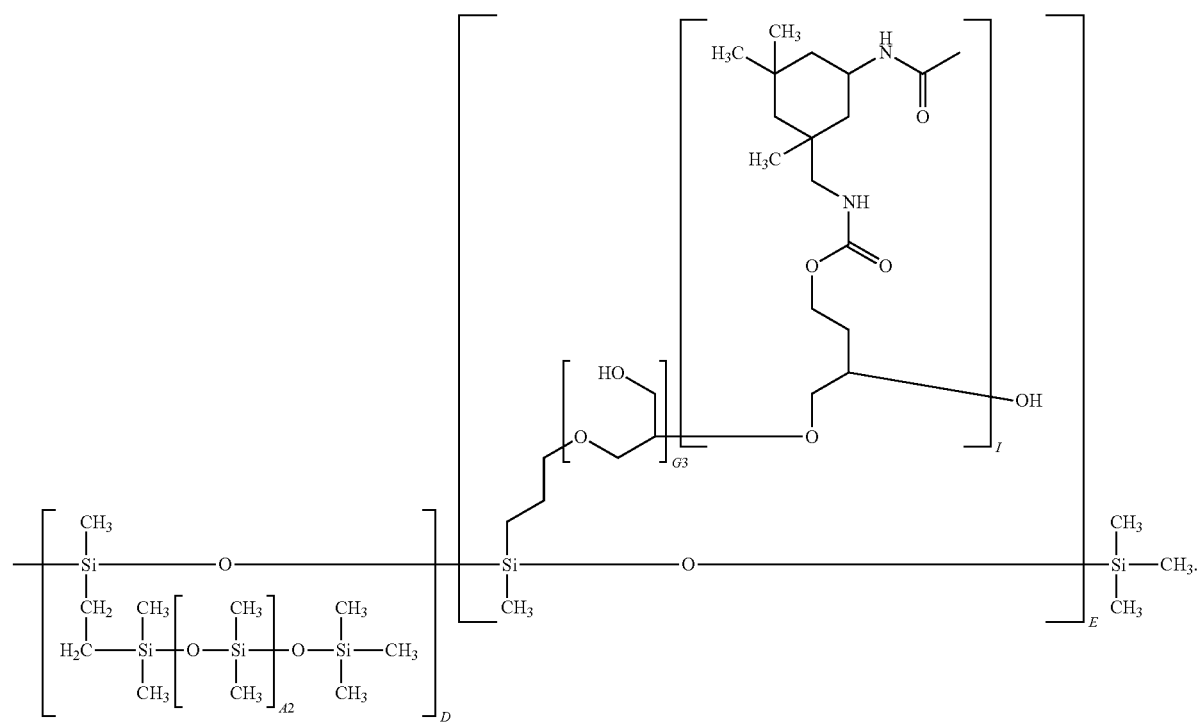

TABLE 26

Monomer lot ID, lens lot number, back vertex power, date of manufacturing, and quantities of sample lenses that were produced and used in the stability study.

| Lens Formulation Lot No. | Lens Lot No. | Lens Lot ID | Back Vertex Power |
|---|---|---|---|
| 68GS-001 | PGS0119001 | A1 | −8.25 |
|  | PGS0119002 | A2 | −3.25 |
|  | PGS0119003 | A3 | +3.00 |
| 68GS-002 | PGS0119004 | A4 | −8.25 |
|  | PGS0119005 | A5 | −3.25 |
|  | PGS0119006 | A6 | +3.00 |
| 68GS-003 | PGS0119007 | A7 | −8.25 |
|  | PGS0119008 | A8 | −3.25 |
|  | PGS0119009 | A9 | +3.00 |

For the stability tests, The lenses were packaged in polypropylene bowls (S-cup), sealed with aluminum laminated foils and filled with phosphate-buffered saline (PBS). Total quantities of the above detailed stability samples were split and placed into three incubators maintained at 25° C.±2° C., 35° C.±2° C. and 45° C.±2° C. Stability study results at baseline and previous intervals (3 months, 6 months, 9 months, and 12 months) were also performed. The following tests were carried out in the 15 month stability study: back vertex power; visual defect; diameter; back vertex radius of curvature; saline pH and osmolality; spectral and luminous transmittance; sterility test; water content; package seal integrity; and extractables and biocompatibility studies. Lenses were collected from 45° C. incubator for testing at 15 months interval. The temperature and humidity of incubators used in this stability study are summarized in Table 27 and Table 28.

TABLE 27

Temperature of incubators from month 12 to month 15.

| Incubator ID/ Calibration Due Date |  | Temperature (° C.) | Month 12 (° C.) | Month 13 (° C.) | Month 14 (° C.) | Month 15 (° C.) |
|---|---|---|---|---|---|---|
| STL-ICU-09/ | 45° C. | Maximum | 44 | 45 | 46 | 45 |
| Apr. 2, 2021 |  | Minimum | 43 | 43 | 44 | 44 |
|  |  | Average | 44 | 44 | 45 | 45 |

TABLE 28

Humidity of incubators from month 12 to month 15.

| Incubator ID/ Calibration Due Date |  | Humidity | Month 12 | Month 13 | Month 14 | Month 15 |
|---|---|---|---|---|---|---|
| STL-ICU-09/ | 45° C. | Maximum | 38% | 39% | 39% | 38% |
| Apr. 2, 2021 |  | Minimum | 36% | 36% | 37% | 35% |
|  |  | Average | 37% | 38% | 38% | 37% |

The shelf life of the stability study can be accelerated by aging at higher temperature and the real time shelf life equivalent at 25° C. is established based on ISO 11987:2012 Clause 9.2.1, as summarized in Table 29.

TABLE 29

Real time shelf life equivalent at 25° C. for contact lens samples incubated under accelerated aging studies at 35° C. and 45° C. as per ISO 11987:2012 Clause 9.2.1.

| | Real time shelf life equivalent at 25° C. | | |
|---|---|---|---|
| Incubation Period | 25° C. ± 2° C. (real time) | 35° C. ± 2° C. (accelerated) | 45° C. ± 2° C. (accelerated) |
| 0 months | | baseline | |
| 3 months | 3 months | 6 months | 12 months |
| 6 months | 6 months | 12 months | 24 months |
| 9 months | 9 months | 18 months | 36 months |
| 12 months | 12 months | 24 months | 48 months |
| 15 months | 15 months | 30 months | 60 months |

The back vertex power of the lenses at 15 months was tested. The specification (e.g., acceptance criteria) identified for the test was ±0.25 D of nominal value measured at baseline. The sampling plan for the tests was that 10 lenses per lens lot per test interval were sampled. The results of the back vertex power test of the lenses that met the acceptance criteria at 15 months are summarized in Table 30. In general, all the lens power are within manufacturing tolerances (i.e., ±0.25 D).

The visual defects of the lenses at 15 months was tested. The specification (e.g., acceptance criteria) identified for the test was no unusual color, surface deposit, and appearance. The sampling plan for the tests was that 10 lenses per lens lot per test interval were sampled. The results of the visual defect test of the lenses that met the acceptance criteria at 15 months are summarized in Table 31. In general, all the lenses did not have any visual defects.

TABLE 30

Results of the back vertex power test of the lenses that met the acceptance criteria at 15 months.

| Monomer Lot No. | Lens Lot ID | | Back Vertex Power (D) | |
|---|---|---|---|---|
| | | | Baseline | 15 months at 45° C. |
| 68GS-001 | A1 | Mean | −8.75 | −8.81 |
| | | Range | 0.13 | 0.25 |
| | | SD | 0.04 | 0.11 |
| | A2 | Mean | −3.50 | −3.54 |
| | | Range | 0.50 | 0.25 |
| | | SD | 0.16 | 0.08 |
| | A3 | Mean | +3.00 | +3.09 |
| | | Range | 0.50 | 0.25 |
| | | SD | 0.12 | 0.12 |
| 68GS-002 | A4 | Mean | −8.75 | −8.85 |
| | | Range | 0.25 | 0.25 |
| | | SD | 0.13 | 0.13 |
| | A5 | Mean | −3.75 | −3.75 |
| | | Range | 0.25 | 0.00 |
| | | SD | 0.11 | 0.00 |
| | A6 | Mean | +3.00 | +3.04 |
| | | Range | 0.25 | 0.25 |
| | | SD | 0.11 | 0.08 |
| 68GS-003 | A7 | Mean | −8.75 | −8.79 |
| | | Range | 0.25 | 0.25 |
| | | SD | 0.12 | 0.08 |
| | A8 | Mean | −3.50 | −3.59 |
| | | Range | 0.25 | 0.25 |
| | | SD | 0.08 | 0.12 |
| | A9 | Mean | +3.00 | +3.18 |
| | | Range | 0.25 | 0.25 |
| | | SD | 0.12 | 0.12 |

Range = Maximum-minimum
SD = Standard Deviation

TABLE 31

Results of the visual defect test of the lenses that met the acceptance criteria at 15 months.

| Monomer Lot No. | Lens Lot ID | Visual Defects | |
|---|---|---|---|
| | | Baseline | 15 months at 45° C. |
| 68GS-001 | A1 | No defects | No defects |
| | A2 | No defects | No defects |
| | A3 | No defects | No defects |
| 68GS-002 | A4 | No defects | No defects |
| | A5 | No defects | No defects |
| | A6 | No defects | No defects |
| 68GS-003 | A7 | No defects | No defects |
| | A8 | No defects | No defects |
| | A9 | No defects | No defects |

The diameter of the lenses at 15 months was tested. The specification (e.g., acceptance criteria) identified for the test was a diameter of 12.0-15.0 mm and ±0.20 mm of nominal value measured at baseline. 10 lenses per lens lot per test interval were sampled. The results of the diameter test of the lenses that met the acceptance criteria at 15 months are summarized in Table 32. In general, lens diameters are within ±0.20 mm of nominal value measured at baseline.

The base curve of the lenses at 15 months was tested. The specification (e.g., acceptance criteria) identified for the test was a base curve of 7.80-10.00 mm and ±0.20 mm of nominal value measured at baseline. The sampling plan for the tests was that 10 lenses per lens lot per test interval were sampled. The results of the base curve test of the lenses that met the acceptance criteria at 15 months are summarized in Table 33. In general, lens base curves are within ±0.20 mm of nominal value measured at baseline.

The saline pH and osmolality of the lenses at 15 months was tested. The specification (e.g., acceptance criteria) identified for the test was a pH of 6.30 to 8.50 and an osmolality of 285±65 mOsm·kg. The sampling plan for the tests was that the saline was pooled from 10 lenses per monomer lot per temperature condition per buy off for sampling. The results of the pH and Osmolality tests of the lenses that met the acceptance criteria at 15 months are summarized in Table 34. In general, the results of saline pH at 15 months are within specification and met the acceptance criteria of the stability study. The saline pH value was found to be within ocular comfort range, which is around 6.3 to 8.5.

TABLE 32

Results of the diameter test of the lenses that met the acceptance criteria at 15 months.

| Monomer Lot No. | Lens Lot ID | | Diameter (mm) | |
|---|---|---|---|---|
| | | | Baseline | 15 months at 45° C. |
| 68GS-001 | A1 | Mean | 14.10 | 14.13 |
| | | Range | 0.40 | 0.35 |
| | | SD | 0.15 | 0.12 |
| | A2 | Mean | 14.10 | 14.19 |
| | | Range | 0.33 | 0.30 |
| | | SD | 0.10 | 0.10 |
| | A3 | Mean | 13.95 | 14.03 |
| | | Range | 0.13 | 0.25 |
| | | SD | 0.05 | 0.09 |
| 68GS-002 | A4 | Mean | 14.05 | 14.11 |
| | | Range | 0.23 | 0.25 |
| | | SD | 0.08 | 0.09 |
| | A5 | Mean | 14.10 | 14.22 |
| | | Range | 0.30 | 0.35 |
| | | SD | 0.11 | 0.10 |
| | A6 | Mean | 14.05 | 14.10 |
| | | Range | 0.23 | 0.25 |
| | | SD | 0.07 | 0.11 |
| 68GS-003 | A7 | Mean | 14.05 | 14.05 |
| | | Range | 0.30 | 0.35 |
| | | SD | 0.10 | 0.10 |
| | A8 | Mean | 14.10 | 14.12 |
| | | Range | 0.25 | 0.40 |
| | | SD | 0.09 | 0.15 |
| | A9 | Mean | 14.10 | 14.03 |
| | | Range | 0.25 | 0.30 |
| | | SD | 0.10 | 0.11 |

Range = Maximum-minimum
SD = Standard Deviation

TABLE 33

Results of the base curve test of the lenses that met the acceptance criteria at 15 months.

| Monomer Lot No. | Lens Lot ID | | Base curve (mm) | |
|---|---|---|---|---|
| | | | Baseline | 15 months at 45° C. |
| 68GS-001 | A1 | Mean | 8.60 | 8.45 |
| | | Range | 0.15 | 0.10 |
| | | SD | 0.06 | 0.05 |
| | A2 | Mean | 8.60 | 8.71 |
| | | Range | 0.23 | 0.20 |
| | | SD | 0.08 | 0.05 |
| | A3 | Mean | 8.50 | 8.66 |
| | | Range | 0.18 | 0.20 |
| | | SD | 0.05 | 0.06 |
| 68GS-002 | A4 | Mean | 8.60 | 8.45 |
| | | Range | 0.20 | 0.20 |
| | | SD | 0.06 | 0.07 |
| | A5 | Mean | 8.60 | 8.63 |
| | | Range | 0.25 | 0.20 |
| | | SD | 0.09 | 0.06 |

TABLE 33-continued

Results of the base curve test of the lenses that met the acceptance criteria at 15 months.

| Monomer Lot No. | Lens Lot ID | | Base curve (mm) | |
|---|---|---|---|---|
| | | | Baseline | 15 months at 45° C. |
| | A6 | Mean | 8.55 | 8.65 |
| | | Range | 0.23 | 0.20 |
| | | SD | 0.07 | 0.08 |
| 68GS-003 | A7 | Mean | 8.60 | 8.50 |
| | | Range | 0.27 | 0.25 |
| | | SD | 0.12 | 0.07 |
| | A8 | Mean | 8.60 | 8.64 |
| | | Range | 0.25 | 0.30 |
| | | SD | 0.09 | 0.08 |
| | A9 | Mean | 8.60 | 8.66 |
| | | Range | 0.20 | 0.25 |
| | | SD | 0.06 | 0.09 |

Range = Maximum-minimum
SD = Standard Deviation

TABLE 34

Results of the saline pH and Osmolality test of the lenses that met the acceptance criteria at 15 months.

| Monomer Lot No. | Test | Baseline | 15 months at 45° C. |
|---|---|---|---|
| 68GS-001 | pH | 7.46 | 7.48 |
| | Osmolality (average; mOsm/kg) | 254 | 268 |
| 68GS-002 | pH | 7.41 | 7.38 |
| | Osmolality (average; mOsm/kg) | 249 | 279 |
| 68GS-003 | pH | 7.43 | 7.42 |
| | Osmolality (average; mOsm/kg) | 257 | 297 |

The spectral luminous transmittance of the lenses at 15 months was tested. The specification (e.g., acceptance criteria) identified for the test was that the light transmittance of the lens measured between 380 nm and 780 nm must be 95% T+5% T. The sampling plan for the tests was that 5 lenses (mid power) per monomer lot per temperature condition per buy off were sampled. The results of the spectral and luminous transmittance of the lenses that met the acceptance criteria at 15 months are summarized in Table 35. In accordance with ISO 18369-3: 2006, visible light transmissibility of the lenses were to be measured for wavelength between 380 nm to 780 nm. Visible light transmissibility of the lenses was tested using Shimadzu UV-VIS spectra photometer UV-2450. The luminous transmittance was calculated from the spectral transmittance value based on standard illuminant CIE A. The spectral and luminous transmittance of the light by the stability lenses at the visible region is greater than 95%.

TABLE 35

Results of the spectral transmissibility at the visible region for the stability studies at 15 months.

| | Visible Light Transmittance | |
|---|---|---|
| Monomer Lot No. | Baseline | 15 months at 45° C. |
| 68GS-001 | 99% T | 99% T |
| 68GS-002 | 99% T | 98% T |
| 68GS-003 | 98% T | 98% T |

The sterility of the lenses at 15 months was tested. The specification (e.g., acceptance criteria) identified for the test was that the lenses were sterile (no growth). The sampling plan for the tests was that 20 lenses of any back vertex power per monomer lot per temperature condition per buy off were sampled. The results of the sterility tests of stability samples at 15 months are summarized in Table 36. Sterility of the lenses was tested and met specification as per USP 32<71>.

TABLE 36

The sterility results of stability samples at 15 months.

| Monomer | Sterility | |
|---|---|---|
| Lot No. | Baseline | 15 months at 45° C. |
| 68GS-001 | No growth (sterile) | No growth (sterile) |
| 68GS-002 | No growth (sterile) | No growth (sterile) |
| 68GS-003 | No growth (sterile) | No growth (sterile) |

The water content of the lenses at 15 months was tested. The specification (e.g., acceptance criteria) identified for the test was that the lenses has a water content of 68±2%. The sampling plan for the tests was that 25 lenses of any back vertex power per monomer lot per temperature condition per buy off were sampled. The results of the lens water content tests at 15 months that met the acceptance criteria are summarized in Table 37. Water content of lens was tested as per ISO 18369-4: 2006. The results of the tests show that the water content of the lens is within specification.

TABLE 37

Results of lens water content at 15 months.

| Monomer | Lens Water Content | |
|---|---|---|
| Lot No. | Baseline | 15 months at 45° C. |
| 68GS-001 | 66% | 67% |
| 68GS-002 | 66% | 67% |
| 68GS-003 | 67% | 67% |

The package integrity of the lenses at 15 months was tested (leak test). The specification (e.g., acceptance criteria) identified for the packaging seal integrity test was that there was no leakage. The sampling plan for the tests was that 10 blisters per back vertex power per monomer per temperature condition per buy off were sampled. The results of the package seal integrity of stability samples at 15 months are summarized in Table 38. The blister packaged lenses that were sample tested at 15 months have no leakage and passed the dye penetration test by using Carleton Integrity Tester.

TABLE 38

Results of package seal integrity tests of stability samples at 15 months.

| Monomer Lot No. | Lens Lot ID | Package Seal Integrity | |
|---|---|---|---|
| | | Baseline | 15 months at 45° C. |
| 68GS-001 | A1 | No leakage | No leakage |
| | A2 | No leakage | No leakage |
| | A3 | No leakage | No leakage |
| 68GS-002 | A4 | No leakage | No leakage |
| | A5 | No leakage | No leakage |
| | A6 | No leakage | No leakage |

TABLE 38-continued

Results of package seal integrity tests of stability samples at 15 months.

| Monomer Lot No. | Lens Lot ID | Package Seal Integrity | |
|---|---|---|---|
| | | Baseline | 15 months at 45° C. |
| 68GS-003 | A7 | No leakage | No leakage |
| | A8 | No leakage | No leakage |
| | A9 | No leakage | No leakage |

The extractables and biocompatibility of the lenses were also tested. For cytotoxicity tests, the specification identified was that there was acceptable cell lysis of toxicity as per ISO 10993-5. For ocular irritation tests, the specification identified was that there was an acceptable irritation scale as per ISO 10993-10. For systemic toxicity tests, the specification identified was that there was an acceptable biological reactivity as per ISO 10993-11. For sensitization tests, the specification identified was that there was an acceptable irritation scale as per ISO 10993-10. For extractables tests, the specification identified was for monitoring purposes.

The sampling plan for the biocompatibility tests was that 250 lenses per monomer lot (for 3 monomer lots) were sampled. The sampling plan for the extractables tests was that 110 lenses per monomer lot (for 2 monomer lots) were sampled. The results of the extractables and biocompatibility studies of stability samples at 15 months are summarized in Table 39. The results of the tests are within specifications and acceptance criteria under ISO 10993 for cytotoxicity, ocular irritation, sensitization, and systemic toxicity.

In conclusion, the sample lenses incubated for 15 months under accelerated aging conditions at 45° C. satisfied all testing specifications and passed the acceptance criteria. 68GS's shelf life is declared as 5 years based on the results of accelerated aging at 45° C. at 15 months testing interval.

TABLE 39

Results of extractables and biocompatibility studies of stability samples at 15 months

| Monomer Lot No. | Lens Lot No. | Test | 15 months at 45° C. |
|---|---|---|---|
| 68GS-001 | PGS0119003 | Cytotoxicity | Pass |
| | | Ocular Irritation | Pass |
| | | Systemic Toxicity | Pass |
| | | Sensitization | Pass |
| | | Extractables (% m/m) | Water: Less than 0.1% Hexane: 0.12% |
| 68GS-002 | PGS0119006 | Cytotoxicity | Pass |
| | | Ocular Irritation | Pass |
| | | Systemic Toxicity | Pass |
| | | Sensitization | Pass |
| 68GS-003 | PGS0119009 | Cytotoxicity | Pass |
| | | Ocular Irritation | Pass |
| | | Systemic Toxicity | Pass |
| | | Sensitization | Pass |
| | | Extractables (% m/m) | Water: Less than 0.1% Hexane: 0.14% |

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions and methods, and aspects of these compositions and methods are specifically described, other compositions and methods and combinations of various features of the compositions and methods are intended to fall within the scope of the appended claims, even if not specifically recited. Thus, a combination of steps, elements, components, or constituents can be explicitly mentioned herein; however, all other combinations of steps, elements, components, and constituents are included, even though not explicitly stated.

What is claimed is:

1. An antimicrobial ophthalmic device comprising:
   a silicone hydrogel composition and an antimicrobial agent,
   wherein the silicone hydrogel composition comprises an actinically-crosslinkable polysiloxane-polyglycerol block copolymer crosslinked with a crosslinker,
   wherein the actinically-crosslinkable polysiloxane-polyglycerol block copolymer is derived from: a polysiloxane prepolymer comprising a polyglycerol side chain, the polyglycerol side chain comprising an ethylenically unsaturated group covalently linked thereto,
   wherein the ethylenically unsaturated group is actinically curable.

2. The antimicrobial ophthalmic device of claim 1, wherein the antimicrobial ophthalmic device comprises a contact lens, an introcular lens, a corneal inlay, an eye bandage, a drug delivery device, a prosthetic device, or a combination thereof.

3. The antimicrobial ophthalmic device of claim 1, wherein the antimicrobial ophthalmic device comprises a contact lens and the contact lens is cosmetically tinted.

4. The antimicrobial ophthalmic device of claim 1, wherein the antimicrobial agent comprises a quaternary ammonium compound, an antimicrobial metal, an antimicrobial monomer, or a combination thereof.

5. The antimicrobial ophthalmic device of claim 1, wherein the antimicrobial agent comprises a quaternary ammonium compound.

6. The antimicrobial ophthalmic device of claim 1, wherein the antimicrobial agent comprises an antimicrobial metal and the antimicrobial metal comprises Ag, Au, Pt, Pd, Ir, Sn, Cu, Sb, Bi, or Zn.

7. The antimicrobial ophthalmic device of claim 1, wherein the antimicrobial agent comprises a plurality of nanoparticles comprising an antimicrobial metal.

8. The antimicrobial ophthalmic device of claim 1, wherein the antimicrobial agent is provided as a coating, wherein the antimicrobial agent is chemically bound to the silicon hydrogel composition, or a combination thereof.

9. The antimicrobial ophthalmic device of claim 1, wherein the antimicrobial ophthalmic device has a high oxygen permeability.

10. The antimicrobial ophthalmic device of claim 1, wherein the polysiloxane prepolymer is linear or branched.

11. The antimicrobial ophthalmic device of claim 1, wherein the ethylenically unsaturated group is covalently linked to the polyglycerol side chain directly or wherein the ethylenically unsaturated group is covalently linked to the polyglycerol side chain through a linking group.

12. The antimicrobial ophthalmic device of claim 1, wherein the ethylenically unsaturated group comprises acryloyl, acrylamide, alkyl acrylamide, dialkyl acrylamide, methacryloyl, allyl, vinyl, styrenyl, or a combination thereof.

13. The antimicrobial ophthalmic device of claim 1, wherein the actinically-crosslinkable polysiloxane-polyglycerol block copolymer is defined by Formula I:

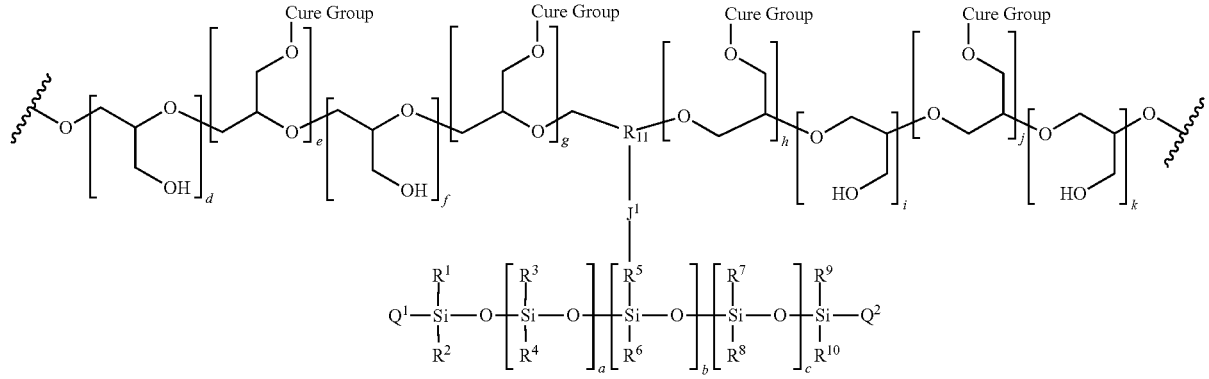

I wherein $R^1$, $R^2$, $R^3$, $R^4$, $R^5$, $R^6$, $R^7$, $R^8$, $R^9$, $R^{10}$, $R^{11}$, and $J^1$ are, independently, alkyl, cycloalkyl, aryl, alkylpolyethylene oxide, or polyglycerol, any of which is optionally substituted with halide, hydroxy, thiol, carbonyl, alkoxy, alkylhydroxy, carboxyl, amino, amido, alkyl, alkenyl, alkynyl, aryl, —$NR^xR^y$, —$C(O)NR^xR^y$, azide, or a combination thereof;

$Q^1$ and $Q^2$ are independently H, OH, amino, alkyl, alkenyl, alkynyl, cycloalkyl, aryl, alkylaryl, or heteroaryl, any of which is optionally substituted with epoxy, hydroxy, thiol, carbonyl, alkoxy, alkylhydroxy, carboxyl, amino, amido, alkyl, alkenyl, alkynyl, aryl, —$NR^xR^y$, —$C(O)NR^xR^y$, azide, or a combination thereof;

$R^x$ and $R^y$ are independently H, OH, alkyl, alkenyl, alkynyl, cycloalkyl, aryl, alkylaryl, or heteroaryl;

Cure Group comprises the ethylenically unsaturated group;

a, c, d, e, f, g, h, i, j, and k are, independently, an integer from 0 to 10,000; with the proviso that: at least one of e, g, h, and j is not 0, and at least one of d, f, i, and k is not 0; and b is an integer from 1 to 10,000.

14. The antimicrobial ophthalmic device of claim 13, wherein:

$R^1$-$R^{11}$ and $J^1$ are, independently, $C_1$-$C_{18}$ alkyl, $C_3$-$C_{18}$ cycloalkyl, $C_3$-$C_{20}$ aryl, alkylpolyethylene oxide, or polyglycerol, any of which is optionally substituted;

$Q^1$ and $Q^2$ are independently $C_1$-$C_{18}$ alkyl, $C_3$-$C_{20}$ aryl, $C_1$-$C_{18}$ perfluoroalkyl, $C_1$-$C_{18}$ alkanol, $C_1$-$C_{18}$ alkylthiol, $C_1$-$C_{18}$ alkylamine, $C_1$-$C_{18}$ dialkylamine, any of which is optionally substituted; and the Cure Group is selected from the group consisting of:

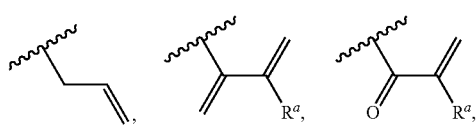

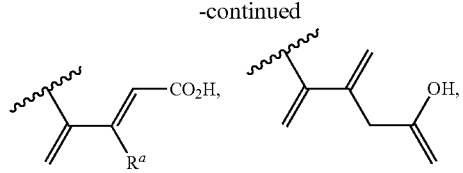

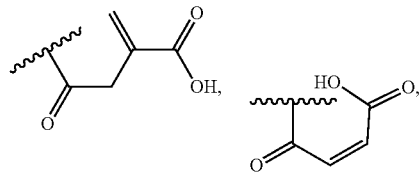

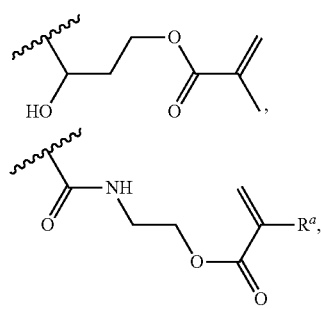

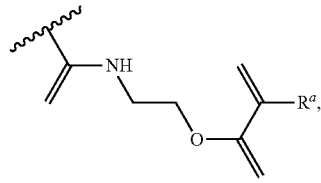

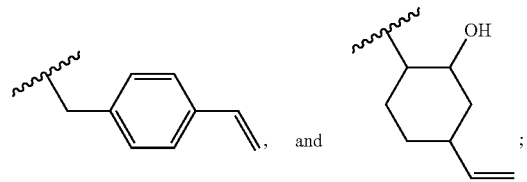

wherein

R$^a$ is H, alkyl, or cycloalkyl, either of which is optionally substituted with halide, hydroxy, alkylthiol, carbonyl, alkoxy, alkylhydroxy, carboxyl, amino, amido, alkyl, alkenyl, alkynyl, aryl, —NR$^x$R$^y$, —C(O)NR$^x$R$^y$, or a combination thereof; and R$^x$ and R$^y$ are independently H, OH, alkyl, alkenyl, alkynyl, cycloalkyl, aryl, alkylaryl, or heteroaryl.

15. The antimicrobial ophthalmic device of claim 1, wherein the polysiloxane prepolymer comprises polydimethylsiloxane.

16. The antimicrobial ophthalmic device of claim 1, wherein the actinically-crosslinkable polysiloxane-polyglycerol block copolymer is defined by Formula IX, Formula X, or Formula XI:

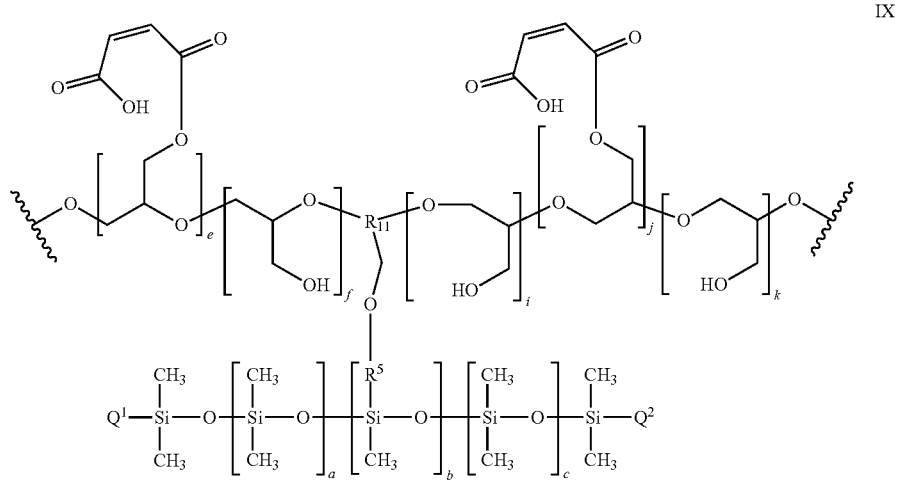

IX

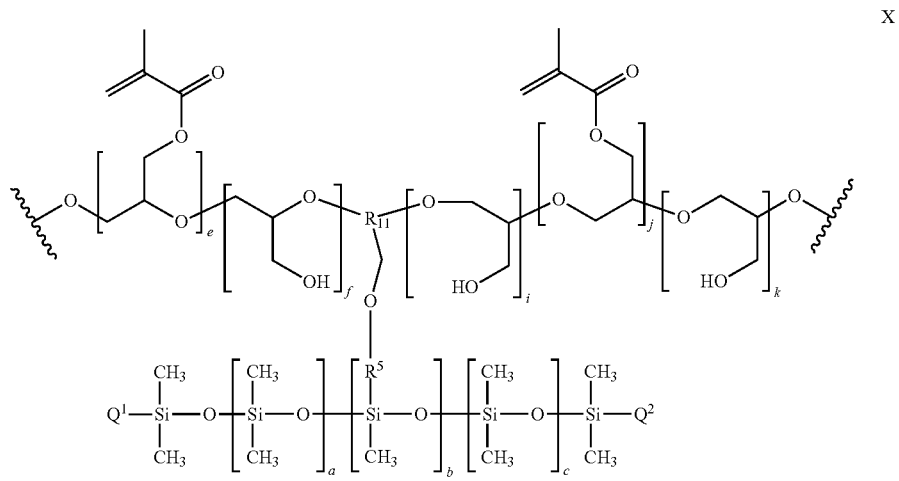

X

-continued

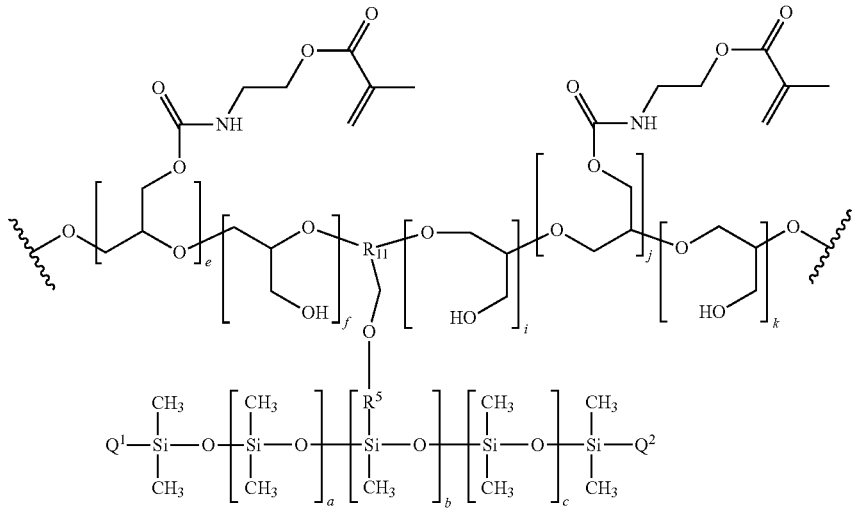

XI wherein
a, c, e, f, i, j and k are, independently, an integer from 0 to 10,000; with the proviso that: at least one of e and j is not 0, and at least one of f, i, and k is not 0; and
b is an integer from 1 to 10,000.

17. The antimicrobial ophthalmic device of claim 1, wherein the actinically-crosslinkable polysiloxane-polyglycerol block copolymer comprises a methacrylated polydimethylsiloxane-polyglycerol block copolymer; a chain extended actinically-crosslinkable polysiloxane-polyglycerol block copolymer; or a combination thereof.

18. The antimicrobial ophthalmic device of claim 1, wherein the actinically-crosslinkable polysiloxane-polyglycerol block copolymer comprises a chain extended actinically-crosslinkable polysiloxane-polyglycerol block copolymer and the chain extended actinically-crosslinkable polysiloxane-polyglycerol block copolymer is defined by Formula XII:

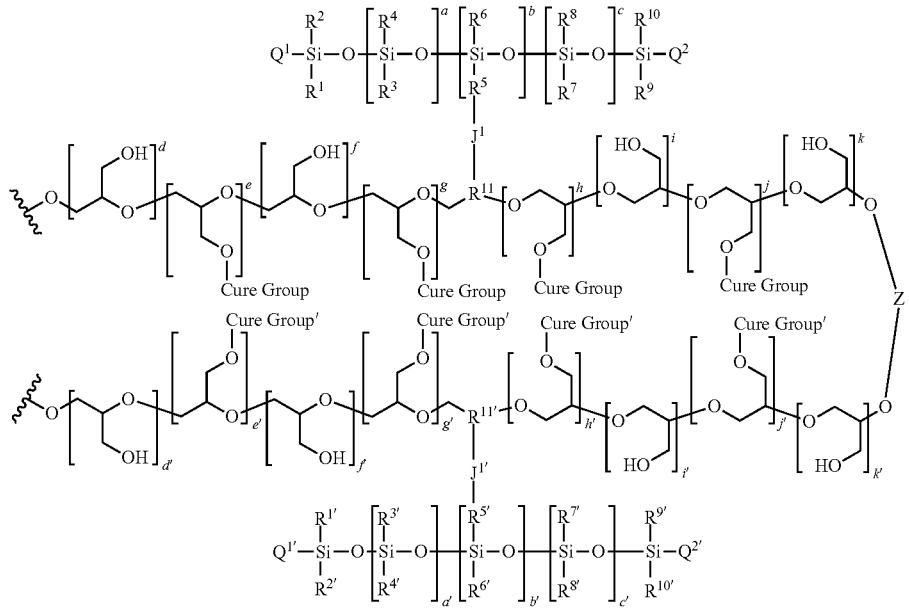

XII wherein
R¹, R¹', R², R²', R³, R³', R⁴, R⁴', R⁵, R⁵', R⁶, R⁶', R⁷, R⁷', R⁸, R⁸', R⁹, R⁹', R¹⁰, R¹⁰', R¹¹, R¹¹', J¹, and J¹' are, independently, alkyl, cycloalkyl, aryl, alkylpolyethylene oxide, or polyglycerol, any of which is optionally substituted with halide, hydroxy, thiol, carbonyl, alkoxy, alkylhydroxy, carboxyl, amino, amido, alkyl, alkenyl, alkynyl, aryl, —NR$^x$R$^y$, —C(O)NR$^x$R$^y$, azide, or a combination thereof;

Q¹, Q¹', Q², and Q²' are independently H, OH, amino, alkyl, alkenyl, alkynyl, cycloalkyl, aryl, alkylaryl, or heteroaryl, any of which is optionally substituted with epoxy, hydroxy, thiol, carbonyl, alkoxy, alkylhydroxy, carboxyl, amino, amido, alkyl, alkenyl, alkynyl, aryl, —NR$^x$R$^y$, —C(O)NR$^x$R$^y$, azide, or a combination thereof;

R$^x$ and R$^y$ are independently H, OH, alkyl, alkenyl, alkynyl, cycloalkyl, aryl, alkylaryl, or heteroaryl;

Cure Group and Cure Group' independently comprise an ethylenically unsaturated group;

Z is a chain extension group;

a, a', c, c', d, d', e, e', f, f', g, g', h, h', i, i', j, j', k, and k' are, independently, an integer from 0 to 10,000, with the proviso that:
at least one of e, g, h, and j is not 0,
at least one of e', g', h', and j' is not 0,
at least one of d, f, i, and k is not 0, and
at least one of d', f', i', and k' is not 0; and b and b' are independently an integer from 1 to 10,000.

19. The antimicrobial ophthalmic device of claim 18, wherein:

R¹-R¹¹, R¹'-R¹¹', J¹, and J¹' are, independently, $C_1$-$C_{18}$ alkyl, $C_3$-$C_{18}$ cycloalkyl, $C_3$-$C_{20}$ aryl, alkylpolyethylene oxide, or polyglycerol, any of which is optionally substituted;

Q¹, Q¹', Q², and Q²' are independently H, OH, aryl, epoxide, alkanol, alkylthio, alkenylthio, arylthio, amine, alkylamine, dialkylamine, (meth)acrylate, (meth)acrylamide, dialkyl (meth)acrylamide, vinyl, ketone, aldehyde, carboxylic acid, anhydride, or azide, any of which is optionally substituted; and Cure Group and Cure Group' are independently selected from the group consisting of:

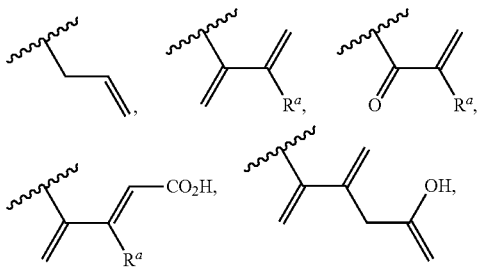

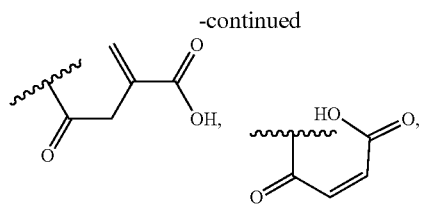

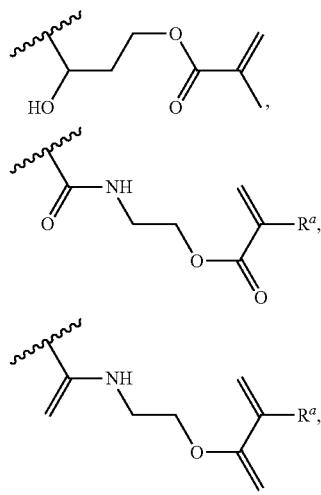

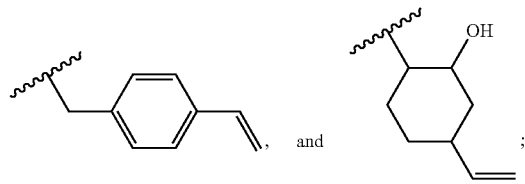

wherein

R$^a$ is H, alkyl, or cycloalkyl, either of which is optionally substituted with halide, hydroxy, alkylthiol, carbonyl, alkoxy, alkylhydroxy, carboxyl, amino, amido, alkyl, alkenyl, alkynyl, aryl, —NR$^x$R$^y$, —C(O)NR$^x$R$^y$, or a combination thereof, and R$^x$ and R$^y$ are independently H, OH, alkyl, alkenyl, alkynyl, cycloalkyl, aryl, alkylaryl, or heteroaryl.

20. The antimicrobial ophthalmic device of claim 1, wherein the silicone hydrogel composition further comprises a hydrophilic monomer, a hydrophobic monomer, an amphiphilic monomer, a zwitterionic monomer, a UV-blocker, a blue light blocker, an antimicrobial monomer, a dye, a pigment, a solvent, or a combination thereof.

* * * * *